US010143748B2

(12) United States Patent
Grosmaire et al.

(10) Patent No.: US 10,143,748 B2
(45) Date of Patent: Dec. 4, 2018

(54) B-CELL REDUCTION USING CD37-SPECIFIC AND CD20-SPECIFIC BINDING MOLECULES

(71) Applicant: Emergent Product Development Seattle, LLC, Seattle, WA (US)

(72) Inventors: Laura Sue Grosmaire, Hobart, WA (US); Martha Susan Hayden-Ledbetter, Shoreline, WA (US); Jeffrey A. Ledbetter, Shoreline, WA (US); Peter Armstrong Thompson, Bellevue, WA (US); Sandy Alexander Simon, Seattle, WA (US); William Brady, Bothell, WA (US)

(73) Assignee: Aptevo Research and Development LLC, Seattle, WA (US)

( * ) Notice: Subject to any disclaimer, the term of this patent is extended or adjusted under 35 U.S.C. 154(b) by 921 days.

(21) Appl. No.: 13/836,103

(22) Filed: Mar. 15, 2013

(65) Prior Publication Data

US 2014/0004117 A1 Jan. 2, 2014

Related U.S. Application Data

(63) Continuation of application No. 11/493,132, filed on Jul. 25, 2006.

(60) Provisional application No. 60/702,499, filed on Jul. 25, 2005, provisional application No. 60/800,595, filed on May 16, 2006.

(51) Int. Cl.

| | |
|---|---|
| ***A61K 38/36*** | (2006.01) |
| ***A61K 39/395*** | (2006.01) |
| ***A61K 45/06*** | (2006.01) |
| ***C07K 16/28*** | (2006.01) |
| ***C07K 16/30*** | (2006.01) |
| *A61K 39/00* | (2006.01) |

(52) U.S. Cl.

CPC .... *A61K 39/3955* (2013.01); *A61K 39/39558* (2013.01); *A61K 45/06* (2013.01); *C07K 16/2887* (2013.01); *C07K 16/2896* (2013.01); *C07K 16/30* (2013.01); *C07K 16/3061* (2013.01); *A61K 2039/505* (2013.01); *A61K 2039/507* (2013.01); *A61K 2039/545* (2013.01); *C07K 2317/24* (2013.01); *C07K 2317/52* (2013.01); *C07K 2317/53* (2013.01); *C07K 2317/56* (2013.01); *C07K 2317/565* (2013.01); *C07K 2317/567* (2013.01); *C07K 2317/622* (2013.01); *C07K 2317/72* (2013.01); *C07K 2317/73* (2013.01); *C07K 2317/732* (2013.01); *C07K 2317/734* (2013.01); *C07K 2317/75* (2013.01); *C07K 2317/76* (2013.01)

(58) Field of Classification Search

None

See application file for complete search history.

(56) References Cited

U.S. PATENT DOCUMENTS

| | | | |
|---|---|---|---|
| 3,927,193 | A | 12/1975 | Hansen et al. |
| 3,929,992 | A | 12/1975 | Sehgal et al. |
| 4,179,337 | A | 12/1979 | Davis et al. |
| 4,301,144 | A | 11/1981 | Iwashita et al. |
| 4,316,885 | A | 2/1982 | Rakhit |
| 4,331,647 | A | 5/1982 | Goldenberg |
| 4,348,376 | A | 9/1982 | Goldenberg |
| 4,361,544 | A | 11/1982 | Goldenberg |
| 4,444,744 | A | 4/1984 | Goldenberg |
| 4,460,459 | A | 7/1984 | Shaw et al. |
| 4,460,559 | A | 7/1984 | Goldenberg |
| 4,460,561 | A | 7/1984 | Goldenberg |
| 4,468,457 | A | 8/1984 | Goldenberg et al. |
| 4,496,689 | A | 1/1985 | Mitra |
| 4,624,846 | A | 11/1986 | Goldenberg |
| 4,640,835 | A | 2/1987 | Shimizu et al. |
| 4,650,803 | A | 3/1987 | Stella et al. |
| 4,670,417 | A | 6/1987 | Iwasaki et al. |
| 4,704,692 | A | 11/1987 | Ladner |
| 4,769,330 | A | 9/1988 | Paoletti et al. |
| 4,782,840 | A | 11/1988 | Martin, Jr. et al. |
| 4,791,192 | A | 12/1988 | Nakagawa et al. |

(Continued)

FOREIGN PATENT DOCUMENTS

| | | | |
|---|---|---|---|
| CA | 2 379 586 | A1 | 10/2003 |
| CA | 2 414 148 | A1 | 6/2004 |

(Continued)

OTHER PUBLICATIONS

De Pascalis, R., et al., "Grafting of'abbreviated' complementarity-determining regions containing specificity-determining residues essential for ligand contact to engineer a less immunogenic humanized monoclonal antibody," J. Immunol. 169(6):3076-3084, 2002.*

(Continued)

*Primary Examiner* — Michail A Belyavskyi

(74) *Attorney, Agent, or Firm* — Cooley LLP

(57) ABSTRACT

The present invention generally provides methods for B-cell reduction in an individual using CD37-specific binding molecules. In particular, the invention provides methods for B-cell reduction using CD37-specific binding molecules alone, or a combination of CD37-specific binding molecules and CD20-specific binding molecules, in some instances a synergistic combination. The invention further provides materials and methods for treatment of diseases involving aberrant B-cell activity. In addition, the invention provides humanized CD37-specific binding molecules.

8 Claims, 39 Drawing Sheets

Specification includes a Sequence Listing.

(56) References Cited

U.S. PATENT DOCUMENTS

| | | | |
|---|---|---|---|
| 4,816,567 | A | 3/1989 | Cabilly et al. |
| 4,818,709 | A | 4/1989 | Primus et al. |
| 4,861,579 | A | 8/1989 | Meyer, Jr. et al. |
| 4,897,268 | A | 1/1990 | Tice et al. |
| 4,906,562 | A | 3/1990 | Hellstrom et al. |
| 4,932,412 | A | 6/1990 | Goldenberg |
| 4,935,495 | A | 6/1990 | Hellstrom et al. |
| 4,946,778 | A | 8/1990 | Ladner et al. |
| 5,017,487 | A | 5/1991 | Stunnenberg et al. |
| 5,023,263 | A | 6/1991 | Von Burg |
| 5,023,264 | A | 6/1991 | Caufield et al. |
| 5,075,109 | A | 12/1991 | Tice et al. |
| 5,091,177 | A | 2/1992 | Hellstrom et al. |
| 5,098,833 | A | 3/1992 | Lasky et al. |
| 5,100,883 | A | 3/1992 | Schiehser |
| 5,118,677 | A | 6/1992 | Caufield |
| 5,118,678 | A | 6/1992 | Kao et al. |
| 5,120,842 | A | 6/1992 | Failli et al. |
| 5,122,368 | A | 6/1992 | Greenfield |
| 5,130,307 | A | 7/1992 | Failli et al. |
| 5,141,736 | A | 8/1992 | Iwasa et al. |
| 5,151,413 | A | 9/1992 | Caufield et al. |
| 5,162,333 | A | 11/1992 | Failli et al. |
| 5,177,203 | A | 1/1993 | Failli et al. |
| 5,217,713 | A | 6/1993 | Iwasa et al. |
| 5,221,670 | A | 6/1993 | Caufield |
| 5,225,539 | A | 7/1993 | Winter |
| 5,233,036 | A | 8/1993 | Hughes |
| 5,256,790 | A | 10/1993 | Nelson |
| 5,258,389 | A | 11/1993 | Goulet et al. |
| 5,260,203 | A | 11/1993 | Ladner et al. |
| 5,260,300 | A | 11/1993 | Hu |
| 5,262,423 | A | 11/1993 | Kao |
| 5,302,584 | A | 4/1994 | Kao et al. |
| 5,362,718 | A | 11/1994 | Skotnicki et al. |
| 5,373,014 | A | 12/1994 | Failli et al. |
| 5,385,908 | A | 1/1995 | Nelson et al. |
| 5,385,909 | A | 1/1995 | Nelson et al. |
| 5,385,910 | A | 1/1995 | Ocain et al. |
| 5,389,639 | A | 2/1995 | Failli et al. |
| 5,391,730 | A | 2/1995 | Skotnicki et al. |
| 5,411,967 | A | 5/1995 | Kao et al. |
| 5,434,131 | A | 7/1995 | Linsley et al. |
| 5,434,260 | A | 7/1995 | Skotnicki et al. |
| 5,455,030 | A | 10/1995 | Ladner et al. |
| 5,463,048 | A | 10/1995 | Skotnicki et al. |
| 5,480,988 | A | 1/1996 | Failli et al. |
| 5,480,989 | A | 1/1996 | Kao et al. |
| 5,489,680 | A | 2/1996 | Failli et al. |
| 5,491,231 | A | 2/1996 | Nelson et al. |
| 5,500,362 | A | 3/1996 | Robinson et al. |
| 5,504,091 | A | 4/1996 | Molnar-Kimber et al. |
| 5,521,288 | A | 5/1996 | Linsley et al. |
| 5,530,101 | A | 6/1996 | Queen et al. |
| 5,563,145 | A | 10/1996 | Failli et al. |
| 5,580,756 | A | 12/1996 | Linsley et al. |
| 5,585,089 | A | 12/1996 | Queen et al. |
| 5,591,828 | A | 1/1997 | Bosslet et al. |
| 5,595,721 | A | 1/1997 | Kaminski et al. |
| 5,597,707 | A | 1/1997 | Marken et al. |
| 5,601,819 | A | 2/1997 | Wong et al. |
| 5,605,690 | A | 2/1997 | Jacobs et al. |
| 5,637,481 | A | 6/1997 | Ledbetter et al. |
| 5,645,835 | A | 7/1997 | Fell, Jr. et al. |
| 5,665,772 | A | 9/1997 | Cottens et al. |
| 5,677,180 | A | 10/1997 | Robinson et al. |
| 5,677,425 | A | 10/1997 | Bodmer et al. |
| 5,693,762 | A | 12/1997 | Queen et al. |
| 5,709,859 | A | 1/1998 | Aruffo et al. |
| 5,714,147 | A | 2/1998 | Capon et al. |
| 5,721,108 | A | 2/1998 | Robinson et al. |
| 5,736,137 | A | 4/1998 | Anderson et al. |
| 5,770,197 | A | 6/1998 | Linsley et al. |
| 5,773,253 | A | 6/1998 | Linsley et al. |
| 5,776,456 | A | 7/1998 | Anderson et al. |
| 5,780,462 | A | 7/1998 | Lee et al. |
| 5,795,572 | A | 8/1998 | Diegel et al. |
| 5,807,734 | A | 9/1998 | Diegel et al. |
| 5,837,243 | A | 11/1998 | Deo et al. |
| 5,843,398 | A | 12/1998 | Kaminski et al. |
| 5,843,439 | A | 12/1998 | Anderson et al. |
| 5,844,093 | A | 12/1998 | Kettleborough et al. |
| 5,844,095 | A | 12/1998 | Linsley et al. |
| 5,849,898 | A | 12/1998 | Seed et al. |
| 5,858,753 | A | 1/1999 | Chantry et al. |
| 5,869,049 | A | 2/1999 | Noelle et al. |
| 5,869,620 | A | 2/1999 | Whitlow et al. |
| 5,876,718 | A | 3/1999 | Noelle et al. |
| 5,876,950 | A | 3/1999 | Siadak et al. |
| 5,882,910 | A | 3/1999 | Chantry et al. |
| 5,885,793 | A | 3/1999 | Griffiths et al. |
| 5,888,773 | A | 3/1999 | Jost et al. |
| 5,892,019 | A | 4/1999 | Schlom et al. |
| 5,897,861 | A | 4/1999 | Fanger et al. |
| 5,916,560 | A | 6/1999 | Larsen et al. |
| 5,922,845 | A | 7/1999 | Deo et al. |
| 5,955,315 | A | 9/1999 | Lee et al. |
| 5,959,083 | A | 9/1999 | Bosslet et al. |
| 5,977,318 | A | 11/1999 | Linsley et al. |
| 5,980,896 | A | 11/1999 | Hellstrom et al. |
| 5,985,589 | A | 11/1999 | Chantry et al. |
| 6,015,542 | A | 1/2000 | Kaminski et al. |
| 6,015,695 | A | 1/2000 | Casterman et al. |
| 6,072,035 | A | 6/2000 | Hardman et al. |
| 6,074,644 | A | 6/2000 | Pastan et al. |
| 6,074,655 | A | 6/2000 | Fowler et al. |
| 6,087,329 | A | 7/2000 | Armitage et al. |
| 6,090,365 | A | 7/2000 | Kaminski et al. |
| 6,090,914 | A | 7/2000 | Linsley et al. |
| 6,105,542 | A | 8/2000 | Efford |
| 6,120,767 | A | 9/2000 | Robinson et al. |
| 6,129,914 | A | 10/2000 | Weiner et al. |
| 6,132,992 | A | 10/2000 | Ledbetter et al. |
| 6,133,426 | A | 10/2000 | Gonzalez et al. |
| 6,136,313 | A | 10/2000 | Stevenson |
| 6,147,203 | A | 11/2000 | Pastan et al. |
| 6,150,584 | A | 11/2000 | Kucherlapati et al. |
| 6,171,586 | B1 | 1/2001 | Lam et al. |
| 6,180,370 | B1 | 1/2001 | Queen et al. |
| 6,193,966 | B1 | 2/2001 | Deo et al. |
| 6,194,551 | B1 | 2/2001 | Idusogie et al. |
| 6,197,294 | B1 | 3/2001 | Tao et al. |
| 6,224,866 | B1 | 5/2001 | Barbera-Guillem |
| 6,242,195 | B1 | 6/2001 | Idusogie et al. |
| 6,262,244 | B1 | 7/2001 | Houchins et al. |
| 6,264,951 | B1 | 7/2001 | Armitage et al. |
| 6,270,765 | B1 | 8/2001 | Deo et al. |
| 6,284,536 | B1 | 9/2001 | Morrison et al. |
| 6,287,537 | B1 | 9/2001 | Kaminski et al. |
| 6,303,755 | B1 | 10/2001 | Deo et al. |
| 6,306,393 | B1 | 10/2001 | Goldenberg |
| 6,312,692 | B1 | 11/2001 | Noelle et al. |
| 6,312,694 | B1 | 11/2001 | Thorpe et al. |
| 6,352,694 | B1 | 3/2002 | June et al. |
| 6,368,596 | B1 | 4/2002 | Ghetie et al. |
| 6,376,459 | B1 | 4/2002 | Aruffo et al. |
| 6,379,966 | B2 | 4/2002 | Monahan et al. |
| 6,379,967 | B1 | 4/2002 | Meredith et al. |
| 6,380,169 | B1 | 4/2002 | Adams et al. |
| 6,380,170 | B1 | 4/2002 | Muller et al. |
| 6,380,362 | B1 | 4/2002 | Watson et al. |
| 6,380,369 | B1 | 4/2002 | Adams et al. |
| 6,380,371 | B1 | 4/2002 | Sassetti et al. |
| 6,380,382 | B1 | 4/2002 | Khodadoust |
| 6,383,138 | B1 | 5/2002 | Sen et al. |
| 6,383,478 | B1 | 5/2002 | Prokop et al. |
| 6,383,481 | B1 | 5/2002 | Ikehara et al. |
| 6,383,512 | B1 | 5/2002 | Ciccarelli et al. |
| 6,383,522 | B1 | 5/2002 | Dupont |
| 6,383,733 | B1 | 5/2002 | Beug et al. |
| 6,383,737 | B2 | 5/2002 | Olsen et al. |
| 6,383,738 | B1 | 5/2002 | Bruni et al. |
| 6,383,743 | B1 | 5/2002 | Kinzler et al. |
| 6,383,746 | B1 | 5/2002 | Guignard et al. |

(56) References Cited

U.S. PATENT DOCUMENTS 6,383,753 B1 5/2002 Thiele et al.
6,383,785 B1 5/2002 Mueller et al.
6,383,794 B1 5/2002 Mountz et al.
6,383,795 B1 5/2002 Carrion et al.
6,383,811 B2 5/2002 Wolff et al.
6,383,814 B1 5/2002 Lee et al.
6,384,018 B1 5/2002 Content et al.
6,384,198 B1 5/2002 Diegel et al.
6,384,202 B1 5/2002 Sedlacek et al.
6,384,203 B1 5/2002 Anderson et al.
6,384,210 B1 5/2002 Blanchard
6,395,272 B1 5/2002 Deo et al.
6,399,061 B1 6/2002 Anderson et al.
6,403,769 B1 6/2002 Larochelle et al.
6,410,319 B1 6/2002 Raubitschek et al.
6,410,391 B1 6/2002 Zelsacher
6,410,690 B1 6/2002 Deo et al.
6,444,792 B1 9/2002 Gray et al.
6,455,043 B1 9/2002 Grillo-Lopez
6,472,179 B2 10/2002 Stahl et al.
6,472,510 B1 10/2002 Aruffo et al.
6,476,198 B1 11/2002 Kang
6,482,919 B2 11/2002 Ledbetter et al.
6,515,110 B1 2/2003 Whitlow et al.
6,518,277 B1 2/2003 Sadhu et al.
6,528,624 B1 3/2003 Idusogie et al.
6,538,124 B1 3/2003 Idusogie et al.
6,586,428 B2 7/2003 Geroni et al.
6,589,527 B1 7/2003 Winter et al.
6,623,940 B1 9/2003 Ledbetter et al.
6,641,809 B1 11/2003 Linsley et al.
6,696,290 B2 2/2004 Fitzpatrick et al.
6,761,889 B2 7/2004 Lowman et al.
6,800,620 B2 10/2004 Sadhu et al.
6,809,185 B1 10/2004 Schoonjans et al.
6,815,540 B1 11/2004 Pluckthun et al.
6,818,213 B1 11/2004 Thorpe et al.
6,881,557 B2 4/2005 Foote
6,893,625 B1 5/2005 Robinson et al.
6,896,885 B2 5/2005 Hanna
7,052,872 B1 5/2006 Hansen et al.
7,074,403 B1 7/2006 Goldenberg et al.
7,122,646 B2 10/2006 Holliger et al.
7,129,330 B1 10/2006 Little et al.
7,148,321 B2 12/2006 Gillies et al.
7,166,707 B2 1/2007 Feige
7,183,076 B2 2/2007 Arathoon et al.
7,612,181 B2 11/2009 Wu et al.
7,754,208 B2 7/2010 Ledbetter et al.
7,754,209 B2 7/2010 Ledbetter et al.
7,820,161 B1 10/2010 Curd et al.
7,829,056 B2 11/2010 Lee
7,829,084 B2 11/2010 Ledbetter et al.
8,106,161 B2 1/2012 Ledbetter et al.
8,147,835 B2 4/2012 Ledbetter et al.
8,188,237 B2 5/2012 Ledbetter et al.
8,197,810 B2 6/2012 Ledbetter et al.
8,333,966 B2 12/2012 Tan et al.
8,361,464 B2 1/2013 Griffiths
8,409,577 B2 4/2013 Thompson et al.
8,853,366 B2 10/2014 Ledbetter et al.
9,005,612 B2 4/2015 Ledbetter et al.
9,101,609 B2 8/2015 Tan et al.
2001/0044135 A1 11/2001 Stahi et al.
2002/0004587 A1 1/2002 Miller et al.
2002/0006404 A1 1/2002 Hanna et al.
2002/0009444 A1 1/2002 Grillo-Lopez
2002/0012665 A1 1/2002 Hanna
2002/0028178 A1 3/2002 Hanna et al.
2002/0031510 A1 3/2002 Larsen et al.
2002/0039557 A1 4/2002 White
2002/0041847 A1 4/2002 Goldenberg
2002/0103345 A1 8/2002 Zhu
2002/0128448 A1 9/2002 Reff
2002/0128488 A1 9/2002 Yamakawa et al.
2002/0155604 A1 10/2002 Ledbetter et al.
2002/0192223 A1 12/2002 Hellstrom et al.
2002/0197255 A1 12/2002 Anderson et al.
2002/0197256 A1 12/2002 Grewal
2003/0008923 A1 1/2003 Dukart et al.
2003/0021781 A1 1/2003 Anderson et al.
2003/0026780 A1 2/2003 Hood et al.
2003/0026801 A1 2/2003 Weiner et al.
2003/0031667 A1 2/2003 Deo et al.
2003/0044423 A1 3/2003 Gillies et al.
2003/0078385 A1 4/2003 Arathoon et al.
2003/0088074 A1 5/2003 Hamers et al.
2003/0115614 A1 6/2003 Kanda et al.
2003/0118592 A1 6/2003 Ledbetter et al.
2003/0133930 A1 7/2003 Goldenberg et al.
2003/0133939 A1 7/2003 Ledbetter et al.
2003/0166868 A1 9/2003 Presta et al.
2003/0219433 A1 11/2003 Hansen et al.
2003/0219436 A1 11/2003 Ledbetter et al.
2003/0219446 A1 11/2003 Linsley et al.
2003/0219876 A1 11/2003 Ledbetter et al.
2004/0018557 A1 1/2004 Qu et al.
2004/0043029 A1 3/2004 Hellstrom et al.
2004/0058445 A1 3/2004 Ledbetter et al.
2004/0071696 A1 4/2004 Adams et al.
2004/0180046 A1 9/2004 Himawan
2004/0191248 A1 9/2004 Goldenberg et al.
2005/0012665 A1 1/2005 Runyon et al.
2005/0031617 A1 2/2005 Ma et al.
2005/0054000 A1 3/2005 Dubel
2005/0084933 A1 4/2005 Schilling et al.
2005/0123540 A1 6/2005 Hanna
2005/0136049 A1 6/2005 Ledbetter et al.
2005/0158829 A1 7/2005 Fandl et al.
2005/0163782 A1 7/2005 Glaser et al.
2005/0164307 A1 7/2005 Kojima et al.
2005/0175614 A1 8/2005 Ledbetter et al.
2005/0180970 A1 8/2005 Ledbetter et al.
2005/0186203 A1 8/2005 Singh et al.
2005/0186216 A1 8/2005 Ledbetter et al.
2005/0202012 A1 9/2005 Ledbetter et al.
2005/0202023 A1 9/2005 Ledbetter et al.
2005/0202028 A1 9/2005 Ledbetter et al.
2005/0202534 A1 9/2005 Ledbetter et al.
2005/0238646 A1 10/2005 Ledbetter et al.
2005/0261317 A1 11/2005 Sadhu et al.
2005/0272758 A1 12/2005 Bayever et al.
2006/0008415 A1 1/2006 Kaisheva et al.
2006/0051844 A1 3/2006 Heavner et al.
2006/0063715 A1 3/2006 Whitlow et al.
2006/0088529 A1 4/2006 Leung et al.
2006/0099205 A1 5/2006 Adams et al.
2006/0104971 A1 5/2006 Garber et al.
2006/0153837 A1 7/2006 Black et al.
2006/0159713 A1 7/2006 Brittain et al.
2006/0210564 A1 9/2006 Kumagai et al.
2006/0263367 A1 11/2006 Fey et al.
2007/0041967 A1 2/2007 Jung et al.
2007/0059206 A1 3/2007 Araki et al.
2007/0059306 A1 3/2007 Grosmaire et al.
2007/0071675 A1 3/2007 Wu et al.
2007/0237779 A1 10/2007 Ledbetter et al.
2008/0213273 A1 9/2008 Burge
2008/0214596 A1 9/2008 Boulay et al.
2008/0279850 A1 11/2008 Brady et al.
2009/0041765 A1 2/2009 Espling et al.
2009/0053225 A1 2/2009 Marzari et al.
2009/0088346 A1 4/2009 Enzelberger et al.
2009/0148447 A1 6/2009 Ledbetter et al.
2009/0162380 A1 6/2009 Glaser et al.
2009/0175867 A1 7/2009 Thompson et al.
2009/0196870 A1 8/2009 Ledbetter et al.
2009/0204489 A1 8/2009 Behrens et al.
2009/0214539 A1 8/2009 Grosmaire et al.
2009/0252729 A1 10/2009 Farrington et al.
2009/0274649 A1 11/2009 Qu et al.
2009/0274692 A1 11/2009 Tan et al.
2010/0034820 A1 2/2010 Ledbetter et al.
2010/0135900 A1 6/2010 Cerveny et al.

(56) References Cited

U.S. PATENT DOCUMENTS

2010/0203052 A1 8/2010 Ledbetter et al.
2010/0272636 A1 10/2010 Byrd et al.
2010/0279932 A1 11/2010 Ledbetter et al.
2011/0033483 A1 2/2011 Thompson et al.
2011/0091461 A1 4/2011 Ledbetter et al.
2011/0105729 A1 5/2011 Ledbetter et al.
2011/0171208 A1 7/2011 Tan et al.
2011/0223164 A1 9/2011 Ledbetter et al.
2012/0034245 A9 2/2012 Thompson et al.
2012/0213773 A1 8/2012 Ledbetter et al.
2013/0142793 A1 6/2013 Ledbetter et al.
2013/0195850 A1 8/2013 Tan et al.
2013/0266561 A1 10/2013 Grosmaire et al.
2014/0010809 A1 1/2014 Ledbetter et al.
2014/0010813 A1 1/2014 Grosmaire et al.
2014/0072562 A1 3/2014 Grosmaire et al.

FOREIGN PATENT DOCUMENTS

EP 0 274 394 A2 7/1988
EP 0 330 191 A2 8/1989
EP 0 332 865 A2 9/1989
EP 0 555 880 A2 8/1993
EP 0 586 002 A2 3/1994
EP 0 682 039 A1 11/1995
EP 0 330 191 B1 10/1996
EP 0 757 099 A2 2/1997
EP 1 186 300 A1 3/2002
EP 0 555 880 B1 8/2004
EP 1 444 268 B1 8/2004
EP 1 654 358 2/2005
EP 0 610 046 B1 12/2005
EP 1 666 500 A1 6/2006
EP 1 746 162 A2 1/2007
EP 1 939 203 A2 7/2008
EP 1 654 358 B1 9/2011
JP 2000-516452 A 12/2000
WO WO 88/04936 A1 7/1988
WO WO 89/01973 A2 3/1989
WO WO 89/01974 A1 3/1989
WO WO 89/07142 A1 8/1989
WO WO 90/07936 A1 7/1990
WO WO 91/00360 A1 1/1991
WO WO 91/02805 A2 3/1991
WO WO 91/04329 A1 4/1991
WO WO 91/09967 A1 7/1991
WO WO 91/11456 A1 8/1991
WO WO 91/13166 A1 9/1991
WO WO 92/00092 A1 1/1992
WO WO 92/08802 A1 5/1992
WO WO 92/21755 A1 12/1992
WO WO 93/00431 A1 1/1993
WO WO 93/03709 A1 3/1993
WO WO 93/25234 A1 12/1993
WO WO 93/25698 A1 12/1993
WO WO 94/03622 A1 2/1994
WO WO 94/04678 A1 3/1994
WO WO 94/05690 A1 3/1994
WO WO 94/09010 A1 4/1994
WO WO 94/09034 A1 4/1994
WO WO 94/11026 A2 5/1994
WO WO 94/13804 A1 6/1994
WO WO 94/25591 A1 11/1994
WO WO 95/03770 A1 2/1995
WO WO 95/08577 A1 3/1995
WO WO 95/09917 A1 4/1995
WO WO 95/16691 A1 6/1995
WO WO 95/24220 A1 9/1995
WO WO 95/30014 A1 11/1995
WO WO 96/34103 A1 10/1996
WO WO 96/40789 A1 12/1996
WO WO 96/41807 A1 12/1996
WO WO 97/09433 A1 3/1997
WO WO 98/02441 A2 1/1998
WO WO 98/02462 A1 1/1998
WO WO 98/02463 A1 1/1998
WO WO 98/23646 A2 6/1998
WO WO 98/31820 A1 7/1998
WO WO 98/56418 A1 12/1998
WO WO 98/58964 A1 12/1998
WO WO 99/02711 A2 1/1999
WO WO 99/10494 A2 3/1999
WO WO 99/15530 A1 4/1999
WO WO 99/22764 A1 5/1999
WO WO 99/37791 A1 7/1999
WO WO 99/42075 A2 8/1999
WO WO 99/42077 A2 8/1999
WO WO 99/43713 A1 9/1999
WO WO 99/51642 A1 10/1999
WO WO 99/57150 A2 11/1999
WO WO 99/57266 A2 11/1999
WO WO 00/06605 A2 2/2000
WO WO 00/09160 A1 2/2000
WO WO 00/20864 A1 4/2000
WO WO 00/27428 A1 5/2000
WO WO 00/27433 A1 5/2000
WO WO 00/27885 A1 5/2000
WO WO 00/42072 A2 7/2000
WO WO 00/44777 A1 8/2000
WO WO 00/44788 A1 8/2000
WO WO 00/67795 A1 11/2000
WO WO 00/67796 A1 11/2000
WO WO 00/69913 A1 11/2000
WO WO 00/74718 A1 12/2000
WO WO 00/76542 A1 12/2000
WO WO 01/03734 A1 1/2001
WO WO 01/09186 A2 2/2001
WO WO 01/09187 A2 2/2001
WO WO 01/09192 A1 2/2001
WO WO 01/10460 A1 2/2001
WO WO 01/10461 A1 2/2001
WO WO 01/10462 A1 2/2001
WO WO 01/13945 A1 3/2001
WO WO 01/14387 A1 3/2001
WO WO 01/34194 A1 5/2001
WO WO 01/72333 A1 10/2001
WO WO 01/74388 A1 10/2001
WO WO 01/77342 A1 10/2001
WO WO 01/80884 A1 11/2001
WO WO 01/85798 A2 11/2001
WO WO 01/97858 A2 12/2001
WO WO 02/02773 A2 1/2002
WO WO 02/04021 A1 1/2002
WO WO 02/08773 A2 1/2002
WO WO 02/34790 A1 5/2002
WO WO 02/056910 A1 7/2002
WO WO 02/060485 A2 8/2002
WO WO 02/060955 A2 8/2002
WO WO 02/064634 A2 8/2002
WO WO 02/072141 A2 9/2002
WO WO 02/072605 A2 9/2002
WO WO 02/079255 A1 10/2002
WO WO 02/096948 A2 12/2002
WO WO 02/100348 A2 12/2002
WO WO 02/102312 A2 12/2002
WO WO 03/020906 A2 3/2003
WO WO 03/025018 A2 3/2003
WO WO 03/026490 A2 4/2003
WO WO 03/027135 A2 4/2003
WO WO 03/030835 A2 4/2003
WO WO 03/042231 A2 5/2003
WO WO 03/048209 A1 6/2003
WO WO 03/057829 A2 7/2003
WO WO 03/074569 A2 9/2003
WO WO 03/083069 A2 10/2003
WO WO 03/106622 A2 12/2003
WO WO 2004/003019 A2 1/2004
WO WO 2004/006955 A1 1/2004
WO WO 2004/016750 A2 2/2004
WO WO 2004/032857 A2 4/2004
WO WO 2004/032961 A1 4/2004
WO WO 2004/035537 A2 4/2004

(56) References Cited

FOREIGN PATENT DOCUMENTS

| | | | |
|---|---|---|---|
| WO | WO 2004/035607 | A2 | 4/2004 |
| WO | WO 2004/056312 | A2 | 7/2004 |
| WO | WO 2004/058171 | A2 | 7/2004 |
| WO | WO 2004/058191 | A2 | 7/2004 |
| WO | WO 2004/072266 | A2 | 8/2004 |
| WO | WO 2004/076489 | A1 | 9/2004 |
| WO | WO 2004/103404 | A1 | 12/2004 |
| WO | WO 2005/000899 | A2 | 1/2005 |
| WO | WO 2005/004809 | A2 | 1/2005 |
| WO | WO 2005/017148 | A1 | 2/2005 |
| WO | WO 2005/018671 | A1 | 3/2005 |
| WO | WO 2005/021710 | A2 | 3/2005 |
| WO | WO 2005/037989 | A2 | 4/2005 |
| WO | WO 2005/040220 | A1 | 5/2005 |
| WO | WO 2005/047334 | A1 | 5/2005 |
| WO | WO 2005/061547 | A2 | 7/2005 |
| WO | WO 2005/063816 | A2 | 7/2005 |
| WO | WO 2005/070966 | A2 | 8/2005 |
| WO | WO 2005/077981 | A2 | 8/2005 |
| WO | WO 2005/077982 | A1 | 8/2005 |
| WO | WO 2005/095460 | A2 | 10/2005 |
| WO | WO 2005/103081 | A2 | 11/2005 |
| WO | WO 2005/117978 | A2 | 12/2005 |
| WO | WO 2005/120437 | A2 | 12/2005 |
| WO | WO 2006/002438 | A2 | 1/2006 |
| WO | WO 2006/008548 | A2 | 1/2006 |
| WO | WO 2006/020258 | A2 | 2/2006 |
| WO | WO 2006/028936 | A2 | 3/2006 |
| WO | WO 2006/041680 | A2 | 4/2006 |
| WO | WO 2006/063150 | A2 | 6/2006 |
| WO | WO 2006/064121 | A2 | 6/2006 |
| WO | WO 2006/074399 | A2 | 7/2006 |
| WO | WO 2006/084264 | A2 | 8/2006 |
| WO | WO 2006/106905 | A1 | 10/2006 |
| WO | WO 2006/113308 | A1 | 10/2006 |
| WO | WO 2006/117782 | A2 | 11/2006 |
| WO | WO 2006/130458 | A2 | 12/2006 |
| WO | WO 2007/011363 | A2 | 1/2007 |
| WO | WO 2007/014238 | A2 | 2/2007 |
| WO | WO 2007/014278 | A2 | 2/2007 |
| WO | WO 2007/011363 | A3 | 7/2007 |
| WO | WO 2007/095338 | A2 | 8/2007 |
| WO | WO 2007/146968 | A2 | 12/2007 |
| WO | WO 2008/052030 | A2 | 5/2008 |
| WO | WO 2008/138834 | A1 | 11/2008 |
| WO | WO 2008/143954 | A2 | 11/2008 |
| WO | WO 2008/152387 | A1 | 12/2008 |
| WO | WO 2008/152390 | A1 | 12/2008 |
| WO | WO 2008/152394 | A1 | 12/2008 |
| WO | WO 2008/153636 | A1 | 12/2008 |
| WO | WO 2009/019312 | A2 | 2/2009 |
| WO | WO 2009/023386 | A2 | 2/2009 |
| WO | WO 2009/036082 | A2 | 3/2009 |
| WO | WO 2009/039140 | A1 | 3/2009 |
| WO | WO 2009/040552 | A2 | 4/2009 |
| WO | WO 2009/042607 | A1 | 4/2009 |
| WO | WO 2009/045174 | A1 | 4/2009 |
| WO | WO 2009/045175 | A1 | 4/2009 |
| WO | WO 2009/046448 | A1 | 4/2009 |
| WO | WO 2009/052145 | A1 | 4/2009 |
| WO | WO 2009/053715 | A1 | 4/2009 |
| WO | WO 2009/053716 | A1 | 4/2009 |
| WO | WO 2009/055418 | A1 | 4/2009 |
| WO | WO 2009/058361 | A1 | 5/2009 |
| WO | WO 2009/059030 | A1 | 5/2009 |
| WO | WO 2009/064802 | A2 | 5/2009 |
| WO | WO 2009/066084 | A1 | 5/2009 |
| WO | WO 2009/068482 | A1 | 6/2009 |
| WO | WO 2009/070524 | A1 | 6/2009 |
| WO | WO 2009/106356 | A1 | 9/2009 |
| WO | WO 2009/126944 | A1 | 10/2009 |
| WO | WO 2010/057047 | A1 | 5/2010 |

OTHER PUBLICATIONS

MacCallum, R.M., et al., "Antibody-antigen Interactions: Contact Analysis and Binding Site Topography," J. Mol. Biol. 262:732-745, 1996.*
Deckert et al., "A novel anti-CD37 antibody-drug conjugate with multiple anti-tumor mechanisms for the treatment of B-cell malignancies", Blood, 122:3500-3510, 2013 (Year: 2013).*
U.S. Appl. No. 12/834,707, filed Jul. 12, 2010.
U.S. Appl. No. 13/396,147, filed Feb. 14, 2012.
U.S. Appl. No. 13/451,641, filed Apr. 20, 2012.
U.S. Appl. No. 13/835,833, filed Mar. 15, 2013.
U.S. Appl. No. 11/493,132, filed Jul. 25, 2006.
U.S. Appl. No. 12/437,507, filed May 7, 2009.
U.S. Appl. No. 13/836,147, filed Mar. 15, 2013.
U.S. Appl. No. 13/836,163, filed Mar. 15, 2013.
U.S. Appl. No. 13/836,377, filed Mar. 15, 2013.
U.S. Appl. No. 12/041,590, filed Mar. 3, 2008.
U.S. Appl. No. 13/815,721, filed Mar. 15, 2013.
U.S. Appl. No. 13/815,722, filed Mar. 15, 2013.
U.S. Appl. No. 13/815,720, filed Mar. 15, 2013.
U.S. Appl. No. 13/815,724, filed Mar. 15, 2013.
U.S. Appl. No. 12/168,875, filed Jul. 7, 2008.
U.S. Appl. No. 12/618,509, filed Nov. 13, 2009.
U.S. Appl. No. 12/422,780, filed Apr. 13, 2009.
U.S. Appl. No. 13/678,128, filed Nov. 15, 2012.
U.S. Appl. No. 13/844,269, filed Mar. 15, 2013.
EP 1 444 268 B1: An English abstract may be found on the equivalent document WO 03/042231 A2.
JP 2000-516452 A: English equivalents are cited herein as U.S. Pat. No. 6,815,540 and WO 98/02462 A1.
WO 00/27885 A1: An English abstract may be found on the front page of the document.
WO 03/042231 A2: An English abstract may be found on the front page of the document.
WO 2006/064121 A2: An English abstract may be found on the front page of the document.
WO 2006/106905 A1: An English abstract may be found on the front page of the document.
Tanpakushitsu VII (Protein VII)—Tanpakushitsu kogaku (Protein Engineering), p. 57 (1993): No English translation is readily available. Applicants believe that this reference discloses the role of cysteine residues in protein stability.
"IUPAC-IUB commission on biochemical nomenclature rules for naming synthetic modification of natural peptides tentative rules," J. Biol. Chem. 242:555-557, 1967.
Adlersberg, J.B, "The immunoglobulin hinge (interdomain) region," Ric. Clin. Lab. 6:191-205, 1976.
Afanasieva, T.A., et al., "Single-chain antibody and its derivatives directed against vascular endothelial growth factor: application for antiangiogenic gene therapy," Gene Ther. 10:1850-1859, 2003.
Aicher, A., et al., "Characterization of human inducible costimulator ligand expression and function," J. Immunol. 164:4689-4696, 2000.
Albrecht, H., et al., "Monospecific bivalent scFv-SH: Effects of linker length and location of an engineered cysteine on production, antigen binding activity and free SH accessibility," J. Immunol. Meth. 310:100-116, 2006.
Amit, A.G., et al., "Three-Dimensional Structure of an Antigen-Antibody Complex at 2.8 angstrom Resolution," Science 233(4765):747-753, 1986.
Anderson, D.R., et al., "Targeting Cytotoxic Immunotherapy: Targeted anti-cancer therapy using rituximab, a chimaeric anti-CD20 antibody (IDEC-C2B8) in the treatment of non-Hodgkin's B-cell lymphoma," Biochem. Soc. Transactions, 25(2):705-708, 1997.
Andritsos, L., et al., "A phase I trial of TRU-016, an anti-CD37 small modular immunopharmaceutical (SMIP) in relapsed and refractory CLL," 2009 Annual Meeting, American Society of Clinical Oncology (ASCO), J. Clin. Oncol. 27(suppl.):15s (Abstract #3017), 2009.
Angal, S., et al., "A single amino acid substitution abolishes the heterogeneity of chimeric mouse/human (IgG4) antibody," Mol. Immunol. 30(1):105-108, 1993.
Anthony, K., Ed., "Selective inhibitors gain traction," Nat. Rev. Cancer 10:160, 2010.

(56) References Cited

OTHER PUBLICATIONS

Barone, D., et al., "Efficacy of SMIP-016, a novel CD37-directed biologic therapy, in human NHL tumor xenograft models," J. Clin. Oncol. 24(18S)(Jun. 20 Suppl.):Abstract #2565, 2006.
Barone, D., et al., "Prolonged Depletion of Circulating B Cells in Cynomolgus Monkeys after a Single Dose of TRU-015, a Novel CD20 Directed Therapeutic," Ann. Rheum. Dis. 64(Suppl. III):159 (Abstract #THU0169), 2005.
Barone, D., et al., "TRU-015, a novel CD20-directed biologic therapy, demonstrates significant anti-tumor activity in human tumor xenograft models," J. Clin. Oncol. 23(16S):178s (Abstract #2549) Jun. 1, 2005.
Barrena et al., "Aberrant expression of tetraspanin molecules in B-cell chronic lymphoproliferative disorders and tis correlation with normal B-cell maturation." Leukemia 19; 1376-1393 (2005).
Batra, J.K., et al., "Single-Chain Immunotoxins Directed at the Human Transferrin Receptor Containing Pseudomonas Exotoxin A or Diphtheria Toxin: Anti-TFR(Fv)-PE40 and DT388-Anti-TFR(Fv)," Mol. Cell. Biol. 11(4):2200-2205, 1991.
Baum, P.R., et al., "Evaluation of the effect of TRU-016, an anti-CD37 directed SMIP, in combination with other therapeutic drugs in models of Non-Hodgkin's Lymphoma," J. Clin. Oncol., 2009 ASCO Annual Meeting Proceedings (Post-Meeting Edition), vol. 27, No. 15S (May 20 Suppl.), Abstract 8571 (2009).
Beavil, A.J., et al., "α-Helical coiled-coil stalks in the low-affinity receptor for IgE (FcεRII/CD23) and related C-type lectins," Proc. Natl. Acad. Sci. USA 89:753-757, 1992.
Beiske, K., et al., "Triggering of neoplastic B cells via surface IgM and the cell surface antigens CD20 and CDw40. Responses differ from normal blood B cells and are restricted to certain morphologic subsets," Int. J. Cancer 42:521-528, 1988.
Belov, L., et al., "Immunophenotyping of Leukemias Using a Cluster of Differentiation Antibody Microarray," Canc. Res. 61:4483-4489, 2001.
Bénistant, C., et al., "A specific function for phosphatidylinositol 3-kinase α (p85α—p110α) in cell survival and for phosphatidylinositol 3-kinase β (p85α—p110β) in de novo DNA synthesis of human colon carcinoma cells," Oncogene 19:5083-5090, 2000.
Benoist, C., and Mathis, D., "A revival of the B cell paradigm for rheumatoid arthritis pathogenesis?" Arthritis Res. 2(2):90-94, 2000.
Bernstein, I.D., et al., "High Dose Radiolabeled Antibody Therapy of Lymphoma," Canc. Res. 50(Suppl.):1017s-1021s, 1990.
Berzofsky, J.A., and Berkower, I.J., "Immunogenicity and Antigen Structure," in Fundamental Immunology, Third Edition, William E. Paul, Ed., Chap. 8, pp. 235-282, Raven Press, Ltd., New York, 1993.
Best, W.R., et al., "Development of a Crohn's Disease Activity Index. National Cooperative Crohn's Disease Study," Gastroenterology 70(3):439-444, 1976.
Better, M., et al., "*Escherichia coli* Secretion of an Active Chimeric Antibody Fragment," Science 240:1041-1043, 1988.
Bloom, J.W., et al., "Intrachain disulfide bond in the core hinge region of human IgG4," Protein Sci. 6:407-415, 1997.
Boehm, M.K., et al., "The Fab and Fc fragments of IgA1 exhibit a different arrangement from that in IgG: a study by X-ray and neutron solution scattering and homology modelling," J. Mol. Biol. 286:1421-1447, 1999.
Bongini, L., et al., "Freezing immunoglobulins to see them move," Proc. Natl. Acad. Sci. USA 101(17):6466-6471, 2004.
Bonnema et al., "Fc Receptor Stimulation of Phosphatidylinositol 3-Kinase in Natural Killer Cells Is Associated with Protein Kinase C-independent Granule Release and Cell-mediated Cytotoxicity," J. Exp. Med. 180:1427-1435 (1994).
Boussif, O., et al., "A versatile vector for gene and oligonucleotide transfer into cells in culture and in vivo: Polyethylenimine," Proc. Natl. Acad. Sci. USA 92:7297-7301, 1995.
Brandl et al., "Bispecific antibody fragments with CD20×CD28 specificity allow effective autologous and allogeneic T-cell activation against malignant cells in peripheral blood and bone marrow cultures from patients with B-cell lineage leukemia and lymphoma," Exp. Hematol. 27:1264-1270 (1999).
Braslawsky, G.R., et al., "Adriamycin(hydrazone)-antibody conjugates require internalization and intracellular acid hydrolysis for antitumor activity," Cancer Immunol. Immunother. 33:367-374, 1991.
Brekke, O.H., et al., "The structural requirements for complement activation by IgG: does it hinge on the hinge?" Immunol. Today 16(2):85-90, 1995.
Brinkmann, U., et al., "Recombinant immunotoxins containing the VH or VL domain of monoclonal antibody B3 fused to Pseudomonas exotoxin," J. Immunol. 150(7):2774-2782, 1993.
Brok, H.P.M., et al., "Prophylactic and therapeutic effects of a humanized monoclonal antibody against the IL-2 receptor (DACLIZUMAB) on collagen-induced arthritis (CIA) in rhesus monkeys," Clin. Exp. Immunol. 124:134-141, 2001.
Brorson, K., et al., "Mutational analysis of avidity and fine specificity of anti-levan antibodies," J. Immunol. 163:6694-6701, 1999.
Brown, R.S., et al., "Intratumoral Microdistribution of [131I]MB-1 in Patients with B-Cell Lymphoma Following Radioimmunotheraphy," Nucl. Med. Biol. 24:657-663, 1997.
Brown, S.L., et al., "Treatment of B-Cell Lymphomas with Anti-idiotype Antibodies Alone and in Combination with Alpha Interferon," Blood 73(3):651-661, 1989.
Brummell, D.A., et al., "Probing the Combining Site of an Anti-Carbohydrate Antibody by Saturation-Mutagenesis: Role of the Heavy-Chain CDR3 Residues," Biochemistry 32:1180-1187, 1993.
Buchsbaum, D.J., et al., "Therapy with Unlabeled and 131I-labeled Pan-B-Cell Monoclonal Antibodies in Nude Mice Bearing Raji Burkitt's Lymphoma Xenografts," Canc. Res. 52:6476-6481, 1992.
Burgess, W.H., et al., "Possible dissociation of the heparin-binding and mitogenic activities of heparin-binding (acidic fibroblast) growth factor-1 from its receptor-binding activities by site-directed mutagenesis of a single lysine residue," J. Cell Biol. 111:2129-2138, 1990.
Burke, J.M., et al., "Radioimmunotherapy for acute leukemia," Cancer Control 9(2):106-113, 2002.
Burks, E.A., et al., "In vitro scanning saturation mutagenesis of an antibody binding pocket," Proc. Natl. Acad. Sci. USA 94:412-417, 1997.
Bussel, J.B., "Overview of Idiopathic Thrombocytopenia Purpura: New Approach to Refractory Patients," Semin. Oncol. 27(6 Suppl 12):91-98, 2000.
Byrd, J.C., et al., "Effect of CD37 small modular immunopharmaceutical (SMIP) on direct apoptosis in chronic lymphocytic leukemia cells via transcriptional up-regulation of the BH3 family member BIM," J. Clin. Oncol., 2009 ASCO Annual Meeting Proceedings (Post-Meeting Edition) vol. 27, No. 15S (May 20 Suppl.), Abstract 3035, (2009).
Cai, X., and Garen, A., "Comparison of fusion phage libraries displaying VH or single-chain Fv antibody fragments derived from the antibody repertoire of a vaccinated melanoma patient as a source of melanoma-specific targeting molecules," Proc. Natl. Acad. Sci. USA 94:9261-9266, 1997.
Calistoga Pharmaceuticals, "Preliminary evidence of clinical activity in a phase 1 study of CAL-101, a potent selective inhibitor of the p110δ isoform of phosphatidylinositol 3-kinase, in patients with B-cell malignancies," European Hematology Association, Berlin, Germany, Jun. 4-7, 2009, Poster Session, 17 pages.
Cambridge, G., et al., "Serologic Changes Following B Lymphocyte Depletion Therapy for Rheumatoid Arthritis," Arthritis Rheum. 48(8):2146-2154, 2003.
Campbell, N.A., et al., "Methods: Monoclonal Antibody Technology," in Biology, 5th Ed., p. 856, Benjamin-Cummings Publ. Co., Menlo Park, CA (1999).
Campo et al., "Non-Hodgkin's Lymphomas of Nasal Cavity and Paranasal Sinuses, An Immunohistochemical Study," Am. J. Clin. Pathol. 96; 184-190 (1991).
Capaldi, R.A., et al., "Changes in Order of Migration of Polypeptides in Complex III and Cytochrome c Oxidase under Different Conditions of SDS Polyacrylamide Gel Electrophoresis," Biochem. Biophys. Res. Commun. 74(2):425-433, 1977.
Capon, D.J., et al., "Designing CD4 immunoadhesins for AIDS therapy," Nature 337:525-531, 1989.

(56) References Cited

OTHER PUBLICATIONS

Carbone et al., "B-Zone Small Lymphocytic Lymphoma: A Morphologic, Immunophenotypic, and Clinical Study With Comparison to "Well-Differentiated" Lymphocytic Disorders," Human Pathology 23; 438-448 (1992).
Carter, P., "Antibody Engineering—IBC's Tenth International Conference, Dec. 6-9, 1999, La Jolla, CA, USA," IDrugs 3(3):259-261, 2000.
Carter, P., "Improving the efficacy of antibody-based cancer therapies," Nature Reviews Cancer 1:118-129, 2001.
Casset, F., et al., "A peptide mimetic of an anti-CD4 monoclonal antibody by rational design," Biochem. Biophys. Res. Commun. 307:198-205, 2003.
Catley et al., "Monoclonal antibodies for the treatment of asthma," Pharmacol. Ther. 132:333-351 (2011).
Cephalon Oncology, "Treanda Prescribing Information," 6 pages, (published in 2008, revised in Mar. 2008).
Chakraborti, T., et al., "Complement activation in heart disease: Role of oxidants," Cell. Signal. 12:607-617, 2000.
Chan H.T.C et al., "CD20-induced lymphoma cell death is independent of both caspases and its redistribution into Triton X-100 insoluble membrane rafts." Cancer Research 63: 5480-5489, 2003.
Chan, O.T.M., et al., "A Novel Mouse with B Cells but Lacking Serum Antibody Reveals an Antibody-Independent Role for B Cells in Murine Lupus," J. Exp. Med. 189(10):1639-1647, 1999.
Chatterjee, M.B., et al., "Idiotypic antibody immunotherapy of cancer," Cancer Immunol. Immunother. 38:75-82, 1994.
Chaudhary, V.K., et al., "A recombinant immunotoxin consisting of two antibody variable domains fused to Pseudomonas exotoxin," Nature 339:394-397, 1989.
Chen, Y., et al., "Selection and Analysis of an Optimized Anti-VEGF Antibody: Crystal Structure of an Affinity-matured Fab in Complex with Antigen," J. Mol. Biol. 293:865-881, 1999.
Cheson, B.D., "CLL Response Criteria," Clin. Adv. Hematol. Oncol. 4(5)(Suppl. 12):4-5, 2006.
Cheson, B.D., et al., "Report of an international working group to standardize response criteria for myelodysplastic syndromes," Blood 96:3671-3674, 2000.
Cheson, B.D., et al., "Report of an International Workshop to Standardize Response Criteria for Non-Hodgkin's Lymphomas," J. Clin. Oncol. 17:1244-1253, 1999.
Cheson, B.D., et al., "Revised Recommendations of the International Working Group for Diagnosis, Standardization of Response Criteria, Treatment Outcomes, and Reporting Standards for Therapeutic Trials in Acute Myeloid Leukemia," J. Clin. Oncol. 21(24):4642-4649, 2003.
Chothia, C., and Lesk, A.M., "Canonical Structures for the Hypervariable Regions of Immunoglobulins," J. Mol. Biol. 196:901-917, 1987.
Chothia, C., et al., "Conformations of immunoglobulin hypervariable regions," Nature 342:877-883, 1989.
Chothia, C., et al., "Domain association in immunoglobulin molecules. The packing of variable domains," J. Mol. Biol. 186(3):651-663, 1985.
Chowdhury, P.S., and Pastan, I., "Improving antibody affinity by mimicking somatic hypermutation in vitro," Nat. Biotechnol. 17:568-572, 1999.
Clackson, T., et al., "Making antibody fragments using phage display libraries," Nature 352:624-628, 1991.
Clark, E.A., and Einfeld, D, "Human B Cell Surface Molecules Defined by an International Workshop Panel of Monoclonal Antibodies," in Leukocyte Typing II (1986), vol. 2, Reinherz, E.L., et al., Eds., pp. 155-167, Springer Verlag, New York, 1986.
Clark, E.A., and Ledbetter, J.A., "Activation of human B cells mediated through two distinct cell surface differentiation antigens, Bp35 and Bp50," Proc. Natl. Acad. Sci. USA 83:4494-4498, 1986.
Clark, E.A., and Ledbetter, J.A., "Structure, function, and genetics of human B cell-associated surface molecules," Adv. Cancer Res. 52:81-149, 1989.
Clark, E.A., et al., "Role of the Bp35 cell surface polypeptide in human B-cell activation," Proc. Natl. Acad. Sci. USA 82:1766-1770, 1985.
Classon et al., "The hinge region of the CD8α chain: structure, antigenicity, and utility in expression of immunoglobulin superfamily domains," Int. Immunol. 4(2):215-225 (1992).
Co, M.S., et al., "Chimeric and Humanized Antibodies with Specificity for the CD33 Antigen," J. Immunol. 148(4):1149-1154, 1992.
Co, M.S., et al., "Genetically Engineered Deglycosylation of the Variable Domain Increases the Affinity of an Anti-CD33 Monoclonal Antibody," Mol. Immunol. 30(15):1361-1367, 1993.
Co, M.S., et al., "Humanized antibodies for antiviral therapy," Proc. Natl. Acad. Sci. USA 88:2869-2873, 1991.
Coffin, J.M., et al., Eds., Retroviruses, "Contents," pp. vii-viii, Cold Spring Harbor Laboratory Press, Plainview, NY, 1997.
Coiffier, B., et al., "Rituximab (Anti-CD-20 Monoclonal Antibody) for the Treatment of Patients With Relapsing or Refractory Aggressive Lymphoma: A Multicenter Phase II Study," Blood 92(6):1927-1932, 1998.
Colman, P.M., "Effects of amino acid sequence changes on antibody-antigen interactions," Res. Immunol. 145:33-36, 1994.
Coloma, M.J., and Morrison, S.L., "Design and production of novel tetravalent bispecific antibodies," Nat. Biotechnol. 15:159-163, 1997.
Coloma, M.J., et al., "The hinge as a spacer contributes to covalent assembly and is required for function of IgG," J. Immunol. 158:733-740, 1997.
Cooke, S.P., et al., "A strategy for antitumor vascular therapy by targeting the vascular endothelial growth factor: receptor complex," Cancer Res. 61:3653-3659, 2001.
Cote, R.J., et al., "Generation of human monoclonal antibodies reactive with cellular antigens," Proc. Natl. Acad. Sci. USA 80:2026-2030, 1983.
Cotten, M., et al., "High-efficiency receptor-mediated delivery of small and large (48 kilobase gene constructs using the endosome-disruption activity of defective or chemically inactivated adenovirus particles," Proc. Natl. Acad. Sci. USA 89:6094-6098, 1992.
Cragg, M.S., and Glennie, M.J., "Antibody specificity controls in vivo effector mechanisms of anti-CD20 reagents," Blood 103(7):2738-2743, 2004.
Cree, B., et al., "Tolerability and Effects of Rituximab (Anti-CD20 Antibody) in Neuromyelitis Optica (NMO) and Rapidly Worsening Multiple Sclerosis (MS)," Neurology 62(Suppl 5):A492 (Abstract P06.090), Apr. 2004.
Cruczman, M.S., et al., "Treatment of Patients With Low-Grade B-Cell Lymphoma With the Combination of Chimeric Anti-CD20 Monoclonal Antibody and CHOP Chemotherapy," J. Clin. Oncol. 17(1):268-276, 1999.
Crunkhorn, S., "Designing selective PI3K inhibitors," Nat. Rev. Drug Discovery 9:105, 2010.
Cruse, J.M., and Lewis, R.E., Illustrated Dictionary of Immunology, p. 157, CRC Press, Inc., 1995.
Curiel, D.T., et al., "High-efficiency gene transfer mediated by adenovirus coupled to DNA-polylysine complexes," Hum. Gene Ther. 3(2):147-154, 1992.
Dall'Acqua, W.F., et al., "Modulation of the Effector Functions of a Human IgG1 through Engineering of it Hinge Region," J. Immunol. 177:1129-1138, 2006.
Damle, N.K., et al., "Direct helper T cell-induced B cell differentiation involves interaction between T cell antigen CD28 and B cell activation antigen B7," Eur. J. Immunol. 21:1277-1282, 1991.
Davies J., and Riechmann, L., "Single antibody domains as small recognition units: design and in vitro antigen selection of camelized, human VH domains with improved protein stability," Protein Eng. 9(6):531-537, 1996.
Davies, J., "Hematological malignancies," American Society of Hematology—45th Annual Meeting and Exposition, Dec. 5-9, 2003, San Diego, CA, USA; iDrugs 7(1):1-3, 2004.
Davies, J., and Riechmann, L., "'Camelising' human antibody fragments: NMR studies on VH domains," FEBS Lett. 339:285-290, 1994.

(56) References Cited

OTHER PUBLICATIONS

Davis, S.J., et al., "High Level Expression in Chinese Hamster Ovary Cells of Soluble Forms of CD4 T Lymphocyte Glycoprotein Including Glycosylation Variants," J. Biol. Chem. 265(18):10410-10418, 1990.
De Vita, S., et al., "Efficacy of Selective B Cell Blockade in the Treatment of Rheumatoid Arthritis. Evidence for a Pathogenic Role of B Cells," Arthritis Rheum. 46(8):2029-2033, 2002.
Deans, J.P., et al., "Association of tyrosine and serine kinases with the B cell surface antigen CD20. Induction via CD20 of tyrosine phosphorylation and activation of phospholipase C-γ1 and PLC phospholipase C-γ2," J. Immunol. 151(9):4494-4504, 1993.
Dechant, M., et al., "Chimeric IgA antibodies against HLA class II effectively trigger lymphoma cell killing," Blood 100(13):4574-4580, 2002.
Decker, T., et al., "A pilot trial of the mTOR (mammalian target of rapamycin) inhibitor RAD001 in patients with advanced B-CLL," Ann. Hematol. 88:221-227, 2009.
Dermer, G.B., "Another Anniversary for the War on Cancer," Bio/Technology 12:320, 1994.
Desmyter, A., et al., "Crystal structure of a camel single-domain VH antibody fragment in complex with lysozyme," Nat. Struct. Biol. 3(9):803-811, 1996.
Dietsch, M.T., et al., "Bispecific receptor globulins, novel tools for the study of cellular interactions. Preparation and characterization of an E-selectin/P-selectin bispecific receptor globulin," J. Immunol. Methods 162:123-132, 1993.
Dietsch, M.T., et al., "Coengagement of CD2 with LFA-1 or VLA-4 by bispecific ligand fusion proteins primes T cells to respond more effectively to T cell receptor-dependent signals," J. Leukoc. Biol. 56:444-452, 1994.
Dillman, R.O., et al., "Continuous infusion of T101 monoclonal antibody in chronic lymphocytic leukemia and cutaneous T-cell lymphoma," J. Biol. Response Mod. 5:394-410, 1986.
Dong, H., et al., "B7-H1, a third member of the B7 family, co-stimulates T-cell proliferation and interleukin-10 secretion," Nat. Med. 5(12):1365-1369, 1999.
Dorai, H., et al., "Role of inter-heavy and light chain disulfide bonds in the effector functions of human immunoglobulin IgG1," Mol. Immunol. 29(12):1487-1491, 1992.
Dorrington, K.J., and Klein, M., "Aspects of immunoglobulin G structure relevant to its interaction with Fc receptors," Arch. Immunol. Ther. Exp. (Warsz.) 29:275-282, 1981.
Dufner, P., et al., "Harnessing phage and ribosome display for antibody optimisation," Trends Biotechnol. 24(11):523-529, 2006.
Duncan, A.R., and Winter, G., "The binding site for C1q on IgG," Nature 332:738-740, 1988.
Durie, F.H., et al., "Prevention of collagen-induced arthritis with an antibody to gp39, the ligand for CD40," Science 261:1328-1330, 1993.
Dyer, M.J., et al., "Effects of CAMPATH-1 antibodies in vivo in patients with lymphoid malignancies: influence of antibody isotype," Blood 73(6):1431-1439, 1989.
Edwards, et al., "Efficacy and Safety of Rituximab, a B-Cell Targeted Chimeric Monoclonal Antibody: A Randomized Placebo-Controlled Trial in Patients with Rheumatoid Arthritis," Arthritis Rheum. 46:S197 (Abstract 446), 2002.
Edwards, J.C.W., "Importance of T cells in Rheumatoid Synovitis: Comment on the Review by Firestein and Zvaifler," Arthritis Rheum. 46(11):3105-3106, 2002.
Edwards, J.C.W., and Cambridge, G., "Rheumatoid Arthritis: The Predictable Effect of Small Immune Complexes in which Antibody Is Also Antigen," Br. J. Rheumatol. 37:126-130, 1998.
Edwards, J.C.W., and Cambridge, G., "Sustained improvement in rheumatoid arthritis following a protocol designed to deplete B lymphocytes," Rheumatology 40:205-211, 2001.
Edwards, J.C.W., et al., "B-lymphocyte depletion therapy in rheumatoid arthritis and other automimmune disorders," Biochem. Soc. Trans. 30(4):824-828, 2002.
Edwards, J.C.W., et al., "Do self-perpetuating B lymphocytes drive human autoimmune disease?" Immunology 97:188-196, 1999.
Edwards, J.C.W., et al., "Efficacy of B-Cell-Targeted Therapy with Rituximab in Patients with Rheumatoid Arthritis," New Engl. J. Med. 350:2572-2581, 2004.
Einfeld, D.A., et al., "Molecular cloning of the human B cell CD20 receptor predicts a hydrophobic protein with multiple transmembrane domains," EMBO J. 7(3):711-717, 1988.
Elsässer, D., et al., "HLA Class II as Potential Target Antigen on Malignant B Cells for Therapy with Bispecific Antibodies in Combination with Granulocyte Colony-Stimulating Factor," Blood 87(9):3803-3812, 1996.
Engelhard, E.K., et al., "The Insect Tracheal System: A Conduit for the Systemic Spread of Autographa Californica M nuclear polyhedrosis virus," Proc. Natl. Acad. Sci. USA 91:3224-3227, 1994.
Faure, P., et al., "Immunohistochemical Profile of Cutaneous B-Cell Lymphoma on Cryostat and Paraffin Sections," Amer. J. Dermatopathol. 12(3):122-133, 1990.
Feldman, M.E., et al., "Active-Site Inhibitors of mTOR Target Rapamycin-Resistant Outputs of mTORC1 and mTORC2," PLoS Biol. 7(2):0371-0383, 2009.
Felgner, P.L., et al., "Lipofection: A highly efficient, lipid-mediated DNA-transfection procedure," Proc. Natl. Acad. Sci. USA 84:7413-7417, 1987.
Fell, H.P., et al., "Chimeric L6 Anti-tumor Antibody. Genomic construction, expression, and characterization of the antigen binding site," J. Biol. Chem. 267(22):15552-15558, 1992.
Fell, H.P., et al., "Genetic construction and characterization of a fusion protein consisting of a chimeric F(ab') with specificity for carcinomas and human IL-2," J. Immunol. 146(7):2446-2452, 1991.
Felson, D.T., et al., "American College of Rheumatology Preliminary Definition of Improvement in Rheumatoid Arthritis," Arthritis Rheum. 38(6):727-735, 1995.
Filpula, et al., "Single-chain Fv designs for protein, cell and gene therapeutics," Exp. Opin. Ther. Patents 9(3):231-245, 1999.
Fischer, K., et al., "Bendamustine in Combination with Rituximab (BR) for Patients with Relapsed Chronic Lymphocytic Leukemia (CLL): A Multicentre Phase II Trial of the German CLL Study Group (GCLLSG)," Blood (ASH Annual Meeting Abstracts) 112:Abstract #330, 2008, 2 pages.
Fix, J.A., "Strategies for Delivery of Peptides Utilizing Absorption-Enhancing Agents," J. Pharmaceut. Sci. 85(12):1282-1285, 1996.
Fonseca, R., et al., "Myeloma and the t(11;14)(q13;q32); evidence for a biologically defined unique subset of patients," Blood 99(10):3735-3741, 2002.
Foster, F.M., et al., "The phosphoinositide (PI) 3-kinase family," J. Cell Sci. 116(15):3037-3040, 2003.
Francisco, J.A., et al., "Activity of a Single-Chain Immunotoxin That Selectively Kills Lymphoma and Other B-Lineage Cells Expressing the CD40 Antigen," Canc. Res. 55:3099-3104, 1995.
Funakoshi, S., et al., "Differential in Vitro and in Vivo Antitumor Effects Mediated by Anti-CD40 and Anti-CD20 Monoclonal Antibodies Against Human B-Cell Lymphomas," J. Immunother. 19(2):93-101, 1996.
Funakoshi, S., et al., "Inhibition of Human B-Cell Lymphoma Growth by CD40 Stimulation," Blood 83(10):2787-2794, 1994.
Gazzano-Santoro, H., et al., "A non-radioactive complement-dependent cytotoxicity assay for anti-CD20 monoclonal antibody," J. Immunol. Meth. 202:163-171, 1997.
Genbank Accession No. L07414, *Homo sapiens* CD40 surface protein mRNA, complete cds, 2 pages, first accessible on Apr. 27, 1993. http://www.ncbi.nlm.nih.gov/nuccore/180123?sat=0&satkey=132107, retrieved May 11, 2015.
Genbank Accession No. M17953, Mouse Ig rearranged H-chain V-region mRNA VJ1, 1 page, first accessible on Apr. 27, 1993. http://www.ncbi.nlm.nih.gov/nuccore/196223?sat=0&satkey=139913, retrieved May 11, 2015.
Genbank Accession No. M17954, Mouse Ig rearranged kappa-chain mRNA VJ5, 1 page, first accessible on Apr. 27, 1993. http://www.ncbi.nlm.nih.gov/nuccore/197015?sat=0&satkey=140324, retrieved May 11, 2015.

(56) References Cited

OTHER PUBLICATIONS

Genbank Accession No. M62541, Mouse CD20 cell surface protein mRNA, complete cds, 1 page, first accessible on Jul. 26, 1993 http://www.ncbi.nlm.nih.gov/nuccore/309155?sat=0&satkey=282899, retrieved May 11, 2015.
Genbank Accession No. M62542, Mouse CD19 gene, complete cds, 2 pages, first accessible on Apr. 27, 1993. http://www.ncbi.nlm.nih.gov/nuccore/192462?sat=0&satkey=137833, retrieved May 11, 2015.
Genbank Accession No. M83312, Mouse CD40 mRNA, complete cds, 2 pages, first accessible on Apr. 27, 1993. http://www.ncbi.nlm.nih.gov/nuccore/192519?sat=0&satkey=137853, retrieved May 11, 2015.
Genbank Accession No. M83312, Mouse CD40 mRNA, complete cds, 2 pages, version first accessible on Sep. 23, 1996. http://www.ncbi.nlm.nih.gov/nuccore/1553058?sat=13&satkey=6581391, retrieved May 11, 2015.
Genbank Accession No. M84371, Human CD19 gene, complete cds, 4 pages, first accessible on Apr. 27, 1993. http://www.ncbi.nlm.nih.gov/nuccore/180024?sat=0&satkey=132070, retrieved May 11, 2015.
Genbank Accession No. M84371, Human CD19 gene, complete cds, 5 pages, version first accessible on Jul. 18, 1995. http://www.ncbi.nlm.nih.gov/nuccore/901822?sat=13&satkey=3082945, retrieved May 11, 2015.
Genbank Accession No. U15637, *Homo sapiens* CD40 binding protein (CD40BP) mRNA, complete cds, 2 pages, first accessible on Dec. 7, 1994. http://www.ncbi.nlm.nih.gov/nuccore/595910?sat=8&satkey=2454153, retrieved May 11, 2015.
Genbank Accession No. X14046, Human mRNA for leukocyte antigen CD37, 2 pages, first accessible on Apr. 21, 1993. http://www.ncbi.nlm.nih.gov/nuccore/29793?sat=0&satkey=18847, retrieved May 11, 2015.
Genbank Accession No. X53517, R. norvegicus mRNA for antigen CD37, 1 page, first accessible on Apr. 21, 1993. http://www.ncbi.nlm.nih.gov/nuccore/55911?sat=0&satkey=32498, retrieved May 11, 2015.
Genbank Accession No. X65453, M. musculus mRNA for CD40 ligand, 2 pages, first accessible on Apr. 21, 1993. http://www.ncbi.nlm.nih.gov/nuccore/50351?sat=0&satkey=29318, retrieved May 11, 2015.
Genbank Accession No. X65453, M. musculus mRNA for CD40 ligand, 2 pages, version first accessible on Apr. 27, 2001. http://www.ncbi.nlm.nih.gov/nuccore/13872516?sat=24&satkey=1347605, retrieved May 11, 2015.
Genbank Accession No. X67878, *H. sapiens* mRNA for CD40 ligand, 2 pages, first accessible on Apr. 21, 1993. http://www.ncbi.nlm.nih.gov/nuccore/38411?sat=0&satkey=23994, retrieved May 11, 2015.
Genbank Accession No. X96710, *H. sapiens* mRNA for CD40 ligand, 1 page, first accessible on Apr. 5, 1996. http://www.ncbi.nlm.nih.gov/nuccore/1255924?sat=0&satkey=2163718, retrieved May 11, 2015.
Genbank Accession No. Y10507, *H. sapiens* mRNA for CD40 protein, 1 page, first accessible on Sep. 9, 1997. http://www.ncbi.nlm.nih.gov/nuccore/2370162?sat=8&satkey=138163, retrieved May 11, 2015.
Gillies, S.D., and Wesolowski, J.S., "Antigen binding and biological activities of engineered mutant chimeric antibodies with human tumor specificities," Hum. Antibod. Hybridomas 1(1):47-54, 1990.
Gillies, S.D., et al., "Improving the efficacy of antibody-interleukin 2 fusion proteins by reducing their interaction with Fc receptors," Cancer Res. 59:2159-2166, 1999.
Gilliland, L.K., et al., "Elimination of the Immunogenicity of Therapeutic Antibodies," J. Immunol. 162:3663-3671, 1999.
Gilliland, L.K., et al., "Rapid and reliable cloning of antibody variable regions and generation of recombinant single chain antibody fragments," Tissue Antigens 47:1-20, 1996.
Gladman, D.D., et al., "Sensitivity to Change of 3 Systemic Lupus Erythematosus Disease Activity Indices: International Validation," J. Rheumatol. 21:1468-1471, 1994.
Gluzman, Y., "SV40-Transformed Simian Cells Support the Replication of Early SV40 Mutants," Cell 23:175-182, 1981.
Gordan, L.N., et al., "Phase II Trial of Individualized Rituximab Dosing for Patients With CD20-Positive Lymphoproliferative Disorders," J. Clin. Oncol. 23(6):1096-1102, 2005.
Gottdiener, J.S., et al., "Cardiac Manifestations in Poliomyositis," Amer. J. Cardiol. 41:1141-1149, 1978.
Graff, C.P., et al., "Directed evolution of an anti-carcinoembryonic antigen scFv with a 4-day monovalent dissociation half-time at 37° C.," Prot. Eng. Des. Sel. 17(4):293-304, 2004.
Griffiths, A.D., et al., "Isolation of high affinity human antibodies directly from large synthetic repertoires," EMBO J. 13(14):3245-3260, 1994.
Grillo-Lopez, A.J., et al., "Response criteria for NHL: Importance of 'normal' lymph node size and correlations with response rates," Ann. Oncol. 11:399-408, 2000.
Grossbard, M.L., et al., "Monoclonal Antibody-Based Therapies of Leukemia and Lymphoma," Blood 80(4):863-878, 1992.
Grünwald, V., et al., "Inhibitors of mTOR Reverse Doxorubicin Resistance Conferred by PTEN Status in Prostate Cancer Cells," Cancer Res. 62:6141-6145, 2002.
Gura, T., "Cancer Models. Systems for Identifying New Drugs Are Often Faulty," Science 278(5340):1041-1042, 1997.
Halin, C., et al., "Tumor-targeting properties of antibody-vascular endothelial growth factor fusion proteins," Int. J. Cancer 102:109-116, 2002.
Hamers-Casterman, C., et al., "Naturally occurring antibodies devoid of light chains," Nature 363:446-448, 1993.
Haritunians, T., et al., "Antiproliferative activity of RAD001 (everolimus) as a single agent and combined with other agents in mantle cell lymphoma," Leukemia 21:333-339, 2007.
Harris, C.L. et al., "Tumor cell killing using chemically engineered antibody constructs specific for tumor cells and the complement inhibitor CD59." Clin Exp Immunol 107; 364-371, 1997.
Harrison, "Phosphoinositide 3-kinase inhibitors," Nat. Rev. Drug Discovery 8:607, 2009.
Hay, N., and Sonenberg, N., "Upstream and downstream of mTOR," Genes Dev. 18:1926-1945, 2004.
Hayden, M.S., et al., "Antibody engineering," Curr. Opin. Immunol. 9:201-212, 1997.
Hayden, M.S., et al., "Costimulation by CD28 sFv expressed on the tumor cell surface or as a soluble bispecific molecule targeted to the L6 carcinoma antigen," Tissue Antigens 48:242-254, 1996.
Hayden, M.S., et al., "Single-chain mono- and bispecific antibody derivatives with novel biological properties and antitumour activity from a COS cell transient expression system," Ther. Immunol. 1:3-15, 1994.
Hayden-Ledbetter, M., et al., "Induction of Apoptosis in B Lymphoma Cell Lines by CytoxB37G, a Small Modular ImmunoPharmaceutical (SMIP) That Binds CD37," Blood 102(11, part 1):432a, Abstract #1572, 2003, and Poster presented at the 45th annual meeting of the American Society of Hematology, Dec. 6-9, 2003 in San Diego, California (18 pages).
Hekman, A., et al., "Initial experience with treatment of human B cell lymphoma with anti-CD19 monoclonal antibody," Cancer Immunol. Immunother. 32:364-372, 1991.
Hellström, I., et al., "Monoclonal Mouse Antibodies Raised against Human Lung Carcinoma," Canc. Res. 46:3917-3923, 1986.
Hemler, M.E., "Targeting of tetraspanin proteins—potential benefits and strategies," Nat. Rev. Drug Discovery 7:747-758, 2008.
Hillmen, P., "MRD in DLL," Clin. Adv. Hematol. Oncol. 4(5)(Suppl. 12):6-7, 2006.
Hinek, A., et al., "The Elastin Receptor: A Galactoside-Binding Protein," Science 239:1539-1541, 1988.
Hollenbaugh, D., et al., "The human T cell antigen gp39, a member of the TNF gene family, is a ligand for the CD40 receptor: expression of a soluble form of gp39 with B cell co-stimulatory activity," EMBO J. 11:4313-4321, 1992.
Holliger, P., and Hudson, P.J., "Engineered antibody fragments and the rise of single domains," Nat. Biotechnol. 23(9):1126-1136, 2005.

(56) References Cited

OTHER PUBLICATIONS

Holm, P., et al., "Functional mapping and single chain construction of the anti-cytokeratin 8 monoclonal antibody TS1," Mol. Immunol. 44:1075-1084, 2007.
Hoogenboom, H.R., and Winter, G., "By-passing Immunisation. Human Antibodies from Synthetic Repertoires of Germline VH Gene Segments Rearranged in Vitro," J. Mol. Biol. 227:381-388, 1992.
Hu, S., et al., "Minibody: a novel engineered anti-carcinoembryonic antigen antibody fragment (single-chain Fv-CH3) which exhibits rapid, high-level targeting of xenografts," Cancer Res. 56:3055-3061, 1996.
Hudson, P.J., "Recombinant antibodies: a novel approach to cancer diagnosis and therapy," Expert Opin. Investig. Drugs 9(6):1231-1242, 2000.
Hudson, P.J., "Recombinant antibody fragments," Curr. Opin. Biotechnol. 9:395-402, 1998.
Huls, G., et al., "Antitumor Immune Effector Mechanisms Recruited by Phage Display-derived Fully Human IgG1 and IgA1 Monoclonal Antibodies," Cancer Res. 59:5778-5784, 1999.
Humphreys et al., "F(ab')2 molecules made from *Escherichia coli* produced Fab' with hinge sequences conferring increased serum survival in an animal model," J. Immunol. Methods 217:1-10 (1998).
Huret, J.-L., "t(11;14)(q13;q32)," Atlas Genet. Cytogenet. Oncol. Haematol., May 1998. URL: http://atlasgeneticsoncology.org/Anomalies/t1114ID2021.html, 5 pages (retrieved Nov. 13, 2008).
Huston, J.S., et al., "Medical applications of single-chain antibodies," Int. Rev. Immunol. 10:195-217, 1993.
Huston, J.S., et al., "Protein engineering of antibody binding sites: Recovery of specific activity in an anti-digoxin single-chain Fv analogue produced in *Escherichia coli*," Proc. Natl. Acad. Sci. USA 85:5879-5883, 1988.
Hwang, W.Y.K., et al., "Use of human germline genes in a CDR homology-based approach to antibody humanization," Methods 36:35-42, 2005.
Ihle, N.T., et al., "Molecular pharmacology and antitumor activity of PX-866, a novel inhibitor of phosphoinositide-3-kinase signaling," Mol. Cancer Ther. 3(7):763-772, 2004.
Isaacs, J.D., et al., "Therapy with monoclonal antibodies. II. The contribution of Fcγ receptor binding and the influence of CH1 and CH3 domains on in vivo effector function," J. Immunol. 161:3862-3869, 1998.
Isenman, D.E., et al., "Correlation between the exposure of aromatic chromophores at the surface of the Fc domains of immunoglobulin G and their ability to bind complement," Biochemistry 16(2):233-240, 1977.
Jacquemin, M., et al., "Variable region heavy chain glycosylation determines the anticoagulant activity of a factor VIII antibody," J. Thromb. Haemost. 4:1047-1055, 2006.
Jain, R.K., "Barriers to drug delivery in solid tumors," Scientific American, 271(1):58-65, Jul. 1994.
Jain, R.K., "Physiological barriers to delivery of monoclonal antibodies and other macromolecules in tumors," Cancer Res. 50(Suppl.):814s-819s, 1990.
Janeway, C.A., et al., Eds., Immunobiology: The Immune System in Health and Disease, 4th ed., Chap. 3, p. 92, Elsevier Science Ltd., London, and Garland Publishing, New York, 1999.
Jang, Y.-J., et al., "The structural basis for DNA binding by an anti-DNA autoantibody," Mol. Immunol. 35:1207-1217, 1998.
Jendreyko, N., et al., "Intradiabodies, Bispecific, Tetravalent Antibodies for the Simultaneous Functional Knockout of Two Cell Surface Receptors," J. Biol. Chem. 278(48):47812-47819, 2003.
Jendreyko, N., et al., "Phenotypic knockout of VEGF-R2 and Tie-2 with an intradiabody reduces tumor growth and angiogenesis in vivo," Proc. Natl. Acad. Sci. USA 102(23):8293-8298, 2005.
Jermutus, L., et al., "Tailoring in vitro evolution for protein affinity of stability," Proc. Natl. Acad. Sci. USA 98(1):75-80, 2001.
Johnson, G., and Wu, T.T., "Kabat Database and its applications: 30 years after the first variability plot," Nucl. Acids Res. 28(1):214-218, 2000.
Jones, P.T., et al., "Replacing the complementarity-determining regions in a human antibody with those from a mouse," Nature 321:522-525, 1986.
Joosten, L.A.B., et al., "Protection against cartilage and bone destruction by systemic interleukin-4 treatment in established murine type II collagen-induced arthritis," Arthritis Res. 1:81-91, 1999.
Jost, C.R., et al., "Mammalian Expression and Secretion of Functional Single-chain Fv Molecules," J. Biol. Chem. 269(42):26267-26273, 1994.
Kalergis, A.M., et al., "Efficient T cell activation requires an optimal dwell-time of interaction between the TCR and the pMHC complex," Nat. Immunol. 2(3):229-234, 2001.
Kaminski, M.S., et al., "Imaging, Dosimetry, and Radioimmunotherapy With Iodine 131-Labeled Anti-CD37 Antibody in B-Cell Lymphoma," J. Clin. Oncol. 10(11):1696-1711, 1992.
Kaminski, M.S., et al., "Radioimmunotherapy of B-Cell Lymphoma with [131I]Anti-B1 (Anti-CD20) Antibody," N. Engl. J. Med. 329(7):459-465, 1993.
Kato, K., et al., "A conformational change in the Fc precludes the binding of two Fcγ receptor molecules to one IgG," Immunol. Today 21:310-312, 2000.
Kersh, E.N., et al., "Fidelity of T Cell Activation Through Multistep T Cell Receptor ζ Phosphorylation," Science 281:572-575, 1998.
Keystone, E., "B cell targeted therapies," Arthritis Res. Ther. 7(Suppl. 3):S13-S18, 2005.
Kiel, C., et al., "Electrostatically optimized Ras-binding Ral guanine dissociation stimulator mutants increase the rate of association by stabilizing the encounter complex," Proc. Natl. Acad. Sci. USA 101(25):9223-9228, 2004.
Kienberger, F., et al., "Following single antibody binding to purple membranes in real time," EMBO Rep. 5(6):579-583, 2004.
Kiesel, S., et al., "Removal of Cells from a Malignant B-Cell Line from Bone Marrow with Immunomagnetic Beads and with Complement and Immunoglobulin Switch Variant Mediated Cytolysis," Leukemia Res. 11:1119-1125, 1987.
Kirschfink, M., "Targeting complement in therapy," Immunol. Rev. 180:177-189, 2001.
Klein, M., et al., "Expression of biological effector functions by immunoglobulin G molecules lacking the hinge region," Proc. Natl. Acad. Sci. USA 78(1):524-528, 1981.
Knobeloch, K.-P., et al., "Targeted Inactivation of the Tetraspanin CD37 Impairs T-Cell-Dependent B-Cell Response under Suboptimal Costimulatory Conditions," Mol. Cell. Biol. 20(15):5363-5369, 2000.
Kobayashi, H., et al., "Tryptophan H33 plays an important role in pyrimidine (6-4) pyrimidone photoproduct binding by a high-affinity antibody," Protein Eng. 12(10):879-884, 1999.
Köhl, J., and Gessner, J.E., "On the role of complement and Fc γ-receptors in the Arthus reaction," Mol. Immunol. 36:893-903, 1999.
Kolls, J., et al., "Prolonged and effective blockade of tumor necrosis factor activity through adenovirus-mediated gene transfer," Proc. Natl. Acad. Sci. USA 91:215-219, 1994.
Koolwijk, P., et al., "Interaction between hybrid mouse monoclonal antibodies and the human high-affinity IgG FcR, huFc gamma RI, on U937. Involvement of only one of the mIgG heavy chains in receptor binding," J. Immunol. 143(5):1656-1662, 1989.
Kortt, A.A., et al., "Dimeric and trimeric antibodies: high avidity scFvs for cancer targeting," Biomol. Eng. 18:95-108, 2001.
Kortt, A.A., et al., "Recombinant anti-sialidase single-chain variable fragment antibody. Characterization, formation of dimer and higher-molecular-mass multimers and the solution of the crystal structure of the single-chain variable fragment/sialidase complex," Eur. J. Biochem. 221:151-157, 1994.
Kost et al., "Production of a urokinase plasminogen activator-IgG fusion protein (uPA-IgG) in the baculovirus expression system," Gene 190:139-144 (1997).
Kozbor, D., and Roder, J.C., "The production of monoclonal antibodies from human lymphocytes," Immunol. Today 4(3):72-79, 1983.

(56) References Cited

OTHER PUBLICATIONS

Kumar, S., et al., "Molecular Cloning and Expression of the Fabs of Human Autoantibodies in *Escherichia coli*," J. Biol. Chem. 275(45):35129-35136, 2000.
Kunkel, T.A., "Rapid and efficient site-specific mutagenesis without phenotypic selection," Proc. Natl. Acad. Sci. USA 82:488-492, 1985.
Kurtzke, J.F., "Rating neurologic impairment in multiple sclerosis: An expanded disability status scale (EDSS)," Neurology 33:1444-1452, 1983.
Kusumi, A., et al., "Confined Lateral Diffusion of Membrane Receptors as Studied by Single Particle Tracking (Nanovid Microscopy). Effects of Calcium-Induced Differentiation in Cultured Epithelial Cells," Biophys. J. 65:2021-2040, 1993.
Ladetto, M., et al., "Rituximab anti-CD20 monoclonal antibody induces marked but transient reductions of peripheral blood lymphocytes in chronic lymphocytic leukaemia patients," Med. Oncol. 17:203-210, 2000.
Lamminmäki, U., and Kankare, J.A., "Crystal Structure of a Recombinant Anti-estradiol Fab Fragment in Complex with 17β-Estradiol," J. Biol. Chem. 276(39):36687-36694, 2001.
Law, C.-L., et al., "Expression and characterization of recombinant soluble human CD3 molecules: presentation of antigenic epitopes defined on the native TCR-CD3 complex," Int. Immunol. 14(4):389-400, 2002.
Layios, N., et al., "Remission of severe cold agglutinin disease after Rituximab therapy," Leukemia 15(1):187-188, 2000.
Lazar, E., et al., "Transforming growth factor α: mutation of aspartic acid 47 and leucine 48 results in different biological activities," Mol. Cell. Biol. 8(3):1247-1252, 1988.
Lazar, G.A., et al., "Engineered antibody Fc variants with enhanced effector function," Proc. Natl. Acad. Sci. USA 103(11):4005-4010, 2006.
Leandro, M.J., et al., "An Open Study of B Lymphocyte Depletion in Systemic Lupus Erythematosus," Arthritis Rheum. 46(10):2673-2677, 2002.
Leandro, M.J., et al., "B Lymphocyte Depletion in Rheumatoid Arthritis: Early Evidence for Safety, Efficacy, and Dose Response," Arthritis Rheum. 44(9):S370 (Abstract #1905), 2001.
Leandro, M.J., et al., "Clinical outcome in 22 patients with rheumatoid arthritis treated with B lymphocyte depletion," Ann. Rheum. Dis. 61:883-888, 2002.
Leatherbarrow, R.J., et al., "Effector Functions of a Monoclonal Aglycosylated Mouse IgG2a: Binding and Activation of Complement Component C1 and Interaction with Human Monocyte Fc Receptor," Mol. Immunol. 22(4):407-415, 1985.
Ledbetter, J.A., et al., "Antibodies to Tp67 and Tp44 Augment and Sustain Proliferative Responses of Activated T Cells," J. Immunol. 135(4):2331-2336, 1985.
Ledbetter, J.A., et al., "Augmentation of normal and malignant B cell proliferation by monoclonal antibody to the B cell-specific antigen BP50 (CDW40)," J. Immunol. 138(3):788-794, 1987.
Ledbetter, J.A., et al., "Binding Constructs and Methods for Use Thereof," filed Jul. 26, 2003, Office Action dated Dec. 8, 2006, for U.S. Appl. No. 10/627,556, 38 pages.
Ledbetter, J.A., et al., "Binding Constructs and Methods for Use Thereof," filed Jul. 26, 2003, Office Action dated Feb. 14, 2008, for U.S. Appl. No. 10/627,556, 22 pages.
Ledbetter, J.A., et al., "Binding Constructs and Methods for Use Thereof," filed Aug. 24, 2006, Office Action dated Feb. 20, 2009, for U.S. Appl. No. 10/566,409, 13 pages.
Ledbetter, J.A., et al., "Binding Constructs and Methods for Use Thereof," filed Aug. 24, 2006, Office Action dated Jul. 10, 2008, for U.S. Appl. No. 10/566,409, 8 pages.
Ledbetter, J.A., et al., "Binding Constructs and Methods for Use Thereof," filed Jul. 26, 2003, Office Action dated Jun. 24, 2009, for U.S. Appl. No. 10/627,556, 14 pages.
Ledbetter, J.A., et al., "Binding Constructs and Methods for Use Thereof," filed Aug. 24, 2006, Office Action dated Jun. 9, 2009, for U.S. Appl. No. 10/566,409, 32 pages.
Ledbetter, J.A., et al., "Binding Constructs and Methods for Use Thereof," filed Jul. 26, 2003, Office Action dated Nov. 26, 2008, for U.S. Appl. No. 10/627,556, 25 pages.
Ledbetter, J.A., et al., "Binding Constructs and Methods for Use Thereof," filed Aug. 24, 2006, Office Action dated Nov. 27, 2009, for U.S. Appl. No. 10/566,409, 12 pages.
Ledbetter, J.A., et al., "Binding Constructs and Methods for Use Thereof," filed Feb. 13, 2009, Office Action dated Nov. 29, 2010, for U.S. Appl. No. 12/371,467, 17 pages.
Ledbetter, J.A., et al., "Binding Constructs and Methods for Use Thereof," filed Jul. 26, 2003, Office Action dated Nov. 6, 2009, for U.S. Appl. No. 10/627,556, 15 pages.
Ledbetter, J.A., et al., "Binding Constructs and Methods for Use Thereof," filed Jul. 26, 2003, Office Action dated Sep. 11, 2007, for U.S. Appl. No. 10/627,556, 19 pages.
Ledbetter, J.A., et al., "Binding Domain-Immunoglobulin Fusion Proteins," filed Jan. 17, 2002, Office Action dated Apr. 19, 2007, for U.S. Appl. No. 10/053,530, 17 pages.
Ledbetter, J.A., et al., "Binding Domain-Immunoglobulin Fusion Proteins," filed Jul. 25, 2002, Office Action dated Apr. 2, 2007, for U.S. Appl. No. 10/207,655, 22 pages.
Ledbetter, J.A., et al., "Binding Domain-Immunoglobulin Fusion Proteins," filed Mar. 23, 2005, Office Action dated Apr. 5, 2007, for U.S. Appl. No. 11/089,367, 11 pages.
Ledbetter, J.A., et al., "Binding Domain-Immunoglobulin Fusion Proteins," filed Jan. 17, 2002, Office Action dated Aug. 27, 2004, for U.S. Appl. No. 10/053,530, 15 pages.
Ledbetter, J.A., et al., "Binding Domain-Immunoglobulin Fusion Proteins," filed Aug. 13, 2009, Office Action dated Dec. 13, 2010, for U.S. Appl. No. 12/541,062, 12 pages.
Ledbetter, J.A., et al., "Binding Domain-Immunoglobulin Fusion Proteins," filed Jan. 17, 2002, Office Action dated Dec. 5, 2007, for U.S. Appl. No. 10/053,530, 11 pages.
Ledbetter, J.A., et al., "Binding Domain-Immunoglobulin Fusion Proteins," filed Mar. 23, 2005, Office Action dated Feb. 28, 2008, for U.S. Appl. No. 11/088,569, 26 pages.
Ledbetter, J.A., et al., "Binding Domain-Immunoglobulin Fusion Proteins," filed Jul. 25, 2002, Office Action dated Jan. 14, 2008, for U.S. Appl. No. 10/207,655, 27 pages.
Ledbetter, J.A., et al., "Binding Domain-Immunoglobulin Fusion Proteins," filed Mar. 23, 2005, Office Action dated Jan. 14, 2008, for U.S. Appl. No. 11/089,511, 30 pages.
Ledbetter, J.A., et al., "Binding Domain-Immunoglobulin Fusion Proteins," filed Mar. 23, 2005, Office Action dated Jan. 14, 2010, for U.S. Appl. No. 11/088,693, 13 pages.
Ledbetter, J.A., et al., "Binding Domain-Immunoglobulin Fusion Proteins," filed Jan. 17, 2002, Office Action dated Jan. 17, 2006, for U.S. Appl. No. 10/053,530, 18 pages.
Ledbetter, J.A., et al., "Binding Domain-Immunoglobulin Fusion Proteins," filed Mar. 23, 2005, Office Action dated Jan. 18, 2011, for U.S. Appl. No. 11/088,693, 8 pages.
Ledbetter, J.A., et al., "Binding Domain-Immunoglobulin Fusion Proteins," filed Jan. 17, 2002, Office Action dated Jan. 2, 2004, for U.S. Appl. No. 10/053,530, 15 pages.
Ledbetter, J.A., et al., "Binding Domain-Immunoglobulin Fusion Proteins," filed Aug. 13, 2009, Office Action dated Jul. 12, 2010, for U.S. Appl. No. 12/541,062, 9 pages.
Ledbetter, J.A., et al., "Binding Domain-Immunoglobulin Fusion Proteins," filed Mar. 23, 2005, Office Action dated Jul. 13, 2006, for U.S. Appl. No. 11/089,511, 7 pages.
Ledbetter, J.A., et al., "Binding Domain-Immunoglobulin Fusion Proteins," filed Jul. 25, 2002, Office Action dated Jul. 25, 2006, for U.S. Appl. No. 10/207,655, 29 pages.
Ledbetter, J.A., et al., "Binding Domain-Immunoglobulin Fusion Proteins," filed Mar. 15, 2010, Office Action dated Jun. 2, 2010, for U.S. Appl. No. 12/724,333, 7 pages.
Ledbetter, J.A., et al., "Binding Domain-Immunoglobulin Fusion Proteins," filed Mar. 23, 2005, Office Action dated Jun. 4, 2007, for U.S. Appl. No. 11/088,569, 24 pages.
Ledbetter, J.A., et al., "Binding Domain-Immunoglobulin Fusion Proteins," filed Mar. 23, 2005, Office Action dated Jun. 4, 2007, for U.S. Appl. No. 11/088,737, 27 pages.

(56) References Cited

OTHER PUBLICATIONS

Ledbetter, J.A., et al., "Binding Domain-Immunoglobulin Fusion Proteins," filed Mar. 23, 2005, Office Action dated Jun. 4, 2007, for U.S. Appl. No. 11/089,190, 27 pages.
Ledbetter, J.A., et al., "Binding Domain-Immunoglobulin Fusion Proteins," filed Mar. 23, 2005, Office Action dated Jun. 6, 2007, for U.S. Appl. No. 11/088,570, 27 pages.
Ledbetter, J.A., et al., "Binding Domain-Immunoglobulin Fusion Proteins," filed Mar. 23, 2005, Office Action dated Jun. 8, 2007, for U.S. Appl. No. 11/089,368, 29 pages.
Ledbetter, J.A., et al., "Binding Domain-Immunoglobulin Fusion Proteins," filed Jan. 17, 2002, Office Action dated Mar. 1, 2005, for U.S. Appl. No. 10/053,530, 11 pages.
Ledbetter, J.A., et al., "Binding Domain-Immunoglobulin Fusion Proteins," filed Aug. 13, 2009, Office Action dated Mar. 22, 2010, for U.S. Appl. No. 12/541,062, 9 pages.
Ledbetter, J.A., et al., "Binding Domain-Immunoglobulin Fusion Proteins," filed Jan. 17, 2002, Office Action dated Mar. 23, 2007, for U.S. Appl. No. 10/053,530, 22 pages.
Ledbetter, J.A., et al., "Binding Domain-Immunoglobulin Fusion Proteins," filed Mar. 23, 2005, Office Action dated Mar. 26, 2007, for U.S. Appl. No. 11/089,511, 34 pages.
Ledbetter, J.A., et al., "Binding Domain-Immunoglobulin Fusion Proteins," filed Mar. 23, 2005, Office Action dated Mar. 28, 2008, for U.S. Appl. No. 11/088,693, 16 pages.
Ledbetter, J.A., et al., "Binding Domain-Immunoglobulin Fusion Proteins," filed Mar. 23, 2005, Office Action dated Mar. 3, 2008, for U.S. Appl. No. 11/088,570, 28 pages.
Ledbetter, J.A., et al., "Binding Domain-Immunoglobulin Fusion Proteins," filed Mar. 23, 2005, Office Action dated Mar. 3, 2008, for U.S. Appl. No. 11/088,737, 29 pages.
Ledbetter, J.A., et al., "Binding Domain-Immunoglobulin Fusion Proteins," filed Mar. 23, 2005, Office Action dated Mar. 3, 2008, for U.S. Appl. No. 11/089,190, 26 pages.
Ledbetter, J.A., et al., "Binding Domain-Immunoglobulin Fusion Proteins," filed Mar. 23, 2005, Office Action dated Mar. 4, 2009, for U.S. Appl. No. 11/088,693, 10 pages.
Ledbetter, J.A., et al., "Binding Domain-Immunoglobulin Fusion Proteins," filed Mar. 23, 2005, Office Action dated Mar. 5, 2008, for U.S. Appl. No. 11/089,368, 30 pages.
Ledbetter, J.A., et al., "Binding Domain-Immunoglobulin Fusion Proteins," filed Mar. 23, 2005, Office Action dated May 14, 2007, for U.S. Appl. No. 11/088,693, 11 pages.
Ledbetter, J.A., et al., "Binding Domain-Immunoglobulin Fusion Proteins," filed Jul. 25, 2002, Office Action dated May 18, 2009, for U.S. Appl. No. 10/207,655, 7 pages.
Ledbetter, J.A., et al., "Binding Domain-Immunoglobulin Fusion Proteins," filed Jan. 17, 2002, Office Action dated May 22, 2003, for U.S. Appl. No. 10/053,530, 17 pages.
Ledbetter, J.A., et al., "Binding Domain-Immunoglobulin Fusion Proteins," filed Jul. 25, 2002, Office Action dated Nov. 20, 2009, for U.S. Appl. No. 10/207,655, 10 pages.
Ledbetter, J.A., et al., "Binding Domain-Immunoglobulin Fusion Proteins," filed Mar. 23, 2005, Office Action dated Nov. 30, 2007, for U.S. Appl. No. 11/089,367, 15 pages.
Ledbetter, J.A., et al., "Binding Domain-Immunoglobulin Fusion Proteins," filed Jul. 25, 2002, Office Action dated Nov. 4, 2008, for U.S. Appl. No. 10/207,655, 20 pages.
Ledbetter, J.A., et al., "Binding Domain-Immunoglobulin Fusion Proteins," filed Jan. 17, 2002, Office Action dated Oct. 12, 2006, for U.S. Appl. No. 10/053,530, 16 pages.
Ledbetter, J.A., et al., "Binding Domain-Immunoglobulin Fusion Proteins," filed Mar. 23, 2005, Office Action dated Sep. 11, 2009, for U.S. Appl. No. 11/088,693, 12 pages.
Ledbetter, J.A., et al., "Binding Domain-Immunoglobulin Fusion Proteins," filed Mar. 23, 2005, Office Action dated Sep. 12, 2006, for U.S. Appl. No. 11/089,368, 8 pages.
Ledbetter, J.A., et al., "Binding Domain-Immunoglobulin Fusion Proteins," filed Mar. 23, 2005, Office Action dated Sep. 14, 2006, for U.S. Appl. No. 11/088,569, 8 pages.
Ledbetter, J.A., et al., "Binding Domain-Immunoglobulin Fusion Proteins," filed Mar. 23, 2005, Office Action dated Sep. 14, 2006, for U.S. Appl. No. 11/088,570, 7 pages.
Ledbetter, J.A., et al., "Binding Domain-Immunoglobulin Fusion Proteins," filed Mar. 23, 2005, Office Action dated Sep. 14, 2006, for U.S. Appl. No. 11/088,737, 7 pages.
Ledbetter, J.A., et al., "Binding Domain-Immunoglobulin Fusion Proteins," filed Mar. 23, 2005, Office Action dated Sep. 14, 2006, for U.S. Appl. No. 11/089,190, 7 pages.
Ledbetter, J.A., et al., "Binding Domain-Immunoglobulin Fusion Proteins," filed Mar. 15, 2010, Office Action dated Sep. 2, 2010, for U.S. Appl. No. 12/724,333, 11 pages.
Ledbetter, J.A., et al., "Monoclonal antibodies to a new gp40-45 (CD37) B-cell-associated cluster group modulate B-cell proliferation," in Leucocyte Typing III: White Cell Differentiation Antigens, A.J. McMichael, Ed., pp. 339-340, Oxford University Press, Oxford (1987).
Lee, E.J., and Kueck, B., "Rituxan in the Treatment of Cold Agglutinin Disease," Blood 92(9):3490-3491, 1998.
Lee, H.S., et al., "Generation and characterization of a novel single-gene-encoded single-chain immunoglobulin molecule with antigen binding activity and effector functions," Mol. Immunol. 36:61-71, 1999.
Leget, G.A., and Czuczman, M.S., "Use of rituximab, the new FDA-approved antibody," Curr. Opin. Oncol. 10:548-551, 1998.
Lehninger, A.L., et al., "Amino Acids and Peptides," Chapter 5, pp. 111-133, Figure 5-6, in Principles of Biochemistry, 2nd Ed., Worth Publishers, New York (1993).
Leigh, B.R., et al., "Preclinical evaluation of chimeric L6 antibody for the treatment of Kaposi's sarcoma with radioimmunotherapy," Cancer Biother. Radiopharm. 14(2):113-119, 1999.
Leonard, P., et al., "High throughput ranking of recombinant avian scFv antibody fragments from crude lysates using the Biacore A100," J. Immunol. Meth. 323:172-179, 2007.
Leseux, L., et al., "Syk-dependent mTOR activation in follicular lymphoma cells," Blood 108(13):4156-4162, 2006.
Levine, T.D., "Rituximab in the Treatment of Dermatomyositis," Arthritis Rheum. 52(2):601-607, 2005.
Levine, T.D., and Pestronk, A., "IgM antibody-related polyneuropathies: B-cell depletion chemotherapy using Rituximab," Neurology 52:1701-1704, 1999.
Li, J.-Y., et al., "Detection of Translocation t(11;14)(q13;q32) in Mantle Cell Lymphoma by Fluorescence in Situ Hybridization," Amer. J. Pathol. 154(5):1449-1452, 1999.
Li, Q., et al., "Assessment of Recombinant Adenoviral Vectors for Hepatic Gene Therapy," Hum. Gene Ther. 4:403-409, 1993.
Li, S.L., et al., "Single-chain antibodies against human insulin-like growth factor I receptor: expression, purification, and effect on tumor growth," Cancer Immunol. Immunother. 49:243-252, 2000.
Lin, M.C, et al., "Structure-Function Relationships in Glucagon: Properties of Highly Purified Des-His1-, Monoiodo-, and [Des-Asn28, Thr29](homoserine lactone27)-glucagon," Biochemistry 14(8):1559-1563, 1975.
Lin, T.S., et al., "Rituximab in B-Cell Chronic Lymphocytic Leukemia," Sem. Oncol. 30(4):483-492, 2003.
Ling et al., "Apoptosis induced by Anthracycline Antibiotics in P388 Parent and Multidrug-resistant Cells," Canc. Res. 53:1845-1852 (1993).
Link, M.P., et al., "A Unique Antigen on Mature B Cells Defined by a Monoclonal Antibody," J. Immunol. 137(9):3013-3018, 1986.
Linsley, P.S., et al., "T-cell antigen CD28 mediates adhesion with B cells by interacting with activation antigen B7/BB-1," Proc. Natl. Acad. Sci. USA 87:5031-5035, 1990.
Liu, A.Y., et al., "Production of a Mouse-Human Chimeric Monoclonal Antibody to CD20 with Potent Fc-Dependent Biologic Activity," J. Immunol. 139(10):3521-3526, 1987.
Looney, R.J., et al., "B Cell Depletion as a Novel Treatment for Systemic Lupus Erythematosus," Arthritis Rheum. 50(8):2580-2589, 2004.
Lu, D., et al., "A Fully Human Recombinant IgG-like Bispecific Antibody to Both the Epidermal Growth Factor Receptor and the Insulin-like Growth Factor Receptor for Enhanced Antitumor Activity," J. Biol. Chem. 280(20):19665-19672, 2005.

(56) References Cited

OTHER PUBLICATIONS

Lu, D., et al., "Di-diabody: a novel tetravalent bispecific antibody molecule by design," J. Immunol. Meth. 279:219-232, 2003.
Lyons, D.S., et al., "A TCR Binds to Antagonist Ligands with Lower Affinities and Faster Dissociation Rates Than to Agonists," Immunity 5:53-61, 1996.
Maloney, D.G., et al., "IDEC-C2B8 (Rituximab) Anti-CD20 Monoclonal Antibody Therapy in Patients with Relapsed Low-Grade Non-Hodgkin's Lymphoma," Blood 90(6):2188-2195, 1997.
Maloney, D.G., et al., "IDEC-C2B8: results of a phase I multiple-dose trial in patients with relapsed non-Hodgkin's lymphoma," J. Clin. Oncol. 15(10):3266-3274, 1997.
Maloney, D.G., et al., "Phase I Clinical Trial Using Escalating Single-Dose Infusion of Chimeric Anti-CD20 Monoclonal Antibody (IDEC-C2B8) in Patients With Recurrent B-Cell Lymphoma," Blood 84(8):2457-2466, 1994.
Marks, J.D., et al., "By-passing Immunization. Human Antibodies from V-gene Libraries Displayed on Phage," J. Mol. Biol. 222:581-597, 1991.
Marques et al., "Phosphoinositide 3-Kinases p110α and p110β Regulate Cell Cycle Entry, Exhibiting Distinct Activation Kinetics in $G_1$ Phase," Mol. Cell. Biol. 28(8):2803-2814 (2008).
Marsh, J.E., et al., "Targeting the complement system," Curr. Opin. Nephrol. Hypertens. 8:557-562, 1999.
Martens, C.L., et al., "Heavy chain genes of rabbit IgG: Isolation of a cDNA encoding γ heavy chain and identification of two genomic Cγ genes," Proc. Natl. Acad. Sci. USA 79:6018-6022, 1982.
Martin, A.C.R., et al., "Modeling antibody hypervariable loops: A combined algorithm," Proc. Natl. Acad. Sci. USA 86:9268-9272, 1989.
Martin, S., et al., "Efficient Neutralization and Disruption of Rhinovirus by Chimeric ICAM-1/Immunoglobulin Molecules," J. Virol. 67(6):3561-3568, 1993.
Marvin, J.S., and Zhu, Z., "Recombinant approaches to IgG-like bispecific antibodies," Acta Pharmacol. Sin. 26(6):649-658, 2005.
Matsui, K., et al., "Kinetics of T-cell receptor binding to peptide/I-Ek complexes: Correlation of the dissociation rate with T-cell responsiveness," Proc. Natl. Acad. Sci. USA 91:12862-12866, 1994.
Mattu, T.S., et al., "The Glycosylation and Structure of Human Serum IgA1, Fab, and Fc Regions and the Role of N-Glycosylation on Fcα Receptor Interactions," J. Biol. Chem. 273(4):2260-2272, 1998.
May et al., "CAL-101, a Selective Inhibitor of the p110 delta Isoform of Phosphatidylinositol 3-Kinase, Effectively Induces Apoptosis in Primary Chronic Lymphocytic Leukemia Cells Providing a Novel Therapeutic Strategy for the Treatment of This Disease," Blood 112(11):1085-1086 (2008).
McFarland et al., "Symmetry Recognizing Asymmetry: Analysis of the Interactions between the C-Type Lectin-like Immunoreceptor NKG2D and MHC Class I=like Ligands," Structure 11:411-422 (2003).
McLaughlin, P., et al., "Clinical Status and Optimal Use of Rituximab for B-Cell Lymphomas," Oncology 12(12):1763-1769, 1998; review by Grossbard, M.L., and Multani, P.S., pp. 1769-1770; review by Raubitschek, A., pp. 1775-1776; review by Molina, A., pp. 1776-1777, 1781.
McLaughlin, P., et al., "IDEC-C2B8 Anti-CD20 Antibody: Final Report on a Phase III Pivotal Trial in Patients (PTS) with Relapsed Low-Grade or Follicular Lymphoma (LG/F NHL)," Blood 88(Suppl. 1):90a (Abstract 349), 1996.
McLaughlin, P., et al., "Pharmacokinetics (PK) and Pharmacodynamics (PD) of the Anti-CD20 Antibody (Mab) IDEC-C2B8 in Patients (Pts) with Relapsed Low-Grade or Follicular Lymphoma (LG/F NHL)," Blood 88(10)(Suppl. 1):90a (Abstract 350), 1996.
Mealy et al., "Annual Update 2004/2005—Treatment of Musculoskeletal Disorders," Drugs of the Future 30(2):181-232 (2005).
Merson, A., and Brochier, J., "Phenotypic heterogeneity of B cell chronic lymphocytic leukaemia," Immunol. Lett. 19:269-272, 1988.
Michaelsen, T.E., et al., "Antibody dependent cell-mediated cytotoxicity induced by chimeric mouse-human IgG subclasses and IgG3 antibodies with altered hinge region," Mol. Immunol. 29(3):319-326, 1992.
Michaelsen, T.E., et al., "Enhancement of complement activation and cytolysis of human IgG3 by deletion of hinge exons," Scand. J. Immunol. 32:517-528, 1990.
Michaelsen, T.E., et al., "One disulfide bond in front of the second heavy chain constant region is necessary and sufficient for effector functions of human IgG3 without a genetic hinge," Proc. Natl. Acad. Sci. USA 91:9243-9247, 1994.
Miller, A.D., "Retrovirus Packaging Cells," Hum. Gene Ther. 1:5-14, 1990.
Miller, F.W., "Classification and Prognosis of Inflammatory Muscle Disease," Rheum. Dis. Clin. North Amer. 20(4):811-826, 1994.
Miller, F.W., "Inflammatory Myopathies: Polymyositis, Dermatomyositis, and Related Conditions," in Arthritis and Allied Conditions: A Textbook of Rheumatology, 15th ed., Koopman, W.J., and Moreland, L.W., Eds., Chap. 75, pp. 1593-1620, Lippincott Williams & Wilkins, Philadelphia, 2005.
Minsavage, G.D., and Dillman III, J.F., "Bifunctional Alkylating Agent-Induced p53 and Nonclassical Nuclear Factor κB Responses and Cell Death Are Altered by Caffeic Acid Phenethyl Ester: A Potential Role for Antioxidant/Electrophilic Response-Element Signaling," J. Pharmacol. Exp. Ther. 321(1):202-212, 2007.
Moldenhauer, G., "CD37," J. Biol. Regul. Homeost. Agents 14:281-283, 2000.
Monson, N.L., et al., "Effect of Rituximab on the Peripheral Blood and Cerebrospinal Fluid B Cells in Patients With Primary Progressive Multiple Sclerosis," Arch. Neurol. 62:258-264, 2005.
Moore, K., et al., "Use of the Monoclonal Antibody WR17, Identifying the CD37 gp40-45 Kd Antigen Complex, in the Diagnosis of B-Lymphoid Malignancy," J. Pathol. 152:13-21, 1987.
Mukai, Y., et al., "Optimization of anti-tumor necrosis factor-α single chain Fv displayed on phages for creation of functional antibodies," Pharmazie 61:889-890, 2006.
Mullinax, R.L., et al., "Identification of human antibody fragment clones specific for tetanus toxoid in a bacteriophage λ immunoexpression library," Proc. Natl. Acad. Sci. USA 87:8095-8099, 1990.
Multani, P.S., and Grossbard, M.L., "Monoclonal antibody-based therapies for hematologic malignancies," J. Clin. Oncol. 16(11):3691-3710, 1998.
Muñoz, E., et al., "The CH1 domain of IgG is not essential for C3 covalent binding: importance of the other constant domains as targets for C3," Int. Immunol. 10(2):97-106, 1998.
Muraoka, S., and Shulman, M.J., "Structural Requirements for IgM Assembly and Cytolytic Activity. Effects of Mutations in the Oligosaccharide Acceptor Site at Asn 402," J. Immunol. 142(2):695-701, 1989.
Muyldermans, S., "Single domain camel antibodies: current status," Rev. Mol. Biotechnol. 74:277-302, 2001.
Muyldermans, S., et al., "Sequence and structure of VH domain from naturally occurring camel heavy chain immunoglobulins lacking light chains," Protein Eng. 7(9):1129-1135, 1994.
Nadler, L.M., "B Cell/Leukemia Panel Workshop: Summary and Comments," in Leukocyte Typing II, vol. 2, Reinherz, E.L., et al., Eds., pp. 3-21, Springer Verlag, New York, 1986.
NCBI Reference Sequence NP_001765.1 for Leukocyte Surface Antigen CD37, 1 page, version first accessible Oct. 31, 2000. http://www.ncbi.nlm.nih.gov/protein/4502663?sat=8&satkey=2733144, retrieved May 11, 2015.
Neve, R.M., et al., "Biological effects of anti-ErbB2 single chain antibodies selected for internalizing function," Biochem. Biophys. Res. Commun. 280:274-279, 2001.
Nguyen, D.T., et al., "IDEC-C2B8 anti-CD20 (Rituximab) immunotherapy in patients with low-grade non-Hodgkin's lymphoma and lymphoproliferative disorders: evaluation of response on 48 patients," Eur. J. Haematol. 62:76-82, 1999.
Nguyen, V.K., et al., "Heavy-chain antibodies in Camelidae; a case of evolutionary innovation," Immunogenetics 54:39-47, 2002.
Nguyen, V.K., et al., "The specific variable domain of camel heavy-chain antibodies is encoded in the germline," J. Mol. Biol. 275:413-418, 1998.

(56) References Cited

OTHER PUBLICATIONS

Nieba, L., et al., "Disrupting the hydrophobic patches at the antibody variable/constant domain interface: improved in vivo folding and physical characterization of an engineered scFv fragment," Protein Eng. 10(4):435-444, 1997.
Niedermeir et al., "Isoform-selective phosphoinositide 3'-kinase inhibitors inhibit CXCR4 signaling and overcome stromal cell-mediated drug resistance in chronic lymphocytic leukemia: a novel therapeutic approach," Blood 113(22):5549-5557 (2009).
Nielsen, U.B., et al., "Targeting of Bivalent Anti-ErbB2 Diabody Antibody Fragments to Tumor Cells Is Independent of the Intrinsic Antibody Affinity," Cancer Res. 60:6434-6440, 2000.
Nikula, T.K., et al., "Impact of the high tyrosine fraction in complementarity determining regions: measured and predicted effects of radioiodination on IgG immunoreactivity," Mol. Immunol. 32(12):865-872, 1995.
Novak, H., et al., "Selective antibody-mediated targeting of class I MHC to EGFR-expressing tumor cells induces potent antitumor CTL activity in vitro and in vivo," Int. J. Cancer 120:329-336, 2007.
Nuttall, S.D., et al., "Immunoglobulin VH domains and beyond: design and selection of single-domain binding and targeting reagents," Curr. Pharm. Biotechnol. 1:253-263, 2000.
O'Brien, S., "Practical Applications of Measuring and Monitoring MRD in Patients With CLL," Clin. Adv. Hematol. Oncol. 4(5)(Suppl. 12):8-9, 2006.
O'Brien, S.O., "New Agents in the Treatment of CLL," 2008 Hematology Am. Soc. Hematol. Educ. Program, 2008(1):457-464 (Jan. 1, 2008).
Ogoshi, M., et al., "In Situ Hybridization Analysis of the Expression of Human Telomerase RNA in Normal and Pathologic Conditions of the Skin," J. Invest. Dermatol. 110:818-823, 1998.
Okazaki, T., et al., "PD-1 immunoreceptor inhibits B cell receptor-mediated signaling by recruiting src homology 2-domain-containing tyrosine phosphatase 2 to phosphotyrosine," Proc. Natl. Acad. Sci. USA 98(24):13866-13871, 2001.
Oki, S., et al., "Augmentation of CTLA-4 expression by wortmannin: involvement of lysosomal sorting properties of CTLA-4," Int. Immunol. 11(9):1563-1571, 1999.
Oliyai, R., and Stella, V.J., et al., "Prodrugs of Peptides and Proteins for Improved Formulation and Delivery," Annu. Rev. Pharmacol. Toxicol. 32:521-544, 1993.
Paar, J.M., et al., "Bivalent Ligands with Rigid Double-Stranded DNA Spacers Reveal Structural Constraints on Signaling by FcεRI," J. Immunol. 169:856-864, 2002.
Padlan, E.A., "A Possible Procedure for Reducing the Immunogenicity of Antibody Variable Domains While Preserving Their Ligand-Binding Properties," Mol. Immunol. 28(4/5):489-498, 1991.
Padlan, E.A., "Anatomy of the Antibody Molecule," Mol. Immunol. 31(3):169-217, 1994.
Pallesen, G., and Hager, H., "The expression of the 40-45 kDa pan-B cluster (CD37) in normal human tissues and in haematopoietic neoplasms as defined by immunohistology," in Leucocyte Typing III: White Cell Differentiation Antigens, A.J. McMichael, Ed., pp. 337-339, Oxford University Press, Oxford (1987).
Panka, D.J., et al., "Variable Region Framework Differences Result in Decreased or Increased Affinity of Variant Anti-Digoxin Antibodies," Proc. Natl. Acad. Sci. USA 85(9):3080-3084, 1988.
Papadakis, K., et al., "Anti-CD20 Chimeric Monoclonal Antibody (Rituximab) Treatment of Immune-Mediated Thrombocytopenia Associated With Crohn's Disease," Gastroenterology 124(2):583, Feb. 2003.
Park, S.S., et al., "Generation and characterization of a novel tetravalent bispecific antibody that binds to hepatitis B virus surface antigens," Mol. Immunol, 37:1123-1130, 2000.
Pawson, R., et al., "Treatment of T-Cell Prolymphocytic Leukemia With Human CD52 Antibody," J. Clin. Oncol. 15(7):2667-2672, 1997.
Pelat, T., et al., "Germline Humanization of a Non-human Primate Antibody that Neutralizes the Anthrax Toxin, by in Vitro and in Silico Engineering," J. Mol. Biol. 384:1400-1407, 2008.
Peter, K. et al., "Construction and functional evaluation of a single-chain antibody fusion protein with fibrin targeting and thrombin inhibition after activation by factor Xa," Circulation 101:1158-1164, 2000.
Petri, M.A., et al., "Effects of Prasterone on Disease Activity and Symptoms in Women With Active Systemic Lupus Erythematosus. Results of a Multicenter Randomized, Double-Blind, Placebo-Controlled Trial," Arthritis Rheum. 50(9):2858-2868, 2004.
Pezzutto, A., et al., "CD19 Monoclonal Antibody HD37 Inhibits Anti-Immunoglobulin-Induced B Cell Activation and Proliferation," J. Immunol. 138(9):2793-2799, 1987.
Piro et al. "Extended Rituximab (anti-CD20 monoclonal antibody) therapy for relapsed or refractory low-grade or follicular non-Hodgkin's lymphoma", Annals of Oncolology 10 (6): 655-661 (1999).
Poljak, R.J., et al., "Three-Dimensional Structure of the Fab' Fragment of a Human Immunoglobulin at 2.8-Å Resolution," Proc. Natl. Acad. Sci. USA 70(12):3305-3310, 1973.
Pollard, H., et al., "Polyethylenimine but Not Cationic Lipids Promotes Transgene Delivery to the Nucleus in Mammalian Cells," J. Biol. Chem. 273(13):7507-7511, 1998.
Portolano, S., et al., "Lack of promiscuity in autoantigen-specific H and L chain combinations as revealed by human H and L chain 'roulette'," J. Immunol. 150(3):880-887, 1993.
Press, O.W., et al., "High-Dose Radioimmunotherapy of B Cell Lymphomas," in the Present and Future Role of Monoclonal Antibodies in Management of Cancer. Front. Radiat. Ther. Oncol., Vaeth, J.M., and Meyer, J.L., Eds., Karger, Basel, Switzerland, 24:204-213, 225-227 (discussion), 1990.
Press, O.W., et al., "Monoclonal Antibody 1F5 (Anti-CD20) Serotherapy of Human B Cell Lymphomas," Blood 69(2):584-591, 1987.
Press, O.W., et al., "Radiolabeled Antibody Therapy of Human B Cell Lymphomas," in Immunobiology of Proteins and Peptides VI, Atassi, M.Z., Ed., Plenum Press, New York, pp. 91-96, 1991.
Press, O.W., et al., "Radiolabeled-Antibody Therapy of B-Cell Lymphoma with Autologous Bone Marrow Support," N. Engl. J. Med. 329(17):1219-1224, 1993.
Press, O.W., et al., "Treatment of refractory non-Hodgkin's lymphoma with radiolabeled MB-1 (anti-CD37) antibody," J. Clin. Oncol. 7(8):1027-1038, 1989.
Presta, L.G., et al., "Engineering therapeutic antibodies for improved function," Biochem. Soc. Trans. 30(4):487-490, 2002.
Protheroe, A., et al., "Remission of inflammatory arthropathy in association with anti-CD20 therapy for non-Hodgkin's lymphoma," Rheumatology 38:1150-1152, 1999.
Prous, J.R., Ed., "Annual Update 2004/2005—Treatment of Musculoskeletal Disorders," Drugs Fut. 30(2):181-232, 2005.
Queen, C., et al., "A humanized antibody that binds to the interleukin 2 receptor," Proc. Natl. Acad. Sci. USA 86:10029-10033, 1989.
Radaev, S., and Sun, P.D., "Recognition of IgG by Fcγ receptor. The role of Fc glycosylation and the binding of peptide inhibitors," J. Biol. Chem. 276(19):16478-16483, 2001.
Radaev, S., et al., "The Structure of a Human Type III Fcγ Receptor in Complex with Fc," J. Biol. Chem. 276(19):16469-16477, 2001.
Rader, C., et al., "A phage display approach for rapid antibody humanization: Designed combinatorial V gene libraries," Proc. Nat. Acad. Sci. USA 95:8910-8915, 1998.
Rai, K.R., et al., "Fludarabine Compared with Chlorambucil as Primary Therapy for Chronic Lymphocytic Leukemia," New Engl. J. Med. 343(24):1750-1757, 2000.
Rastetter, W., et al., "Rituximab: Expanding Role in Therapy for Lymphomas and Autoimmune Diseases," Annu. Rev. Med. 55:477-503, 2004.
Ratanatharathorn, V., et al., "Anti-CD20 Chimeric Monoclonal Treatment of Refractory Immune-Mediated Thrombocytopenia in a Patient with Chronic Graft-versus-Host Disease," Ann. Intern. Med. 133(4):275-279, 2000.
Redpath, S., et al., "The influence of the hinge region length in binding of human IgG to human Fcγ receptors," Hum. Immunol. 59:720-727, 1998.
Reff, M.E., et al., "Depletion of B Cells in Vivo by a Chimeric Mouse Human Monoclonal Antibody to CD20," Blood 83(2):435-445, 1994.

(56) References Cited

OTHER PUBLICATIONS

Rider, L.G., et al., "International Consensus on Preliminary Definitions of Improvement in Adult and Juvenile Myositis," Arthritis Rheum. 50(7):2281-2290, 2004.

Riechmann, L., "Rearrangement of the former VL interface in the solution structure of a camelised, single antibody VH domain," J. Mol. Biol. 259:957-969, 1996.

Riechmann, L., et al., "Reshaping human antibodies for therapy," Nature 332:323-327, 1988.

Roguska, M.A., et al., "A comparison of two murine monoclonal antibodies humanized by CDR-grafting and variable domain resurfacing," Protein Eng. 9(10):895-904, 1996.

Rothe, C., et al., "The human combinatorial antibody library HuCAL GOLD combines diversification of all six CDRs according to the natural immune system with a novel display method for efficient selection of high-affinity antibodies," J. Mol. Biol. 376:1182-1200, 2008.

Roux, K.H., et al., "Comparisons of the ability of human IgG3 hinge mutants, IgM, IgE, and IgA2, to form small immune complexes: a role for flexibility and geometry," J. Immunol. 161:4083-4090, 1998.

Roux, K.H., et al., "Flexibility of Human IgG Subclasses," J. Immunol. 159:3372-3382, 1997.

Roux, K.H., et al., "Structural analysis of the nurse shark (new) antigen receptor (NAR): Molecular convergence of NAR and unusual mammalian immunoglobulins," Proc. Natl. Acad. Sci. USA 95:11804-11809, 1998.

Rudick, R.A., et al., "Impact of interferon beta-1a on neurologic disability in relapsing multiple sclerosis," Neurology 49:358-363, 1997.

Rudikoff, S., et al., "Single amino acid substitution altering antigen-binding specificity," Proc. Natl. Acad. Sci. USA 79:1979-1983, 1982.

Rummel, M.J., "German Experience With Bendamustine Treating Relapsed/Refractory Indolent B-Cell and Mantle Cell Lymphomas," Semin. Hematol. 44:S22-S26, 2007.

Rummel, M.J., et al., "Bendamustine Plus Rituximab Versus CHOP Plus Rituximab in the First-Line Treatment of Patients with Indolent and Mantle Cell Lymphomas—First Interim Results of a Randomized Phase III Study of the StiL (Study Group Indolent Lymphomas, Germany)," Blood 110(11):120a, Abstract #385, (2007) American Society of Hematology, Forty-ninth annual meeting program and abstracts, Atlanta Georgia, Dec. 8-11, 2007.

Saldanha, J.W., et al., "A single backmutation in the human kIV framework of a previously unsuccessfully humanized antibody restores the binding activity and increases the secretion in cos cells," Mol. Immunol. 36:709-719, 1999.

Saleh, M.N., et al., A Pilot Study of the Anti-CD20 Monoclonal Antibody Rituximab in Patients With Refractory Immune Thrombocytopenia, Semin. Oncol. 27(6)(Suppl 12):99-103, 2000.

Santos, L., et al., "Role of macrophage migration inhibitory factor (MIF) in murine antigen-induced arthritis: interaction with glucocorticoids," Clin. Exp. Immunol. 123:309-314, 2001.

Scheinberg, D.A., et al., "A phase I toxicity, pharmacology, and dosimetry trial of monoclonal antibody OKB7 in patients with non-Hodgkin's lymphoma: effects of tumor burden and antigen expression," J. Clin. Oncol. 8(5):792-803, 1990.

Schmidt, M., et al., "Suppression of metastasis formation by a recombinant single chain antibody-toxin targeted to full-length and oncogenic variant EGF receptors," Oncogene 18:1711-1721, 1999.

Schuster, M., et al., "Improved Effector Functions of a Therapeutic Monoclonal Lewis Y-Specific Antibody by Glycoform Engineering," Cancer Res. 65(17):7934-7941, 2005.

Schwartz, G.P., et al., "A superactive insulin: [B10-aspartic acid]insulin(human)," Proc. Natl. Acad. Sci. USA 84:6408-6411, 1987.

Schwartz-Albiez, R., et al., "The B Cell-Associated CD37 Antigen (gp40-52). Structure and Subcellular Expression of an Extensively Glycosylated Glycoprotein," J. Immunol. 140(3):905-914, 1988.

Seaver, S.S., "Monoclonal Antibodies in Industry: More Difficult Than Originally Thought," Genet. Eng. News 14(14):pp. 10 and 21, 1994.

Segal, D.M., et al., "Introduction: bispecific antibodies," J. Immunol. Methods 248:1-6, 2001.

Selzer, T., et al., "Rational design of faster associating and tighter binding protein complexes," Nat. Struct. Biol. 7(7):537-541, 2000.

Sensel, M.G., et al., "Engineering novel antibody molecules," Chem. Immunol. 65:129-158, 1997.

Shahied, L.S., et al., "Bispecific Minibodies Targeting HER2/neu and CD16 Exhibit Improved Tumor Lysis When Placed in a Divalent Tumor Antigen Binding Format," J. Biol. Chem. 279(52):53907-53914, 2004.

Shan, D., et al., "Apoptosis of Malignant Human B Cells by Ligation of CD20 with Monoclonal Antibody," Blood 91(5):1644-1652, 1998.

Shan, D., et al., "Characterization of scFv-Ig Constructs from the Anti-CD20 mAb 1F5 Using Linker Peptides of Varying Lengths," J. Immunol. 162:6589-6595, 1999.

Shankar, S., et al., "Antiepidermal growth factor variant III scFv fragment: effect of radioiodination method on tumor targeting and normal tissue clearance," Nucl. Med. Biol. 33:101-110, 2006.

Shegogue, D., and Trojanowska, M., "Mammalian Target of Rapamycin Positively Regulates Collagen Type I Production via a Phosphatidylinositol 3-Kinase-independent Pathway," J. Biol. Chem. 279(22):23166-23175, 2004.

Shimoni, A., et al., "Autologous T Cells Control B-Chronic Lymphocytic Leukemia Tumor Progression in Human → Mouse Radiation Chimera," Cancer Res. 59:5968-5974, 1999.

Shin, S.-U., et al., "Genetically-Engineered Antibodies: Tools for the Study of Diverse Properties of the Antibody Molecule," Immunol. Rev. 130:87-107 (1992).

Shin, S.-U., et al., "Hybrid antibodies," Int. Rev. Immunol. 10:177-186 (1993).

Shipp, M.A., et al., "A Predictive Model for Aggressive Non-Hodgkin's Lymphoma," New Engl. J. Med. 329:987-994, 1993.

Shlomchik, M.J., et al., "The Role of B Cells in Ipr/Ipr-induced Autoimmunity," J. Exp. Med. 180:1295-1306, 1994.

Shu, L., et al., Secretion of a single-gene-encoded immunoglobulin from myeloma cells, Proc. Natl. Acad. Sci. USA 90:7995-7999, 1993.

Simonds, H.M., and Miles, D., "Adjuvant treatment of breast cancer: impact of monoclonal antibody therapy directed against the HER2 receptor," Expert Opin. Biol. Ther. 7(4):487-491, 2007.

Simonis, B., et al., "Evaluation and Validation of a Crohn's Disease Inflammatory Activity Index Reflecting Pattern of Endoscopic Severity," Scand. J. Gastroenterol. 33(3):283-288, 1998.

Smellie, W.J.B., et al., "Radioimmunotherapy of breast cancer xenografts with monoclonal antibody ICR12 against c-erbB2 p185: comparison of iodogen and N-succinimidyl 4-methyl-3-(tri-n-butylstannyl)benzoate radioiodination methods," Cancer Res. 55(Suppl):5842s-5846s, 1995.

Smith, G.E., et al., "Molecular Engineering of the Autographa californica Nuclear Polyhedrosis Virus Genome: Deletion Mutations Within the Polyhedrin Gene," J. Virol. 46(2):584-593, 1983.

Smith, K.A., et al., "Isolation and characterization of vascular endothelial growth factor-165 specific scFv fragments by phage display," Int. J. Oncol. 22:333-338, 2003.

Smith-Gill, S.J., et al., "Contributions of immunoglobulin heavy and light chains to antibody specificity for lysozyme and two haptens," J. Immunol. 139:4135-4144, 1987.

Sonderman, P., et al., "The 3.2-Å crystal structure of the human IgG1 Fc fragment-FcγRIII complex," Nature 406:267-273, 2000.

Song, M.-K., et al., "Light chain of natural antibody plays a dominant role in protein antigen binding," Biochem. Biophys. Res. Commun. 268:390-394, 2000.

Souriau, C., and Hudson, P.J., "Recombinant antibodies for cancer diagnosis and therapy," Expert Opin. Biol. Ther. 3(2):305-318, 2003.

Speth, C., et al., "The complement system: Pathophysiology and clinical relevance," Wien. Klin. Wochenschr. 111(10):378-391, 1999.

(56) References Cited

OTHER PUBLICATIONS

Spiro, R.G., "Protein glycosylation: nature, distribution, enzymatic formation, and disease implications of glycopeptide bonds," Glycobiology 12(4):43R-56R, 2002.
Sporici, R.A., et al., "ICOS ligand costimulation is required for T-cell encephalitogenicity," Clin. Immunol. 100(3):277-288, 2001.
Stamenkovic, I., and Seed, B., "Analysis of Two cDNA Clones Encoding the B Lymphocyte Antigen CD20 (B1, Bp35), A Type III Integral Membrane Protein," J. Exp. Med. 167:1975-1980, 1988.
Stasi, R. et al., "Rituximab chimeric anti-CD20 monoclonal antibody treatment for adults with chronic idiopathic thrombocytopenic purpura," Blood 98:952-957, 2001.
Steukers, M., et al., "Rapid kinetic-based screening of human Fab fragments," J. Immunol. Meth. 310:126-135, 2006.
Stevenson, G.T., et al., "Conjugation of Human Fcγ in Closed-Hinge or Open-Hinge Configuration to Fab'γ and Analogous Ligands," J. Immunol. 158:2242-2250, 1997.
Stevenson, G.T., et al., "Mechanisms in Removal of Tumor by Antibody," Cell Biophys. 24/25:45-50, 1994.
Stolovich, M., et al., "Transduction of Growth or Mitogenic Signals into Translational Activation of TOP mRNAs Is Fully Reliant on the Phosphatidylinositol 3-Kinase-Mediated Pathway but Requires neither S6K1 nor rpS6 Phosphorylation," Mol. Cell Biol. 22(23):8101-8113, 2002.
Su, B., et al., "Automated high-throughput purification of antibody fragments to facilitate evaluation in functional and kinetic based assays," J. Immunol. Meth. 322:94-103, 2007.
Takemura, S., et al., "Lymphoid Neogenesis in Rheumatoid Synovitis," J. Immunol. 167:1072-1080, 2001.
Tamburini, J., et al., "Mammalian target of rapamycin (mTOR) inhibition activates phosphatidylinositol 3-kinase/Akt by up-regulating insulin-like growth factor-1 receptor signaling in acute myeloid leukemia: rationale for therapeutic inhibition of both pathways," Blood 111:379-382, 2008.
Tamura, H., et al., "B7-H1 costimulation preferentially enhances CD28-independent T-helper cell function," Blood 97(6):1809-1816, 2001.
Tan, E.M., et al., "The 1982 Revised Criteria for the Classification of System Lupus Erythematosus," Arthritis Rheum. 25(11):1271-1277, 1982.
Tan, L.K., et al., "Influence of the hinge region on complement activation, C1q binding, and segmental flexibility in chimeric human immunoglobulins," Proc. Natl. Acad. Sci. USA 87:162-166, 1990.
Tan, P., et al., "'Superhumanized' Antibodies: Reduction of Immunogenic Potential by Complementarity-Determining Region Grafting with Human Germline Sequences: Application to an Anti-CD28," J. Immunol. 169:1119-1125, 2002.
Tannock, "Experimental Chemotherapy," Chapter 19. in the Basic Science of Oncology, Tannock and Hill, eds., McGraw-Hill, Inc., New York, pp. 338-359 (1992).
Tao, M.H., and Morrison, S.L., "Studies of aglycosylated chimeric mouse-human IgG. Role of carbohydrate in the structure and effector functions mediated by the human IgG constant region," J. Immunol. 143(8):2595-2601, 1989.
Targoff, I.N., "Dermatomyositis and Polymyositis," Curr. Probl. Dermatol., 3(5):134-180, Sep./Oct. 1991.
Taylor, A.K., and Wall, R., "Selective Removal of α Heavy-Chain Glycosylation Sites Causes Immunoglobulin A Degradation and Reduced Secretion," Mol. Cell. Biol. 8(10):4197-4203, 1988.
Tedder, T.F., et al., "Cloning of a Complementary DNA Encoding a New Mouse B Lymphocyte Differentiation Antigen, Homologous to the Human B1 (CD20) Antigen, and Localization of the Gene to Chromosome 19," J. Immunol. 141(12):4388-4394, 1988.
Tempest, P.R., et al., "Reshaping a Human Monoclonal Antibody to Inhibit Human Respiratory Syncytial Virus Infection in Vivo," Bio/Technology 9:266-271, 1991.
Terry, L.A., et al., "The monoclonal antibody, UCHL1, recognizes a 180,000 MW component of the human leucocyte-common antigen, CD45," Immunol. 64:331-336, 1988.
Thommesen, J.E., et al., "Lysine 322 in the human IgG3 C(H)2 domain is crucial for antibody dependent complement activation," Mol. Immunol. 37:995-1004, 2000.
Thompson et al., "Single-Chain Multivalent Binding Proteins With Effector Function," Office Action dated Dec. 16, 2011, for U.S. Appl. No. 12/304,562, filed Jul. 22, 2010, 23 pages.
Thompson et al., "Single-Chain Multivalent Binding Proteins With Effector Function," Office Action dated Jun. 1, 2012, for U.S. Appl. No. 12/304,562, filed Jul. 22, 2010, 24 pages.
Thompson et al., "Single-Chain Multivalent Binding Proteins With Effector Function," Office Action dated Jun. 24, 2011, for U.S. Appl. No. 12/304,562, filed Jul. 22, 2010, 7 pages.
Thompson et al., "Single-Chain Multivalent Binding Proteins with Effector Function," Office Action dated Mar. 5, 2012, for U.S. Appl. No. 12/041,590, filed Mar. 3, 2008, 12 pages.
Thompson, P.A., et al., "Single-Chain Multivalent Binding Proteins with Effector Function," Office Action dated May 5, 2011, for U.S. Appl. No. 12/041,590, filed Mar. 3, 2008, 8 pages.
Thoreen, C.C., et al., "An ATP-competitive Mammalian Target of Rapamycin Inhibitor Reveals Rapamycin-resistant Functions of mTORC1," J. Biol. Chem. 284(12):8023-8032, 2009.
Traunecker, A., et al., "Bispecific single chain molecules (Janusins) target cytotoxic lymphocytes on HIV infected cells," EMBO J. 10(12):3655-3659, 1991.
Treon, S.P., and Anderson, K.C., "The Use of Rituximab in the Treatment of Malignant and Nonmalignant Plasma Cell Disorders," Semin. Oncol. 27(Suppl 12):79-85, 2000.
Treon, S.P., et al., "CD2O-Directed Antibody-Mediated Immunotherapy Induces Responses and Facilitates Hematologic Recovery in Patients With Waldenstrom's Macroglobulinemia," J. Immunother. 24(3):272-279, 2001.
Trubion, "Data on Trubion's Drug Candidate TRU-016 Presented at ASCO 2006," Trubion Pharmaceuticals, PR Newswire press release dated Jun. 4, 2006, 1 page.
Trubion, "Trubion Announces Positive Data for Two Product Candidates at Upcoming American Society of Hematology Meeting; Abstracts to be Published in Nov. 16, 2003 Issue of Blood," PR Newswire press release, Nov. 20, 2003, 2 pages.
Tuscano, J.M., "Successful Treatment of Infliximab-Refractory Rheumatoid Arthritis with Rituximab," Annual Scientific Meeting of the American College of Rheumatology, New Orleans, LA (Oct. 24-29, 2002), vol. 46, p. 3420, Abstract #LB11, 1 page.
Vajdos, F.F., et al., "Comprehensive Functional Maps of the Antigen-binding Site of an Anti-ErbB2 Antibody Obtained with Shotgun Scanning Mutagenesis," J. Mol. Biol. 320:415-428, 2002.
Van Den Abbeele, A.D., et al., "Antigen-binding site protection during radiolabeling leads to a higher immunoreactive fraction," J. Nucl. Med. 32(1):116-122, 1991.
Van Den Beucken, T., et al., "Building novel binding ligands of B7.1 and B7.2 based on human antibody single variable light chain domains," J. Mol. Biol. 310:591-601, 2001.
Van Der Kolk, et al., "Complement activation plays a key role in the side-effects of rituximab treatment," Brit. J. Haematol. 115:807-811, 2001.
Van Spriel, A.B., et al., "A Regulatory Role for CD37 in T Cell Proliferation," J. Immunol. 172:2953-2961, 2004.
Vanhove et al., "Selective blockade of CD28 and not CTLA-4 with a single-chain Fv-α1-antitrypsin fusion antibody," Blood 102:564-570 (2003).
Vaswani, S.K., and Hamilton, R.G., "Humanized antibodies as potential therapeutic drugs," Ann. Allergy Asthma Immunol. 81:105-119, 1998.
Verhoeyen, M., et al., "Reshaping Human Antibodies: Grafting an Antilysozyme Activity," Science 239:1534-1536, 1988.
Vincent, N., et al., "Long-term correction of mouse dystrophic degeneration by adenovirus-mediated transfer of a minidystrophin gene," Nat. Genet. 5:130-134, 1993.
Vitaliti, A., et al., "Inhibition of tumor angiogenesis by a single-chain antibody directed against vascular endothelial growth factor," Cancer Res. 60:4311-4314, 2000.
Vlasveld, L.T., et al., "Treatment of low-grade non-Hodgkin's lymphoma with continuous infusion of low-dose recombinant

(56) References Cited

OTHER PUBLICATIONS interleukin-2 in combination with the B-cell-specific monoclonal antibody CLB-CD19," Cancer Immunol. Immunother. 40:37-47, 1995.
Walker, M.R., et al., "Aglycosylation of human IgG1 and IgG3 monoclonal antibodies can eliminate recognition by human cells expressing Fcγ RI and/or Fcγ RII receptors," Biochem. J. 259:347-353, 1989.
Walther, W., and Stein, U., Eds., "Contents," pp. vii-x, in Gene Therapy of Cancer: Methods and Protocols, Humana Press, Totowa, NJ, 2000.
Wang, B., et al., "Human single-chain Fv immunoconjugates targeted to a melanoma-associated chondroitin sulfate proteoglycan mediate specific lysis of human melanoma cells by natural killer cells and complement," Proc. Natl. Acad. Sci. USA 96:1627-1632, 1999.
Wang, C.-Y., and Huang, L., "pH-sensitive immunoliposomes mediate target-cell-specific delivery and controlled expression of a foreign gene in mouse," Proc. Natl. Acad. Sci. USA 84:7851-7855, 1987.
Wang, J., et al., "Generation and Characterization of CD20-Specific CD8+ Cytotoxic T Lymphocytes (CTL) Genetically Modified by Introduction of an scFvFc:zeta Chimeric T Cell Receptor Gene: Preclinical Studies Prior to a Phase I Trial of Cellular Immunotherapy of Follicular Lymphoma," American Society of Hematology, 44th Annual Meeting programs and abstracts, Dec. 6-10, 2002, Philadelphia, Pennsylvania, Blood 100(11):201a, Abstract No. 755, Nov. 16, 2002, 1 page.
Ward, E.S., and Ghetie, V., "The effector functions of immunoglobulins: implications for therapy," Ther. Immunol. 2:77-94, 1995.
Ward, E.S., et al., "Binding activities of a repertoire of single immunoglobulin variable domains secreted from *Escherichia coli*," Nature 341:544-546, 1989.
Warnock, D., et al., "In Vitro Galactosylation of Human IgG at 1 kg Scale Using Recombinant Galactosyltransferase," Biotechnol. Bioeng. 92(7):831-842, 2005.
Welschof, M., et al., "The Antigen Binding Domain of Non-idiotypic Human Anti-F(ab')2 Autoantibodies: Study of their Interaction with IgG Hinge Region Epitopes," Hum. Immunol. 60:282-290, 1999.
Weston, K.M., et al., "In vivo binding of mouse IgG via polyreactive surface IgM abrogates progressive lymphocytosis in prolymphocytic leukemia," Leuk. Lymphoma 29:361-373, 1998.
White, C.A., et al., "Anti-CD20 monoclonal antibodies as novel treatments for non-Hodgkin's lymphoma," Pharm. Sci. Technol. Today 2(3):95-101, 1999.
White, M.W., et al., "Activation of Dense Human Tonsilar B Cells. Induction of c-myc Gene Expression via Two Distinct Signal Transduction," J. Immunol. 146(3):846-853, 1991.
Willems et al., "CD3 ×CD28 cross-interacting bispecific antibodies improve tumor cell dependent T-cell activation," Cancer Immunol. Immunother. 54:1059-1071 (2005).
Wilson, I.A., and Stanfield, R.L., "A Trojan horse with a sweet tooth," Nat. Struct. Biol. 2:433-436, 1995.
Winberg, G., et al., "Surface Expression of CD28 Single Chain Fv for Costimulation by Tumor Cells," Immunol. Rev. 153:209-223, 1996.
Wlodarski, P., et al., "Activation of Mammalian Target of Rapamycin in Transformed B Lymphocytes Is Nutrient Dependent but Independent of Akt, Mitogen-Activated Protein Kinase/Extracellular Signal-Regulated Kinase Kinase, Insulin Growth Factor-I, and Serum," Cancer Res. 65(17):7800-7808, 2005.
Wörn, A., and Plückthun, A., "Stability engineering of antibody single-chain Fv fragments," J. Mol. Biol. 305(5):989-1010, 2001.
Wu, A.M., et al., "Multimerization of a chimeric anti-CD20 single-chain Fv-Fc fusion protein is mediated through variable domain exchange," Protein Eng. 14(12):1025-1033, 2001.
Wu, C.H., et al., "Targeting Genes: Delivery and Persistent Expression of a Foreign Gene Driven by Mammalian Regulatory Elements in Vivo," J. Biol. Chem. 264(29):16985-16987, 1989.
Wu, H., et al., "Humanization of a murine monoclonal antibody by simultaneous optimization of framework and CDR residues," J. Mol. Biol. 294:151-162, 1999.
Xavier, K.A., and Willson, R.C., "Association and Dissociation Kinetics of Anti-Hen Egg Lysozyme Monoclonal Antibodies HyHEL-5 and HyHEL-10," Biophys. J. 74:2036-2045, 1998.
Yang, D., et al., "Human neutrophil defensins selectively chemoattract naïve T and immature dendritic cells," J. Leukoc. Biol. 68:9-14, 2000.
Ye, Z., et al., "Gene therapy for cancer using single-chain Fv fragments specific for 4-1BB," Nat. Med. 8(4):343-348, 2002.
Yokota, T., et al., "Rapid Tumor Penetration of a Single-Chain Fv and Comparison with Other Immunoglobulin Forms," Canc. Res. 52:3402-3408, 1992.
Yokoyama et al., "Immune Functions Encoded by the Natural Killer Gene Complex," Nature Reviews Immunology 3:304-316 (2003).
Yoshinaga, S.K., et al., "Characterization of a new human B7-related protein: B7RP-1 is the ligand to the co-stimulatory protein ICOS," Int. Immunol. 12(10):1439-1447, 2000.
Zaja, F., et al., "Rituximab for myasthenia gravis developing after bone marrow transplant," Neurology 55:1062-1063, 2000.
Zarling, J.M., et al., "Lysis of Cells Infected with HIV-1 by Human Lymphocytes Targeted with Monoclonal Antibody Heteroconjugates," J. Immunol. 140(8):2609-2613, 1988.
Zhao, X., et al., "Targeting CD37-positive lymphoid malignancies with a novel engineered small modular immunopharmaceutical," Blood 110(7):2569-2577, 2007.
Zhao, X.B., et al., "Novel Anti-CD37 Small Modular Immunopharmaceutical (SMIP) Induces B-Cell-Specific, Caspase-Independent Apoptosis in Human CLL Cells," Blood (ASH Annual Meeting Abstracts) 104:Abstract #2515, 2004, 1 page.
Zhorov, O.V., et al., "Oxidative iodination of rabbit IgG: localization of markers in an Fc-fragment and effects of modification," Biokhimiia 56(5):828-838, 1991 (with PubMed Abstract, PMID: 1747412).
"Glycosylation," Google cache of http://www.biocrawler.com/encyclopedia/Glycosylation,http://www.google.com/search?q=cache:FbsvjEyDcIUJ:www.biocrawler.com/encyclopedia/Glycosylation+serine+and+O-linked+glycosylation&hl=en&gl=us&ct=clnk&cd=14, 3 pages, retrieved May 20, 2006, page last modified Apr. 7, 2005.
AFINITOR (everolimus) tablets for oral administration, Highlights of Prescribing Information, Novartis Pharma Stein AG, Novartis Pharmaceuticals Corporation, retrieved from http://www.miochol.org/product/pi/pdf/afinitor.pdf, 12 pages (Published Mar. 2009).
Barbas et al., "Focused Mutagenesis," in Phage Display, A Laboratory Manual, Chapter 13, pp. 13.11 and 13.12, Cold Spring Harbor Laboratory Press, USA (2001).
Belikov, V.G., Pharmaceutical Chemistry, Moscow: Vysshaya Shkola, 1993, pp. 43-47.
Bleyl et al., "Komplette Remission eines langjährig therapierefraktären sekundär hochmalignen Non-Hodgkin-Lymphoms nach Therapie mit Bendamustin und CD 20-Ak (Rituximab)," TumorDiagn u Ther 2001; 22(2): 15-19 (abstract front page).
Brekke and Sandlie, "Therapeutic Antibodies for Human Diseases at the Dawn of the Twenty-First Century," Nat. Rev. Drug Disc. 2:52-62 (2003).
Brennan et al., "Phosphatidylinositol 3-kinase is essential for the proliferation of lymphoblastoid cells," Oncogene 21:1263-1271 (2002).
Brown et al., "Rapamycin is active against B-precursor leukemia in vitro and in vivo, an effect that is modulated by IL-7-mediated signaling," Proc. Natl. Acad. Sci. USA, vol. 100, No. 25, pp. 15113-15118 (2003).
Calistoga Pharmaceuticals, "About Calistoga," 7 pages, promotional material, Calistoga Pharmaceuticals, (published in 2009).
Cragg et al., "Complement-mediated lysis by anti-CD20 mAb correlates with segregation into lipid rafts," Blood 101:1045-1052 (published online Sep. 2002).
Emergent Biosolutions "Emergent Biosolutions' Otlertuzumab (TRU-016) Shows Positive Results in Combination with Rituximab in People with CLL" News Release, 3 pages, http://investors.

(56) References Cited

OTHER PUBLICATIONS emergentbiosolutions.com/phoenix.zhtml?c=202582&p=irol-newsArticle&ID=1883404 (Published online Dec. 10, 2013).
Emergent Biosolutions, "ADAPTIRTM Mono-Specific Protein Therapeutic," http://emergentbiosolutions.com/pipeline/technologies, 2 pages (retrieved May 12, 2015).
Emergent Biosolutions, "SMIP™ Mono-Specific Protein Therapeutic," http://www.emergentbiosolutions.com/?q=node/48 (retrieved Apr. 20, 2012).
Emergent Product Development Seattle LLC, "Phase 1/1b Study of TRU-016 in Patients With Previously Treated CLL or Select Subtypes of Non-Hodgkin's Lymphoma," ClinicalTrials.gov Identifier: NCT00614042, http://clinicaltrials.gov/show/NCT00614042, 3 pages (First received: Jan. 25, 2008).
Endo, K., "Current status of nuclear medicine in Japan," Gan to Kagaku Ryoho 26(6):744-748, May 1999. PubMed Abstract only, PMID: 10410141, http://www.ncbi.nlm.nih.gov/pubmed/10410141 (Article in Japanese).
European Medicines Agency, "MabThera," http://www.emea.europa.eu/docs/en_GB/document_library/EPAR_-_Summary_for_the_public/human/000165/WC500025815.pdf, 4 pages (first available in 2009, updated Oct. 2010).
European Search Report, EP appl. No. 11182404.1, filed Sep. 22, 2011, "Single-chain multivalent binding proteins with effector function," Applicant: Emergent Product Development Seattle, LLC, Inventors: William Brady et al., 11 pages (Dec. 19, 2012).
European Search Report, EP appl. No. 12185719.7, filed Sep. 24, 2012, "B-cell reduction using CD37-specific and CD20-specific binding molecules," Applicant: Emergent Product Development Seattle, LLC, Inventors: Laura Sue Grosmaire et al., (Jul. 5, 2013).
Fischer et al., "Bendamustine in Combination with Rituximab (BR) for Patients with Relapsed Chronic Lymphocytic Leukemia (CLL): A Multicentre Phase II Trial of the German CLL Study Group (GCLLSG)," American Society of Hematology, Forty-ninth annual meeting program and abstracts, Dec. 8-11, 2007, Atlanta, Georgia, Blood 118(11 pt. 1):913A, abstract # 3106 (2007).
George et al., "An analysis of protein domain linkers: their classification and role in protein folding," Prot. Eng. 15(11):871-879 (2002).
Gorter et al., "Immune evasion of tumor cells using membrane-bound complement regulatory proteins," Immunology Today 20(12):576-582 (1999).
Herold et al., "Bendamustine, vincristine and prednisone (BOP) versus cyclophosphamide, vincristine and prednisone (COP) in advanced indolent non-Hodgkin's lymphoma and mantle cell lymphoma: results of a randomised phase III trial (OSHO# 19)," J. Cancer Res. Clin. Oncol. Feb. 2006;132(2):105-12. Epub Aug. 9, 2005.
Higashida, et al., "Treatment of DMARD-Refractory Rheumatoid Arthritis With Rituximab," Annual Scientific Meeting of the American College of Rheumatology (Abstract #LB11), New Orleans, LA (Oct. 2002). (Best available copy).
International Non-Hodgkin's Lymphoma Prognostic Factors Project, "A Predictive Model for Aggressive Non-Hodgkin's Lymphoma," New Engl. J. Med. 329(14):987-994, 1993.
International Preliminary Examination Report, dated Aug. 4, 2006, for PCT appl. No. PCT/US03/41600, "Binding Constructs and Methods for Use Thereof," Trubion Pharmaceuticals, Inc. et al., 5 pages.
International Preliminary Examination Report, dated Feb. 26, 2003, for PCT appl. No. PCT/US02/01487, "Binding Domain-Immunoglobulin Fusion Proteins," Genecraft, Inc. et al., 4 pages.
International Preliminary Examination Report, dated Nov. 28, 2007, for PCT appl. No. PCT/US03/24918, "Binding Domain-Immunoglobulin Fusion Proteins," Genecraft, Inc. et al., 5 pages.
International Search Report, dated Apr. 17, 2008, and Written Opinion for PCT appl. No. PCT/US2007/071052, "Single-Chain Multivalent Binding Proteins With Effector Function," Trubion Pharmaceuticals, Inc. et al., 29 pages.
International Search Report, dated Jan. 22, 2007, for PCT appl. No. PCT/US03/24918, "Binding Domain-Immunoglobulin Fusion Proteins," Trubion Pharmaceuticals, Inc. et al., 4 pages.
International Search Report, dated Jul. 16, 2007, for PCT appl. No. PCT/US2006/029038, "B-Cell Reduction Using CD37-Specific and CD20-Specific Binding Molecules," Trubion Pharmaceuticals, Inc. et al., 10 pages.
International Search Report, dated Mar. 2, 2010, for PCT appl. No. PCT/US2009/064470, "CD37 Immunotherapeutic Combination Therapies and Uses Thereof," Trubion Pharmaceuticals, Inc. et al., 4 pages.
International Search Report, dated May 9, 2002, for PCT appl. No. PCT/US02/01487, "Binding Domain-Immunoglobulin Fusion Proteins," Genecraft, Inc. et al., 3 pages.
International Search Report, dated Nov. 2, 2004, for PCT appl. No. PCT/US03/41600, "Binding Constructs and Methods for Use Thereof," Trubion Pharmaceuticals, Inc. et al., 4 pages.
International Search Report, dated Oct. 1, 2009, and Written Opinion for PCT appl. No. PCT/US2008/069378, "Binding Peptides Having a C-Terminally Disposed Specific Binding Domain," Trubion Pharmaceuticals, Inc. et al., 14 pages.
International Search Report, dated Sep. 18, 2002, for PCT appl. No. PCT/US02/07011, "Expression Technology for Proteins Containing a Hybrid Isotype Antibody Moiety," Lexigen Pharmaceuticals Corp. et al., 3 pages.
International Search Report, dated Sep. 23, 2009, and Written Opinion for PCT appl. No. PCT/US2009/040288, "CD37 Immunotherapeutic and Combination With Bifunctional Chemotherapeutic Thereof," Trubion Pharmaceuticals, Inc. et al., 15 pages.
Jespers et al., "Guiding the Selection of Human Antibodies from Phage Display Repertoires to a Single Epitope of an Antigen," Bio/Technology 12:899-903 (1994).
Konterman, R., and Dübel, S., Eds., "Antibody Engineering," Springer-Verlag, Berlin, 2001 (title pages and Table of Contents only) pp. VII-XII.
Kumagai and Taumoto, "Generation of Novel Functional Antibody Molecules by in vitro Selection System," Proteins, Nucleic Acids, and Enzymes 43(2):159-167 (1998).
Larche et al., "Costimulation Through CD86 Is Involved in Airway Antigen-Presenting Cell and T Cell Responses to Allergen in Atopic Asthmatics," J. Immunol. 161:6375-6382 (1998).
Li et al., "Expressions of CD37 and CD53 in three kinds of human cancer cell lines," J. Henan Medical University 35(2):108-110 (2000) (Abstract front).
Linsley et al., "CTLA-4 Is a Second Receptor for the B Cell Activation Antigen B7," J. Exp. Med. 174:561-569 (1991).
Maddocks et al., "Phase 1b Study of Otlertuzumab (TRU-016), an Anti-CD37 ADAPTIR™ Protein, in Combination with Rituximab in Patients with Previously Untreated Chronic Lymphocytic Leukemia (CLL)," Poster presented at American Society of Hematology Annual Meeting (Dec. 7-10, 2013).
Maddocks et al., "Phase 1b Study of Otlertuzumab (TRU-016), an Anti-CD37 ADAPTIR™ Protein, in Combination with Rituximab in Patients with Previously Untreated Chronic Lymphocytic Leukemia (CLL)," Blood 122(21):Abstract #4165, 2 pages (Nov. 15, 2013).
Mashkovsky, M.D., Medicaments, Moscow: Novaya Volna, Part 1, p. 11 (2001).
Matthews, R., "Medical Heretics," New Scientist, issue 2285, pp. 34-37, Apr. 7, 2001.
Office Action, dated Jul. 10, 2012, 7 pages, Notice of Reasons for Rejection, Japanese Application Serial No. 2009-515618, "Single-Chain Multivalent Binding Proteins With Effector Function," filed Feb. 3, 2009.
Partial European Search Report, 9 pages, EP appl. No. 12185719.7, "B-cell reduction using CD37-specific and CD20-specific binding molecules," Applicants: Emergent Product Development Seattle, LLC et al., filed Sep. 24, 2012 (dated Apr. 3, 2013).
Pfizer, "Study Evaluating Temsirolimus (CCI-779) in Mantle Cell Lymphoma (MCL) (Optimal)," ClinicalTrials.gov Identifier:NCT00117598, http://clinicaltrials.gov/show/NCT00117598, 4 pages (First received: Jun. 30, 2005).

(56) References Cited

OTHER PUBLICATIONS

Polyak and Deans, "Alanine-170 and proline-172 are critical determinants for extracellular CD20 epitopes; heterogeneity in the fine specificity of CD20 monoclonal antibodies is defined by additional requirements imposed by both amino acid sequence and quaternary structure," Blood 99:3256-3262 (2002).

PubMed (NCBI) search for "des-leucine", accessed Nov. 14, 2006, 1 page, in Office action dated Dec. 8, 2006 in U.S. Appl. No. 10/627,556, "Binding Constructs and Methods for Use Thereof," Jeffrey A. Ledbetter et al., filed Jul. 26, 2003, now U.S. Pat. No. 7,829,084.

RAPAMUNE (sirolimus) Oral Solution and Tablets, Highlights of Prescribing Information (1 page) and Full Prescribing Information (47 pages), Wyeth Pharmaceuticals Inc., retrieved from http://www.wyeth.com/content/showlabeling.asp?id=139, 2009, 48 pages.

Rizzieri et al., "A Phase 2 Clinical Trial of Deforolimus (AP23573, MK-8669), a Novel Mammalian Target of Rapamycin Inhibitor, in Patients with Relapsed or Refractory Hematologic Malignancies," Clin. Cancer Res. 14:2756-2762 (2008).

Roque et al., "Antibodies and Genetically Engineered Related Molecules: Production and Purification," Biotechnol. Prog. 20:639-654 (2004).

Rummel et al., "In vitro studies with bendamustine: enhanced activity in combination with rituximab," Semin Oncol. Aug. 2002;29(4 Suppl 13):12-4.

Schwänen et al., "In vitro evaluation of bendamustine induced apoptosis in B-chronic lymphocytic leukemia," Leukemia. Oct. 2002;16(10):2096-2105.

Search Output from ATCC Website for Hybridomas: 2H7 (pp. 1-2), 1D8 (p. 1), HD37 (p. 1), G28-1 (p. 1), 4.4.220 (p. 1), Fc2-2 (p. 1), UCHL-1 (p. 1), 5B9 (p. 1), L6 (p. 1), 10A8 (p. 1), 2e12 (p. 1). 40.2.36 (p. 1) and G19-4 (p. 1), in Office action dated Dec. 8, 2006 in U.S. Appl. No. 10/627,556, "Binding Constructs and Methods for Use Thereof," Jeffrey A. Ledbetter et al., filed Jul. 26, 2003, now U.S. Pat. No. 7,829,084. http://www.atcc.org/common/catalog/wordSearch/results.cfm, accessed Nov. 4, 2006.

Stone et al., "Autoantibody Activity in Waldenstrom's Macroglobulinemia," Clin. Lymphoma 5(4):225-229 (2005) (Abstract only).

Tang et al., "Regulation of Antibody-Dependent Cellular Cytotoxicity by IgG Intrinsic and Apparent Affinity for Target Antigen," J. Immunol. 179:2815-2823 (2007).

Tanpakushitsu VII (Protein VII)—Tanpakushitsu kogaku (Protein Engineering), p. 57 (1993).

Thurber et al., "Antibody tumor penetration: Transport opposed by systemic and antigen-mediated clearance," Adv. Drug Deliv. Rev. 60(12):1421, 32 pages (2008).

Trubion, "Trubion Pharmaceuticals Announces Upcoming Presentations at the 2006 American Society of Hematology (ASH) Annual Meeting," PR Newswire press release, Dec. 4, 2006, 2 pages.

Trubion, "Trubion Announces Presentation of Positive TRU-016 Data at ASCO," PR Newswire press release, Jun. 2, 2008, 2 pages.

Trubion, "Trubion Announces Upcoming Presentation at the 2007 American Society of Hematology (ASH) Annual Meeting," PR Newswire press release, Dec. 6, 2007, 2 pages.

Trubion, "Trubion Initiates Phase 1/2 Study of TRU-016 in CLL, Announces Next-Generation Product Candidate for RA and Provides Product Pipeline Update," PR Newswire press release, Mar. 27, 2008, 3 pages.

Trubion, "Trubion Pharmaceuticals, Inc. Announces Upcoming Presentation at the 2007 ASCO Annual Meeting," PR Newswire press release, May 31, 2007, 2 pages.

Trubion, "Trubion Presents Positive Data on First Pre-Clinical Product Candidates at ASH; Molecules Demonstrate Effective Depletion of Targeted B Cells," PR Newswire press release, Dec. 8, 2003, 3 pages.

Wanner et al., "Mammalian target of rapamycin inhibition induces cell cycle arrest in diffuse large B cell lymphoma (DLBCL) cells and sensitises DLBCL to rituximab," Br. J. Haematol.. vol. 134, No. 5, pp. 475-484 (2006).

Wriggers et al., "Control of Protein Functional Dynamics by Peptide Linkers," Biopolymers 80(6):736-746 (2005).

Written Opinion, dated Aug. 19, 2005, for PCT appl. No. PCT/US03/41600, "Binding Constructs and Methods for Use Thereof," Trubion Pharmaceuticals, Inc. et al., 4 pages.

Written Opinion, dated Jul. 16, 2007, for PCT appl. No. PCT/US2006/029038, "B-Cell Reduction Using CD37-Specific and CD20-Specific Binding Molecules," Trubion Pharmaceuticals, Inc. et al., 11 pages.

Written Opinion, dated Nov. 20, 2002, for PCT appl. No. PCT/US02/01487, "Binding Domain-Immunoglobulin Fusion Proteins," Genecraft, Inc., et al., 4 pages.

Xu and Davis, "Diversity in the CDR3 Region of VH Is Sufficient for Most Antibody Specificities," Immunity 13:37-45 (2000).

* cited by examiner

Anti-Class II

Anti-CD19

C. Anti-CD45

D. CTLA4Ig

- ♦ A, B, C, or D + Media
- ■ A, B, C, or D + Rituxan (0.05 mg/ml)
- ▲ A, B, C, or D + TRU016 (2 µg/ml)
- X Media alone
- ✳ Rituxan alone (2 and 0.5 µg/ml)
- ✳ TRU016 alone (2 and 0.5 µg/ml)

```
                            L-FR1              L-CDR1          L-FR2
              1                                                            49
  016_-_G28-1 DIQMTQSPASLSASVGETVTITC RTSENVYSYLA WYQQKQGKSPQLLVS
 H016_-_019001 EIVLTQSPATLSLSPGERATLSC RTSENVYSYLA WYQQKPGQAPRLLIY

    Consensus  I  TQSPA LS S GE  T  C RTSENVYSYLA WYQQK G  P LL

              L-CDR2            L-FR3                           L-CDR3
              50                                                      97
  016_-_G28-1 FAKTLAE GVPSRFSGSGSGTQFSLKISSLQPEDSGSYFC QHHSDNPWT
 H016_-_019001 FAKTLAE GIPARFSGSGSGTDFTLTISSLEPEDFAVYYC QHHSDNPWT

    Consensus FAKTLAE G P RFSGSGSGT F L ISSL PED   Y C QHHSDNPWT

               L-FR4     (G4S)3 linker                 H-FR1
              98                           1                           30
  016_-_G28-1 FGGGTELEIK GGGGSGGGGSGGGGSS AVQLQQSGPESEKPGASVKISCKASGYSFT
 H016_-_019001 FGQGTKVEIK GGGGSGGGGSGGGGTG EVQLVQSGAEVKKPGESLKISCKGSGYSFT

    Consensus FG GT  EIK GGGGSGGGGSGGGG    VQL QSG E  KPG S KISCK SGYSFT

              H-CDR1    H-FR2            H-CDR2
              31                                                   76
  016_-_G28-1 GYNMN WVKQNNGKSLEWIG NIDPYYGGTTYNRKFKG KATLTVDKSSS
 H016_-_019001 GYNMN WVRQMPGKGLEWMG NIDPYYGGTTYNRKFKG QVTISADKSIS

    Consensus GYNMN WV Q  GK LEW G NIDPYYGGTTYNRKFKG   T   DKS S

                H-FR3                  H-CDR3    H-FR4
              77                                      113
  016_-_G28-1 TAYMQLKSLTSEDSAVYYCAR SVGPMDY WGQGTSVTVSS
 H016_-_019001 TAYLQWSSLKASDTAMYYCAR SVGPMDY WGRGTLVTVSS

    Consensus TAY Q  SL   D A YYCAR SVGPMDY WG GT VTVSS
```

*FIG. 30A*

```
               1                                                50
H016_-_019001  EIVLTQSPATLSLSPGERATLSCRTSENVYSYLAWYQQKPGQAPRLLIYF
H016_-_019008  EIVLTQSPATLSLSPGERATLSCRTSENVYSYLAWYQQKPGQAPRLLIYF
H016_-_019009  EIVLTQSPATLSLSPGERATLSCRTSENVYSYLAWYQQKPGQAPRLLIYF

               51                                              100
H016_-_019001  AKTLAEGIPARFSGSGSGTDFTLTISSLEPEDFAVYYCQHHSDNPWTFGQ
H016_-_019008  AKTLAEGIPARFSGSGSGTDFTLTISSLEPEDFAVYYCQHHSDNPWTFGQ
H016_-_019009  AKTLAEGIPARFSGSGSGTDFTLTISSLEPEDFAVYYCQHHSDNPWTFGQ

               101                                             150
H016_-_019001  GTKVEIKGGGGSGGGGSGGGGTGEVQLVQSGAEVKKPGESLKISCKGSGY
H016_-_019008  GTKVEIKGGGGSGGGGSGGGGASEVQLVQSGAESKKPGESLKISCKGSGY
H016_-_019009  GTKVEIKGGGGSGGGGSGGGGASEVQLVQSGAESKKPGESLRISCKGSGY
                                    **                  *

               151                                             200
H016_-_019001  SFTGYNMNWVRQMPGKGLEWMGNIDPYYGGTTYNRKFKGQVTISADKSIS
H016_-_019008  SFTGYNMNWVRQMPGKGLEWMGNIDPYYGGTTYNRKFKGQVTISADKSIS
H016_-_019009  SFTGYNMNWVRQMPGKGLEWMGNIDPYYGGTTYNRKFKGHVTISADKSIS
                                                      *

               201                                   239
H016_-_019001  TAYLQWSSLKASDTAMYYCARSVGPMDYWGRGTLVTVSS
H016_-_019008  TAYLQWSSLKASDTAMYYCARSVGPMDYWGRGTLVTVSS
H016_-_019009  TAYLQWSSLKASDTAMYYCARSVGPMDYWGRGTLVTVSS
```

*FIG. 30B*

| Construct ID | Description | Hinge | DNA Sequence |
| --- | --- | --- | --- |
| 019001 | Vk3:VH5-51 | SSC-P | atggaagccccagctcagcttctcttcctcctgctactctggctcccag |
| 019041 | Vk3:VH5-51 | SSC-P | aagcttgccgccatggaagccccagcgcagcttctcttcctcctgcta |
| 019044 | Vk3:VH5-51 | SSC-P | aagcttgccgccatggaagccccagcgcagcttctcttcctcctgcta |

Amino Acid Sequence meapaqllflllwlpdttgeivltqspatlslspgeratlscrtsenvysylawyqqkpgqaprlliyfaktlaegiparfsgsgsgtdftltisslepedfavyycqhhsdnpwtfgqgtkveikggggsggggsggggtgev
meapaqllflllwlpdttgeivltqspatlslspgeratlscrasenvysylawyqqkpgqaprlliyfaktlaegiparfsgsgsgtdftltisslepedfavyycqhhsdnpwtfgqgtkveikggggsggggsggggtge
meapaqllflllwlpdttgeivltqspatlslspgeratlscrasenvysylawyqqkpgqaprlliyfaktlaegiparfsgsgsgtdftltisslepedfavyycqhhsdnpwtfgqgtkveikggggsggggsggggtge vqlvqsgaevkkpgeslkisckgsgysftgynmnwvrqmpgkglewmgnidpyyggttynrkfkgqvtisadksistaylqwsslkasdtamyycarsvgpmdywgrgtlvtvssdqepkssdkthtsppcpap
vqlvqsgaevkkpgeslkisckgsgysftgynmnwvrqmpgkglewmgnidpyyggttynrkfkgqvtisadksistaylqwsslkasdtamyycarsvgpfdywgqgtlvtvssdqepkssdkthtsppcpap
vqlvqsgaevkkpgeslkisckgsgysftgynmnwvrqmpgkglewmgnidpyyggttynrkfkgqvtisadksistaylqwsslkasdtamyycarsvgpfdswgqgtlvtvssdqepkssdkthtsppcpap ellggpsvflfppkpkdtlmisrtpevtcvvvdvshedpevkfnwyvdgvevhnaktkpreeqynstyrvvsvltvlhqdwlngkeykckvsnkalpapiektiskakgqprepqvytlppsrdeltknqvsltclvkgfy
ellggpsvflfppkpkdtlmisrtpevtcvvvdvshedpevkfnwyvdgvevhnaktkpreeqynstyrvvsvltvlhqdwlngkeykckvsnkalpapiektiskakgqprepqvytlppsrdeltknqvsltclvkgfy
ellggpsvflfppkpkdtlmisrtpevtcvvvdvshedpevkfnwyvdgvevhnaktkpreeqynstyrvvsvltvlhqdwlngkeykckvsnkalpapiektiskakgqprepqvytlppsrdeltknqvsltclvkgfy psdiavewesngqpennykttppvldsdgsfflyskltvdksrwqqgnvfscsvmhealhnhytqkslslspgk
psdiavewesngqpennykttppvldsdgsfflyskltvdksrwqqgnvfscsvmhealhnhytqkslslspgk*
psdiavewesngqpennykttppvldsdgsfflyskltvdksrwqqgnvfscsvmhealhnhytqkslslspgk*

```
LIGHT CHAIN   ........FR1...........  ___CDR1_____  ......FR2......
019041        EIVLTQSPATLSLSPGERATLSC RASENVYSYLA  WYQQKPGQAPRLLIY
019044        EIVLTQSPATLSLSPGERATLSC RASENVYSYLA  WYQQKPGQAPRLLIY
019001        EIVLTQSPATLSLSPGERATLSC RTSENVYSYLA  WYQQKPGQAPRLLIY

              _CDR2___  ..............FR3...............  ___CDR3____  ....FR4...
019041        FAKTLAE  GIPARFSGSGSGTDFTLTISSLEPEDFAVYYC QHHSDNPWT  FGQGTKVEIK
019044        FAKTLAE  GIPARFSGSGSGTDFTLTISSLEPEDFAVYYC QHHSDNPWT  FGQGTKVEIK
019001        FAKTLAE  GIPARFSGSGSGTDFTLTISSLEPEDFAVYYC QHHSDNPWT  FGQGTKVEIK

HEAVY CHAIN   ..............FR1............ CDR1  .....FR2......
019041        EVQLVQSGAEVKKPGESLKISCKGSGYSFT GYNMN WVRQMPGKGLEWMG
019044        EVQLVQSGAEVKKPGESLKISCKGSGYSFT GYNMN WVRQMPGKGLEWMG
019001        EVQLVQSGAEVKKPGESLKISCKGSGYSFT GYNMN WVRQMPGKGLEWMG

              ________CDR2_______ ...............FR3..............
019041        NIDPYYGGTTYNRKFKG QVTISADKSISTAYLQWSSLKASDTAMYYCAR
019044        NIDPYYGGTTYNRKFKG QVTISADKSISTAYLQWSSLKASDTAMYYCAR
019001        NIDPYYGGTTYNRKFKG QVTISADKSISTAYLQWSSLKASDTAMYYCAR

              __CDR3_ .....FR4...
019041        SVGPFDY WGQGTLVTVSS
019044        SVGPFDS WGQGTLVTVSS
019001        SVGPMDY WGRGTLVTVSS

CLUSTAL W (1.83) multiple sequence alignment

019041        ------------ATGGAAGCCCCAGCGCAGCTTCTCTTCCTCCTGCTACTCTGGCTCCCA 48
019044        ------------ATGGAAGCCCCAGCGCAGCTTCTCTTCCTCCTGCTACTCTGGCTCCCA 48
019001        AAGCTTGCCGCCATGGAAGCCCCAGCTCAGCTTCTCTTCCTCCTGCTACTCTGGCTCCCA 60
```

```
                         ************** *********************************

019041     GATACCACCGGAGAAATTGTGTTGACACAGTCTCCAGCCACCCTGTCTTTGTCTCCAGGC 108
019044     GATACCACCGGAGAAATTGTGTTGACACAGTCTCCAGCCACCCTGTCTTTGTCTCCAGGC 108
019001     GATACCACCGGAGAAATTGTGTTGACACAGTCTCCAGCCACCCTGTCTTTGTCTCCAGGC 120
           ************************************************************

019041     GAAAGAGCCACCCTCTCCTGCCGAGCAAGTGAAAATGTTTACAGCTACTTAGCCTGGTAC 168
019044     GAAAGAGCCACCCTCTCCTGCCGAGCAAGTGAAAATGTTTACAGCTACTTAGCCTGGTAC 168
019001     GAAAGAGCCACCCTCTCCTGCCGAACAAGTGAAAATGTTTACAGCTACTTAGCCTGGTAC 180
           ************************ ***********************************

019041     CAACAGAAACCTGGCCAGGCTCCTAGGCTCCTCATCTATTTTGCAAAAACCTTAGCAGAA 228
019044     CAACAGAAACCTGGCCAGGCTCCTAGGCTCCTCATCTATTTTGCAAAAACCTTAGCAGAA 228
019001     CAACAGAAACCTGGCCAGGCTCCTAGGCTCCTCATCTATTTTGCAAAAACCTTAGCAGAA 240
           ************************************************************

019041     GGAATTCCAGCCAGGTTCAGTGGCAGTGGATCCGGGACAGACTTCACTCTCACCATCAGC 288
019044     GGAATTCCAGCCAGGTTCAGTGGCAGTGGATCCGGGACAGACTTCACTCTCACCATCAGC 288
019001     GGAATTCCAGCCAGGTTCAGTGGCAGTGGATCCGGGACAGACTTCACTCTCACCATCAGC 300
           ************************************************************

019041     AGCCTAGAGCCTGAAGATTTTGCAGTTTATTACTGTCAACATCATTCCGATAATCCGTGG 348
019044     AGCCTAGAGCCTGAAGATTTTGCAGTTTATTACTGTCAACATCATTCCGATAATCCGTGG 348
019001     AGCCTAGAGCCTGAAGATTTTGCAGTTTATTACTGTCAACATCATTCCGATAATCCGTGG 360
           ************************************************************

019041     ACATTCGGCCAAGGGACCAAGGTGGAAATCAAAGGTGGCGGCGGCTCGGGCGGTGGTGGA 408
019044     ACATTCGGCCAAGGGACCAAGGTGGAAATCAAAGGTGGCGGTGGCTCGGGCGGTGGTGGA 408
019001     ACATTCGGCCAAGGGACCAAGGTGGAAATCAAAGGTGGCGGTGGCTCGGGCGGTGGTGGA 420
           ***************************************** ******************

019041     TCTGGAGGAGGTGGGACCGGTGAGGTGCAGCTGGTGCAGTCTGGAGCAGAGGTGAAAAAG 468
019044     TCTGGAGGAGGTGGGACCGGTGAGGTGCAGCTGGTGCAGTCTGGAGCAGAGGTGAAAAAG 468
019001     TCTGGAGGAGGTGGGACCGGTGAGGTGCAGCTGGTGCAGTCTGGAGCAGAGGTGAAAAAG 480
           ************************************************************

019041     CCCGGAGAGTCTCTGAAGATTTCCTGTAAGGGATCCGGTTACTCATTCACTGGCTACAAT 528
019044     CCCGGAGAGTCTCTGAAGATTTCCTGTAAGGGATCCGGTTACTCATTCACTGGCTACAAT 528
019001     CCCGGAGAGTCTCTGAAGATTTCCTGTAAGGGATCCGGTTACTCATTCACTGGCTACAAT 540
           ************************************************************

019041     ATGAACTGGGTGCGCCAGATGCCCGGGAAAGGCCTCGAGTGGATGGGCAATATTGATCCT 588
019044     ATGAACTGGGTGCGCCAGATGCCCGGGAAAGGCCTCGAGTGGATGGGCAATATTGATCCT 588
019001     ATGAACTGGGTGCGCCAGATGCCCGGGAAAGGCCTCGAGTGGATGGGCAATATTGATCCT 600
           ************************************************************

019041     TATTATGGTGGTACTACCTACAACCGGAAGTTCAAGGGCCAGGTCACTATCTCCGCCGAC 648
```

```
019044      TATTATGGTGGTACTACCTACAACCGGAAGTTCAAGGGCCAGGTCACTATCTCCGCCGAC 648
019001      TATTATGGTGGTACTACCTACAACCGGAAGTTCAAGGGCCAGGTCACTATCTCCGCCGAC 660
            ************************************************************

019041      AAGTCCATCAGCACCGCCTACCTGCAATGGAGCAGCCTGAAGGCCTCGGACACCGCCATG 708
019044      AAGTCCATCAGCACCGCCTACCTGCAATGGAGCAGCCTGAAGGCCTCGGACACCGCCATG 708
019001      AAGTCCATCAGCACCGCCTACCTGCAATGGAGCAGCCTGAAGGCCTCGGACACCGCCATG 720
            ************************************************************

019041      TATTACTGTGCACGCTCAGTCGGCCCTTTCGACTACTGGGGCCAGGGCACCCTGGTCACT 768
019044      TATTACTGTGCACGCTCAGTCGGCCCTTTCGACTCCTGGGGCCAGGGCACCCTGGTCACT 768
019001      TATTACTGTGCACGCTCAGTCGGCCCTATGGACTACTGGGGCCGCGGCACCCTGGTCACT 780
            *************************** * **** ********  ***************

019041      GTCTCCTCTGATCAGGAGCCCAAATCTTCTGACAAAACTCACACATCTCCACCGTGCCCA 828
019044      GTCTCCTCTGATCAGGAGCCCAAATCTTCTGACAAAACTCACACATCTCCACCGTGCCCA 828
019001      GTCTCCTCTGATCAGGAGCCCAAATCTTCTGACAAAACTCACACATCTCCACCGTGCCCA 840
            ************************************************************

019041      GCACCTGAACTCCTGGGTGGACCGTCAGTCTTCCTCTTCCCCCCAAAACCCAAGGACACC 888
019044      GCACCTGAACTCCTGGGTGGACCGTCAGTCTTCCTCTTCCCCCCAAAACCCAAGGACACC 888
019001      GCACCTGAACTCCTGGGTGGACCGTCAGTCTTCCTCTTCCCCCCAAAACCCAAGGACACC 900
            ************************************************************

019041      CTCATGATCTCCCGGACCCCTGAGGTCACATGCGTGGTGGTGGACGTGAGCCACGAAGAC 948
019044      CTCATGATCTCCCGGACCCCTGAGGTCACATGCGTGGTGGTGGACGTGAGCCACGAAGAC 948
019001      CTCATGATCTCCCGGACCCCTGAGGTCACATGCGTGGTGGTGGACGTGAGCCACGAAGAC 960
            ************************************************************

019041      CCTGAGGTCAAGTTCAACTGGTACGTGGACGGCGTGGAGGTGCATAATGCCAAGACAAAG 1008
019044      CCTGAGGTCAAGTTCAACTGGTACGTGGACGGCGTGGAGGTGCATAATGCCAAGACAAAG 1008
019001      CCTGAGGTCAAGTTCAACTGGTACGTGGACGGCGTGGAGGTGCATAATGCCAAGACAAAG 1020
            ************************************************************

019041      CCGCGGGAGGAGCAGTACAACAGCACGTACCGTGTGGTCAGCGTCCTCACCGTCCTGCAC 1068
019044      CCGCGGGAGGAGCAGTACAACAGCACGTACCGTGTGGTCAGCGTCCTCACCGTCCTGCAC 1068
019001      CCGCGGGAGGAGCAGTACAACAGCACGTACCGTGTGGTCAGCGTCCTCACCGTCCTGCAC 1080
            ************************************************************

019041      CAGGACTGGCTGAATGGCAAGGAGTACAAGTGCAAGGTCTCCAACAAAGCCCTCCCAGCC 1128
019044      CAGGACTGGCTGAATGGCAAGGAGTACAAGTGCAAGGTCTCCAACAAAGCCCTCCCAGCC 1128
019001      CAGGACTGGCTGAATGGCAAGGAGTACAAGTGCAAGGTCTCCAACAAAGCCCTCCCAGCC 1140
            ************************************************************

019041      CCCATCGAGAAAACCATCTCCAAAGCCAAAGGGCAGCCCCGAGAACCACAGGTGTACACC 1188
019044      CCCATCGAGAAAACCATCTCCAAAGCCAAAGGGCAGCCCCGAGAACCACAGGTGTACACC 1188
019001      CCCATCGAGAAAACCATCTCCAAAGCCAAAGGGCAGCCCCGAGAACCACAGGTGTACACC 1200
            ************************************************************
```

D

C

```
019041   CTGCCCCCATCCCGGGATGAGCTGACCAAGAACCAGGTCAGCCTGACCTGCCTGGTCAAA 1248
019044   CTGCCCCCATCCCGGGATGAGCTGACCAAGAACCAGGTCAGCCTGACCTGCCTGGTCAAA 1248
019001   CTGCCCCCATCCCGGGATGAGCTGACCAAGAACCAGGTCAGCCTGACCTGCCTGGTCAAA 1260
         ************************************************************

019041   GGCTTCTATCCAAGCGACATCGCCGTGGAGTGGGAGAGCAATGGGCAGCCGGAGAACAAC 1308
019044   GGCTTCTATCCAAGCGACATCGCCGTGGAGTGGGAGAGCAATGGGCAGCCGGAGAACAAC 1308
019001   GGCTTCTATCCAAGCGACATCGCCGTGGAGTGGGAGAGCAATGGGCAGCCGGAGAACAAC 1320
         ************************************************************

019041   TACAAGACCACGCCTCCCGTGCTGGACTCCGACGGCTCCTTCTTCCTCTACAGCAAGCTC 1368
019044   TACAAGACCACGCCTCCCGTGCTGGACTCCGACGGCTCCTTCTTCCTCTACAGCAAGCTC 1368
019001   TACAAGACCACGCCTCCCGTGCTGGACTCCGACGGCTCCTTCTTCCTCTACAGCAAGCTC 1380
         ************************************************************

019041   ACCGTGGACAAGAGCAGGTGGCAGCAGGGGAACGTCTTCTCATGCTCCGTGATGCATGAG 1428
019044   ACCGTGGACAAGAGCAGGTGGCAGCAGGGGAACGTCTTCTCATGCTCCGTGATGCATGAG 1428
019001   ACCGTGGACAAGAGCAGGTGGCAGCAGGGGAACGTCTTCTCATGCTCCGTGATGCATGAG 1440
         ************************************************************

019041   GCTCTGCACAACCACTACACGCAGAAGAGCCTCTCCCTGTCTCCGGGTAAATGA------ 1482
019044   GCTCTGCACAACCACTACACGCAGAAGAGCCTCTCCCTGTCTCCGGGTAAATGA------ 1482
019001   GCTCTGCACAACCACTACACGCAGAAGAGCCTCTCCCTGTCTCCGGGTAAATGATCTAGA 1500
         ******************************************************
```

*FIG. 32D*

SEQUENCE LISTING

<160> NUMBER OF SEQ ID NOS: 226

<210> SEQ ID NO 1
<211> LENGTH: 1510
<212> TYPE: DNA
<213> ORGANISM: Artificial sequence
<220> FEATURE:
<223> OTHER INFORMATION: TRU-016 polynucleotide

<400> SEQUENCE: 1

```
aagcttgccg ccatggattt tcaagtgcag attttcagct tcctgctaat cagtgcttca     60
gtcataattg ccagaggagt cgacatccag atgactcagt ctccagcctc cctatctgca    120
tctgtgggag agactgtcac catcacatgt cgaacaagtg aaaatgttta cagttatttg    180
gcttggtatc agcagaaaca gggaaaatct cctcagctcc tggtctcttt tgcaaaaacc    240
ttagcagaag gtgtgccatc aaggttcagt ggcagtggat caggcacaca gttttctctg    300
aagatcagca gcctgcagcc tgaagattct ggaagttatt tctgtcaaca tcattccgat    360
aatccgtgga cgttcggtgg aggcaccgaa ctggagatca aaggtggcgg tggctcgggc    420
ggtggtgggt cgggtggcgg cggatcgtca gcggtccagc tgcagcagtc tggacctgag    480
tcggaaaagc ctggcgcttc agtgaagatt tcctgcaagg cttctggtta ctcattcact    540
ggctacaata tgaactgggt gaagcagaat aatggaaaga gccttgagtg gattggaaat    600
attgatcctt attatggtgg tactacctac aaccggaagt tcaagggcaa ggccacattg    660
actgtagaca aatcctccag cacagcctac atgcagctca agagtctgac atctgaggac    720
tctgcagtct attactgtgc aagatcggtc ggccctatgg actactgggg tcaaggaacc    780
tcagtcaccg tctcttcaga tctggagccc aaatcttctg acaaaactca cacatctcca    840
```

```
ccgtgcccag cacctgaact cttgggtgga ccgtcagtct tcctcttccc cccaaaaccc    900

aaggacaccc tcatgatctc ccggacccct gaggtcacat gcgtggtggt ggacgtgagc    960

cacgaagacc ctgaggtcaa gttcaactgg tacgtggacg gcgtggaggt gcataatgcc   1020

aagacaaagc cgcgggagga gcagtacaac agcacgtacc gtgtggtcag cgtcctcacc   1080

gtcctgcacc aggactggct gaatggcaag gagtacaagt gcaaggtctc caacaaagcc   1140

ctcccagccc ccatcgagaa aaccatctcc aaagccaaag ggcagccccg agaaccacag   1200

gtgtacaccc tgcccccatc ccgggatgag ctgaccaaga accaggtcag cctgacctgc   1260

ctggtcaaag gcttctatcc aagcgacatc gccgtggagt gggagagcaa tgggcaaccg   1320

gagaacaact acaagaccac gcctcccgtg ctggactccg acggctcctt cttcctctac   1380

agcaagctca ccgtggacaa gagcaggtgg cagcagggga acgtcttctc atgctccgtg   1440

atgcatgagg ctctgcacaa ccactacacg cagaagagcc tctccctgtc tccgggtaaa   1500

tgagtctaga                                                          1510
```

<210> SEQ ID NO 2
<211> LENGTH: 496
<212> TYPE: PRT
<213> ORGANISM: Artificial sequence
<220> FEATURE:
<223> OTHER INFORMATION: TRU-016 peptide

<400> SEQUENCE: 2

```
Met Asp Phe Gln Val Gln Ile Phe Ser Phe Leu Leu Ile Ser Ala Ser
1               5                   10                  15

Val Ile Ile Ala Arg Gly Val Asp Ile Gln Met Thr Gln Ser Pro Ala
            20                  25                  30

Ser Leu Ser Ala Ser Val Gly Glu Thr Val Thr Ile Thr Cys Arg Thr
        35                  40                  45

Ser Glu Asn Val Tyr Ser Tyr Leu Ala Trp Tyr Gln Gln Lys Gln Gly
    50                  55                  60

Lys Ser Pro Gln Leu Leu Val Ser Phe Ala Lys Thr Leu Ala Glu Gly
65                  70                  75                  80

Val Pro Ser Arg Phe Ser Gly Ser Gly Ser Gly Thr Gln Phe Ser Leu
                85                  90                  95

Lys Ile Ser Ser Leu Gln Pro Glu Asp Ser Gly Ser Tyr Phe Cys Gln
            100                 105                 110

His His Ser Asp Asn Pro Trp Thr Phe Gly Gly Gly Thr Glu Leu Glu
        115                 120                 125

Ile Lys Gly Gly Gly Gly Ser Gly Gly Gly Gly Ser Gly Gly Gly Gly
    130                 135                 140

Ser Ser Ala Val Gln Leu Gln Gln Ser Gly Pro Glu Ser Glu Lys Pro
145                 150                 155                 160

Gly Ala Ser Val Lys Ile Ser Cys Lys Ala Ser Gly Tyr Ser Phe Thr
                165                 170                 175

Gly Tyr Asn Met Asn Trp Val Lys Gln Asn Asn Gly Lys Ser Leu Glu
            180                 185                 190

Trp Ile Gly Asn Ile Asp Pro Tyr Tyr Gly Gly Thr Thr Tyr Asn Arg
        195                 200                 205

Lys Phe Lys Gly Lys Ala Thr Leu Thr Val Asp Lys Ser Ser Ser Thr
    210                 215                 220

Ala Tyr Met Gln Leu Lys Ser Leu Thr Ser Glu Asp Ser Ala Val Tyr
225                 230                 235                 240
```

-continued

```
Tyr Cys Ala Arg Ser Val Gly Pro Met Asp Tyr Trp Gly Gln Gly Thr
                245                 250                 255

Ser Val Thr Val Ser Ser Asp Leu Glu Pro Lys Ser Ser Asp Lys Thr
            260                 265                 270

His Thr Ser Pro Pro Cys Pro Ala Pro Glu Leu Leu Gly Gly Pro Ser
        275                 280                 285

Val Phe Leu Phe Pro Pro Lys Pro Lys Asp Thr Leu Met Ile Ser Arg
    290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr
        355                 360                 365

Lys Cys Lys Val Ser Asn Lys Ala Leu Pro Ala Pro Ile Glu Lys Thr
    370                 375                 380

Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
                405                 410                 415

Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
        435                 440                 445

Ser Asp Gly Ser Phe Phe Leu Tyr Ser Lys Leu Thr Val Asp Lys Ser
    450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
                485                 490                 495
```

<210> SEQ ID NO 3
<211> LENGTH: 1518
<212> TYPE: DNA
<213> ORGANISM: Artificial sequence
<220> FEATURE:
<223> OTHER INFORMATION: TRU-015 polynucleotide

<400> SEQUENCE: 3

```
aagcttgccg ccatggattt tcaagtgcag attttcagct tcctgctaat cagtgcttca     60

gtcataatgt ccagaggaca aattgttctc tcccagtctc cagcaatcct gtctgcatct    120

ccaggggaga aggtcacaat gacttgcagg gccagctcaa gtgtaagtta catgcactgg    180

taccagcaga agccaggatc ctcccccaaa ccctggattt atgccccatc caacctggct    240

tctggagtcc ctgctcgctt cagtggcagt gggtctggga cctcttactc tctcacaatc    300

agcagagtgg aggctgaaga tgctgccact tattactgcc agcagtggag ttttaaccca    360

cccacgttcg gtgctgggac caagctggag ctgaaagatg gcggtggctc gggcggtggt    420

ggatctggag gaggtgggag ctctcaggct tatctacagc agtctggggc tgagtcggtg    480

aggcctgggg cctcagtgaa gatgtcctgc aaggcttctg gctacacatt taccagttac    540

aatatgcact gggtaaagca gacacctaga cagggcctgg aatggattgg agctatttat    600
```

-continued

```
ccaggaaatg gtgatacttc ctacaatcag aagttcaagg gcaaggccac actgactgta    660

gacaaatcct ccagcacagc ctacatgcag ctcagcagcc tgacatctga agactctgcg    720

gtctatttct gtgcaagagt ggtgtactat agtaactctt actggtactt cgatgtctgg    780

ggcacaggga ccacggtcac cgtctctgat caggagccca aatcttgtga caaaactcac    840

acatctccac cgtgctcagc acctgaactc ctgggtggac cgtcagtctt cctcttcccc    900

ccaaaaccca aggacaccct catgatctcc cggacccctg aggtcacatg cgtggtggtg    960

gacgtgagcc acgaagaccc tgaggtcaag ttcaactggt acgtggacgg cgtggaggtg   1020

cataatgcca agacaaagcc gcgggaggag cagtacaaca gcacgtaccg tgtggtcagc   1080

gtcctcaccg tcctgcacca ggactggctg aatggcaagg agtacaagtg caaggtctcc   1140

aacaaagccc tcccagcccc catcgagaaa accatctcca aagccaaagg gcagccccga   1200

gaaccacagg tgtacaccct gcccccatcc cgggatgagc tgaccaagaa ccaggtcagc   1260

ctgacctgcc tggtcaaagg cttctatcca agcgacatcg ccgtggagtg ggagagcaat   1320

gggcagccgg agaacaacta caagaccacg cctcccgtgc tggactccga cggctccttc   1380

ttcctctaca gcaagctcac cgtggacaag agcaggtggc agcaggggaa cgtcttctca   1440

tgctccgtga tgcatgaggc tctgcacaac cactacacgc agaagagcct ctccctgtct   1500

ccgggtaaat gatctaga                                                 1518
```

<210> SEQ ID NO 4
<211> LENGTH: 499
<212> TYPE: PRT
<213> ORGANISM: Artificial sequence
<220> FEATURE:
<223> OTHER INFORMATION: TRU-015 peptide

<400> SEQUENCE: 4

```
Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Trp Tyr Gln Gln Lys Pro Gly Ser Ser
    50                  55                  60

Pro Lys Pro Trp Ile Tyr Ala Pro Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Ser Phe Asn Pro Pro Thr Phe Gly Ala Gly Thr Lys Leu Glu Leu Lys
        115                 120                 125

Asp Gly Gly Gly Ser Gly Gly Gly Gly Ser Gly Gly Gly Gly Ser Ser
    130                 135                 140

Gln Ala Tyr Leu Gln Gln Ser Gly Ala Glu Ser Val Arg Pro Gly Ala
145                 150                 155                 160

Ser Val Lys Met Ser Cys Lys Ala Ser Gly Tyr Thr Phe Thr Ser Tyr
                165                 170                 175

Asn Met His Trp Val Lys Gln Thr Pro Arg Gln Gly Leu Glu Trp Ile
            180                 185                 190

Gly Ala Ile Tyr Pro Gly Asn Gly Asp Thr Ser Tyr Asn Gln Lys Phe
```

-continued

```
        195                 200                 205

Lys Gly Lys Ala Thr Leu Thr Val Asp Lys Ser Ser Ser Thr Ala Tyr
    210                 215                 220

Met Gln Leu Ser Ser Leu Thr Ser Glu Asp Ser Ala Val Tyr Phe Cys
225                 230                 235                 240

Ala Arg Val Val Tyr Tyr Ser Asn Ser Tyr Trp Tyr Phe Asp Val Trp
                245                 250                 255

Gly Thr Gly Thr Thr Val Thr Val Ser Asp Gln Glu Pro Lys Ser Cys
            260                 265                 270

Asp Lys Thr His Thr Ser Pro Pro Cys Ser Ala Pro Glu Leu Leu Gly
        275                 280                 285

Gly Pro Ser Val Phe Leu Phe Pro Pro Lys Pro Lys Asp Thr Leu Met
    290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
        355                 360                 365

Lys Glu Tyr Lys Cys Lys Val Ser Asn Lys Ala Leu Pro Ala Pro Ile
    370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
        435                 440                 445

Val Leu Asp Ser Asp Gly Ser Phe Phe Leu Tyr Ser Lys Leu Thr Val
    450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Gly Lys


<210> SEQ ID NO 5
<211> LENGTH: 1482
<212> TYPE: DNA
<213> ORGANISM: Artificial sequence
<220> FEATURE:
<223> OTHER INFORMATION: Humanized TRU-016

<400> SEQUENCE: 5

atggaagccc cagctcagct tctcttcctc ctgctactct ggctcccaga taccaccgga      60

gaaattgtgt tgacacagtc tccagccacc ctgtctttgt ctccaggcga aagagccacc     120

ctctcctgcc gaacaagtga aaatgtttac agctacttag cctggtacca acagaaacct     180

ggccaggctc ctaggctcct catctatttt gcaaaaacct tagcagaagg aattccagcc     240

aggttcagtg gcagtggatc cgggacagac ttcactctca ccatcagcag cctagagcct     300

gaagattttg cagtttatta ctgtcaacat cattccgata atccgtggac attcggccaa     360
```

-continued

```
gggaccaagg tggaaatcaa aggtggcggt ggctcgggcg gtggtggatc tggaggaggt    420

gggaccggtg aggtgcagct ggtgcagtct ggagcagagg tgaaaaagcc cggagagtct    480

ctgaagattt cctgtaaggg atccggttac tcattcactg gctacaatat gaactgggtg    540

cgccagatgc ccgggaaagg cctcgagtgg atgggcaata ttgatcctta ttatggtggt    600

actacctaca accggaagtt caagggccag gtcactatct ccgccgacaa gtccatcagc    660

accgcctacc tgcaatggag cagcctgaag gcctcggaca ccgccatgta ttactgtgca    720

cgctcagtcg gccctatgga ctactggggc cgcggcaccc tggtcactgt ctcctctgat    780

caggagccca aatcttctga caaaactcac acatctccac cgtgcccagc acctgaactc    840

ctgggtggac cgtcagtctt cctcttcccc ccaaaaccca aggacaccct catgatctcc    900

cggacccctg aggtcacatg cgtggtggtg gacgtgagcc acgaagaccc tgaggtcaag    960

ttcaactggt acgtggacgg cgtggaggtg cataatgcca agacaaagcc gcgggaggag   1020

cagtacaaca gcacgtaccg tgtggtcagc gtcctcaccg tcctgcacca ggactggctg   1080

aatggcaagg agtacaagtg caaggtctcc aacaaagccc tcccagcccc catcgagaaa   1140

accatctcca aagccaaagg gcagccccga gaaccacagg tgtacaccct gcccccatcc   1200

cgggatgagc tgaccaagaa ccaggtcagc ctgacctgcc tggtcaaagg cttctatcca   1260

agcgacatcg ccgtggagtg ggagagcaat gggcagccgg agaacaacta caagaccacg   1320

cctcccgtgc tggactccga cggctccttc ttcctctaca gcaagctcac cgtggacaag   1380

agcaggtggc agcaggggaa cgtcttctca tgctccgtga tgcatgaggc tctgcacaac   1440

cactacacgc agaagagcct ctccctgtct ccgggtaaat ga                      1482
```

<210> SEQ ID NO 6
<211> LENGTH: 493
<212> TYPE: PRT
<213> ORGANISM: Artificial sequence
<220> FEATURE:
<223> OTHER INFORMATION: Humanized TRU-016

<400> SEQUENCE: 6

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Thr Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Gly Ser Gly Gly Gly Gly Thr Gly Glu
    130                 135                 140

Val Gln Leu Val Gln Ser Gly Ala Glu Val Lys Lys Pro Gly Glu Ser
145                 150                 155                 160
```

-continued

```
Leu Lys Ile Ser Cys Lys Gly Ser Gly Tyr Ser Phe Thr Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240

Arg Ser Val Gly Pro Met Asp Tyr Trp Gly Arg Gly Thr Leu Val Thr
                245                 250                 255

Val Ser Ser Asp Gln Glu Pro Lys Ser Ser Asp Lys Thr His Thr Ser
            260                 265                 270

Pro Pro Cys Pro Ala Pro Glu Leu Leu Gly Gly Pro Ser Val Phe Leu
        275                 280                 285

Phe Pro Pro Lys Pro Lys Asp Thr Leu Met Ile Ser Arg Thr Pro Glu
    290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Ala Leu Pro Ala Pro Ile Glu Lys Thr Ile Ser Lys
    370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Tyr Ser Lys Leu Thr Val Asp Lys Ser Arg Trp Gln
    450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490
```

<210> SEQ ID NO 7
<211> LENGTH: 1482
<212> TYPE: DNA
<213> ORGANISM: Artificial sequence
<220> FEATURE:
<223> OTHER INFORMATION: Humanized TRU-016

<400> SEQUENCE: 7

```
atggaagccc cagctcagct tctcttcctc ctgctactct ggctcccaga taccaccgga      60

gaaattgtgt tgacacagtc tccagccacc ctgtctttgt ctccaggcga aagagccacc     120

ctctcctgcc gaacaagtga aaatgtttac agctacttag cctggtacca acagaaacct     180
```

-continued

```
ggccaggctc ctaggctcct catctatttt gcaaaaacct tagcagaagg aattccagcc    240

aggttcagtg gcagtggatc cgggacagac ttcactctca ccatcagcag cctagagcct    300

gaagattttg cagtttatta ctgtcaacat cattccgata atccgtggac attcggccaa    360

gggaccaagg tggaaatcaa aggtggcggt ggctcgggcg gtggtggatc tggaggaggt    420

gggagctctg aggtgcagct ggtgcagtct ggagcagagg tgaaaaagcc cggagagtct    480

ctgaagattt cctgtaaggg atccggttac tcattcactg gctacaatat gaactgggtg    540

cgccagatgc ccgggaaagg cctcgagtgg atgggcaata ttgatcctta ttatggtggt    600

actacctaca accggaagtt caagggccag gtcactatct ccgccgacaa gtccatcagc    660

accgcctacc tgcaatggag cagcctgaag gcctcggaca ccgccatgta ttactgtgca    720

cgctcagtcg gccctatgga ctactggggc cgcggcaccc tggtcactgt ctcctctgat    780

caggagccca aatcttctga caaaactcac acatctccac cgtgcccagc acctgaactc    840

ctgggtggac cgtcagtctt cctcttcccc ccaaaaccca aggacaccct catgatctcc    900

cggacccctg aggtcacatg cgtggtggtg gacgtgagcc acgaagaccc tgaggtcaag    960

ttcaactggt acgtggacgg cgtggaggtg cataatgcca agacaaagcc gcgggaggag   1020

cagtacaaca gcacgtaccg tgtggtcagc gtcctcaccg tcctgcacca ggactggctg   1080

aatggcaagg agtacaagtg caaggtctcc aacaaagccc tcccagcccc catcgagaaa   1140

accatctcca aagccaaagg gcagccccga gaaccacagg tgtacaccct gcccccatcc   1200

cgggatgagc tgaccaagaa ccaggtcagc ctgacctgcc tggtcaaagg cttctatcca   1260

agcgacatcg ccgtggagtg ggagagcaat gggcagccgg agaacaacta caagaccacg   1320

cctcccgtgc tggactccga cggctccttc ttcctctaca gcaagctcac cgtggacaag   1380

agcaggtggc agcaggggaa cgtcttctca tgctccgtga tgcatgaggc tctgcacaac   1440

cactacacgc agaagagcct ctccctgtct ccgggtaaat ga                      1482
```

```
<210> SEQ ID NO 8
<211> LENGTH: 493
<212> TYPE: PRT
<213> ORGANISM: Artificial sequence
<220> FEATURE:
<223> OTHER INFORMATION: Humanized TRU-016

<400> SEQUENCE: 8

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Thr Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Gly Ser Gly Gly Gly Gly Ser Ser Glu
```

-continued

```
    130                 135                 140

Val Gln Leu Val Gln Ser Gly Ala Glu Val Lys Lys Pro Gly Glu Ser
145                 150                 155                 160

Leu Lys Ile Ser Cys Lys Gly Ser Gly Tyr Ser Phe Thr Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240

Arg Ser Val Gly Pro Met Asp Tyr Trp Gly Arg Gly Thr Leu Val Thr
                245                 250                 255

Val Ser Ser Asp Gln Glu Pro Lys Ser Ser Asp Lys Thr His Thr Ser
            260                 265                 270

Pro Pro Cys Pro Ala Pro Glu Leu Leu Gly Gly Pro Ser Val Phe Leu
        275                 280                 285

Phe Pro Pro Lys Pro Lys Asp Thr Leu Met Ile Ser Arg Thr Pro Glu
    290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Ala Leu Pro Ala Pro Ile Glu Lys Thr Ile Ser Lys
    370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Tyr Ser Lys Leu Thr Val Asp Lys Ser Arg Trp Gln
    450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490
```

<210> SEQ ID NO 9
<211> LENGTH: 1482
<212> TYPE: DNA
<213> ORGANISM: Artificial sequence
<220> FEATURE:
<223> OTHER INFORMATION: Humanized TRU-016

<400> SEQUENCE: 9
atggaagccc cagctcagct tctcttcctc ctgctactct ggctcccaga taccaccgga     60

```
gaaattgtgt tgacacagtc tccagccacc ctgtctttgt ctccaggcga aagagccacc    120

ctctcctgcc gaacaagtga aaatgtttac agctacttag cctggtacca acagaaacct    180

ggccaggctc ctaggctcct catctatttt gcaaaaacct tagcagaagg aattccagcc    240

aggttcagtg gcagtggatc cgggacagac ttcactctca ccatcagcag cctagagcct    300

gaagattttg cagtttatta ctgtcaacat cattccgata atccgtggac attcggccaa    360

gggaccaagg tggaaatcaa aggtggcggt ggctcgggcg gtggtggatc tggaggaggt    420

gggaccggtg aggtgcagct ggtgcagtct ggagcagagt cgaaaaagcc cggagagtct    480

ctgaagattt cctgtaaggg atccggttac tcattcactg gctacaatat gaactgggtg    540

cgccagatgc ccgggaaagg cctcgagtgg atgggcaata ttgatcctta ttatggtggt    600

actacctaca accggaagtt caagggccag gtcactatct ccgccgacaa gtccatcagc    660

accgcctacc tgcaatggag cagcctgaag gcctcggaca ccgccatgta ttactgtgca    720

cgctcagtcg gccctatgga ctactggggc cgcggcaccc tggtcactgt ctcctctgat    780

caggagccca aatcttctga caaaactcac acatctccac cgtgcccagc acctgaactc    840

ctgggtggac cgtcagtctt cctcttcccc ccaaaaccca aggacaccct catgatctcc    900

cggacccctg aggtcacatg cgtggtggtg gacgtgagcc acgaagaccc tgaggtcaag    960

ttcaactggt acgtggacgg cgtggaggtg cataatgcca agacaaagcc gcgggaggag   1020

cagtacaaca gcacgtaccg tgtggtcagc gtcctcaccg tcctgcacca ggactggctg   1080

aatggcaagg agtacaagtg caaggtctcc aacaaagccc tcccagcccc catcgagaaa   1140

accatctcca aagccaaagg gcagccccga gaaccacagg tgtacaccct gcccccatcc   1200

cgggatgagc tgaccaagaa ccaggtcagc ctgacctgcc tggtcaaagg cttctatcca   1260

agcgacatcg ccgtggagtg ggagagcaat gggcagccgg agaacaacta caagaccacg   1320

cctcccgtgc tggactccga cggctccttc ttcctctaca gcaagctcac cgtggacaag   1380

agcaggtggc agcaggggaa cgtcttctca tgctccgtga tgcatgaggc tctgcacaac   1440

cactacacgc agaagagcct ctccctgtct ccgggtaaat ga                      1482
```

<210> SEQ ID NO 10
<211> LENGTH: 493
<212> TYPE: PRT
<213> ORGANISM: Artificial sequence
<220> FEATURE:
<223> OTHER INFORMATION: Humanized TRU-016

<400> SEQUENCE: 10

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Thr Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110
```

```
Asp Asn Pro Trp Thr Phe Gly Gln Gly Thr Lys Val Glu Ile Lys Gly
        115                 120                 125

Gly Gly Gly Ser Gly Gly Gly Gly Ser Gly Gly Gly Gly Thr Gly Glu
    130                 135                 140

Val Gln Leu Val Gln Ser Gly Ala Glu Ser Lys Lys Pro Gly Glu Ser
145                 150                 155                 160

Leu Lys Ile Ser Cys Lys Gly Ser Gly Tyr Ser Phe Thr Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240

Arg Ser Val Gly Pro Met Asp Tyr Trp Gly Arg Gly Thr Leu Val Thr
                245                 250                 255

Val Ser Ser Asp Gln Glu Pro Lys Ser Ser Asp Lys Thr His Thr Ser
            260                 265                 270

Pro Pro Cys Pro Ala Pro Glu Leu Leu Gly Gly Pro Ser Val Phe Leu
        275                 280                 285

Phe Pro Pro Lys Pro Lys Asp Thr Leu Met Ile Ser Arg Thr Pro Glu
    290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Ala Leu Pro Ala Pro Ile Glu Lys Thr Ile Ser Lys
    370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Tyr Ser Lys Leu Thr Val Asp Lys Ser Arg Trp Gln
    450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490
```

<210> SEQ ID NO 11
<211> LENGTH: 1482
<212> TYPE: DNA
<213> ORGANISM: Artificial sequence
<220> FEATURE:

<223> OTHER INFORMATION: Humanized TRU-016

<400> SEQUENCE: 11

```
atggaagccc cagctcagct tctcttcctc ctgctactct ggctcccaga taccaccgga      60
gaaattgtgt tgacacagtc tccagccacc ctgtctttgt ctccaggcga aagagccacc     120
ctctcctgcc gaacaagtca aaatgtttac agctacttag cctggtacca acagaaacct     180
ggccaggctc ctaggctcct catctatttt gcaaaaacct tagcagaagg aattccagcc     240
aggttcagtg gcagtggatc cgggacagac ttcactctca ccatcagcag cctagagcct     300
gaagattttg cagtttatta ctgtcaacat cattccgata atccgtggac attcggccaa     360
gggaccaagg tggaaatcaa aggtggcggt ggctcgggcg gtggtggatc tggaggaggt     420
gggaccggtg aggtgcagct ggtgcagtct ggagcagagg tgaaaaagcc cggagagtct     480
ctgaagattt cctgtaaggg atccggttac tcattcactg gctacaatat gaactgggtg     540
cgccagatgc ccgggaaagg cctcgagtgg atgggcaata ttgatcctta ttatggtggt     600
actacctaca accggaagtt caagggccag gtcactatct ccgccgacaa gtccatcagc     660
accgcctacc tgcaatggag cagcctgaag gcctcggaca ccgccatgta ttactgtgca     720
cgctcagtcg gccctatgga ctactggggc cgcggcaccc tggtcactgt ctcctctgat     780
caggagccca aatcttctga caaaactcac acatctccac cgtgcccagc acctgaactc     840
ctgggtggac cgtcagtctt cctcttcccc ccaaaaccca aggacaccct catgatctcc     900
cggacccctg aggtcacatg cgtggtggtg gacgtgagcc acgaagaccc tgaggtcaag     960
ttcaactggt acgtggacgg cgtggaggtg cataatgcca agacaaagcc gcgggaggag    1020
cagtacaaca gcacgtaccg tgtggtcagc gtcctcaccg tcctgcacca ggactggctg    1080
aatggcaagg agtacaagtg caaggtctcc aacaaagccc tcccagcccc catcgagaaa    1140
accatctcca aagccaaagg gcagccccga gaaccacagg tgtacaccct gcccccatcc    1200
cgggatgagc tgaccaagaa ccaggtcagc ctgacctgcc tggtcaaagg cttctatcca    1260
agcgacatcg ccgtggagtg ggagagcaat gggcagccgg agaacaacta caagaccacg    1320
cctcccgtgc tggactccga cggctccttc ttcctctaca gcaagctcac cgtggacaag    1380
agcaggtggc agcaggggaa cgtcttctca tgctccgtga tgcatgaggc tctgcacaac    1440
cactacacgc agaagagcct ctccctgtct ccgggtaaat ga                       1482
```

<210> SEQ ID NO 12
<211> LENGTH: 493
<212> TYPE: PRT
<213> ORGANISM: Artificial sequence
<220> FEATURE:
<223> OTHER INFORMATION: Humanized TRU-016

<400> SEQUENCE: 12

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Thr Ser Gln Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80
```

-continued

```
Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Gly Ser Gly Gly Gly Gly Thr Gly Glu
    130                 135                 140

Val Gln Leu Val Gln Ser Gly Ala Glu Val Lys Lys Pro Gly Glu Ser
145                 150                 155                 160

Leu Lys Ile Ser Cys Lys Gly Ser Gly Tyr Ser Phe Thr Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240

Arg Ser Val Gly Pro Met Asp Tyr Trp Gly Arg Gly Thr Leu Val Thr
                245                 250                 255

Val Ser Ser Asp Gln Glu Pro Lys Ser Ser Asp Lys Thr His Thr Ser
            260                 265                 270

Pro Pro Cys Pro Ala Pro Glu Leu Leu Gly Gly Pro Ser Val Phe Leu
        275                 280                 285

Phe Pro Pro Lys Pro Lys Asp Thr Leu Met Ile Ser Arg Thr Pro Glu
    290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Ala Leu Pro Ala Pro Ile Glu Lys Thr Ile Ser Lys
    370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Tyr Ser Lys Leu Thr Val Asp Lys Ser Arg Trp Gln
    450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490
```

-continued

<210> SEQ ID NO 13
<211> LENGTH: 1482
<212> TYPE: DNA
<213> ORGANISM: Artificial sequence
<220> FEATURE:
<223> OTHER INFORMATION: Humanized TRU-016

<400> SEQUENCE: 13

```
atggaagccc cagctcagct tctcttcctc ctgctactct ggctcccaga taccaccgga     60
gaaattgtgt tgacacagtc tccagccacc ctgtctttgt ctccaggcga aagagccacc    120
ctctcctgcc gaacaagtga aagtgtttac agctacttag cctggtacca acagaaacct    180
ggccaggctc ctaggctcct catctatttt gcaaaaacct tagcagaagg aattccagcc    240
aggttcagtg gcagtggatc cgggacagac ttcactctca ccatcagcag cctagagcct    300
gaagattttg cagtttatta ctgtcaacat cattccgata atccgtggac attcggccaa    360
gggaccaagg tggaaatcaa aggtggcggt ggctcgggcg gtggtggatc tggaggaggt    420
gggaccggtg aggtgcagct ggtgcagtct ggagcagagg tgaaaaagcc cggagagtct    480
ctgaagattt cctgtaaggg atccggttac tcattcactg gctacaatat gaactgggtg    540
cgccagatgc ccgggaaagg cctcgagtgg atgggcaata ttgatcctta ttatggtggt    600
actacctaca accggaagtt caagggccag gtcactatct ccgccgacaa gtccatcagc    660
accgcctacc tgcaatggag cagcctgaag gcctcggaca ccgccatgta ttactgtgca    720
cgctcagtcg gccctatgga ctactggggc cgcggcaccc tggtcactgt ctcctctgat    780
caggagccca aatcttctga caaaactcac acatctccac cgtgcccagc acctgaactc    840
ctgggtggac cgtcagtctt cctcttcccc ccaaaaccca aggacaccct catgatctcc    900
cggacccctg aggtcacatg cgtggtggtg gacgtgagcc acgaagaccc tgaggtcaag    960
ttcaactggt acgtggacgg cgtggaggtg cataatgcca agacaaagcc gcgggaggag   1020
cagtacaaca gcacgtaccg tgtggtcagc gtcctcaccg tcctgcacca ggactggctg   1080
aatggcaagg agtacaagtg caaggtctcc aacaaagccc tcccagcccc catcgagaaa   1140
accatctcca aagccaaagg gcagccccga gaaccacagg tgtacaccct gcccccatcc   1200
cgggatgagc tgaccaagaa ccaggtcagc ctgacctgcc tggtcaaagg cttctatcca   1260
agcgacatcg ccgtggagtg ggagagcaat gggcagccgg agaacaacta caagaccacg   1320
cctcccgtgc tggactccga cggctccttc ttcctctaca gcaagctcac cgtggacaag   1380
agcaggtggc agcaggggaa cgtcttctca tgctccgtga tgcatgaggc tctgcacaac   1440
cactacacgc agaagagcct ctccctgtct ccgggtaaat ga                      1482
```

<210> SEQ ID NO 14
<211> LENGTH: 493
<212> TYPE: PRT
<213> ORGANISM: Artificial sequence
<220> FEATURE:
<223> OTHER INFORMATION: Humanized TRU-016

<400> SEQUENCE: 14

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Thr Ser Glu Ser
        35                  40                  45

Val Tyr Ser Tyr Leu Ala Trp Tyr Gln Gln Lys Pro Gly Gln Ala Pro
```

-continued

```
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Gly Ser Gly Gly Gly Gly Thr Gly Glu
    130                 135                 140

Val Gln Leu Val Gln Ser Gly Ala Glu Val Lys Lys Pro Gly Glu Ser
145                 150                 155                 160

Leu Lys Ile Ser Cys Lys Gly Ser Gly Tyr Ser Phe Thr Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240

Arg Ser Val Gly Pro Met Asp Tyr Trp Gly Arg Gly Thr Leu Val Thr
                245                 250                 255

Val Ser Ser Asp Gln Glu Pro Lys Ser Ser Asp Lys Thr His Thr Ser
            260                 265                 270

Pro Pro Cys Pro Ala Pro Glu Leu Leu Gly Gly Pro Ser Val Phe Leu
        275                 280                 285

Phe Pro Pro Lys Pro Lys Asp Thr Leu Met Ile Ser Arg Thr Pro Glu
    290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Ala Leu Pro Ala Pro Ile Glu Lys Thr Ile Ser Lys
    370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Tyr Ser Lys Leu Thr Val Asp Lys Ser Arg Trp Gln
    450                 455                 460

Gln Gly Asn Val Phe Ser Cys Ser Val Met His Glu Ala Leu His Asn
465                 470                 475                 480
```

-continued

His Tyr Thr Gln Lys Ser Leu Ser Leu Ser Pro Gly Lys
485 490

<210> SEQ ID NO 15
<211> LENGTH: 1482
<212> TYPE: DNA
<213> ORGANISM: Artificial sequence
<220> FEATURE:
<223> OTHER INFORMATION: Humanized TRU-016

<400> SEQUENCE: 15
atggaagccc cagctcagct tctcttcctc ctgctactct ggctcccaga taccaccgga 60
gaaattgtgt tgacacagtc tccagccacc ctgtctttgt ctccaggcga aagagccacc 120
ctctcctgcc gagcaagtga aaatgtttac agctacttag cctggtacca acagaaacct 180
ggccaggctc ctaggctcct catctatttt gcaaaaacct tagcagaagg aattccagcc 240
aggttcagtg gcagtggatc cgggacagac ttcactctca ccatcagcag cctagagcct 300
gaagattttg cagtttatta ctgtcaacat cattccgata atccgtggac attcggccaa 360
gggaccaagg tggaaatcaa aggtggcggt ggctcgggcg gtggtggatc tggaggaggt 420
gggaccggtg aggtgcagct ggtgcagtct ggagcagagg tgaaaaagcc cggagagtct 480
ctgaagattt cctgtaaggg atccggttac tcattcactg gctacaatat gaactgggtg 540
cgccagatgc ccgggaaagg cctcgagtgg atgggcaata ttgatcctta ttatggtggt 600
actacctaca accggaagtt caagggccag gtcactatct ccgccgacaa gtccatcagc 660
accgcctacc tgcaatggag cagcctgaag gcctcggaca ccgccatgta ttactgtgca 720
cgctcagtcg gccctatgga ctactggggc cgcggcaccc tggtcactgt ctcctctgat 780
caggagccca aatcttctga caaaactcac acatctccac cgtgcccagc acctgaactc 840
ctgggtggac cgtcagtctt cctcttcccc ccaaaaccca aggacaccct catgatctcc 900
cggacccctg aggtcacatg cgtggtggtg gacgtgagcc acgaagaccc tgaggtcaag 960
ttcaactggt acgtggacgg cgtggaggtg cataatgcca agacaaagcc gcgggaggag 1020
cagtacaaca gcacgtaccg tgtggtcagc gtcctcaccg tcctgcacca ggactggctg 1080
aatggcaagg agtacaagtg caaggtctcc aacaaagccc tcccagcccc catcgagaaa 1140
accatctcca aagccaaagg gcagccccga gaaccacagg tgtacaccct gcccccatcc 1200
cgggatgagc tgaccaagaa ccaggtcagc ctgacctgcc tggtcaaagg cttctatcca 1260
agcgacatcg ccgtggagtg ggagagcaat gggcagccgg agaacaacta caagaccacg 1320
cctcccgtgc tggactccga cggctccttc ttcctctaca gcaagctcac cgtggacaag 1380
agcaggtggc agcaggggaa cgtcttctca tgctccgtga tgcatgaggc tctgcacaac 1440
cactacacgc agaagagcct ctccctgtct ccgggtaaat ga 1482

<210> SEQ ID NO 16
<211> LENGTH: 493
<212> TYPE: PRT
<213> ORGANISM: Artificial sequence
<220> FEATURE:
<223> OTHER INFORMATION: Humanized TRU-016

<400> SEQUENCE: 16

Met Glu Ala Pro Ala Gln Leu Leu Phe Leu Leu Leu Leu Trp Leu Pro
1 5 10 15

Asp Thr Thr Gly Glu Ile Val Leu Thr Gln Ser Pro Ala Thr Leu Ser
20 25 30

-continued

```
Leu Ser Pro Gly Glu Arg Ala Thr Leu Ser Cys Arg Ala Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Gly Ser Gly Gly Gly Gly Thr Gly Glu
    130                 135                 140

Val Gln Leu Val Gln Ser Gly Ala Glu Val Lys Lys Pro Gly Glu Ser
145                 150                 155                 160

Leu Lys Ile Ser Cys Lys Gly Ser Gly Tyr Ser Phe Thr Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240

Arg Ser Val Gly Pro Met Asp Tyr Trp Gly Arg Gly Thr Leu Val Thr
                245                 250                 255

Val Ser Ser Asp Gln Glu Pro Lys Ser Ser Asp Lys Thr His Thr Ser
            260                 265                 270

Pro Pro Cys Pro Ala Pro Glu Leu Leu Gly Gly Pro Ser Val Phe Leu
        275                 280                 285

Phe Pro Pro Lys Pro Lys Asp Thr Leu Met Ile Ser Arg Thr Pro Glu
    290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Ala Leu Pro Ala Pro Ile Glu Lys Thr Ile Ser Lys
    370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445
```

```
Ser Phe Phe Leu Tyr Ser Lys Leu Thr Val Asp Lys Ser Arg Trp Gln
    450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490


<210> SEQ ID NO 17
<211> LENGTH: 1479
<212> TYPE: DNA
<213> ORGANISM: Artificial sequence
<220> FEATURE:
<223> OTHER INFORMATION: Humanized TRU-016

<400> SEQUENCE: 17

atggaagcac cagcgcagct tctcttcctc ctgctactct ggctcccaga taccaccggt     60

gacatccaga tgactcagtc tccagcctcc ctatctgcat ctgtgggaga gactgtcacc    120

atcacatgtc gaacaagtga aaatgtttac agttatttgg cttggtatca gcagaaacag    180

ggaaaatctc ctcagctcct ggtctctttt gcaaaaacct tagcagaagg tgtgccatca    240

aggttcagtg gcagtggatc aggcacacag ttttctctga agatcagcag cctgcagcct    300

gaagattctg gaagttattt ctgtcaacat cattccgata atccgtggac gttcggtgga    360

ggcaccgaac tggagatcaa aggtggcggt ggctcgggcg gtggtgggtc gggtggcggc    420

ggagctagcg aggtgcagct ggtgcagtct ggagcagagg tgaaaaagcc cggagagtct    480

ctgaggattt cctgtaaggg atccggttac tcattcactg gctacaatat gaactgggtg    540

cgccagatgc ccgggaaagg cctggagtgg atgggcaata ttgatcctta ttatggtggt    600

actacctaca accggaagtt caagggccag gtcactatct ccgccgacaa gtccatcagc    660

accgcctacc tgcaatggag cagcctgaag gcctcggaca ccgccatgta ttactgtgca    720

cgctcagtcg gccctatgga ctactggggc cgcggcaccc tggtcactgt ctcctcgagc    780

gagcccaaat cttctgacaa aactcacaca tctccaccgt gcccagcacc tgaactcctg    840

ggtggaccgt cagtcttcct cttcccccca aaacccaagg acaccctcat gatctcccgg    900

acccctgagg tcacatgcgt ggtggtggac gtgagccacg aagaccctga ggtcaagttc    960

aactggtacg tggacggcgt ggaggtgcat aatgccaaga caaagccgcg ggaggagcag   1020

tacaacagca cgtaccgtgt ggtcagcgtc ctcaccgtcc tgcaccagga ctggctgaat   1080

ggcaaggagt acaagtgcaa ggtctccaac aaagccctcc cagcccccat cgagaaaacc   1140

atctccaaag ccaaagggca gccccgagaa ccacaggtgt acaccctgcc cccatcccgg   1200

gatgagctga ccaagaacca ggtcagcctg acctgcctgg tcaaaggctt ctatccaagc   1260

gacatcgccg tggagtggga gagcaatggg cagccggaga acaactacaa gaccacgcct   1320

cccgtgctgg actccgacgg ctccttcttc ctctacagca agctcaccgt ggacaagagc   1380

aggtggcagc aggggaacgt cttctcatgc tccgtgatgc atgaggctct gcacaaccac   1440

tacacgcaga agagcctctc cctgtctccg ggtaaatga                          1479


<210> SEQ ID NO 18
<211> LENGTH: 492
<212> TYPE: PRT
<213> ORGANISM: Artificial sequence
<220> FEATURE:
<223> OTHER INFORMATION: Humanized TRU-016

<400> SEQUENCE: 18
```

-continued

```
Met Glu Ala Pro Ala Gln Leu Leu Phe Leu Leu Leu Leu Trp Leu Pro
1               5                   10                  15

Asp Thr Thr Gly Asp Ile Gln Met Thr Gln Ser Pro Ala Ser Leu Ser
            20                  25                  30

Ala Ser Val Gly Glu Thr Val Thr Ile Thr Cys Arg Thr Ser Glu Asn
        35                  40                  45

Val Tyr Ser Tyr Leu Ala Trp Tyr Gln Gln Lys Gln Gly Lys Ser Pro
    50                  55                  60

Gln Leu Leu Val Ser Phe Ala Lys Thr Leu Ala Glu Gly Val Pro Ser
65                  70                  75                  80

Arg Phe Ser Gly Ser Gly Ser Gly Thr Gln Phe Ser Leu Lys Ile Ser
                85                  90                  95

Ser Leu Gln Pro Glu Asp Ser Gly Ser Tyr Phe Cys Gln His His Ser
            100                 105                 110

Asp Asn Pro Trp Thr Phe Gly Gly Gly Thr Glu Leu Glu Ile Lys Gly
        115                 120                 125

Gly Gly Gly Ser Gly Gly Gly Gly Ser Gly Gly Gly Gly Ala Ser Glu
    130                 135                 140

Val Gln Leu Val Gln Ser Gly Ala Glu Val Lys Lys Pro Gly Glu Ser
145                 150                 155                 160

Leu Arg Ile Ser Cys Lys Gly Ser Gly Tyr Ser Phe Thr Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240

Arg Ser Val Gly Pro Met Asp Tyr Trp Gly Arg Gly Thr Leu Val Thr
                245                 250                 255

Val Ser Ser Ser Glu Pro Lys Ser Ser Asp Lys Thr His Thr Ser Pro
            260                 265                 270

Pro Cys Pro Ala Pro Glu Leu Leu Gly Gly Pro Ser Val Phe Leu Phe
        275                 280                 285

Pro Pro Lys Pro Lys Asp Thr Leu Met Ile Ser Arg Thr Pro Glu Val
    290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365

Ser Asn Lys Ala Leu Pro Ala Pro Ile Glu Lys Thr Ile Ser Lys Ala
    370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
```

```
            420                 425                 430

Glu Asn Asn Tyr Lys Thr Thr Pro Pro Val Leu Asp Ser Asp Gly Ser
        435                 440                 445

Phe Phe Leu Tyr Ser Lys Leu Thr Val Asp Lys Ser Arg Trp Gln Gln
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys
                485                 490


<210> SEQ ID NO 19
<211> LENGTH: 1479
<212> TYPE: DNA
<213> ORGANISM: Artificial sequence
<220> FEATURE:
<223> OTHER INFORMATION: Humanized TRU-016

<400> SEQUENCE: 19

atggaagcac cagcgcagct tctcttcctc ctgctactct ggctcccaga taccaccggt     60

gaaattgtgt tgacacagtc tccagccacc ctgtctttgt ctccaggcga aagagccacc    120

ctctcctgcc gaacaagtga aaatgtttac agctacttag cctggtacca acagaaacct    180

ggccaggctc ctaggctcct catctatttt gcaaaaacct tagcagaagg aattccagcc    240

aggttcagtg gcagtggatc cgggacagac ttcactctca ccatcagcag cctagagcct    300

gaagattttg cagtttatta ctgtcaacat cattccgata atccgtggac attcggccaa    360

gggaccaagg tggaaatcaa aggtggcggt ggctcgggcg gtagtggatc tggaggaggt    420

ggagctagcg cggtccagct gcagcagtct ggacctgagt cggaaaagcc tggcgcttca    480

gtgaagattt cctgcaaggc ttctggttac tcattcactg gctacaatat gaactgggtg    540

aagcagaata atggaaagag ccttgagtgg attggaaata ttgatcctta ttatggtggt    600

actacctaca accggaagtt caagggcaag gccacattga ctgtagacaa atcctccagc    660

acagcctaca tgcagctcaa gagtctgaca tctgaggact ctgcagtcta ttactgtgca    720

agatcggtcg gccctatgga ctactggggt caaggaacct cagtcaccgt ctcctcgagc    780

gagcccaaat cttctgacaa aactcacaca tctccaccgt gcccagcacc tgaactcctg    840

ggtggaccgt cagtcttcct cttcccccca aaacccaagg acaccctcat gatctcccgg    900

acccctgagg tcacatgcgt ggtggtggac gtgagccacg aagaccctga ggtcaagttc    960

aactggtacg tggacggcgt ggaggtgcat aatgccaaga caaagccgcg ggaggagcag   1020

tacaacagca cgtaccgtgt ggtcagcgtc ctcaccgtcc tgcaccagga ctggctgaat   1080

ggcaaggagt acaagtgcaa ggtctccaac aaagccctcc cagcccccat cgagaaaacc   1140

atctccaaag ccaaagggca gccccgagaa ccacaggtgt acaccctgcc cccatcccgg   1200

gatgagctga ccaagaacca ggtcagcctg acctgcctgg tcaaaggctt ctatccaagc   1260

gacatcgccg tggagtggga gagcaatggg cagccggaga acaactacaa gaccacgcct   1320

cccgtgctgg actccgacgg ctccttcttc ctctacagca agctcaccgt ggacaagagc   1380

aggtggcagc aggggaacgt cttctcatgc tccgtgatgc atgaggctct gcacaaccac   1440

tacacgcaga agagcctctc cctgtctccg ggtaaatga                          1479


<210> SEQ ID NO 20
<211> LENGTH: 492
<212> TYPE: PRT
<213> ORGANISM: Artificial sequence
```

<220> FEATURE:
<223> OTHER INFORMATION: Humanized TRU-016

<400> SEQUENCE: 20

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Thr Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Ser Gly Ser Gly Gly Gly Gly Ala Ser Ala
    130                 135                 140

Val Gln Leu Gln Gln Ser Gly Pro Glu Ser Glu Lys Pro Gly Ala Ser
145                 150                 155                 160

Val Lys Ile Ser Cys Lys Ala Ser Gly Tyr Ser Phe Thr Gly Tyr Asn
                165                 170                 175

Met Asn Trp Val Lys Gln Asn Asn Gly Lys Ser Leu Glu Trp Ile Gly
            180                 185                 190

Asn Ile Asp Pro Tyr Tyr Gly Gly Thr Thr Tyr Asn Arg Lys Phe Lys
        195                 200                 205

Gly Lys Ala Thr Leu Thr Val Asp Lys Ser Ser Ser Thr Ala Tyr Met
    210                 215                 220

Gln Leu Lys Ser Leu Thr Ser Glu Asp Ser Ala Val Tyr Tyr Cys Ala
225                 230                 235                 240

Arg Ser Val Gly Pro Met Asp Tyr Trp Gly Gln Gly Thr Ser Val Thr
                245                 250                 255

Val Ser Ser Ser Glu Pro Lys Ser Ser Asp Lys Thr His Thr Ser Pro
            260                 265                 270

Pro Cys Pro Ala Pro Glu Leu Leu Gly Gly Pro Ser Val Phe Leu Phe
        275                 280                 285

Pro Pro Lys Pro Lys Asp Thr Leu Met Ile Ser Arg Thr Pro Glu Val
    290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365

Ser Asn Lys Ala Leu Pro Ala Pro Ile Glu Lys Thr Ile Ser Lys Ala
    370                 375                 380

Lys Gly Gln Pro Arg Glu Pro Gln Val Tyr Thr Leu Pro Pro Ser Arg
385                 390                 395                 400
```

```
Asp Glu Leu Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
        435                 440                 445

Phe Phe Leu Tyr Ser Lys Leu Thr Val Asp Lys Ser Arg Trp Gln Gln
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys
                485                 490


<210> SEQ ID NO 21
<211> LENGTH: 1479
<212> TYPE: DNA
<213> ORGANISM: Artificial sequence
<220> FEATURE:
<223> OTHER INFORMATION: Humanized TRU-016

<400> SEQUENCE: 21

atggaagcac cagcgcagct tctcttcctc ctgctactct ggctcccaga taccaccggt     60

gaaattgtgt tgacacagtc tccagccacc ctgtctttgt ctccaggcga aagagccacc    120

ctctcctgcc gaacaagtga aaatgtttac agctacttag cctggtacca acagaaacct    180

ggccaggctc ctaggctcct catctatttt gcaaaaacct tagcagaagg aattccagcc    240

aggttcagtg gcagtggatc cgggacagac ttcactctca ccatcagcag cctagagcct    300

gaagattttg cagtttatta ctgtcaacat cattccgata atccgtggac attcggccaa    360

gggaccaagg tggaaatcaa aggtggcggt ggctcgggcg gtggtggatc tggaggaggt    420

ggagctagcc aggtgcagct ggtggagtct ggtggaggcg tggtccagcc tgggaggtcc    480

ctgagactct cctgtgcagc ctctggattc accttcagtg gctacaatat gaactgggtc    540

cgccagatgc ccgggaaagg cctggagtgg atgggcaata ttgatcctta ttatggtggt    600

actacctaca accggaagtt caagggccag gtcactatct ccgccgacaa gtccatcagc    660

accgcctacc tgcaatggag cagcctgaag gcctcggaca ccgccatgta ttactgtgca    720

cgctcagtcg gccctatgga ctactggggc cgcggcaccc tggtcactgt ctcctcgagc    780

gagcccaaat cttctgacaa aactcacaca tctccaccgt gcccagcacc tgaactcctg    840

ggtggaccgt cagtcttcct cttcccccca aaacccaagg acaccctcat gatctcccgg    900

acccctgagg tcacatgcgt ggtggtggac gtgagccacg aagaccctga ggtcaagttc    960

aactggtacg tggacggcgt ggaggtgcat aatgccaaga caaagccgcg ggaggagcag   1020

tacaacagca cgtaccgtgt ggtcagcgtc ctcaccgtcc tgcaccagga ctggctgaat   1080

ggcaaggagt acaagtgcaa ggtctccaac aaagccctcc cagcccccat cgagaaaacc   1140

atctccaaag ccaaagggca gccccgagaa ccacaggtgt acaccctgcc cccatcccgg   1200

gatgagctga ccaagaacca ggtcagcctg acctgcctgg tcaaaggctt ctatccaagc   1260

gacatcgccg tggagtggga gagcaatggg cagccggaga acaactacaa gaccacgcct   1320

cccgtgctgg actccgacgg ctccttcttc ctctacagca agctcaccgt ggacaagagc   1380

aggtggcagc aggggaacgt cttctcatgc tccgtgatgc atgaggctct gcacaaccac   1440

tacacgcaga agagcctctc cctgtctccg ggtaaatga                          1479
```

<210> SEQ ID NO 22
<211> LENGTH: 492
<212> TYPE: PRT
<213> ORGANISM: Artificial sequence
<220> FEATURE:
<223> OTHER INFORMATION: Humanized TRU-016

<400> SEQUENCE: 22

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Thr Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Gly Ser Gly Gly Gly Gly Ala Ser Gln
    130                 135                 140

Val Gln Leu Val Glu Ser Gly Gly Gly Val Val Gln Pro Gly Arg Ser
145                 150                 155                 160

Leu Arg Leu Ser Cys Ala Ala Ser Gly Phe Thr Phe Ser Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240

Arg Ser Val Gly Pro Met Asp Tyr Trp Gly Arg Gly Thr Leu Val Thr
                245                 250                 255

Val Ser Ser Ser Glu Pro Lys Ser Ser Asp Lys Thr His Thr Ser Pro
            260                 265                 270

Pro Cys Pro Ala Pro Glu Leu Leu Gly Gly Pro Ser Val Phe Leu Phe
        275                 280                 285

Pro Pro Lys Pro Lys Asp Thr Leu Met Ile Ser Arg Thr Pro Glu Val
    290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365
```

-continued

```
Ser Asn Lys Ala Leu Pro Ala Pro Ile Glu Lys Thr Ile Ser Lys Ala
    370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
        435                 440                 445

Phe Phe Leu Tyr Ser Lys Leu Thr Val Asp Lys Ser Arg Trp Gln Gln
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys
                485                 490


<210> SEQ ID NO 23
<211> LENGTH: 1503
<212> TYPE: DNA
<213> ORGANISM: Artificial sequence
<220> FEATURE:
<223> OTHER INFORMATION: Humanized TRU-016

<400> SEQUENCE: 23

atggaagcac cagcgcagct tctcttcctc ctgctactct ggctcccaga taccaccggt     60

gcggtccagc tgcagcagtc tggacctgag tcggaaaagc ctggcgcttc agtgaagatt    120

tcctgcaagg cttctggtta ctcattcact ggctacaata tgaactgggt gaagcagaat    180

aatggaaaga gccttgagtg gattggaaat attgatcctt attatggtgg tactacctac    240

aaccggaagt tcaagggcaa ggccacattg actgtagaca aatcctccag cacagcctac    300

atgcagctca agagtctgac atctgaggac tctgcagtct attactgtgc aagatcggtc    360

ggccctatgg actactgggg tcaaggaacc tcagtcaccg tctcttctgg tggcggtggc    420

tcgggcggtg gtgggtcggg tggcggcgga tcaggaggag gcgggagtgc tagcgaaatt    480

gtgttgacac agtctccagc caccctgtct ttgtctccag gcgaaagagc caccctctcc    540

tgccgaacaa gtgaaaatgt ttacagctac ttagcctggt accaacagaa acctggccag    600

gctcctaggc tcctcatcta ttttgcaaaa accttagcag aaggaattcc agccaggttc    660

agtggcagtg gatccgggac agacttcact ctcaccatca gcagcctaga gcctgaagat    720

tttgcagttt attactgtca acatcattcc gataatccgt ggacattcgg ccaagggacc    780

aaggtggaaa tcaaaggctc gagcgagccc aaatcttctg acaaaactca cacatctcca    840

ccgtgcccag cacctgaact cctgggtgga ccgtcagtct tcctcttccc cccaaaaccc    900

aaggacaccc tcatgatctc ccggacccct gaggtcacat gcgtggtggt ggacgtgagc    960

cacgaagacc ctgaggtcaa gttcaactgg tacgtggacg gcgtggaggt gcataatgcc   1020

aagacaaagc cgcgggagga gcagtacaac agcacgtacc gtgtggtcag cgtcctcacc   1080

gtcctgcacc aggactggct gaatggcaag gagtacaagt gcaaggtctc caacaaagcc   1140

ctcccagccc ccatcgagaa aaccatctcc aaagccaaag ggcagccccg agaaccacag   1200

gtgtacaccc tgcccccatc ccgggatgag ctgaccaaga accaggtcag cctgacctgc   1260

ctggtcaaag gcttctatcc aagcgacatc gccgtggagt gggagagcaa tgggcagccg   1320

gagaacaact acaagaccac gcctcccgtg ctggactccg acggctcctt cttcctctac   1380
```

```
agcaagctca ccgtggacaa gagcaggtgg cagcagggga acgtcttctc atgctccgtg   1440

atgcatgagg ctctgcacaa ccactacacg cagaagagcc tctccctgtc tccgggtaaa   1500

tga                                                                 1503


<210> SEQ ID NO 24
<211> LENGTH: 500
<212> TYPE: PRT
<213> ORGANISM: Artificial sequence
<220> FEATURE:
<223> OTHER INFORMATION: Humanized TRU-016

<400> SEQUENCE: 24

Met Glu Ala Pro Ala Gln Leu Leu Phe Leu Leu Leu Leu Trp Leu Pro
1               5                   10                  15

Asp Thr Thr Gly Ala Val Gln Leu Gln Gln Ser Gly Pro Glu Ser Glu
            20                  25                  30

Lys Pro Gly Ala Ser Val Lys Ile Ser Cys Lys Ala Ser Gly Tyr Ser
        35                  40                  45

Phe Thr Gly Tyr Asn Met Asn Trp Val Lys Gln Asn Asn Gly Lys Ser
    50                  55                  60

Leu Glu Trp Ile Gly Asn Ile Asp Pro Tyr Tyr Gly Gly Thr Thr Tyr
65                  70                  75                  80

Asn Arg Lys Phe Lys Gly Lys Ala Thr Leu Thr Val Asp Lys Ser Ser
                85                  90                  95

Ser Thr Ala Tyr Met Gln Leu Lys Ser Leu Thr Ser Glu Asp Ser Ala
            100                 105                 110

Val Tyr Tyr Cys Ala Arg Ser Val Gly Pro Met Asp Tyr Trp Gly Gln
        115                 120                 125

Gly Thr Ser Val Thr Val Ser Ser Gly Gly Gly Gly Ser Gly Gly Gly
    130                 135                 140

Gly Ser Gly Gly Gly Gly Ser Gly Gly Gly Gly Ser Ala Ser Glu Ile
145                 150                 155                 160

Val Leu Thr Gln Ser Pro Ala Thr Leu Ser Leu Ser Pro Gly Glu Arg
                165                 170                 175

Ala Thr Leu Ser Cys Arg Thr Ser Glu Asn Val Tyr Ser Tyr Leu Ala
            180                 185                 190

Trp Tyr Gln Gln Lys Pro Gly Gln Ala Pro Arg Leu Leu Ile Tyr Phe
        195                 200                 205

Ala Lys Thr Leu Ala Glu Gly Ile Pro Ala Arg Phe Ser Gly Ser Gly
    210                 215                 220

Ser Gly Thr Asp Phe Thr Leu Thr Ile Ser Ser Leu Glu Pro Glu Asp
225                 230                 235                 240

Phe Ala Val Tyr Tyr Cys Gln His His Ser Asp Asn Pro Trp Thr Phe
                245                 250                 255

Gly Gln Gly Thr Lys Val Glu Ile Lys Gly Ser Ser Glu Pro Lys Ser
            260                 265                 270

Ser Asp Lys Thr His Thr Ser Pro Pro Cys Pro Ala Pro Glu Leu Leu
        275                 280                 285

Gly Gly Pro Ser Val Phe Leu Phe Pro Pro Lys Pro Lys Asp Thr Leu
    290                 295                 300

Met Ile Ser Arg Thr Pro Glu Val Thr Cys Val Val Val Asp Val Ser
305                 310                 315                 320

His Glu Asp Pro Glu Val Lys Phe Asn Trp Tyr Val Asp Gly Val Glu
                325                 330                 335
```

```
Val His Asn Ala Lys Thr Lys Pro Arg Glu Glu Gln Tyr Asn Ser Thr
            340                 345                 350

Tyr Arg Val Val Ser Val Leu Thr Val Leu His Gln Asp Trp Leu Asn
        355                 360                 365

Gly Lys Glu Tyr Lys Cys Lys Val Ser Asn Lys Ala Leu Pro Ala Pro
    370                 375                 380

Ile Glu Lys Thr Ile Ser Lys Ala Lys Gly Gln Pro Arg Glu Pro Gln
385                 390                 395                 400

Val Tyr Thr Leu Pro Pro Ser Arg Asp Glu Leu Thr Lys Asn Gln Val
                405                 410                 415

Ser Leu Thr Cys Leu Val Lys Gly Phe Tyr Pro Ser Asp Ile Ala Val
            420                 425                 430

Glu Trp Glu Ser Asn Gly Gln Pro Glu Asn Asn Tyr Lys Thr Thr Pro
        435                 440                 445

Pro Val Leu Asp Ser Asp Gly Ser Phe Phe Leu Tyr Ser Lys Leu Thr
    450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Pro Gly Lys
            500


<210> SEQ ID NO 25
<211> LENGTH: 1488
<212> TYPE: DNA
<213> ORGANISM: Artificial sequence
<220> FEATURE:
<223> OTHER INFORMATION: Humanized TRU-016

<400> SEQUENCE: 25

atggattttc aagtgcagat tttcagcttc ctgctaatca gtgcttcagt cataattgcc     60

agaggagtcg aaattgtgtt gacacagtct ccagccaccc tgtctttgtc tccaggcgaa    120

agagccaccc tctcctgccg aacaagtgaa aatgtttaca gctacttagc ctggtaccaa    180

cagaaacctg gccaggctcc taggctcctc atctattttg caaaaacctt agcagaagga    240

attccagcca ggttcagtgg cagtggatcc gggacagact tcactctcac catcagcagc    300

ctagagcctg aagattttgc agtttattac tgtcaacatc attccgataa tccgtggaca    360

ttcggccaag ggaccaaggt ggaaatcaaa ggtggcggtg gctcgggcgg tggtggatct    420

ggaggaggtg gagctagcgc ggtccagctg cagcagtctg gacctgagtc ggaaaagcct    480

ggcgcttcag tgaagatttc ctgcaaggct tctggttact cattcactgg ctacaatatg    540

aactgggtga agcagaataa tggaaagagc cttgagtgga ttggaaatat tgatccttat    600

tatggtggta ctacctacaa ccggaagttc aagggcaagg ccacattgac tgtagacaaa    660

tcctccagca cagcctacat gcagctcaag agtctgacat ctgaggactc tgcagtctat    720

tactgtgcaa gatcggtcgg ccctatggac tactggggtc aaggaacctc agtcaccgtc    780

tcctcgagcg agcccaaatc ttctgacaaa actcacacat ctccaccgtg cccagcacct    840

gaactcctgg gtggaccgtc agtcttcctc ttccccccaa aacccaagga caccctcatg    900

atctcccgga cccctgaggt cacatgcgtg gtggtggacg tgagccacga agaccctgag    960

gtcaagttca actggtacgt ggacggcgtg gaggtgcata atgccaagac aaagccgcgg   1020

gaggagcagt acaacagcac gtaccgtgtg gtcagcgtcc tcaccgtcct gcaccaggac   1080
```

```
tggctgaatg gcaaggagta caagtgcaag gtctccaaca aagccctccc agcccccatc   1140

gagaaaacca tctccaaagc caaagggcag ccccgagaac cacaggtgta caccctgccc   1200

ccatcccggg atgagctgac caagaaccag gtcagcctga cctgcctggt caaaggcttc   1260

tatccaagcg acatcgccgt ggagtgggag agcaatgggc agccggagaa caactacaag   1320

accacgcctc ccgtgctgga ctccgacggc tccttcttcc tctacagcaa gctcaccgtg   1380

gacaagagca ggtggcagca ggggaacgtc ttctcatgct ccgtgatgca tgaggctctg   1440

cacaaccact acacgcagaa gagcctctcc ctgtctccgg gtaaatga                1488


<210> SEQ ID NO 26
<211> LENGTH: 495
<212> TYPE: PRT
<213> ORGANISM: Artificial sequence
<220> FEATURE:
<223> OTHER INFORMATION: Humanized TRU-016

<400> SEQUENCE: 26

Met Asp Phe Gln Val Gln Ile Phe Ser Phe Leu Leu Ile Ser Ala Ser
1               5                   10                  15

Val Ile Ile Ala Arg Gly Val Glu Ile Val Leu Thr Gln Ser Pro Ala
            20                  25                  30

Thr Leu Ser Leu Ser Pro Gly Glu Arg Ala Thr Leu Ser Cys Arg Thr
        35                  40                  45

Ser Glu Asn Val Tyr Ser Tyr Leu Ala Trp Tyr Gln Gln Lys Pro Gly
    50                  55                  60

Gln Ala Pro Arg Leu Leu Ile Tyr Phe Ala Lys Thr Leu Ala Glu Gly
65                  70                  75                  80

Ile Pro Ala Arg Phe Ser Gly Ser Gly Ser Gly Thr Asp Phe Thr Leu
                85                  90                  95

Thr Ile Ser Ser Leu Glu Pro Glu Asp Phe Ala Val Tyr Tyr Cys Gln
            100                 105                 110

His His Ser Asp Asn Pro Trp Thr Phe Gly Gln Gly Thr Lys Val Glu
        115                 120                 125

Ile Lys Gly Gly Gly Gly Ser Gly Gly Gly Gly Ser Gly Gly Gly Gly
    130                 135                 140

Ala Ser Ala Val Gln Leu Gln Gln Ser Gly Pro Glu Ser Glu Lys Pro
145                 150                 155                 160

Gly Ala Ser Val Lys Ile Ser Cys Lys Ala Ser Gly Tyr Ser Phe Thr
                165                 170                 175

Gly Tyr Asn Met Asn Trp Val Lys Gln Asn Asn Gly Lys Ser Leu Glu
            180                 185                 190

Trp Ile Gly Asn Ile Asp Pro Tyr Tyr Gly Gly Thr Thr Tyr Asn Arg
        195                 200                 205

Lys Phe Lys Gly Lys Ala Thr Leu Thr Val Asp Lys Ser Ser Ser Thr
    210                 215                 220

Ala Tyr Met Gln Leu Lys Ser Leu Thr Ser Glu Asp Ser Ala Val Tyr
225                 230                 235                 240

Tyr Cys Ala Arg Ser Val Gly Pro Met Asp Tyr Trp Gly Gln Gly Thr
                245                 250                 255

Ser Val Thr Val Ser Ser Ser Glu Pro Lys Ser Ser Asp Lys Thr His
            260                 265                 270

Thr Ser Pro Pro Cys Pro Ala Pro Glu Leu Leu Gly Gly Pro Ser Val
        275                 280                 285
```

-continued

```
Phe Leu Phe Pro Pro Lys Pro Lys Asp Thr Leu Met Ile Ser Arg Thr
    290                 295                 300

Pro Glu Val Thr Cys Val Val Val Asp Val Ser His Glu Asp Pro Glu
305                 310                 315                 320

Val Lys Phe Asn Trp Tyr Val Asp Gly Val Glu Val His Asn Ala Lys
                325                 330                 335

Thr Lys Pro Arg Glu Glu Gln Tyr Asn Ser Thr Tyr Arg Val Val Ser
            340                 345                 350

Val Leu Thr Val Leu His Gln Asp Trp Leu Asn Gly Lys Glu Tyr Lys
        355                 360                 365

Cys Lys Val Ser Asn Lys Ala Leu Pro Ala Pro Ile Glu Lys Thr Ile
    370                 375                 380

Ser Lys Ala Lys Gly Gln Pro Arg Glu Pro Gln Val Tyr Thr Leu Pro
385                 390                 395                 400

Pro Ser Arg Asp Glu Leu Thr Lys Asn Gln Val Ser Leu Thr Cys Leu
                405                 410                 415

Val Lys Gly Phe Tyr Pro Ser Asp Ile Ala Val Glu Trp Glu Ser Asn
            420                 425                 430

Gly Gln Pro Glu Asn Asn Tyr Lys Thr Thr Pro Pro Val Leu Asp Ser
        435                 440                 445

Asp Gly Ser Phe Phe Leu Tyr Ser Lys Leu Thr Val Asp Lys Ser Arg
    450                 455                 460

Trp Gln Gln Gly Asn Val Phe Ser Cys Ser Val Met His Glu Ala Leu
465                 470                 475                 480

His Asn His Tyr Thr Gln Lys Ser Leu Ser Leu Ser Pro Gly Lys
                485                 490                 495
```

<210> SEQ ID NO 27
<211> LENGTH: 1503
<212> TYPE: DNA
<213> ORGANISM: Artificial sequence
<220> FEATURE:
<223> OTHER INFORMATION: Humanized TRU-016

<400> SEQUENCE: 27

```
atggaagcac cagcgcagct tctcttcctc ctgctactct ggctcccaga taccaccggt     60

gcggtccagc tgcagcagtc tggacctgag tcggaaaagc ctggcgcttc agtgaagatt    120

tcctgcaagg cttctggtta ctcattcact ggctacaata tgaactgggt gaagcagaat    180

aatggaaaga gccttgagtg gattggaaat attgatcctt attatggtgg tactacctac    240

aaccggaagt tcaagggcaa ggccacattg actgtagaca aatcctccag cacagcctac    300

atgcagctca agagtctgac atctgaggac tctgcagtct attactgtgc aagatcggtc    360

ggccctatgg actactgggg tcaaggaacc tcagtcaccg tctcttctgg tggcggtggc    420

tcgggcggtg gtgggtcggg tggcggcgga tcaggaggag gcgggagtgc tagcgaaatt    480

gtgttgacac agtctccagc caccctgtct ttgtctccag gcgaaagagc caccctctcc    540

tgccgaacaa gtgaaaatgt ttacagctac ttagcctggt accaacagaa acctggccag    600

gctcctaggc tcctcatcta ttttgcaaaa accttagcag aaggaattcc agccaggttc    660

agtggcagtg gatccgggac agacttcact ctcaccatca gcagcctaga gcctgaagat    720

tttgcagttt attactgtca acatcattcc gataatccgt ggacattcgg ccaagggacc    780

aaggtggaaa tcaaaggctc gagcgagccc aaatcttctg acaaaactca cacatgccca    840

ccgtgcccag cacctgaact cctgggtgga ccgtcagtct tcctcttccc cccaaaaccc    900
```

-continued aaggacaccc tcatgatctc ccggacccct gaggtcacat gcgtggtggt ggacgtgagc 960
cacgaagacc ctgaggtcaa gttcaactgg tacgtggacg gcgtggaggt gcataatgcc 1020
aagacaaagc cgcgggagga gcagtacaac agcacgtacc gtgtggtcag cgtcctcacc 1080
gtcctgcacc aggactggct gaatggcaag gagtacaagt gcaaggtctc caacaaagcc 1140
ctcccagccc ccatcgagaa aaccatctcc aaagccaaag ggcagccccg agaaccacag 1200
gtgtacaccc tgcccccatc ccgggatgag ctgaccaaga accaggtcag cctgacctgc 1260
ctggtcaaag gcttctatcc aagcgacatc gccgtggagt gggagagcaa tgggcagccg 1320
gagaacaact acaagaccac gcctcccgtg ctggactccg acggctcctt cttcctctac 1380
agcaagctca ccgtggacaa gagcaggtgg cagcagggga acgtcttctc atgctccgtg 1440
atgcatgagg ctctgcacaa ccactacacg cagaagagcc tctccctgtc tccgggtaaa 1500
tga 1503

<210> SEQ ID NO 28
<211> LENGTH: 500
<212> TYPE: PRT
<213> ORGANISM: Artificial sequence
<220> FEATURE:
<223> OTHER INFORMATION: Humanized TRU-016

<400> SEQUENCE: 28

Met Glu Ala Pro Ala Gln Leu Leu Phe Leu Leu Leu Leu Trp Leu Pro
1 5 10 15

Asp Thr Thr Gly Ala Val Gln Leu Gln Gln Ser Gly Pro Glu Ser Glu
20 25 30

Lys Pro Gly Ala Ser Val Lys Ile Ser Cys Lys Ala Ser Gly Tyr Ser
35 40 45

Phe Thr Gly Tyr Asn Met Asn Trp Val Lys Gln Asn Asn Gly Lys Ser
50 55 60

Leu Glu Trp Ile Gly Asn Ile Asp Pro Tyr Tyr Gly Gly Thr Thr Tyr
65 70 75 80

Asn Arg Lys Phe Lys Gly Lys Ala Thr Leu Thr Val Asp Lys Ser Ser
85 90 95

Ser Thr Ala Tyr Met Gln Leu Lys Ser Leu Thr Ser Glu Asp Ser Ala
100 105 110

Val Tyr Tyr Cys Ala Arg Ser Val Gly Pro Met Asp Tyr Trp Gly Gln
115 120 125

Gly Thr Ser Val Thr Val Ser Ser Gly Gly Gly Gly Ser Gly Gly Gly
130 135 140

Gly Ser Gly Gly Gly Gly Ser Gly Gly Gly Gly Ser Ala Ser Glu Ile
145 150 155 160

Val Leu Thr Gln Ser Pro Ala Thr Leu Ser Leu Ser Pro Gly Glu Arg
165 170 175

Ala Thr Leu Ser Cys Arg Thr Ser Glu Asn Val Tyr Ser Tyr Leu Ala
180 185 190

Trp Tyr Gln Gln Lys Pro Gly Gln Ala Pro Arg Leu Leu Ile Tyr Phe
195 200 205

Ala Lys Thr Leu Ala Glu Gly Ile Pro Ala Arg Phe Ser Gly Ser Gly
210 215 220

Ser Gly Thr Asp Phe Thr Leu Thr Ile Ser Ser Leu Glu Pro Glu Asp
225 230 235 240

Phe Ala Val Tyr Tyr Cys Gln His His Ser Asp Asn Pro Trp Thr Phe
245 250 255

```
Gly Gln Gly Thr Lys Val Glu Ile Lys Gly Ser Ser Glu Pro Lys Ser
            260                 265                 270

Ser Asp Lys Thr His Thr Cys Pro Pro Cys Pro Ala Pro Glu Leu Leu
        275                 280                 285

Gly Gly Pro Ser Val Phe Leu Phe Pro Pro Lys Pro Lys Asp Thr Leu
    290                 295                 300

Met Ile Ser Arg Thr Pro Glu Val Thr Cys Val Val Val Asp Val Ser
305                 310                 315                 320

His Glu Asp Pro Glu Val Lys Phe Asn Trp Tyr Val Asp Gly Val Glu
                325                 330                 335

Val His Asn Ala Lys Thr Lys Pro Arg Glu Glu Gln Tyr Asn Ser Thr
            340                 345                 350

Tyr Arg Val Val Ser Val Leu Thr Val Leu His Gln Asp Trp Leu Asn
        355                 360                 365

Gly Lys Glu Tyr Lys Cys Lys Val Ser Asn Lys Ala Leu Pro Ala Pro
    370                 375                 380

Ile Glu Lys Thr Ile Ser Lys Ala Lys Gly Gln Pro Arg Glu Pro Gln
385                 390                 395                 400

Val Tyr Thr Leu Pro Pro Ser Arg Asp Glu Leu Thr Lys Asn Gln Val
                405                 410                 415

Ser Leu Thr Cys Leu Val Lys Gly Phe Tyr Pro Ser Asp Ile Ala Val
            420                 425                 430

Glu Trp Glu Ser Asn Gly Gln Pro Glu Asn Asn Tyr Lys Thr Thr Pro
        435                 440                 445

Pro Val Leu Asp Ser Asp Gly Ser Phe Phe Leu Tyr Ser Lys Leu Thr
    450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Pro Gly Lys
            500
```

<210> SEQ ID NO 29
<211> LENGTH: 1479
<212> TYPE: DNA
<213> ORGANISM: Artificial sequence
<220> FEATURE:
<223> OTHER INFORMATION: Humanized TRU-016

<400> SEQUENCE: 29

```
atggaagcac cagcgcagct tctcttcctc ctgctactct ggctcccaga taccaccggt      60

gaaattgtgt tgacacagtc tccagccacc ctgtctttgt ctccaggcga aagagccacc     120

ctctcctgcc gaacaagtga aaatgtttac agctacttag cctggtacca acagaaacct     180

ggccaggctc ctaggctcct catctatttt gcaaaaacct tagcagaagg aattccagcc     240

aggttcagtg gcagtggatc cgggacagac ttcactctca ccatcagcag cctagagcct     300

gaagattttg cagtttatta ctgtcaacat cattccgata atccgtggac attcggccaa     360

gggaccaagg tggaaatcaa aggtggcggt ggctcgggcg gtggtggatc tggaggaggt     420

ggagctagcg cggtccagct gcagcagtct ggacctgagt cggaaaagcc tggcgcttca     480

gtgaagattt cctgcaaggc ttctggttac tcattcactg gctacaatat gaactgggtg     540

aagcagaata atggaaagag ccttgagtgg attggaaata ttgatcctta ttatggtggt     600
```

-continued

```
actacctaca accggaagtt caagggcaag gccacattga ctgtagacaa atcctccagc    660

acagcctaca tgcagctcaa gagtctgaca tctgaggact ctgcagtcta ttactgtgca    720

agatcggtcg gccctatgga ctactggggt caaggaacct cagtcaccgt ctcctcgagc    780

gagcccaaat cttctgacaa aactcacaca tctccaccgt gcccagcacc tgaactcctg    840

ggtggaccgt cagtcttcct cttcccccca aaacccaagg acaccctcat gatctcccgg    900

acccctgagg tcacatgcgt ggtggtggac gtgagccacg aagaccctga ggtcaagttc    960

aactggtacg tggacggcgt ggaggtgcat aatgccaaga caaagccgcg ggaggagcag   1020

tacaacagca cgtaccgtgt ggtcagcgtc ctcaccgtcc tgcaccagga ctggctgaat   1080

ggcaaggagt acaagtgcaa ggtctccaac aaagccctcc cagcccccat cgagaaaacc   1140

atctccaaag ccaaagggca gccccgagaa ccacaggtgt acaccctgcc cccatcccgg   1200

gatgagctga ccaagaacca ggtcagcctg acctgcctgg tcaaaggctt ctatccaagc   1260

gacatcgccg tggagtggga gagcaatggg cagccggaga acaactacaa gaccacgcct   1320

cccgtgctgg actccgacgg ctccttcttc ctctacagca agctcaccgt ggacaagagc   1380

aggtggcagc aggggaacgt cttctcatgc tccgtgatgc atgaggctct gcacaaccac   1440

tacacgcaga agagcctctc cctgtctccg ggtaaatga                           1479
```

<210> SEQ ID NO 30
<211> LENGTH: 492
<212> TYPE: PRT
<213> ORGANISM: Artificial sequence
<220> FEATURE:
<223> OTHER INFORMATION: Humanized TRU-016

<400> SEQUENCE: 30

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Thr Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Gly Ser Gly Gly Gly Gly Ala Ser Ala
    130                 135                 140

Val Gln Leu Gln Gln Ser Gly Pro Glu Ser Glu Lys Pro Gly Ala Ser
145                 150                 155                 160

Val Lys Ile Ser Cys Lys Ala Ser Gly Tyr Ser Phe Thr Gly Tyr Asn
                165                 170                 175

Met Asn Trp Val Lys Gln Asn Asn Gly Lys Ser Leu Glu Trp Ile Gly
            180                 185                 190

Asn Ile Asp Pro Tyr Tyr Gly Gly Thr Thr Tyr Asn Arg Lys Phe Lys
        195                 200                 205
```

-continued

```
Gly Lys Ala Thr Leu Thr Val Asp Lys Ser Ser Ser Thr Ala Tyr Met
    210                 215                 220

Gln Leu Lys Ser Leu Thr Ser Glu Asp Ser Ala Val Tyr Tyr Cys Ala
225                 230                 235                 240

Arg Ser Val Gly Pro Met Asp Tyr Trp Gly Gln Gly Thr Ser Val Thr
                245                 250                 255

Val Ser Ser Ser Glu Pro Lys Ser Ser Asp Lys Thr His Thr Ser Pro
            260                 265                 270

Pro Cys Pro Ala Pro Glu Leu Leu Gly Gly Pro Ser Val Phe Leu Phe
        275                 280                 285

Pro Pro Lys Pro Lys Asp Thr Leu Met Ile Ser Arg Thr Pro Glu Val
    290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365

Ser Asn Lys Ala Leu Pro Ala Pro Ile Glu Lys Thr Ile Ser Lys Ala
    370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
        435                 440                 445

Phe Phe Leu Tyr Ser Lys Leu Thr Val Asp Lys Ser Arg Trp Gln Gln
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys
                485                 490
```

<210> SEQ ID NO 31
<211> LENGTH: 1479
<212> TYPE: DNA
<213> ORGANISM: Artificial sequence
<220> FEATURE:
<223> OTHER INFORMATION: Humanized TRU-016

<400> SEQUENCE: 31

```
atggaagcac cagcgcagct tctcttcctc ctgctactct ggctcccaga taccaccggt     60

gaaattgtgt tgacacagtc tccagccacc ctgtctttgt ctccaggcga aagagccacc    120

ctctcctgcc gaacaagtga aaatgtttac agctacttag cctggtacca acagaaacct    180

ggccaggctc ctaggctcct catctatttt gcaaaaacct tagcagaagg aattccagcc    240

aggttcagtg gcagtggatc cgggacagac ttcactctca ccatcagcag cctagagcct    300

gaagattttg cagtttatta ctgtcaacat cattccgata atccgtggac attcggccaa    360

gggaccaagg tggaaatcaa aggtggcggt ggctcgggcg gtggtggatc tggaggaggt    420

ggagctagcg cggtccagct gcagcagtct ggacctgagt cggaaaagcc tggcgcttca    480
```

-continued

```
gtgaagattt cctgcaaggc ttctggttac tcattcactg gctacaatat gaactgggtg    540

aagcagaata atggaaagag ccttgagtgg attggaaata ttgatcctta ttatggtggt    600

actacctaca accggaagtt caagggcaag gccacattga ctgtagacaa atcctccagc    660

acagcctaca tgcagctcaa gagtctgaca tctgaggact ctgcagtcta ttactgtgca    720

agatcggtcg gccctatgga ctactggggt caaggaacct cagtcaccgt ctcctcgagc    780

gagcccaaat cttctgacaa aactcacaca tgcccaccgt gcccagcacc tgaactcctg    840

ggtggaccgt cagtcttcct cttcccccca aaacccaagg acaccctcat gatctcccgg    900

acccctgagg tcacatgcgt ggtggtggac gtgagccacg aagaccctga ggtcaagttc    960

aactggtacg tggacggcgt ggaggtgcat aatgccaaga caaagccgcg ggaggagcag   1020

tacaacagca cgtaccgtgt ggtcagcgtc ctcaccgtcc tgcaccagga ctggctgaat   1080

ggcaaggagt acaagtgcaa ggtctccaac aaagccctcc cagcccccat cgagaaaacc   1140

atctccaaag ccaaagggca gccccgagaa ccacaggtgt acaccctgcc cccatcccgg   1200

gatgagctga ccaagaacca ggtcagcctg acctgcctgg tcaaaggctt ctatccaagc   1260

gacatcgccg tggagtggga gagcaatggg cagccggaga acaactacaa gaccacgcct   1320

cccgtgctgg actccgacgg ctccttcttc ctctacagca agctcaccgt ggacaagagc   1380

aggtggcagc aggggaacgt cttctcatgc tccgtgatgc atgaggctct gcacaaccac   1440

tacacgcaga agagcctctc cctgtctccg ggtaaatga                          1479
```

<210> SEQ ID NO 32
<211> LENGTH: 492
<212> TYPE: PRT
<213> ORGANISM: Artificial sequence
<220> FEATURE:
<223> OTHER INFORMATION: Humanized TRU-016

<400> SEQUENCE: 32

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Thr Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Gly Ser Gly Gly Gly Gly Ala Ser Ala
    130                 135                 140

Val Gln Leu Gln Gln Ser Gly Pro Glu Ser Glu Lys Pro Gly Ala Ser
145                 150                 155                 160

Val Lys Ile Ser Cys Lys Ala Ser Gly Tyr Ser Phe Thr Gly Tyr Asn
                165                 170                 175

Met Asn Trp Val Lys Gln Asn Asn Gly Lys Ser Leu Glu Trp Ile Gly
```

-continued

```
            180                 185                 190

Asn Ile Asp Pro Tyr Tyr Gly Gly Thr Thr Tyr Asn Arg Lys Phe Lys
        195                 200                 205

Gly Lys Ala Thr Leu Thr Val Asp Lys Ser Ser Ser Thr Ala Tyr Met
    210                 215                 220

Gln Leu Lys Ser Leu Thr Ser Glu Asp Ser Ala Val Tyr Tyr Cys Ala
225                 230                 235                 240

Arg Ser Val Gly Pro Met Asp Tyr Trp Gly Gln Gly Thr Ser Val Thr
                245                 250                 255

Val Ser Ser Ser Glu Pro Lys Ser Ser Asp Lys Thr His Thr Cys Pro
            260                 265                 270

Pro Cys Pro Ala Pro Glu Leu Leu Gly Gly Pro Ser Val Phe Leu Phe
        275                 280                 285

Pro Pro Lys Pro Lys Asp Thr Leu Met Ile Ser Arg Thr Pro Glu Val
    290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365

Ser Asn Lys Ala Leu Pro Ala Pro Ile Glu Lys Thr Ile Ser Lys Ala
    370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
        435                 440                 445

Phe Phe Leu Tyr Ser Lys Leu Thr Val Asp Lys Ser Arg Trp Gln Gln
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys
                485                 490
```

<210> SEQ ID NO 33
<211> LENGTH: 1479
<212> TYPE: DNA
<213> ORGANISM: Artificial sequence
<220> FEATURE:
<223> OTHER INFORMATION: Humanized TRU-016

<400> SEQUENCE: 33

```
atggaagcac cagcgcagct tctcttcctc ctgctactct ggctcccaga taccaccggt      60

gaaattgtgt tgacacagtc tccagccacc ctgtctttgt ctccaggcga aagagccacc     120

ctctcctgcc gaacaagtga aaatgtttac agctacttag cctggtacca acagaaacct     180

ggccaggctc ctaggctcct catctatttt gcaaaaacct tagcagaagg aattccagcc     240

aggttcagtg gcagtggatc cgggacagac ttcactctca ccatcagcag cctagagcct     300
```

-continued

```
gaagattttg cagtttatta ctgtcaacat cattccgata atccgtggac attcggccaa    360

gggaccaagg tggaaatcaa aggtggcggt ggctcgggcg gtggtggatc tggaggaggt    420

ggagctagcc aggtgcagct ggtggagtct ggtggaggcg tggtccagcc tgggaggtcc    480

ctgagactct cctgtgcagc ctctggattc accttcagtg gctacaatat gaactgggtc    540

cgccagatgc ccgggaaagg cctggagtgg atgggcaata ttgatcctta ttatggtggt    600

actacctaca accggaagtt caagggccag gtcactatct ccgccgacaa gtccatcagc    660

accgcctacc tgcaatggag cagcctgaag gcctcggaca ccgccatgta ttactgtgca    720

cgctcagtcg gccctatgga ctactggggc cgcggcaccc tggtcactgt ctcctcgagc    780

gagcccaaat cttctgacaa aactcacaca tgcccaccgt gcccagcacc tgaactcctg    840

ggtggaccgt cagtcttcct cttcccccca aaacccaagg acaccctcat gatctcccgg    900

acccctgagg tcacatgcgt ggtggtggac gtgagccacg aagaccctga ggtcaagttc    960

aactggtacg tggacggcgt ggaggtgcat aatgccaaga caaagccgcg ggaggagcag   1020

tacaacagca cgtaccgtgt ggtcagcgtc ctcaccgtcc tgcaccagga ctggctgaat   1080

ggcaaggagt acaagtgcaa ggtctccaac aaagccctcc cagcccccat cgagaaaacc   1140

atctccaaag ccaaagggca gccccgagaa ccacaggtgt acaccctgcc cccatcccgg   1200

gatgagctga ccaagaacca ggtcagcctg acctgcctgg tcaaaggctt ctatccaagc   1260

gacatcgccg tggagtggga gagcaatggg cagccggaga acaactacaa gaccacgcct   1320

cccgtgctgg actccgacgg ctccttcttc ctctacagca agctcaccgt ggacaagagc   1380

aggtggcagc aggggaacgt cttctcatgc tccgtgatgc atgaggctct gcacaaccac   1440

tacacgcaga agagcctctc cctgtctccg ggtaaatga                          1479
```

```
<210> SEQ ID NO 34
<211> LENGTH: 492
<212> TYPE: PRT
<213> ORGANISM: Artificial sequence
<220> FEATURE:
<223> OTHER INFORMATION: Humanized TRU-016

<400> SEQUENCE: 34

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Thr Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Gly Ser Gly Gly Gly Gly Ala Ser Gln
    130                 135                 140

Val Gln Leu Val Glu Ser Gly Gly Gly Val Val Gln Pro Gly Arg Ser
145                 150                 155                 160
```

-continued

Leu Arg Leu Ser Cys Ala Ala Ser Gly Phe Thr Phe Ser Gly Tyr Asn
165 170 175

Met Asn Trp Val Arg Gln Met Pro Gly Lys Gly Leu Glu Trp Met Gly
180 185 190

Asn Ile Asp Pro Tyr Tyr Gly Gly Thr Thr Tyr Asn Arg Lys Phe Lys
195 200 205

Gly Gln Val Thr Ile Ser Ala Asp Lys Ser Ile Ser Thr Ala Tyr Leu
210 215 220

Gln Trp Ser Ser Leu Lys Ala Ser Asp Thr Ala Met Tyr Tyr Cys Ala
225 230 235 240

Arg Ser Val Gly Pro Met Asp Tyr Trp Gly Arg Gly Thr Leu Val Thr
245 250 255

Val Ser Ser Ser Glu Pro Lys Ser Ser Asp Lys Thr His Thr Cys Pro
260 265 270

Pro Cys Pro Ala Pro Glu Leu Leu Gly Gly Pro Ser Val Phe Leu Phe
275 280 285

Pro Pro Lys Pro Lys Asp Thr Leu Met Ile Ser Arg Thr Pro Glu Val
290 295 300

Thr Cys Val Val Val Asp Val Ser His Glu Asp Pro Glu Val Lys Phe
305 310 315 320

Asn Trp Tyr Val Asp Gly Val Glu Val His Asn Ala Lys Thr Lys Pro
325 330 335

Arg Glu Glu Gln Tyr Asn Ser Thr Tyr Arg Val Val Ser Val Leu Thr
340 345 350

Val Leu His Gln Asp Trp Leu Asn Gly Lys Glu Tyr Lys Cys Lys Val
355 360 365

Ser Asn Lys Ala Leu Pro Ala Pro Ile Glu Lys Thr Ile Ser Lys Ala
370 375 380

Lys Gly Gln Pro Arg Glu Pro Gln Val Tyr Thr Leu Pro Pro Ser Arg
385 390 395 400

Asp Glu Leu Thr Lys Asn Gln Val Ser Leu Thr Cys Leu Val Lys Gly
405 410 415

Phe Tyr Pro Ser Asp Ile Ala Val Glu Trp Glu Ser Asn Gly Gln Pro
420 425 430

Glu Asn Asn Tyr Lys Thr Thr Pro Pro Val Leu Asp Ser Asp Gly Ser
435 440 445

Phe Phe Leu Tyr Ser Lys Leu Thr Val Asp Lys Ser Arg Trp Gln Gln
450 455 460

Gly Asn Val Phe Ser Cys Ser Val Met His Glu Ala Leu His Asn His
465 470 475 480

Tyr Thr Gln Lys Ser Leu Ser Leu Ser Pro Gly Lys
485 490

<210> SEQ ID NO 35
<211> LENGTH: 1479
<212> TYPE: DNA
<213> ORGANISM: Artificial sequence
<220> FEATURE:
<223> OTHER INFORMATION: Humanized TRU-016

<400> SEQUENCE: 35
atggaagcac cagcgcagct tctcttcctc ctgctactct ggctcccaga taccaccggt 60
gaaattgtgt tgacacagtc tccagccacc ctgtctttgt ctccaggcga aagagccacc 120
ctctcctgcc gaacaagtga aaatgtttac agctacttag cctggtacca acagaaacct 180

```
ggccaggctc ctaggctcct catctatttt gcaaaaacct tagcagaagg aattccagcc    240

aggttcagtg gcagtggatc cgggacagac ttcactctca ccatcagcag cctagagcct    300

gaagattttg cagtttatta ctgtcaacat cattccgata atccgtggac attcggccaa    360

gggaccaagg tggaaatcaa aggtggcggt ggctcgggcg gtggtggatc tggaggaggt    420

ggagctagcc aggtgcagct ggtggagtct ggtggaggcg tggtccagcc tgggaggtcc    480

ctgagactct cctgtgcagc ctctggattc accttcagtg gctacaatat gaactgggtc    540

cgccagatgc ccgggaaagg cctggagtgg atgggcaata ttgatcctta ttatggtggt    600

actacctaca accggaagtt caagggccag gtcactatct ccgccgacaa gtccatcagc    660

accgcctacc tgcaatggag cagcctgaag gcctcggaca ccgccatgta ttactgtgca    720

cgctcagtcg gccctatgga ctactggggc cgcggcaccc tggtcactgt ctcctcgagc    780

gagcccaaat cttctgacaa aactcacaca tgcccaccgt gcccagcacc tgaactcctg    840

ggtggaccgt cagtcttcct cttcccccca aaacccaagg acaccctcat gatctcccgg    900

acccctgagg tcacatgcgt ggtggtggac gtgagccacg aagaccctga ggtcaagttc    960

aactggtacg tggacggcgt ggaggtgcat aatgccaaga caaagccgcg ggaggagcag   1020

tacaacagca cgtaccgtgt ggtcagcgtc ctcaccgtcc tgcaccagga ctggctgaat   1080

ggcaaggagt acaagtgcaa ggtctccaac aaagccctcc cagcccccat cgagaaaacc   1140

atctccaaag ccaaagggca gccccgagaa ccacaggtgt acaccctgcc cccatcccgg   1200

gatgagctga ccaagaacca ggtcagcctg acctgcctgg tcaaaggctt ctatccaagc   1260

gacatcgccg tggagtggga gagcaatggg cagccggaga acaactacaa gaccacgcct   1320

cccgtgctgg actccgacgg ctccttcttc ctctacagca agctcaccgt ggacaagagc   1380

aggtggcagc aggggaacgt cttctcatgc tccgtgatgc atgaggctct gcacaaccac   1440

tacacgcaga agagcctctc cctgtctccg ggtaaatga                          1479
```

<210> SEQ ID NO 36
<211> LENGTH: 492
<212> TYPE: PRT
<213> ORGANISM: Artificial sequence
<220> FEATURE:
<223> OTHER INFORMATION: Humanized TRU-016

<400> SEQUENCE: 36

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Thr Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125
```

-continued

```
Gly Gly Gly Ser Gly Gly Gly Gly Ser Gly Gly Gly Gly Ala Ser Gln
    130                 135                 140

Val Gln Leu Val Glu Ser Gly Gly Gly Val Val Gln Pro Gly Arg Ser
145                 150                 155                 160

Leu Arg Leu Ser Cys Ala Ala Ser Gly Phe Thr Phe Ser Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240

Arg Ser Val Gly Pro Met Asp Tyr Trp Gly Arg Gly Thr Leu Val Thr
                245                 250                 255

Val Ser Ser Ser Glu Pro Lys Ser Ser Asp Lys Thr His Thr Ser Pro
            260                 265                 270

Pro Cys Pro Ala Pro Glu Leu Leu Gly Gly Pro Ser Val Phe Leu Phe
        275                 280                 285

Pro Pro Lys Pro Lys Asp Thr Leu Met Ile Ser Arg Thr Pro Glu Val
    290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365

Ser Asn Lys Ala Leu Pro Ala Pro Ile Glu Lys Thr Ile Ser Lys Ala
    370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
        435                 440                 445

Phe Phe Leu Tyr Ser Lys Leu Thr Val Asp Lys Ser Arg Trp Gln Gln
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys
                485                 490
```

<210> SEQ ID NO 37
<211> LENGTH: 1476
<212> TYPE: DNA
<213> ORGANISM: Artificial sequence
<220> FEATURE:
<223> OTHER INFORMATION: Humanized TRU-016

<400> SEQUENCE: 37

```
atggaagcac cagcgcagct tctcttcctc ctgctactct ggctcccaga taccaccggt     60

gaaattgtgt tgacacagtc tccagccacc ctgtctttgt ctccaggcga aagagccacc    120

ctctcctgcc gaacaagtga aaatgtttac agctacttag cctggtacca acagaaacct    180

ggccaggctc ctaggctcct catctatttt gcaaaaacct tagcagaagg aattccagcc    240

aggttcagtg gcagtggatc cgggacagac ttcactctca ccatcagcag cctagagcct    300

gaagattttg cagtttatta ctgtcaacat cattccgata atccgtggac attcggccaa    360

gggaccaagg tggaaatcaa aggtggcggt ggctcgggcg gtggtggatc tggaggaggt    420

ggggctagcg aggtgcagct ggtggagtct ggtggaggct tggtccagcc tggagggtcc    480

ctgagactct cctgtgcagc ctctggattc accttcagtg gctacaatat gaactgggtc    540

cgccagatgc ccgggaaagg cctggagtgg atgggcaata ttgatcctta ttatggtggt    600

actacctaca accggaagtt caagggccag gtcactatct ccgccgacaa gtccatcagc    660

accgcctacc tgcaatggag cagcctgaag gcctcggaca ccgccatgta ttactgtgca    720

cgctcagtcg gccctatgga ctactggggc cgcggcaccc tggtcactgt ctcctcgagc    780

gagcccaaat cttctgacaa aactcacaca tctccaccgt gcccagcacc tgaactcctg    840

ggtggaccgt cagtcttcct cttcccccca aaacccaagg acaccctcat gatctcccgg    900

acccctgagg tcacatgcgt ggtggtggac gtgagccacg aagaccctga ggtcaagttc    960

aactggtacg tggacggcgt ggaggtgcat aatgccaaga caaagccgcg ggaggagcag   1020

tacaacagca cgtaccgtgt ggtcagcgtc ctcaccgtcc tgcaccagga ctggctgaat   1080

ggcaaggagt acaagtgcaa ggtctccaac aaagccctcc cagcccccat cgagaaaacc   1140

atctccaaag ccaaagggca gccccgagaa ccacaggtgt acaccctgcc cccatcccgg   1200

gatgagctga ccaagaacca ggtcagcctg acctgcctgg tcaaaggctt ctatccaagc   1260

gacatcgccg tggagtggga gagcaatggg cagccggaga acaactacaa gaccacgcct   1320

cccgtgctgg actccgacgg ctccttcttc ctctacagca agctcaccgt ggacaagagc   1380

aggtggcagc aggggaacgt cttctcatgc tccgtgatgc atgaggctct gcacaaccac   1440

tacacgcaga agagcctctc cctgtctccg ggtaaa                             1476
```

```
<210> SEQ ID NO 38
<211> LENGTH: 492
<212> TYPE: PRT
<213> ORGANISM: Artificial sequence
<220> FEATURE:
<223> OTHER INFORMATION: Humanized TRU-016

<400> SEQUENCE: 38

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Thr Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
```

```
            100                 105                 110

Asp Asn Pro Trp Thr Phe Gly Gln Gly Thr Lys Val Glu Ile Lys Gly
        115                 120                 125

Gly Gly Gly Ser Gly Gly Gly Gly Ser Gly Gly Gly Gly Ala Ser Glu
    130                 135                 140

Val Gln Leu Val Glu Ser Gly Gly Gly Leu Val Gln Pro Gly Gly Ser
145                 150                 155                 160

Leu Arg Leu Ser Cys Ala Ala Ser Gly Phe Thr Phe Ser Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240

Arg Ser Val Gly Pro Met Asp Tyr Trp Gly Arg Gly Thr Leu Val Thr
                245                 250                 255

Val Ser Ser Ser Glu Pro Lys Ser Ser Asp Lys Thr His Thr Ser Pro
            260                 265                 270

Pro Cys Pro Ala Pro Glu Leu Leu Gly Gly Pro Ser Val Phe Leu Phe
        275                 280                 285

Pro Pro Lys Pro Lys Asp Thr Leu Met Ile Ser Arg Thr Pro Glu Val
    290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365

Ser Asn Lys Ala Leu Pro Ala Pro Ile Glu Lys Thr Ile Ser Lys Ala
    370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
        435                 440                 445

Phe Phe Leu Tyr Ser Lys Leu Thr Val Asp Lys Ser Arg Trp Gln Gln
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys
                485                 490
```

<210> SEQ ID NO 39
<211> LENGTH: 1476
<212> TYPE: DNA
<213> ORGANISM: Artificial sequence
<220> FEATURE:
<223> OTHER INFORMATION: Humanized TRU-016

<400> SEQUENCE: 39
atggaagcac cagcgcagct tctcttcctc ctgctactct ggctcccaga taccaccggt 60
gaaattgtgt tgacacagtc tccagccacc ctgtctttgt ctccaggcga aagagccacc 120
ctctcctgcc gaacaagtga aaatgtttac agctacttag cctggtacca acagaaacct 180
ggccaggctc ctaggctcct catctatttt gcaaaaacct tagcagaagg aattccagcc 240
aggttcagtg gcagtggatc cgggacagac ttcactctca ccatcagcag cctagagcct 300
gaagattttg cagtttatta ctgtcaacat cattccgata atccgtggac attcggccaa 360
gggaccaagg tggaaatcaa aggtggcggt ggctcgggcg gtggtggatc tggaggaggt 420
ggggctagcg aggtgcagct ggtggagtct ggtggaggct tggtccagcc tggagggtcc 480
ctgagactct cctgtgcagc ctctggattc accttcagtg gctacaatat gaactgggtc 540
cgccagatgc ccgggaaagg cctggagtgg atgggcaata ttgatcctta ttatggtggt 600
actacctaca accggaagtt caagggccag gtcactatct ccgccgacaa gtccatcagc 660
accgcctacc tgcaatggag cagcctgaag gcctcggaca ccgccatgta ttactgtgca 720
cgctcagtcg gccctatgga ctactggggc cgcggcaccc tggtcactgt ctcctcgagc 780
gagcccaaat cttctgacaa aactcacaca tgcccaccgt gcccagcacc tgaactcctg 840
ggtggaccgt cagtcttcct cttcccccca aaacccaagg acaccctcat gatctcccgg 900
acccctgagg tcacatgcgt ggtggtggac gtgagccacg aagaccctga ggtcaagttc 960
aactggtacg tggacggcgt ggaggtgcat aatgccaaga caaagccgcg ggaggagcag 1020
tacaacagca cgtaccgtgt ggtcagcgtc ctcaccgtcc tgcaccagga ctggctgaat 1080
ggcaaggagt acaagtgcaa ggtctccaac aaagccctcc cagcccccat cgagaaaacc 1140
atctccaaag ccaaagggca gccccgagaa ccacaggtgt acaccctgcc cccatcccgg 1200
gatgagctga ccaagaacca ggtcagcctg acctgcctgg tcaaaggctt ctatccaagc 1260
gacatcgccg tggagtggga gagcaatggg cagccggaga acaactacaa gaccacgcct 1320
cccgtgctgg actccgacgg ctccttcttc ctctacagca agctcaccgt ggacaagagc 1380
aggtggcagc aggggaacgt cttctcatgc tccgtgatgc atgaggctct gcacaaccac 1440
tacacgcaga agagcctctc cctgtctccg ggtaaa 1476

<210> SEQ ID NO 40
<211> LENGTH: 492
<212> TYPE: PRT
<213> ORGANISM: Artificial sequence
<220> FEATURE:
<223> OTHER INFORMATION: Humanized TRU-016

<400> SEQUENCE: 40

Met Glu Ala Pro Ala Gln Leu Leu Phe Leu Leu Leu Leu Trp Leu Pro
1 5 10 15

Asp Thr Thr Gly Glu Ile Val Leu Thr Gln Ser Pro Ala Thr Leu Ser
20 25 30

Leu Ser Pro Gly Glu Arg Ala Thr Leu Ser Cys Arg Thr Ser Glu Asn
35 40 45

Val Tyr Ser Tyr Leu Ala Trp Tyr Gln Gln Lys Pro Gly Gln Ala Pro
50 55 60

Arg Leu Leu Ile Tyr Phe Ala Lys Thr Leu Ala Glu Gly Ile Pro Ala
65 70 75 80

-continued

```
Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Gly Ser Gly Gly Gly Gly Ala Ser Glu
    130                 135                 140

Val Gln Leu Val Glu Ser Gly Gly Gly Leu Val Gln Pro Gly Gly Ser
145                 150                 155                 160

Leu Arg Leu Ser Cys Ala Ala Ser Gly Phe Thr Phe Ser Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240

Arg Ser Val Gly Pro Met Asp Tyr Trp Gly Arg Gly Thr Leu Val Thr
                245                 250                 255

Val Ser Ser Ser Glu Pro Lys Ser Ser Asp Lys Thr His Thr Cys Pro
            260                 265                 270

Pro Cys Pro Ala Pro Glu Leu Leu Gly Gly Pro Ser Val Phe Leu Phe
        275                 280                 285

Pro Pro Lys Pro Lys Asp Thr Leu Met Ile Ser Arg Thr Pro Glu Val
    290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365

Ser Asn Lys Ala Leu Pro Ala Pro Ile Glu Lys Thr Ile Ser Lys Ala
    370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
        435                 440                 445

Phe Phe Leu Tyr Ser Lys Leu Thr Val Asp Lys Ser Arg Trp Gln Gln
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys
                485                 490
```

<210> SEQ ID NO 41
<211> LENGTH: 1476
<212> TYPE: DNA
<213> ORGANISM: Artificial sequence
<220> FEATURE:
<223> OTHER INFORMATION: Humanized TRU-016

<400> SEQUENCE: 41

```
atggaagcac cagcgcagct tctcttcctc ctgctactct ggctcccaga taccaccggt     60

gaaattgtgt tgacacagtc tccagccacc ctgtctttgt ctccaggcga aagagccacc    120

ctctcctgcc gaacaagtga aaatgtttac agctacttag cctggtacca acagaaacct    180

ggccaggctc ctaggctcct catctatttt gcaaaaacct tagcagaagg aattccagcc    240

aggttcagtg gcagtggatc cgggacagac ttcactctca ccatcagcag cctagagcct    300

gaagattttg cagtttatta ctgtcaacat cattccgata atccgtggac attcggccaa    360

gggaccaagg tggaaatcaa aggtggcggt ggctcgggcg gtggtggatc tggaggaggt    420

ggggctagcg aggtgcagct ggtggagtct ggtggaggct ctgtccagcc tggagggtcc    480

ctgagactct cctgtgcagc ctctggattc accttcagtg gctacaatat gaactgggtc    540

cgccagatgc ccgggaaagg cctggagtgg atgggcaata ttgatcctta ttatggtggt    600

actacctaca accggaagtt caagggccag gtcactatct ccgccgacaa gtccatcagc    660

accgcctacc tgcaatggag cagcctgaag gcctcggaca ccgccatgta ttactgtgca    720

cgctcagtcg gccctatgga ctactggggc cgcggcaccc tggtcactgt ctcctcgagc    780

gagcccaaat cttctgacaa aactcacaca tctccaccgt gcccagcacc tgaactcctg    840

ggtggaccgt cagtcttcct cttcccccca aaacccaagg acaccctcat gatctcccgg    900

acccctgagg tcacatgcgt ggtggtggac gtgagccacg aagaccctga ggtcaagttc    960

aactggtacg tggacggcgt ggaggtgcat aatgccaaga caaagccgcg ggaggagcag   1020

tacaacagca cgtaccgtgt ggtcagcgtc ctcaccgtcc tgcaccagga ctggctgaat   1080

ggcaaggagt acaagtgcaa ggtctccaac aaagccctcc cagcccccat cgagaaaacc   1140

atctccaaag ccaaagggca gccccgagaa ccacaggtgt acaccctgcc cccatcccgg   1200

gatgagctga ccaagaacca ggtcagcctg acctgcctgg tcaaaggctt ctatccaagc   1260

gacatcgccg tggagtggga gagcaatggg cagccggaga acaactacaa gaccacgcct   1320

cccgtgctgg actccgacgg ctccttcttc ctctacagca agctcaccgt ggacaagagc   1380

aggtggcagc aggggaacgt cttctcatgc tccgtgatgc atgaggctct gcacaaccac   1440

tacacgcaga agagcctctc cctgtctccg ggtaaa                             1476
```

<210> SEQ ID NO 42
<211> LENGTH: 492
<212> TYPE: PRT
<213> ORGANISM: Artificial sequence
<220> FEATURE:
<223> OTHER INFORMATION: Humanized TRU-016

<400> SEQUENCE: 42

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Thr Ser Glu Asn
        35                  40                  45
```

-continued

```
Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Gly Ser Gly Gly Gly Gly Ala Ser Glu
    130                 135                 140

Val Gln Leu Val Glu Ser Gly Gly Gly Ser Val Gln Pro Gly Gly Ser
145                 150                 155                 160

Leu Arg Leu Ser Cys Ala Ala Ser Gly Phe Thr Phe Ser Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240

Arg Ser Val Gly Pro Met Asp Tyr Trp Gly Arg Gly Thr Leu Val Thr
                245                 250                 255

Val Ser Ser Ser Glu Pro Lys Ser Ser Asp Lys Thr His Thr Ser Pro
            260                 265                 270

Pro Cys Pro Ala Pro Glu Leu Leu Gly Gly Pro Ser Val Phe Leu Phe
        275                 280                 285

Pro Pro Lys Pro Lys Asp Thr Leu Met Ile Ser Arg Thr Pro Glu Val
    290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365

Ser Asn Lys Ala Leu Pro Ala Pro Ile Glu Lys Thr Ile Ser Lys Ala
    370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
        435                 440                 445

Phe Phe Leu Tyr Ser Lys Leu Thr Val Asp Lys Ser Arg Trp Gln Gln
    450                 455                 460

Gly Asn Val Phe Ser Cys Ser Val Met His Glu Ala Leu His Asn His
```

```
465                 470                 475                 480

Tyr Thr Gln Lys Ser Leu Ser Leu Ser Pro Gly Lys
                485                 490


<210> SEQ ID NO 43
<211> LENGTH: 1476
<212> TYPE: DNA
<213> ORGANISM: Artificial sequence
<220> FEATURE:
<223> OTHER INFORMATION: Humanized TRU-016

<400> SEQUENCE: 43

atggaagcac cagcgcagct tctcttcctc ctgctactct ggctcccaga taccaccggt      60

gaaattgtgt tgacacagtc tccagccacc ctgtctttgt ctccaggcga aagagccacc     120

ctctcctgcc gaacaagtga aaatgtttac agctacttag cctggtacca acagaaacct     180

ggccaggctc ctaggctcct catctatttt gcaaaaacct tagcagaagg aattccagcc     240

aggttcagtg gcagtggatc cgggacagac ttcactctca ccatcagcag cctagagcct     300

gaagattttg cagtttatta ctgtcaacat cattccgata atccgtggac attcggccaa     360

gggaccaagg tggaaatcaa aggtggcggt ggctcgggcg gtggtggatc tggaggaggt     420

ggggctagcg aggtgcagct ggtggagtct ggtggaggct ctgtccagcc tggagggtcc     480

ctgagactct cctgtgcagc ctctggattc accttcagtg gctacaatat gaactgggtc     540

cgccagatgc ccgggaaagg cctggagtgg atgggcaata ttgatcctta ttatggtggt     600

actacctaca accggaagtt caagggccag gtcactatct ccgccgacaa gtccatcagc     660

accgcctacc tgcaatggag cagcctgaag gcctcggaca ccgccatgta ttactgtgca     720

cgctcagtcg gccctatgga ctactggggc cgcggcaccc tggtcactgt ctcctcgagc     780

gagcccaaat cttctgacaa aactcacaca tgcccaccgt gcccagcacc tgaactcctg     840

ggtggaccgt cagtcttcct cttcccccca aaacccaagg acaccctcat gatctcccgg     900

acccctgagg tcacatgcgt ggtggtggac gtgagccacg aagaccctga ggtcaagttc     960

aactggtacg tggacggcgt ggaggtgcat aatgccaaga caaagccgcg ggaggagcag    1020

tacaacagca cgtaccgtgt ggtcagcgtc ctcaccgtcc tgcaccagga ctggctgaat    1080

ggcaaggagt acaagtgcaa ggtctccaac aaagccctcc cagcccccat cgagaaaacc    1140

atctccaaag ccaaagggca gccccgagaa ccacaggtgt acaccctgcc cccatcccgg    1200

gatgagctga ccaagaacca ggtcagcctg acctgcctgg tcaaaggctt ctatccaagc    1260

gacatcgccg tggagtggga gagcaatggg cagccggaga acaactacaa gaccacgcct    1320

cccgtgctgg actccgacgg ctccttcttc ctctacagca agctcaccgt ggacaagagc    1380

aggtggcagc aggggaacgt cttctcatgc tccgtgatgc atgaggctct gcacaaccac    1440

tacacgcaga agagcctctc cctgtctccg ggtaaa                              1476


<210> SEQ ID NO 44
<211> LENGTH: 492
<212> TYPE: PRT
<213> ORGANISM: Artificial sequence
<220> FEATURE:
<223> OTHER INFORMATION: Humanized TRU-016

<400> SEQUENCE: 44

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
```

```
                20                  25                  30

Leu Ser Pro Gly Glu Arg Ala Thr Leu Ser Cys Arg Thr Ser Glu Asn
            35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Gly Ser Gly Gly Gly Gly Ala Ser Glu
    130                 135                 140

Val Gln Leu Val Glu Ser Gly Gly Gly Ser Val Gln Pro Gly Gly Ser
145                 150                 155                 160

Leu Arg Leu Ser Cys Ala Ala Ser Gly Phe Thr Phe Ser Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240

Arg Ser Val Gly Pro Met Asp Tyr Trp Gly Arg Gly Thr Leu Val Thr
                245                 250                 255

Val Ser Ser Ser Glu Pro Lys Ser Ser Asp Lys Thr His Thr Cys Pro
            260                 265                 270

Pro Cys Pro Ala Pro Glu Leu Leu Gly Gly Pro Ser Val Phe Leu Phe
        275                 280                 285

Pro Pro Lys Pro Lys Asp Thr Leu Met Ile Ser Arg Thr Pro Glu Val
    290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365

Ser Asn Lys Ala Leu Pro Ala Pro Ile Glu Lys Thr Ile Ser Lys Ala
    370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
        435                 440                 445
```

Phe Phe Leu Tyr Ser Lys Leu Thr Val Asp Lys Ser Arg Trp Gln Gln
450 455 460

Gly Asn Val Phe Ser Cys Ser Val Met His Glu Ala Leu His Asn His
465 470 475 480

Tyr Thr Gln Lys Ser Leu Ser Leu Ser Pro Gly Lys
485 490

<210> SEQ ID NO 45
<211> LENGTH: 1482
<212> TYPE: DNA
<213> ORGANISM: Artificial sequence
<220> FEATURE:
<223> OTHER INFORMATION: Humanized TRU-016

<400> SEQUENCE: 45
atggaagccc cagctcagct tctcttcctc ctgctactct ggctcccaga taccaccgga 60
gaaattgtgt tgacacagtc tccagccacc ctgtctttgt ctccaggcga aagagccacc 120
ctctcctgcc gagcaagtca aagtgtttac agctacttag cctggtacca acagaaacct 180
ggccaggctc ctaggctcct catctatttt gcaaaaacct tagcagaagg aattccagcc 240
aggttcagtg gcagtggatc cgggacagac ttcactctca ccatcagcag cctagagcct 300
gaagattttg cagtttatta ctgtcaacat cattccgata atccgtggac attcggccaa 360
gggaccaagg tggaaatcaa aggtggcggt ggctcgggcg gtggtggatc tggaggaggt 420
gggaccggtg aggtgcagct ggtgcagtct ggagcagagg tgaaaaagcc cggagagtct 480
ctgaagattt cctgtaaggg atccggttac tcattcactg gctacaatat gaactgggtg 540
cgccagatgc ccgggaaagg cctcgagtgg atgggcaata ttgatcctta ttatggtggt 600
actacctaca accggaagtt caagggccag gtcactatct ccgccgacaa gtccatcagc 660
accgcctacc tgcaatggag cagcctgaag gcctcggaca ccgccatgta ttactgtgca 720
cgctcagtcg gccctatgga ctactggggc cgcggcaccc tggtcactgt ctcctctgat 780
caggagccca aatcttctga caaaactcac acatctccac cgtgcccagc acctgaactc 840
ctgggtggac cgtcagtctt cctcttcccc ccaaaaccca aggacaccct catgatctcc 900
cggacccctg aggtcacatg cgtggtggtg gacgtgagcc acgaagaccc tgaggtcaag 960
ttcaactggt acgtggacgg cgtggaggtg cataatgcca agacaaagcc gcgggaggag 1020
cagtacaaca gcacgtaccg tgtggtcagc gtcctcaccg tcctgcacca ggactggctg 1080
aatggcaagg agtacaagtg caaggtctcc aacaaagccc tcccagcccc catcgagaaa 1140
accatctcca aagccaaagg gcagccccga gaaccacagg tgtacaccct gcccccatcc 1200
cgggatgagc tgaccaagaa ccaggtcagc ctgacctgcc tggtcaaagg cttctatcca 1260
agcgacatcg ccgtggagtg ggagagcaat gggcagccgg agaacaacta caagaccacg 1320
cctcccgtgc tggactccga cggctccttc ttcctctaca gcaagctcac cgtggacaag 1380
agcaggtggc agcaggggaa cgtcttctca tgctccgtga tgcatgaggc tctgcacaac 1440
cactacacgc agaagagcct ctccctgtct ccgggtaaat ga 1482

<210> SEQ ID NO 46
<211> LENGTH: 493
<212> TYPE: PRT
<213> ORGANISM: Artificial sequence
<220> FEATURE:
<223> OTHER INFORMATION: Humanized TRU-016

<400> SEQUENCE: 46

-continued

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Gly Ser Gly Gly Gly Gly Thr Gly Glu
    130                 135                 140

Val Gln Leu Val Gln Ser Gly Ala Glu Val Lys Lys Pro Gly Glu Ser
145                 150                 155                 160

Leu Lys Ile Ser Cys Lys Gly Ser Gly Tyr Ser Phe Thr Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240

Arg Ser Val Gly Pro Met Asp Tyr Trp Gly Arg Gly Thr Leu Val Thr
                245                 250                 255

Val Ser Ser Asp Gln Glu Pro Lys Ser Ser Asp Lys Thr His Thr Ser
            260                 265                 270

Pro Pro Cys Pro Ala Pro Glu Leu Leu Gly Gly Pro Ser Val Phe Leu
        275                 280                 285

Phe Pro Pro Lys Pro Lys Asp Thr Leu Met Ile Ser Arg Thr Pro Glu
    290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Ala Leu Pro Ala Pro Ile Glu Lys Thr Ile Ser Lys
    370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415
```

-continued

```
Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Tyr Ser Lys Leu Thr Val Asp Lys Ser Arg Trp Gln
    450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490


<210> SEQ ID NO 47
<211> LENGTH: 1500
<212> TYPE: DNA
<213> ORGANISM: Artificial sequence
<220> FEATURE:
<223> OTHER INFORMATION: Humanized TRU-016

<400> SEQUENCE: 47

aagcttgccg ccatggaagc cccagcgcag cttctcttcc tcctgctact ctggctccca      60

gataccaccg gagaaattgt gttgacacag tctccagcca ccctgtcttt gtctccaggc     120

gaaagagcca ccctctcctg ccgagcaagt gaaaatgttt acagctactt agcctggtac     180

caacagaaac ctggccaggc tcctaggctc ctcatctatt ttgcaaaaac cttagcagaa     240

ggaattccag ccaggttcag tggcagtgga tccgggacag acttcactct caccatcagc     300

agcctagagc ctgaagattt tgcagtttat tactgtcaac atcattccga taatccgtgg     360

acattcggcc aagggaccaa ggtggaaatc aaaggtggcg gcggctcggg cggtggtgga     420

tctggaggag gtgggaccgg tgaggtgcag ctggtgcagt ctggagcaga ggtgaaaaag     480

cccggagagt ctctgaagat ttcctgtaag ggatccggtt actcattcac tggctacaat     540

atgaactggg tgcgccagat gcccgggaaa ggcctcgagt ggatgggcaa tattgatcct     600

tattatggtg gtactaccta caaccggaag ttcaagggcc aggtcactat ctccgccgac     660

aagtccatca gcaccgccta cctgcaatgg agcagcctga aggcctcgga caccgccatg     720

tattactgtg cacgctcagt cggccctttc gactactggg gccagggcac cctggtcact     780

gtctcctctg atcaggagcc caaatcttct gacaaaactc acacatctcc accgtgccca     840

gcacctgaac tcctgggtgg accgtcagtc ttcctcttcc ccccaaaacc caaggacacc     900

ctcatgatct cccggacccc tgaggtcaca tgcgtggtgg tggacgtgag ccacgaagac     960

cctgaggtca agttcaactg gtacgtggac ggcgtggagg tgcataatgc caagacaaag    1020

ccgcgggagg agcagtacaa cagcacgtac cgtgtggtca gcgtcctcac cgtcctgcac    1080

caggactggc tgaatggcaa ggagtacaag tgcaaggtct ccaacaaagc cctcccagcc    1140

cccatcgaga aaaccatctc caaagccaaa gggcagcccc gagaaccaca ggtgtacacc    1200

ctgcccccat cccgggatga gctgaccaag aaccaggtca gcctgacctg cctggtcaaa    1260

ggcttctatc caagcgacat cgccgtggag tgggagagca atgggcagcc ggagaacaac    1320

tacaagacca cgcctcccgt gctggactcc gacggctcct tcttcctcta cagcaagctc    1380

accgtggaca agagcaggtg gcagcagggg aacgtcttct catgctccgt gatgcatgag    1440

gctctgcaca accactacac gcagaagagc ctctccctgt ctccgggtaa atgatctaga    1500


<210> SEQ ID NO 48
<211> LENGTH: 493
<212> TYPE: PRT
```

<213> ORGANISM: Artificial sequence
<220> FEATURE:
<223> OTHER INFORMATION: Humanized TRU-016

<400> SEQUENCE: 48

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Gly Ser Gly Gly Gly Gly Thr Gly Glu
    130                 135                 140

Val Gln Leu Val Gln Ser Gly Ala Glu Val Lys Lys Pro Gly Glu Ser
145                 150                 155                 160

Leu Lys Ile Ser Cys Lys Gly Ser Gly Tyr Ser Phe Thr Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240

Arg Ser Val Gly Pro Phe Asp Tyr Trp Gly Gln Gly Thr Leu Val Thr
                245                 250                 255

Val Ser Ser Asp Gln Glu Pro Lys Ser Ser Asp Lys Thr His Thr Ser
            260                 265                 270

Pro Pro Cys Pro Ala Pro Glu Leu Leu Gly Gly Pro Ser Val Phe Leu
        275                 280                 285

Phe Pro Pro Lys Pro Lys Asp Thr Leu Met Ile Ser Arg Thr Pro Glu
    290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Ala Leu Pro Ala Pro Ile Glu Lys Thr Ile Ser Lys
    370                 375                 380

Ala Lys Gly Gln Pro Arg Glu Pro Gln Val Tyr Thr Leu Pro Pro Ser
```

-continued 385 390 395 400

Arg Asp Glu Leu Thr Lys Asn Gln Val Ser Leu Thr Cys Leu Val Lys
405 410 415

Gly Phe Tyr Pro Ser Asp Ile Ala Val Glu Trp Glu Ser Asn Gly Gln
420 425 430

Pro Glu Asn Asn Tyr Lys Thr Thr Pro Pro Val Leu Asp Ser Asp Gly
435 440 445

Ser Phe Phe Leu Tyr Ser Lys Leu Thr Val Asp Lys Ser Arg Trp Gln
450 455 460

Gln Gly Asn Val Phe Ser Cys Ser Val Met His Glu Ala Leu His Asn
465 470 475 480

His Tyr Thr Gln Lys Ser Leu Ser Leu Ser Pro Gly Lys
485 490

<210> SEQ ID NO 49
<211> LENGTH: 356
<212> TYPE: DNA
<213> ORGANISM: Artificial sequence
<220> FEATURE:
<223> OTHER INFORMATION: Humanized TRU-016

<400> SEQUENCE: 49
gctagcgagg tgcagctggt gcagtctgga gcagaggtga aaaagcccgg agagtctctg 60
aagatttcct gtaagggatc cggttactca ttcactggct acaatatgaa ctgggtgcgc 120
cagatgcccg ggaaaggcct ggagtggatg ggcaatattg atccttatta tggtggtact 180
acctacaacc ggaagttcaa gggccaggtc actatctccg ccgacaagtc catcagcacc 240
gcctacctgc aatggagcag cctgaaggcc tcggacaccg ccatgtatta ctgtgcgcgc 300
tcagtcggcc ctatggacgt ctggggccaa ggcaccactg tcactgtctc ctcgag 356

<210> SEQ ID NO 50
<211> LENGTH: 143
<212> TYPE: PRT
<213> ORGANISM: Artificial sequence
<220> FEATURE:
<223> OTHER INFORMATION: Humanized TRU-016

<400> SEQUENCE: 50

Met Glu Ala Pro Ala Gln Leu Leu Phe Leu Leu Leu Leu Trp Leu Pro
1 5 10 15

Asp Thr Thr Gly Glu Ile Val Leu Thr Gln Ser Pro Ala Thr Leu Ser
20 25 30

Leu Ser Pro Gly Glu Arg Ala Thr Leu Ser Cys Arg Ala Ser Glu Asn
35 40 45

Val Tyr Ser Tyr Leu Ala Trp Tyr Gln Gln Lys Pro Gly Gln Ala Pro
50 55 60

Arg Leu Leu Ile Tyr Phe Ala Lys Thr Leu Ala Glu Gly Ile Pro Ala
65 70 75 80

Arg Phe Ser Gly Ser Gly Ser Gly Thr Asp Phe Thr Leu Thr Ile Ser
85 90 95

Ser Leu Glu Pro Glu Asp Phe Ala Val Tyr Tyr Cys Gln His His Ser
100 105 110

Asp Asn Pro Trp Thr Phe Gly Gln Gly Thr Lys Val Glu Ile Lys Gly
115 120 125

Gly Gly Gly Ser Gly Gly Gly Gly Ser Gly Gly Gly Gly Thr Gly
130 135 140

<210> SEQ ID NO 51
<211> LENGTH: 1381
<212> TYPE: DNA
<213> ORGANISM: Artificial sequence
<220> FEATURE:
<223> OTHER INFORMATION: Humanized TRU-016

<400> SEQUENCE: 51
aagcttgccg ccatggaagc cccagcgcag cttctcttcc tcctgctact ctggctccca 60
gataccaccg gagaaattgt gttgacacag tctccagcca ccctgtcttt gtctccaggc 120
gaaagagcca ccctctcctg ccgagcaagt gaaaatgttt acagctactt agcctggtac 180
caacagaaac ctggccaggc tcctaggctc ctcatctatt ttgcaaaaac cttagcagaa 240
ggaattccag ccaggttcag tggcagtgga tccgggacag acttcactct caccatcagc 300
agcctagagc ctgaagattt tgcagtttat tactgtcaac atcattccga taatccgtgg 360
acattcggcc aagggaccaa ggtggaaatc aaaggtggcg gtggctcggg cggtggtgga 420
tctggaggag gtgggaccgg tgaggtgcag ctggtgcagt ctggagcaga ggtgaaaaag 480
cccggagagt ctctgaagat ttcctgtaag ggatccggtt actcattcac tggctacaat 540
atgaactggg tgcgccagat gcccgggaaa ggcctcgagt ggatgggcaa tattgatcct 600
tattatggtg gtactaccta caaccggaag ttcaagggcc aggtcactat ctccgccgac 660
aagtccatca gcaccgccta cctgcaatgg agcagcctga aggcctcgga caccgccatg 720
tattactgtg cacgctcagt cggccctttc gactcctggg gccagggcac cctggtcact 780
gtctcctctg atcaggagcc caaatcttct gacaaaactc acacatctcc accgtgccca 840
gcacctgaac tcctgggtgg accgtcagtc ttcctcttcc ccccaaaacc caaggacacc 900
ctcatgatct cccggacccc tgaggtcaca tgcgtggtgg tggacgtgag ccacgaagac 960
cctgaggtca agttcaactg gtacgtggac ggcgtggagg tgcataatgc caagacaaag 1020
ccgcgggagg agcagtacaa cagcacgtac cgtgtggtca gcgtcctcac cgtcctgcac 1080
caggactggc tgaatggcaa ggagtacaag tgcaaggtct ccaacaaagc cctcccagcc 1140
cccatcgaga aaaccatctc caaagccaaa gggcagcccc gagaaccaca ggtgtacacc 1200
ctgcccccat cccgggatga gctgaccaag aaccaggtca gcctgacctg cctggtcaaa 1260
ggcttctatc caagcgacat cgccgtggag tgggagagca atgggcagcc ggagaacaac 1320
tacaagacca cgcctcccgt gctggactcc gacggctcct tcttcctcta cagcaagctc 1380
a 1381

<210> SEQ ID NO 52
<211> LENGTH: 493
<212> TYPE: PRT
<213> ORGANISM: Artificial sequence
<220> FEATURE:
<223> OTHER INFORMATION: Humanized TRU-016

<400> SEQUENCE: 52

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Glu Asn
        35                  40                  45

Val Tyr Ser Tyr Leu Ala Trp Tyr Gln Gln Lys Pro Gly Gln Ala Pro
    50                  55                  60

-continued

Arg Leu Leu Ile Tyr Phe Ala Lys Thr Leu Ala Glu Gly Ile Pro Ala
65 70 75 80

Arg Phe Ser Gly Ser Gly Ser Gly Thr Asp Phe Thr Leu Thr Ile Ser
85 90 95

Ser Leu Glu Pro Glu Asp Phe Ala Val Tyr Tyr Cys Gln His His Ser
100 105 110

Asp Asn Pro Trp Thr Phe Gly Gln Gly Thr Lys Val Glu Ile Lys Gly
115 120 125

Gly Gly Gly Ser Gly Gly Gly Gly Ser Gly Gly Gly Gly Thr Gly Glu
130 135 140

Val Gln Leu Val Gln Ser Gly Ala Glu Val Lys Lys Pro Gly Glu Ser
145 150 155 160

Leu Lys Ile Ser Cys Lys Gly Ser Gly Tyr Ser Phe Thr Gly Tyr Asn
165 170 175

Met Asn Trp Val Arg Gln Met Pro Gly Lys Gly Leu Glu Trp Met Gly
180 185 190

Asn Ile Asp Pro Tyr Tyr Gly Gly Thr Thr Tyr Asn Arg Lys Phe Lys
195 200 205

Gly Gln Val Thr Ile Ser Ala Asp Lys Ser Ile Ser Thr Ala Tyr Leu
210 215 220

Gln Trp Ser Ser Leu Lys Ala Ser Asp Thr Ala Met Tyr Tyr Cys Ala
225 230 235 240

Arg Ser Val Gly Pro Phe Asp Ser Trp Gly Gln Gly Thr Leu Val Thr
245 250 255

Val Ser Ser Asp Gln Glu Pro Lys Ser Ser Asp Lys Thr His Thr Ser
260 265 270

Pro Pro Cys Pro Ala Pro Glu Leu Leu Gly Gly Pro Ser Val Phe Leu
275 280 285

Phe Pro Pro Lys Pro Lys Asp Thr Leu Met Ile Ser Arg Thr Pro Glu
290 295 300

Val Thr Cys Val Val Val Asp Val Ser His Glu Asp Pro Glu Val Lys
305 310 315 320

Phe Asn Trp Tyr Val Asp Gly Val Glu Val His Asn Ala Lys Thr Lys
325 330 335

Pro Arg Glu Glu Gln Tyr Asn Ser Thr Tyr Arg Val Val Ser Val Leu
340 345 350

Thr Val Leu His Gln Asp Trp Leu Asn Gly Lys Glu Tyr Lys Cys Lys
355 360 365

Val Ser Asn Lys Ala Leu Pro Ala Pro Ile Glu Lys Thr Ile Ser Lys
370 375 380

Ala Lys Gly Gln Pro Arg Glu Pro Gln Val Tyr Thr Leu Pro Pro Ser
385 390 395 400

Arg Asp Glu Leu Thr Lys Asn Gln Val Ser Leu Thr Cys Leu Val Lys
405 410 415

Gly Phe Tyr Pro Ser Asp Ile Ala Val Glu Trp Glu Ser Asn Gly Gln
420 425 430

Pro Glu Asn Asn Tyr Lys Thr Thr Pro Pro Val Leu Asp Ser Asp Gly
435 440 445

Ser Phe Phe Leu Tyr Ser Lys Leu Thr Val Asp Lys Ser Arg Trp Gln
450 455 460

Gln Gly Asn Val Phe Ser Cys Ser Val Met His Glu Ala Leu His Asn
465 470 475 480

```
His Tyr Thr Gln Lys Ser Leu Ser Leu Ser Pro Gly Lys
                485                 490
```

<210> SEQ ID NO 53
<211> LENGTH: 356
<212> TYPE: DNA
<213> ORGANISM: Artificial sequence
<220> FEATURE:
<223> OTHER INFORMATION: Humanized TRU-016

<400> SEQUENCE: 53

```
gctagcgagg tgcagctggt gcagtctgga gcagaggtga aaaagcccgg agagtctctg      60

aagatttcct gtaagggatc cggttactca ttcactggct acaatatgaa ctgggtgcgc     120

cagatgcccg ggaaaggcct ggagtggatg ggcaatattg atccttatta tggtggtact     180

acctacaacc ggaagttcaa gggccaggtc actatctccg ccgacaagtc catcagcacc     240

gcctacctgc aatggagcag cctgaaggcc tcggacaccg ccatgtatta ctgtgcgcgc     300

tcagtcggcc cttttgaccc ctggggccaa ggcaccctgg tcactgtctc ctcgag         356
```

<210> SEQ ID NO 54
<211> LENGTH: 143
<212> TYPE: PRT
<213> ORGANISM: Artificial sequence
<220> FEATURE:
<223> OTHER INFORMATION: Humanized TRU-016

<400> SEQUENCE: 54

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Gly Ser Gly Gly Gly Gly Thr Gly
    130                 135                 140
```

<210> SEQ ID NO 55
<211> LENGTH: 356
<212> TYPE: DNA
<213> ORGANISM: Artificial sequence
<220> FEATURE:
<223> OTHER INFORMATION: Humanized TRU-016

<400> SEQUENCE: 55

```
gctagcgagg tgcagctggt gcagtctgga gcagaggtga aaaagcccgg agagtctctg      60

aagatttcct gtaagggatc cggttactca ttcactggct acaatatgaa ctgggtgcgc     120

cagatgcccg ggaaaggcct ggagtggatg ggcaatattg atccttatta tggtggtact     180

acctacaacc ggaagttcaa gggccaggtc actatctccg ccgacaagtc catcagcacc     240
```

gcctacctgc aatggagcag cctgaaggcc tcggacaccg ccatgtatta ctgtgcgcgc 300
tcagtcggcc cttttcagca ctggggccaa ggcaccctcg tcactgtctc ctcgag 356

<210> SEQ ID NO 56
<211> LENGTH: 143
<212> TYPE: PRT
<213> ORGANISM: Artificial sequence
<220> FEATURE:
<223> OTHER INFORMATION: Humanized TRU-016

<400> SEQUENCE: 56

Met Glu Ala Pro Ala Gln Leu Leu Phe Leu Leu Leu Leu Trp Leu Pro
1 5 10 15

Asp Thr Thr Gly Glu Ile Val Leu Thr Gln Ser Pro Ala Thr Leu Ser
20 25 30

Leu Ser Pro Gly Glu Arg Ala Thr Leu Ser Cys Arg Ala Ser Glu Asn
35 40 45

Val Tyr Ser Tyr Leu Ala Trp Tyr Gln Gln Lys Pro Gly Gln Ala Pro
50 55 60

Arg Leu Leu Ile Tyr Phe Ala Lys Thr Leu Ala Glu Gly Ile Pro Ala
65 70 75 80

Arg Phe Ser Gly Ser Gly Ser Gly Thr Asp Phe Thr Leu Thr Ile Ser
85 90 95

Ser Leu Glu Pro Glu Asp Phe Ala Val Tyr Tyr Cys Gln His His Ser
100 105 110

Asp Asn Pro Trp Thr Phe Gly Gln Gly Thr Lys Val Glu Ile Lys Gly
115 120 125

Gly Gly Gly Ser Gly Gly Gly Gly Ser Gly Gly Gly Gly Thr Gly
130 135 140

<210> SEQ ID NO 57
<211> LENGTH: 356
<212> TYPE: DNA
<213> ORGANISM: Artificial sequence
<220> FEATURE:
<223> OTHER INFORMATION: Humanized TRU-016

<400> SEQUENCE: 57
gctagcgagg tgcagctggt gcagtctgga gcagaggtga aaaagcccgg agagtctctg 60
aagatttcct gtaagggatc cggttactca ttcactggct acaatatgaa ctgggtgcgc 120
cagatgcccg ggaaaggcct ggagtggatg ggcaatattg atccttatta tggtggtact 180
acctacaacc ggaagttcaa gggccaggtc actatctccg ccgacaagtc catcagcacc 240
gcctacctgc aatggagcag cctgaaggcc tcggacaccg ccatgtatta ctgtgcgcgc 300
tcagtcggcc cttttgacgt ctggggccaa ggcaccatgg tcactgtctc ctcgag 356

<210> SEQ ID NO 58
<211> LENGTH: 143
<212> TYPE: PRT
<213> ORGANISM: Artificial sequence
<220> FEATURE:
<223> OTHER INFORMATION: Humanized TRU-016

<400> SEQUENCE: 58

Met Glu Ala Pro Ala Gln Leu Leu Phe Leu Leu Leu Leu Trp Leu Pro
1 5 10 15

Asp Thr Thr Gly Glu Ile Val Leu Thr Gln Ser Pro Ala Thr Leu Ser
20 25 30

```
Leu Ser Pro Gly Glu Arg Ala Thr Leu Ser Cys Arg Ala Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Gly Ser Gly Gly Gly Gly Thr Gly
    130                 135                 140
```

<210> SEQ ID NO 59
<211> LENGTH: 356
<212> TYPE: DNA
<213> ORGANISM: Artificial sequence
<220> FEATURE:
<223> OTHER INFORMATION: Humanized TRU-016

<400> SEQUENCE: 59

```
gctagcgagg tgcagctggt gcagtctgga gcagaggtga aaaagcccgg agagtctctg     60

aagatttcct gtaagggatc cggttactca ttcactggct acaatatgaa ctgggtgcgc    120

cagatgcccg ggaaaggcct ggagtggatg ggcaatattg atccttatta tggtggtact    180

acctacaacc ggaagttcaa gggccaggtc actatctccg ccgacaagtc catcagcacc    240

gcctacctgc aatggagcag cctgaaggcc tcggacaccg ccatgtatta ctgtgcgcgc    300

tcagtcggcc cttttgacat ctggggccaa ggcaccatgg tcactgtctc ctcgag        356
```

<210> SEQ ID NO 60
<211> LENGTH: 143
<212> TYPE: PRT
<213> ORGANISM: Artificial sequence
<220> FEATURE:
<223> OTHER INFORMATION: Humanized TRU-016

<400> SEQUENCE: 60

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Gly Ser Gly Gly Gly Gly Thr Gly
```

130 135 140

<210> SEQ ID NO 61
<211> LENGTH: 11
<212> TYPE: PRT
<213> ORGANISM: Artificial sequence
<220> FEATURE:
<223> OTHER INFORMATION: Humanized TRU-016

<400> SEQUENCE: 61

Arg Ala Ser Glu Asn Val Tyr Ser Tyr Leu Ala
1 5 10

<210> SEQ ID NO 62
<211> LENGTH: 11
<212> TYPE: PRT
<213> ORGANISM: Artificial sequence
<220> FEATURE:
<223> OTHER INFORMATION: Humanized TRU-016

<400> SEQUENCE: 62

Arg Thr Ser Glu Asn Val Tyr Ser Tyr Leu Ala
1 5 10

<210> SEQ ID NO 63
<211> LENGTH: 5
<212> TYPE: PRT
<213> ORGANISM: Artificial sequence
<220> FEATURE:
<223> OTHER INFORMATION: Humanized TRU-016

<400> SEQUENCE: 63

Gly Tyr Asn Met Asn
1 5

<210> SEQ ID NO 64
<211> LENGTH: 7
<212> TYPE: PRT
<213> ORGANISM: Artificial sequence
<220> FEATURE:
<223> OTHER INFORMATION: Humanized TRU-016

<400> SEQUENCE: 64

Phe Ala Lys Thr Leu Ala Glu
1 5

<210> SEQ ID NO 65
<211> LENGTH: 17
<212> TYPE: PRT
<213> ORGANISM: Artificial sequence
<220> FEATURE:
<223> OTHER INFORMATION: Humanized TRU-016

<400> SEQUENCE: 65

Asn Ile Asp Pro Tyr Tyr Gly Gly Thr Thr Tyr Asn Arg Lys Phe Lys
1 5 10 15

Gly

<210> SEQ ID NO 66
<211> LENGTH: 9
<212> TYPE: PRT
<213> ORGANISM: Artificial sequence
<220> FEATURE:
<223> OTHER INFORMATION: Humanized TRU-016

<400> SEQUENCE: 66

Gln His His Ser Asp Asn Pro Trp Thr
1 5

<210> SEQ ID NO 67
<211> LENGTH: 7
<212> TYPE: PRT
<213> ORGANISM: Artificial sequence
<220> FEATURE:
<223> OTHER INFORMATION: Humanized TRU-016

<400> SEQUENCE: 67

Ser Val Gly Pro Phe Asp Tyr
1 5

<210> SEQ ID NO 68
<211> LENGTH: 7
<212> TYPE: PRT
<213> ORGANISM: Artificial sequence
<220> FEATURE:
<223> OTHER INFORMATION: Humanized TRU-016

<400> SEQUENCE: 68

Ser Val Gly Pro Phe Asp Ser
1 5

<210> SEQ ID NO 69
<211> LENGTH: 7
<212> TYPE: PRT
<213> ORGANISM: Artificial sequence
<220> FEATURE:
<223> OTHER INFORMATION: Humanized TRU-016

<400> SEQUENCE: 69

Ser Val Gly Pro Met Asp Tyr
1 5

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79
<211> LENGTH: 1500
<212> TYPE: DNA
<213> ORGANISM: Artificial sequence
<220> FEATURE:
<223> OTHER INFORMATION: Humanized TRU-016

<400> SEQUENCE: 79
aagcttgccg ccatggaagc cccagcgcag cttctcttcc tcctgctact ctggctccca 60
gataccaccg gagaaattgt gttgacacag tctccagcca ccctgtcttt gtctccaggc 120
gaaagagcca ccctctcctg ccgagcaagt gaaaatgttt acagctactt agcctggtac 180
caacagaaac ctggccaggc tcctaggctc ctcatctatt ttgcaaaaac cttagcagaa 240
ggaattccag ccaggttcag tggcagtgga tccgggacag acttcactct caccatcagc 300
agcctagagc ctgaagattt tgcagtttat tactgtcaac atcattccga taatccgtgg 360
acattcggcc aagggaccaa ggtggaaatc aaaggtggcg gtggctcggg cggtggtgga 420
tctggaggag gtgggaccgg tgaggtgcag ctggtgcagt ctggagcaga ggtgaaaaag 480
cccggagagt ctctgaagat ttcctgtaag ggatccggtt actcattcac tggctacaat 540
atgaactggg tgcgccagat gcccgggaaa ggcctcgagt ggatgggcaa tattgatcct 600
tattatggtg gtactaccta caaccggaag ttcaagggcc aggtcactat ctccgccgac 660
aagtccatca gcaccgccta cctgcaatgg agcagcctga aggcctcgga caccgccatg 720
tattactgtg cacgctcagt cggccctttc gacctctggg gcagaggcac cctggtcact 780
gtctcctctg atcaggagcc caaatcttct gacaaaactc acacatctcc accgtgccca 840
gcacctgaac tcctgggtgg accgtcagtc ttcctcttcc ccccaaaacc caaggacacc 900
ctcatgatct cccggacccc tgaggtcaca tgcgtggtgg tggacgtgag ccacgaagac 960
cctgaggtca agttcaactg gtacgtggac ggcgtggagg tgcataatgc caagacaaag 1020
ccgcgggagg agcagtacaa cagcacgtac cgtgtggtca gcgtcctcac cgtcctgcac 1080
caggactggc tgaatggcaa ggagtacaag tgcaaggtct ccaacaaagc cctcccagcc 1140
cccatcgaga aaaccatctc caaagccaaa gggcagcccc gagaaccaca ggtgtacacc 1200
ctgcccccat cccgggatga gctgaccaag aaccaggtca gcctgacctg cctggtcaaa 1260
ggcttctatc caagcgacat cgccgtggag tgggagagca atgggcagcc ggagaacaac 1320

```
tacaagacca cgcctcccgt gctggactcc gacggctcct tcttcctcta cagcaagctc   1380

accgtggaca agagcaggtg gcagcagggg aacgtcttct catgctccgt gatgcatgag   1440

gctctgcaca accactacac gcagaagagc ctctccctgt ctccgggtaa atgatctaga   1500


<210> SEQ ID NO 80
<211> LENGTH: 493
<212> TYPE: PRT
<213> ORGANISM: Artificial sequence
<220> FEATURE:
<223> OTHER INFORMATION: Humanized TRU-016

<400> SEQUENCE: 80

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Gly Ser Gly Gly Gly Gly Thr Gly Glu
    130                 135                 140

Val Gln Leu Val Gln Ser Gly Ala Glu Val Lys Lys Pro Gly Glu Ser
145                 150                 155                 160

Leu Lys Ile Ser Cys Lys Gly Ser Gly Tyr Ser Phe Thr Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240

Arg Ser Val Gly Pro Phe Asp Leu Trp Gly Arg Gly Thr Leu Val Thr
                245                 250                 255

Val Ser Ser Asp Gln Glu Pro Lys Ser Ser Asp Lys Thr His Thr Ser
            260                 265                 270

Pro Pro Cys Pro Ala Pro Glu Leu Leu Gly Gly Pro Ser Val Phe Leu
        275                 280                 285

Phe Pro Pro Lys Pro Lys Asp Thr Leu Met Ile Ser Arg Thr Pro Glu
    290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335
```

-continued

Pro Arg Glu Glu Gln Tyr Asn Ser Thr Tyr Arg Val Val Ser Val Leu
340 345 350

Thr Val Leu His Gln Asp Trp Leu Asn Gly Lys Glu Tyr Lys Cys Lys
355 360 365

Val Ser Asn Lys Ala Leu Pro Ala Pro Ile Glu Lys Thr Ile Ser Lys
370 375 380

Ala Lys Gly Gln Pro Arg Glu Pro Gln Val Tyr Thr Leu Pro Pro Ser
385 390 395 400

Arg Asp Glu Leu Thr Lys Asn Gln Val Ser Leu Thr Cys Leu Val Lys
405 410 415

Gly Phe Tyr Pro Ser Asp Ile Ala Val Glu Trp Glu Ser Asn Gly Gln
420 425 430

Pro Glu Asn Asn Tyr Lys Thr Thr Pro Pro Val Leu Asp Ser Asp Gly
435 440 445

Ser Phe Phe Leu Tyr Ser Lys Leu Thr Val Asp Lys Ser Arg Trp Gln
450 455 460

Gln Gly Asn Val Phe Ser Cys Ser Val Met His Glu Ala Leu His Asn
465 470 475 480

His Tyr Thr Gln Lys Ser Leu Ser Leu Ser Pro Gly Lys
485 490

<210> SEQ ID NO 81
<211> LENGTH: 1494
<212> TYPE: DNA
<213> ORGANISM: Artificial sequence
<220> FEATURE:
<223> OTHER INFORMATION: Humanized TRU-016

<400> SEQUENCE: 81
aagcttgccg ccatggaagc cccagctcag cttctcttcc tcctgctact ctggctccca 60
gataccaccg gagaaattgt gttgacacag tctccagcca ccctgtcttt gtctccaggc 120
gaaagagcca ccctctcctg ccgagcaagt gaaaatgttt acagctactt agcctggtac 180
caacagaaac ctggccaggc tcctaggctc ctcatctatt ttgcaaaaac cttagcagaa 240
ggaattccag ccaggttcag tggcagtgga tccgggacag acttcactct caccatcagc 300
agcctagagc ctgaagattt tgcagtttat tactgtcaac atcattccga taatccgtgg 360
acattcggcc aagggaccaa ggtggaaatc aaaggtggcg gtggctcggg cggtggtgga 420
tctggaggag gtggggctag cgaggtgcag ctggtgcagt ctggagcaga ggtgaaaaag 480
cccggagagt ctctgaagat ttcctgtaag ggatccggtt actcattcac tagctacaat 540
atgaactggg tgcgccagat gcccgggaaa ggcctggagt ggatgggcaa tattgatcct 600
tattatggtg gtactaacta cgcccagaag ttccagggcc aggtcactat ctccgccgac 660
aagtccatca gcaccgccta cctgcaatgg agcagcctga aggcctcgga caccgccatg 720
tattactgtg cacgctcagt cggccctatg gactactggg gccgcggcac cctggtcact 780
gtctcctctg atcaggagcc caaatcttct gacaaaactc acacatctcc accgtgccca 840
gcacctgaac tcctgggtgg accgtcagtc ttcctcttcc ccccaaaacc caaggacacc 900
ctcatgatct cccggacccc tgaggtcaca tgcgtggtgg tggacgtgag ccacgaagac 960
cctgaggtca agttcaactg gtacgtggac ggcgtggagg tgcataatgc caagacaaag 1020
ccgcgggagg agcagtacaa cagcacgtac cgtgtggtca gcgtcctcac cgtcctgcac 1080
caggactggc tgaatggcaa ggagtacaag tgcaaggtct ccaacaaagc cctcccagcc 1140
cccatcgaga aaaccatctc caaagccaaa gggcagcccc gagaaccaca ggtgtacacc 1200
ctgcccccat cccgggatga gctgaccaag aaccaggtca gcctgacctg cctggtcaaa 1260
ggcttctatc caagcgacat cgccgtggag tgggagagca atgggcagcc ggagaacaac 1320
tacaagacca cgcctcccgt gctggactcc gacggctcct tcttcctcta cagcaagctc 1380
accgtggaca agagcaggtg gcagcagggg aacgtcttct catgctccgt gatgcatgag 1440
gctctgcaca accactacac gcagaagagc ctctccctgt ctccgggtaa atga 1494

<210> SEQ ID NO 82
<211> LENGTH: 493
<212> TYPE: PRT
<213> ORGANISM: Artificial sequence
<220> FEATURE:
<223> OTHER INFORMATION: Humanized TRU-016

<400> SEQUENCE: 82

Met Glu Ala Pro Ala Gln Leu Leu Phe Leu Leu Leu Leu Trp Leu Pro
1 5 10 15

Asp Thr Thr Gly Glu Ile Val Leu Thr Gln Ser Pro Ala Thr Leu Ser
20 25 30

Leu Ser Pro Gly Glu Arg Ala Thr Leu Ser Cys Arg Ala Ser Glu Asn
35 40 45

Val Tyr Ser Tyr Leu Ala Trp Tyr Gln Gln Lys Pro Gly Gln Ala Pro
50 55 60

Arg Leu Leu Ile Tyr Phe Ala Lys Thr Leu Ala Glu Gly Ile Pro Ala
65 70 75 80

Arg Phe Ser Gly Ser Gly Ser Gly Thr Asp Phe Thr Leu Thr Ile Ser
85 90 95

Ser Leu Glu Pro Glu Asp Phe Ala Val Tyr Tyr Cys Gln His His Ser
100 105 110

Asp Asn Pro Trp Thr Phe Gly Gln Gly Thr Lys Val Glu Ile Lys Gly
115 120 125

Gly Gly Gly Ser Gly Gly Gly Gly Ser Gly Gly Gly Gly Ala Ser Glu
130 135 140

Val Gln Leu Val Gln Ser Gly Ala Glu Val Lys Lys Pro Gly Glu Ser
145 150 155 160

Leu Lys Ile Ser Cys Lys Gly Ser Gly Tyr Ser Phe Thr Ser Tyr Asn
165 170 175

Met Asn Trp Val Arg Gln Met Pro Gly Lys Gly Leu Glu Trp Met Gly
180 185 190

Asn Ile Asp Pro Tyr Tyr Gly Gly Thr Asn Tyr Ala Gln Lys Phe Gln
195 200 205

Gly Gln Val Thr Ile Ser Ala Asp Lys Ser Ile Ser Thr Ala Tyr Leu
210 215 220

Gln Trp Ser Ser Leu Lys Ala Ser Asp Thr Ala Met Tyr Tyr Cys Ala
225 230 235 240

Arg Ser Val Gly Pro Met Asp Tyr Trp Gly Arg Gly Thr Leu Val Thr
245 250 255

Val Ser Ser Asp Gln Glu Pro Lys Ser Ser Asp Lys Thr His Thr Ser
260 265 270

Pro Pro Cys Pro Ala Pro Glu Leu Leu Gly Gly Pro Ser Val Phe Leu
275 280 285

Phe Pro Pro Lys Pro Lys Asp Thr Leu Met Ile Ser Arg Thr Pro Glu
290 295 300

-continued

```
Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Ala Leu Pro Ala Pro Ile Glu Lys Thr Ile Ser Lys
    370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Tyr Ser Lys Leu Thr Val Asp Lys Ser Arg Trp Gln
    450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490


<210> SEQ ID NO 83
<211> LENGTH: 1476
<212> TYPE: DNA
<213> ORGANISM: Artificial sequence
<220> FEATURE:
<223> OTHER INFORMATION: Humanized TRU-016

<400> SEQUENCE: 83

aagcttgccg ccatggaagc cccagcgcag cttctcttcc tcctgctact ctggctccca     60

gataccaccg gagaaattgt gttgacacag tctccagcca ccctgtcttt gtctccaggc    120

gaaagagcca ccctctcctg ccgagcaagt gagaatgttt acagctactt agcctggtac    180

caacagaaac ctggccaggc tcctaggctc ctcatctatt ttgcaaaaac cttagcagaa    240

gggattccag ccagattcag tggcagtggt tccgggacag acttcactct caccatcagc    300

agcctagagc ctgaagattt tgcagtttat tactgtcaac atcattccga taatccgtgg    360

acattcggcc aagggaccaa ggtggaaatc aaaggtggcg gtggctcggg cggtggtgga    420

tctggaggag gtgggagcgg aggaggagct agcgaggtgc agctggtgca gtctggagca    480

gaggtgaaaa agcccggaga gtctctgaag atttcctgta agggatccgg ttactcattc    540

actggctaca atatgaactg ggtgcgccag atgcccggga aaggcctcga atggatgggc    600

aatattgatc cttattatgg tggtactacc tacaaccgga agttcaaggg ccaggtcact    660

atctccgccg acaagtccat cagcaccgcc tacctgcaag gagcagcctg aaggcctcgg    720

acaccgccat gtattactgt gcacgctcag tcggcccttt cgactcctgg ggccagggca    780

ccctggtcac tgtctcgagt tgtccaccgt gcccagcacc tgaactcctg ggtggaccgt    840

cagtcttcct cttcccccca aaacccaagg acaccctcat gatctcccgg acccctgagg    900

tcacatgcgt ggtggtggac gtgagccacg aagaccctga ggtcaagttc aactggtacg    960

tggacggcgt ggaggtgcat aatgccaaga caaagccgcg ggaggagcag tacaacagca   1020
```

```
cgtaccgtgt ggtcagcgtc ctcaccgtcc tgcaccagga ctggctgaat ggcaaggagt   1080

acaagtgcaa ggtctccaac aaagccctcc cagcccccat cgagaaaacc atctccaaag   1140

ccaaagggca gccccgagaa ccacaggtgt acaccctgcc cccatcccgg gatgagctga   1200

ccaagaacca ggtcagcctg acctgcctgg tcaaaggctt ctatccaagc gacatcgccg   1260

tggagtggga gagcaatggg cagccggaga acaactacaa gaccacgcct cccgtgctgg   1320

actccgacgg ctccttcttc ctctacagca agctcaccgt ggacaagagc aggtggcagc   1380

aggggaacgt cttctcatgc tccgtgatgc atgaggctct gcacaaccac tacacgcaga   1440

agagcctctc cctgtctccg ggtaaatgac tctaga                             1476
```

<210> SEQ ID NO 84
<211> LENGTH: 485
<212> TYPE: PRT
<213> ORGANISM: Artificial sequence
<220> FEATURE:
<223> OTHER INFORMATION: Humanized TRU-016

<400> SEQUENCE: 84

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Gly Ser Gly Gly Gly Gly Ser Gly Gly
    130                 135                 140

Gly Ala Ser Glu Val Gln Leu Val Gln Ser Gly Ala Glu Val Lys Lys
145                 150                 155                 160

Pro Gly Glu Ser Leu Lys Ile Ser Cys Lys Gly Ser Gly Tyr Ser Phe
                165                 170                 175

Thr Gly Tyr Asn Met Asn Trp Val Arg Gln Met Pro Gly Lys Gly Leu
            180                 185                 190

Glu Trp Met Gly Asn Ile Asp Pro Tyr Tyr Gly Gly Thr Thr Tyr Asn
        195                 200                 205

Arg Lys Phe Lys Gly Gln Val Thr Ile Ser Ala Asp Lys Ser Ile Ser
    210                 215                 220

Thr Ala Tyr Leu Gln Trp Ser Ser Leu Lys Ala Ser Asp Thr Ala Met
225                 230                 235                 240

Tyr Tyr Cys Ala Arg Ser Val Gly Pro Phe Asp Ser Trp Gly Gln Gly
                245                 250                 255

Thr Leu Val Thr Val Ser Ser Cys Pro Pro Cys Pro Ala Pro Glu Leu
            260                 265                 270

Leu Gly Gly Pro Ser Val Phe Leu Phe Pro Pro Lys Pro Lys Asp Thr
```

```
        275                 280                 285

Leu Met Ile Ser Arg Thr Pro Glu Val Thr Cys Val Val Val Asp Val
    290                 295                 300

Ser His Glu Asp Pro Glu Val Lys Phe Asn Trp Tyr Val Asp Gly Val
305                 310                 315                 320

Glu Val His Asn Ala Lys Thr Lys Pro Arg Glu Glu Gln Tyr Asn Ser
                325                 330                 335

Thr Tyr Arg Val Val Ser Val Leu Thr Val Leu His Gln Asp Trp Leu
            340                 345                 350

Asn Gly Lys Glu Tyr Lys Cys Lys Val Ser Asn Lys Ala Leu Pro Ala
        355                 360                 365

Pro Ile Glu Lys Thr Ile Ser Lys Ala Lys Gly Gln Pro Arg Glu Pro
    370                 375                 380

Gln Val Tyr Thr Leu Pro Pro Ser Arg Asp Glu Leu Thr Lys Asn Gln
385                 390                 395                 400

Val Ser Leu Thr Cys Leu Val Lys Gly Phe Tyr Pro Ser Asp Ile Ala
                405                 410                 415

Val Glu Trp Glu Ser Asn Gly Gln Pro Glu Asn Asn Tyr Lys Thr Thr
            420                 425                 430

Pro Pro Val Leu Asp Ser Asp Gly Ser Phe Phe Leu Tyr Ser Lys Leu
        435                 440                 445

Thr Val Asp Lys Ser Arg Trp Gln Gln Gly Asn Val Phe Ser Cys Ser
    450                 455                 460

Val Met His Glu Ala Leu His Asn His Tyr Thr Gln Lys Ser Leu Ser
465                 470                 475                 480

Leu Ser Pro Gly Lys
                485
```

<210> SEQ ID NO 85
<211> LENGTH: 1494
<212> TYPE: DNA
<213> ORGANISM: Artificial sequence
<220> FEATURE:
<223> OTHER INFORMATION: Humanized TRU-016

<400> SEQUENCE: 85

```
aagcttgccg ccatggaagc cccagctcag cttctcttcc tcctgctact ctggctccca      60

gataccaccg gagaaattgt gttgacacag tctccagcca ccctgtcttt gtctccaggc     120

gaaagagcca ccctctcctg ccgaacaagt gaaaatgttt acagctactt agcctggtac     180

caacagaaac ctggccaggc tcctaggctc ctcatctatt ttgcaaaaac cttagcagaa     240

ggaattccag ccaggttcag tggcagtgga tccgggacag acttcactct caccatcagc     300

agcctagagc ctgaagattt tgcagtttat tactgtcaac atcattccga taatccgtgg     360

acattcggcc aagggaccaa ggtggaaatc aaaggtggcg gtggctcggg cggtggtgga     420

tctggaggag gtgggaccgg tgaggtgcag ctggtgcagt ctggagcaga ggtgaaaaag     480

cccggagagt ctctgaagat ttcctgtaag ggatccggtt actcattcac tggctacaat     540

atgaactggg tgcgccagat gcccgggaaa ggcctggagt ggatgggcaa tattgatcct     600

tattatggtg gtactaccta caaccggaag ttcaagggcc aggtcactat ctccgccgac     660

aagtccatca gcaccgccta cctgcaatgg agcagcctga aggcctcgga caccgccatg     720

tattactgtg cacgctcagt cggccctatg gactactggg gccgcggcac cctggtcact     780

gtctcctctg atcaggagcc caaatcttct gacaaaactc acacatctcc accgtgccca     840
```

-continued

```
gcacctgaac tcctgggtgg accgtcagtc ttcctcttcc ccccaaaacc caaggacacc    900

ctcatgatct cccggacccc tgaggtcaca tgcgtggtgg tggacgtgag ccacgaagac    960

cctgaggtca agttcaactg gtacgtggac ggcgtggagg tgcataatgc caagacaaag   1020

ccgcgggagg agcagtacaa cagcacgtac cgtgtggtca gcgtcctcac cgtcctgcac   1080

caggactggc tgaatggcaa ggagtacaag tgcaaggtct ccaacaaagc cctcccagcc   1140

cccatcgaga aaaccatctc caaagccaaa gggcagcccc gagaaccaca ggtgtacacc   1200

ctgcccccat cccgggatga gctgaccaag aaccaggtca gcctgacctg cctggtcaaa   1260

ggcttctatc caagcgacat cgccgtggag tgggagagca atgggcagcc ggagaacaac   1320

tacaagacca cgcctcccgt gctggactcc gacggctcct tcttcctcta cagcaagctc   1380

accgtggaca agagcaggtg gcagcagggg aacgtcttct catgctccgt gatgcatgag   1440

gctctgcaca accactacac gcagaagagc ctctccctgt ctccgggtaa atga         1494
```

<210> SEQ ID NO 86
<211> LENGTH: 493
<212> TYPE: PRT
<213> ORGANISM: Artificial sequence
<220> FEATURE:
<223> OTHER INFORMATION: Humanized TRU-016

<400> SEQUENCE: 86

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Thr Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Gly Ser Gly Gly Gly Gly Ala Ser Glu
    130                 135                 140

Val Gln Leu Val Gln Ser Gly Ala Glu Val Lys Lys Pro Gly Glu Ser
145                 150                 155                 160

Leu Lys Ile Ser Cys Lys Gly Ser Gly Tyr Ser Phe Thr Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205

Gly Gln Val Thr Ile Ser Ala Asp Lys Ser Ile Ser Thr Ala Tyr Leu
    210                 215                 220

Gln Trp Ser Ser Leu Lys Ala Ser Asp Thr Ala Met Tyr Tyr Cys Ala
225                 230                 235                 240

Arg Ser Val Gly Pro Met Asp Tyr Trp Gly Arg Gly Thr Leu Val Thr
                245                 250                 255
```

-continued

Val Ser Ser Asp Gln Glu Pro Lys Ser Ser Asp Lys Thr His Thr Ser
260 265 270

Pro Pro Cys Pro Ala Pro Glu Leu Leu Gly Gly Pro Ser Val Phe Leu
275 280 285

Phe Pro Pro Lys Pro Lys Asp Thr Leu Met Ile Ser Arg Thr Pro Glu
290 295 300

Val Thr Cys Val Val Val Asp Val Ser His Glu Asp Pro Glu Val Lys
305 310 315 320

Phe Asn Trp Tyr Val Asp Gly Val Glu Val His Asn Ala Lys Thr Lys
325 330 335

Pro Arg Glu Glu Gln Tyr Asn Ser Thr Tyr Arg Val Val Ser Val Leu
340 345 350

Thr Val Leu His Gln Asp Trp Leu Asn Gly Lys Glu Tyr Lys Cys Lys
355 360 365

Val Ser Asn Lys Ala Leu Pro Ala Pro Ile Glu Lys Thr Ile Ser Lys
370 375 380

Ala Lys Gly Gln Pro Arg Glu Pro Gln Val Tyr Thr Leu Pro Pro Ser
385 390 395 400

Arg Asp Glu Leu Thr Lys Asn Gln Val Ser Leu Thr Cys Leu Val Lys
405 410 415

Gly Phe Tyr Pro Ser Asp Ile Ala Val Glu Trp Glu Ser Asn Gly Gln
420 425 430

Pro Glu Asn Asn Tyr Lys Thr Thr Pro Pro Val Leu Asp Ser Asp Gly
435 440 445

Ser Phe Phe Leu Tyr Ser Lys Leu Thr Val Asp Lys Ser Arg Trp Gln
450 455 460

Gln Gly Asn Val Phe Ser Cys Ser Val Met His Glu Ala Leu His Asn
465 470 475 480

His Tyr Thr Gln Lys Ser Leu Ser Leu Ser Pro Gly Lys
485 490

<210> SEQ ID NO 87
<211> LENGTH: 1494
<212> TYPE: DNA
<213> ORGANISM: Artificial sequence
<220> FEATURE:
<223> OTHER INFORMATION: Humanized TRU-016

<400> SEQUENCE: 87
aagcttgccg ccatggaagc cccagctcag cttctcttcc tcctgctact ctggctccca 60
gataccaccg gtgaaattgt gttgacacag tctccagcca ccctgtcttt gtctccaggc 120
gaaagagcca ccctctcctg ccgaacaagt gaaaatgttt acagctactt agcctggtac 180
caacagaaac ctggccaggc tcctaggctc ctcatctatt ttgcaaaaac cttagcagaa 240
ggaattccag ccaggttcag tggcagtgga tccgggacag acttcactct caccatcagc 300
agcctagagc ctgaagattt tgcagtttat tactgtcaac atcattccga taatccgtgg 360
acattcggcc aagggaccaa ggtggaaatc aaaggtggcg gtggctcggg cggtggtgga 420
tctggaggag gtggggctag cgaggtgcag ctggtgcagt ctggagcaga ggtgaaaaag 480
cccggagagt ctctgaggat ttcctgtaag ggatccggtt actcattcac tggctacaat 540
atgaactggg tgcgccagat gcccgggaaa ggcctggagt ggatgggcaa tattgatcct 600
tattatggtg gtactaccta caaccggaag ttcaagggcc aggtcactat ctccgccgac 660
aagtccatca gcaccgccta cctgcaatgg agcagcctga aggcctcgga caccgccatg 720

```
tattactgtg cacgctcagt cggccctatg gactactggg gccgcggcac cctggtcact    780

gtctcctctg atcaggagcc caaatcttct gacaaaactc acacatctcc accgtgccca    840

gcacctgaac tcctgggtgg accgtcagtc ttcctcttcc ccccaaaacc caaggacacc    900

ctcatgatct cccggacccc tgaggtcaca tgcgtggtgg tggacgtgag ccacgaagac    960

cctgaggtca agttcaactg gtacgtggac ggcgtggagg tgcataatgc caagacaaag   1020

ccgcgggagg agcagtacaa cagcacgtac cgtgtggtca gcgtcctcac cgtcctgcac   1080

caggactggc tgaatggcaa ggagtacaag tgcaaggtct ccaacaaagc cctcccagcc   1140

cccatcgaga aaaccatctc caaagccaaa gggcagcccc gagaaccaca ggtgtacacc   1200

ctgcccccat cccgggatga gctgaccaag aaccaggtca gcctgacctg cctggtcaaa   1260

ggcttctatc caagcgacat cgccgtggag tgggagagca atgggcagcc ggagaacaac   1320

tacaagacca cgcctcccgt gctggactcc gacggctcct tcttcctcta cagcaagctc   1380

accgtggaca agagcaggtg gcagcagggg aacgtcttct catgctccgt gatgcatgag   1440

gctctgcaca accactacac gcagaagagc ctctccctgt ctccgggtaa atga         1494
```

<210> SEQ ID NO 88
<211> LENGTH: 493
<212> TYPE: PRT
<213> ORGANISM: Artificial sequence
<220> FEATURE:
<223> OTHER INFORMATION: Humanized TRU-016

<400> SEQUENCE: 88

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Thr Ser Glu Asn
        35                  40                  45

Val Tyr Ser Tyr Leu Ala Trp Tyr Gln Gln Lys Pro Gly Gln Ala Pro
    50                  55                  60

Arg Leu Leu Ile Tyr Phe Ala Lys Thr Leu Ala Glu Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln His His Ser
            100                 105                 110

Asp Asn Pro Trp Thr Phe Gly Gln Gly Thr Lys Val Glu Ile Lys Gly
        115                 120                 125

Gly Gly Gly Ser Gly Gly Gly Gly Ser Gly Gly Gly Gly Ala Ser Glu
    130                 135                 140

Val Gln Leu Val Gln Ser Gly Ala Glu Val Lys Lys Pro Gly Glu Ser
145                 150                 155                 160

Leu Arg Ile Ser Cys Lys Gly Ser Gly Tyr Ser Phe Thr Gly Tyr Asn
                165                 170                 175

Met Asn Trp Val Arg Gln Met Pro Gly Lys Gly Leu Glu Trp Met Gly
            180                 185                 190

Asn Ile Asp Pro Tyr Tyr Gly Gly Thr Thr Tyr Asn Arg Lys Phe Lys
        195                 200                 205

Gly Gln Val Thr Ile Ser Ala Asp Lys Ser Ile Ser Thr Ala Tyr Leu
    210                 215                 220
```

-continued

```
Gln Trp Ser Ser Leu Lys Ala Ser Asp Thr Ala Met Tyr Tyr Cys Ala
225                 230                 235                 240

Arg Ser Val Gly Pro Met Asp Tyr Trp Gly Arg Gly Thr Leu Val Thr
                245                 250                 255

Val Ser Ser Asp Gln Glu Pro Lys Ser Ser Asp Lys Thr His Thr Ser
            260                 265                 270

Pro Pro Cys Pro Ala Pro Glu Leu Leu Gly Gly Pro Ser Val Phe Leu
        275                 280                 285

Phe Pro Pro Lys Pro Lys Asp Thr Leu Met Ile Ser Arg Thr Pro Glu
    290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Ala Leu Pro Ala Pro Ile Glu Lys Thr Ile Ser Lys
    370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Tyr Ser Lys Leu Thr Val Asp Lys Ser Arg Trp Gln
    450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490


<210> SEQ ID NO 89
<211> LENGTH: 45
<212> TYPE: DNA
<213> ORGANISM: Artificial sequence
<220> FEATURE:
<223> OTHER INFORMATION: Humanized TRU-016

<400> SEQUENCE: 89

gagcccaaat cttgtgacaa aactcacaca tgtccaccgt gccca                    45


<210> SEQ ID NO 90
<211> LENGTH: 15
<212> TYPE: PRT
<213> ORGANISM: Artificial sequence
<220> FEATURE:
<223> OTHER INFORMATION: Humanized TRU-016

<400> SEQUENCE: 90

Glu Pro Lys Ser Cys Asp Lys Thr His Thr Cys Pro Pro Cys Pro
1               5                   10                  15


<210> SEQ ID NO 91
<211> LENGTH: 45
```

<212> TYPE: DNA
<213> ORGANISM: Artificial sequence
<220> FEATURE:
<223> OTHER INFORMATION: Humanized TRU-016

<400> SEQUENCE: 91
gagcccaaat cttctgacaa aactcacaca tgtccaccgt gccca 45

<210> SEQ ID NO 92
<211> LENGTH: 15
<212> TYPE: PRT
<213> ORGANISM: Artificial sequence
<220> FEATURE:
<223> OTHER INFORMATION: Humanized TRU-016

<400> SEQUENCE: 92

Glu Pro Lys Ser Ser Asp Lys Thr His Thr Cys Pro Pro Cys Pro
1 5 10 15

<210> SEQ ID NO 93
<211> LENGTH: 45
<212> TYPE: DNA
<213> ORGANISM: Artificial sequence
<220> FEATURE:
<223> OTHER INFORMATION: Humanized TRU-016

<400> SEQUENCE: 93
gagcccaaat cttctgacaa aactcacaca tgtccaccgt gctca 45

<210> SEQ ID NO 94
<211> LENGTH: 15
<212> TYPE: PRT
<213> ORGANISM: Artificial sequence
<220> FEATURE:
<223> OTHER INFORMATION: Humanized TRU-016

<400> SEQUENCE: 94

Glu Pro Lys Ser Ser Asp Lys Thr His Thr Cys Pro Pro Cys Ser
1 5 10 15

<210> SEQ ID NO 95
<211> LENGTH: 45
<212> TYPE: DNA
<213> ORGANISM: Artificial sequence
<220> FEATURE:
<223> OTHER INFORMATION: Humanized TRU-016

<400> SEQUENCE: 95
gagcccaaat cttgtgacaa aactcacaca tgtccaccga gctca 45

<210> SEQ ID NO 96
<211> LENGTH: 15
<212> TYPE: PRT
<213> ORGANISM: Artificial sequence
<220> FEATURE:
<223> OTHER INFORMATION: Humanized TRU-016

<400> SEQUENCE: 96

Glu Pro Lys Ser Ser Asp Lys Thr His Thr Cys Pro Pro Ser Ser
1 5 10 15

<210> SEQ ID NO 97
<211> LENGTH: 45
<212> TYPE: DNA
<213> ORGANISM: Artificial sequence
<220> FEATURE:
<223> OTHER INFORMATION: Humanized TRU-016

<400> SEQUENCE: 97
gagcccaaat cttctgacaa aactcacaca tctccaccga gccca 45

<210> SEQ ID NO 98
<211> LENGTH: 15
<212> TYPE: PRT
<213> ORGANISM: Artificial sequence
<220> FEATURE:
<223> OTHER INFORMATION: Humanized TRU-016

<400> SEQUENCE: 98

Glu Pro Lys Ser Ser Asp Lys Thr His Thr Ser Pro Pro Ser Pro
1 5 10 15

<210> SEQ ID NO 99
<211> LENGTH: 45
<212> TYPE: DNA
<213> ORGANISM: Artificial sequence
<220> FEATURE:
<223> OTHER INFORMATION: Humanized TRU-016

<400> SEQUENCE: 99
gagcccaaat cttctgacaa aactcacaca tctccaccga gctca 45

<210> SEQ ID NO 100
<211> LENGTH: 15
<212> TYPE: PRT
<213> ORGANISM: Artificial sequence
<220> FEATURE:
<223> OTHER INFORMATION: Humanized TRU-016

<400> SEQUENCE: 100

Glu Pro Lys Ser Ser Asp Lys Thr His Thr Ser Pro Pro Ser Ser
1 5 10 15

<210> SEQ ID NO 101
<211> LENGTH: 45
<212> TYPE: DNA
<213> ORGANISM: Artificial sequence
<220> FEATURE:
<223> OTHER INFORMATION: Humanized TRU-016

<400> SEQUENCE: 101
gagcccaaat cttgtgacaa aactcacaca tctccaccgt gccca 45

<210> SEQ ID NO 102
<211> LENGTH: 15
<212> TYPE: PRT
<213> ORGANISM: Artificial sequence
<220> FEATURE:
<223> OTHER INFORMATION: Humanized TRU-016

<400> SEQUENCE: 102

Glu Pro Lys Ser Cys Asp Lys Thr His Thr Ser Pro Pro Cys Pro
1 5 10 15

<210> SEQ ID NO 103
<211> LENGTH: 45
<212> TYPE: DNA
<213> ORGANISM: Artificial sequence
<220> FEATURE:
<223> OTHER INFORMATION: Humanized TRU-016

<400> SEQUENCE: 103
gagcccaaat cttgtgacaa aactcacaca tctccaccgt gctca 45

<210> SEQ ID NO 104
<211> LENGTH: 15
<212> TYPE: PRT
<213> ORGANISM: Artificial sequence
<220> FEATURE:
<223> OTHER INFORMATION: Humanized TRU-016

<400> SEQUENCE: 104

Glu Pro Lys Ser Cys Asp Lys Thr His Thr Ser Pro Pro Cys Ser
1 5 10 15

<210> SEQ ID NO 105
<211> LENGTH: 45
<212> TYPE: DNA
<213> ORGANISM: Artificial sequence
<220> FEATURE:
<223> OTHER INFORMATION: Humanized TRU-016

<400> SEQUENCE: 105
gagcccaaat cttctgacaa aactcacaca tctccaccgt gccca 45

<210> SEQ ID NO 106
<211> LENGTH: 15
<212> TYPE: PRT
<213> ORGANISM: Artificial sequence
<220> FEATURE:
<223> OTHER INFORMATION: Humanized TRU-016

<400> SEQUENCE: 106

Glu Pro Lys Ser Ser Asp Lys Thr His Thr Ser Pro Pro Cys Pro
1 5 10 15

<210> SEQ ID NO 107
<211> LENGTH: 45
<212> TYPE: DNA
<213> ORGANISM: Artificial sequence
<220> FEATURE:
<223> OTHER INFORMATION: Humanized TRU-016

<400> SEQUENCE: 107
gagcccaaat cttctgacaa aactcacaca tctccaccgt gctca 45

<210> SEQ ID NO 108
<211> LENGTH: 15
<212> TYPE: PRT
<213> ORGANISM: Artificial sequence
<220> FEATURE:
<223> OTHER INFORMATION: Humanized TRU-016

<400> SEQUENCE: 108

Glu Pro Lys Ser Ser Asp Lys Thr His Thr Ser Pro Pro Cys Ser
1 5 10 15

<210> SEQ ID NO 109
<211> LENGTH: 45
<212> TYPE: DNA
<213> ORGANISM: Artificial sequence
<220> FEATURE:
<223> OTHER INFORMATION: Humanized TRU-016

<400> SEQUENCE: 109
gagcccaaat cttgtgacaa aactcacaca tctccaccga gccca 45

<210> SEQ ID NO 110
<211> LENGTH: 15

-continued

<212> TYPE: PRT
<213> ORGANISM: Artificial sequence
<220> FEATURE:
<223> OTHER INFORMATION: Humanized TRU-016

<400> SEQUENCE: 110

Glu Pro Lys Ser Cys Asp Lys Thr His Thr Ser Pro Pro Ser Pro
1 5 10 15

<210> SEQ ID NO 111
<211> LENGTH: 45
<212> TYPE: DNA
<213> ORGANISM: Artificial sequence
<220> FEATURE:
<223> OTHER INFORMATION: Humanized TRU-016

<400> SEQUENCE: 111
gagcccaaat cttgtgacaa aactcacaca tctccaccga gctca 45

<210> SEQ ID NO 112
<211> LENGTH: 15
<212> TYPE: PRT
<213> ORGANISM: Artificial sequence
<220> FEATURE:
<223> OTHER INFORMATION: Humanized TRU-016

<400> SEQUENCE: 112

Glu Pro Lys Ser Cys Asp Lys Thr His Thr Ser Pro Pro Ser Ser
1 5 10 15

<210> SEQ ID NO 113

<400> SEQUENCE: 113

000

<210> SEQ ID NO 114

<400> SEQUENCE: 114

000

<210> SEQ ID NO 115
<211> LENGTH: 19
<212> TYPE: PRT
<213> ORGANISM: Artificial sequence
<220> FEATURE:
<223> OTHER INFORMATION: Humanized TRU-016

<400> SEQUENCE: 115

Val Pro Ser Thr Pro Pro Thr Pro Ser Pro Ser Thr Pro Pro Thr Pro
1 5 10 15

Ser Pro Ser

<210> SEQ ID NO 116
<211> LENGTH: 6
<212> TYPE: PRT
<213> ORGANISM: Artificial sequence
<220> FEATURE:
<223> OTHER INFORMATION: Humanized TRU-016

<400> SEQUENCE: 116

Val Pro Pro Pro Pro Pro
1 5

<210> SEQ ID NO 117

-continued

<211> LENGTH: 186
<212> TYPE: DNA
<213> ORGANISM: Artificial sequence
<220> FEATURE:
<223> OTHER INFORMATION: Humanized TRU-016

<400> SEQUENCE: 117
gagctcaaaa ctcctctcgg ggatacgacc catacgtgtc cccgctgtcc tgaaccgaag 60
tcctgcgata cgcctccgcc atgtccacgg tgcccagagc ccaaatcatg cgatacgccc 120
ccaccgtgtc cccgctgtcc tgaaccaaag tcatgcgata ccccaccacc atgtccaaga 180
tgccca 186

<210> SEQ ID NO 118
<211> LENGTH: 62
<212> TYPE: PRT
<213> ORGANISM: Artificial sequence
<220> FEATURE:
<223> OTHER INFORMATION: Humanized TRU-016

<400> SEQUENCE: 118

Glu Leu Lys Thr Pro Leu Gly Asp Thr Thr His Thr Cys Pro Arg Cys
1               5                   10                  15

Pro Glu Pro Lys Ser Cys Asp Thr Pro Pro Pro Cys Pro Arg Cys Pro
            20                  25                  30

Glu Pro Lys Ser Cys Asp Thr Pro Pro Pro Cys Pro Arg Cys Pro Glu
        35                  40                  45

Pro Lys Ser Cys Asp Thr Pro Pro Pro Cys Pro Arg Cys Pro
    50                  55                  60

<210> SEQ ID NO 119
<211> LENGTH: 45
<212> TYPE: DNA
<213> ORGANISM: Artificial sequence
<220> FEATURE:
<223> OTHER INFORMATION: Humanized TRU-016

<400> SEQUENCE: 119
gagcccaaat cttctgacac acctccccca tgcccacggt gcccc 45

<210> SEQ ID NO 120
<211> LENGTH: 15
<212> TYPE: PRT
<213> ORGANISM: Artificial sequence
<220> FEATURE:
<223> OTHER INFORMATION: Humanized TRU-016

<400> SEQUENCE: 120

Glu Pro Lys Ser Ser Asp Thr Pro Pro Pro Cys Pro Arg Cys Pro
1               5                   10                  15

<210> SEQ ID NO 121
<211> LENGTH: 45
<212> TYPE: DNA
<213> ORGANISM: Artificial sequence
<220> FEATURE:
<223> OTHER INFORMATION: Humanized TRU-016

<400> SEQUENCE: 121
gagcccaaat cttgtgacac acctccccca tccccacggt cccca 45

<210> SEQ ID NO 122
<211> LENGTH: 15
<212> TYPE: PRT

<213> ORGANISM: Artificial sequence
<220> FEATURE:
<223> OTHER INFORMATION: Humanized TRU-016

<400> SEQUENCE: 122

Glu Pro Lys Ser Cys Asp Thr Pro Pro Pro Ser Pro Arg Ser Pro
1 5 10 15

<210> SEQ ID NO 123
<211> LENGTH: 45
<212> TYPE: DNA
<213> ORGANISM: Artificial sequence
<220> FEATURE:
<223> OTHER INFORMATION: Humanized TRU-016

<400> SEQUENCE: 123
gagcccaaat cttctgacac acctccccca tccccacggt cccca 45

<210> SEQ ID NO 124
<211> LENGTH: 15
<212> TYPE: PRT
<213> ORGANISM: Artificial sequence
<220> FEATURE:
<223> OTHER INFORMATION: Humanized TRU-016

<400> SEQUENCE: 124

Glu Pro Lys Ser Ser Asp Thr Pro Pro Pro Ser Pro Arg Ser Pro
1 5 10 15

<210> SEQ ID NO 125
<211> LENGTH: 45
<212> TYPE: DNA
<213> ORGANISM: Artificial sequence
<220> FEATURE:
<223> OTHER INFORMATION: Humanized TRU-016

<400> SEQUENCE: 125
gagcccaaat cttgtgacac acctccccca tccccacggt gccca 45

<210> SEQ ID NO 126
<211> LENGTH: 15
<212> TYPE: PRT
<213> ORGANISM: Artificial sequence
<220> FEATURE:
<223> OTHER INFORMATION: Humanized TRU-016

<400> SEQUENCE: 126

Glu Pro Lys Ser Cys Asp Thr Pro Pro Pro Ser Pro Arg Cys Pro
1 5 10 15

<210> SEQ ID NO 127
<211> LENGTH: 58
<212> TYPE: PRT
<213> ORGANISM: Artificial sequence
<220> FEATURE:
<223> OTHER INFORMATION: Humanized TRU-016

<400> SEQUENCE: 127

Glu Ser Pro Lys Ala Gln Ala Ser Ser Val Pro Thr Ala Gln Pro Gln
1 5 10 15

Ala Glu Gly Ser Leu Ala Lys Ala Thr Thr Ala Pro Ala Thr Thr Arg
20 25 30

Asn Thr Gly Arg Gly Gly Glu Glu Lys Lys Lys Glu Lys Glu Lys Glu
35 40 45

Glu Gln Glu Glu Arg Glu Thr Lys Thr Pro 50 55

<210> SEQ ID NO 128
<211> LENGTH: 11
<212> TYPE: PRT
<213> ORGANISM: Artificial sequence
<220> FEATURE:
<223> OTHER INFORMATION: Humanized TRU-016

<400> SEQUENCE: 128

Arg Thr Ser Gln Asn Val Tyr Ser Tyr Leu Ala
1 5 10

<210> SEQ ID NO 129
<211> LENGTH: 11
<212> TYPE: PRT
<213> ORGANISM: Artificial sequence
<220> FEATURE:
<223> OTHER INFORMATION: Humanized TRU-016

<400> SEQUENCE: 129

Arg Thr Ser Glu Ser Val Tyr Ser Tyr Leu Ala
1 5 10

<210> SEQ ID NO 130
<211> LENGTH: 11
<212> TYPE: PRT
<213> ORGANISM: Artificial sequence
<220> FEATURE:
<223> OTHER INFORMATION: Humanized TRU-016

<400> SEQUENCE: 130

Arg Ala Ser Gln Ser Val Tyr Ser Tyr Leu Ala
1 5 10

<210> SEQ ID NO 131
<211> LENGTH: 11
<212> TYPE: PRT
<213> ORGANISM: Artificial sequence
<220> FEATURE:
<223> OTHER INFORMATION: Humanized TRU-016

<400> SEQUENCE: 131

Arg Ala Ser Gln Ser Val Ser Ser Tyr Leu Ala
1 5 10

<210> SEQ ID NO 132
<211> LENGTH: 11
<212> TYPE: PRT
<213> ORGANISM: Artificial sequence
<220> FEATURE:
<223> OTHER INFORMATION: Humanized TRU-016

<400> SEQUENCE: 132

Arg Ala Ser Gln Ser Val Ser Tyr Tyr Leu Ala
1 5 10

<210> SEQ ID NO 133
<211> LENGTH: 5
<212> TYPE: PRT
<213> ORGANISM: Artificial sequence
<220> FEATURE:
<223> OTHER INFORMATION: Humanized TRU-016

<400> SEQUENCE: 133

Ser Tyr Met Asn Met
1 5

<210> SEQ ID NO 134
<211> LENGTH: 5
<212> TYPE: PRT
<213> ORGANISM: Artificial sequence
<220> FEATURE:
<223> OTHER INFORMATION: Humanized TRU-016

<400> SEQUENCE: 134

Ser Tyr Trp Ile Gly
1               5

<210> SEQ ID NO 135
<211> LENGTH: 7
<212> TYPE: PRT
<213> ORGANISM: Artificial sequence
<220> FEATURE:
<223> OTHER INFORMATION: Humanized TRU-016

<400> SEQUENCE: 135

Ala Ala Ser Ser Leu Gln Ser
1               5

<210> SEQ ID NO 136
<211> LENGTH: 7
<212> TYPE: PRT
<213> ORGANISM: Artificial sequence
<220> FEATURE:
<223> OTHER INFORMATION: Humanized TRU-016

<400> SEQUENCE: 136

Gly Ala Ser Thr Arg Ala Thr
1               5

<210> SEQ ID NO 137
<211> LENGTH: 7
<212> TYPE: PRT
<213> ORGANISM: Artificial sequence
<220> FEATURE:
<223> OTHER INFORMATION: Humanized TRU-016

<400> SEQUENCE: 137

Asp Ala Ser Asn Arg Ala Thr
1               5

<210> SEQ ID NO 138
<211> LENGTH: 17
<212> TYPE: PRT
<213> ORGANISM: Artificial sequence
<220> FEATURE:
<223> OTHER INFORMATION: Humanized TRU-016

<400> SEQUENCE: 138

Ile Ile Tyr Pro Gly Asp Ser Asp Thr Arg Tyr Ser Pro Ser Phe Gln
1               5                   10                  15

Gly

<210> SEQ ID NO 139
<211> LENGTH: 17
<212> TYPE: PRT
<213> ORGANISM: Artificial sequence
<220> FEATURE:
<223> OTHER INFORMATION: Humanized TRU-016

<400> SEQUENCE: 139

Arg Ile Asp Pro Ser Asp Ser Tyr Thr Asn Tyr Ser Pro Ser Phe Gln 1 5 10 15

Gly

<210> SEQ ID NO 140
<211> LENGTH: 30
<212> TYPE: PRT
<213> ORGANISM: Artificial sequence
<220> FEATURE:
<223> OTHER INFORMATION: Humanized TRU-016

<400> SEQUENCE: 140

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr
20 25 30

<210> SEQ ID NO 141
<211> LENGTH: 30
<212> TYPE: PRT
<213> ORGANISM: Artificial sequence
<220> FEATURE:
<223> OTHER INFORMATION: Humanized TRU-016

<400> SEQUENCE: 141

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser
20 25 30

<210> SEQ ID NO 142

<400> SEQUENCE: 142

000

<210> SEQ ID NO 143
<211> LENGTH: 30
<212> TYPE: PRT
<213> ORGANISM: Artificial sequence
<220> FEATURE:
<223> OTHER INFORMATION: Humanized TRU-016

<400> SEQUENCE: 143

Glu Val Gln Leu Val Gln Ser Gly Ala Glu Val Lys Lys Pro Gly Ala
1 5 10 15

Thr Val Lys Ile Ser Cys Lys Val Ser Gly Tyr Thr Phe Thr
20 25 30

<210> SEQ ID NO 144
<211> LENGTH: 30
<212> TYPE: PRT
<213> ORGANISM: Artificial sequence
<220> FEATURE:
<223> OTHER INFORMATION: Humanized TRU-016

<400> SEQUENCE: 144

Glu Val Gln Leu Val Gln Ser Gly Ala Glu Val Lys Lys Pro Gly Glu
1 5 10 15

Ser Leu Lys Ile Ser Cys Lys Gly Ser Gly Tyr Ser Phe Thr
20 25 30

<210> SEQ ID NO 145
<211> LENGTH: 30
<212> TYPE: PRT

<213> ORGANISM: Artificial sequence
<220> FEATURE:
<223> OTHER INFORMATION: Humanized TRU-016

<400> SEQUENCE: 145

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr
            20                  25                  30

<210> SEQ ID NO 146
<211> LENGTH: 30
<212> TYPE: PRT
<213> ORGANISM: Artificial sequence
<220> FEATURE:
<223> OTHER INFORMATION: Humanized TRU-016

<400> SEQUENCE: 146

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr
            20                  25                  30

<210> SEQ ID NO 147
<211> LENGTH: 14
<212> TYPE: PRT
<213> ORGANISM: Artificial sequence
<220> FEATURE:
<223> OTHER INFORMATION: Humanized TRU-016

<400> SEQUENCE: 147

Trp Val Arg Gln Ala Pro Gly Gln Gly Leu Glu Trp Met Gly
1               5                   10

<210> SEQ ID NO 148

<400> SEQUENCE: 148

000

<210> SEQ ID NO 149

<400> SEQUENCE: 149

000

<210> SEQ ID NO 150
<211> LENGTH: 14
<212> TYPE: PRT
<213> ORGANISM: Artificial sequence
<220> FEATURE:
<223> OTHER INFORMATION: Humanized TRU-016

<400> SEQUENCE: 150

Trp Val Gln Gln Ala Pro Gly Lys Gly Leu Glu Trp Met Gly
1               5                   10

<210> SEQ ID NO 151
<211> LENGTH: 14
<212> TYPE: PRT
<213> ORGANISM: Artificial sequence
<220> FEATURE:
<223> OTHER INFORMATION: Humanized TRU-016

<400> SEQUENCE: 151

Trp Val Arg Gln Met Pro Gly Lys Gly Leu Glu Trp Met Gly 1 5 10

<210> SEQ ID NO 152

<400> SEQUENCE: 152

000

<210> SEQ ID NO 153

<400> SEQUENCE: 153

000

<210> SEQ ID NO 154
<211> LENGTH: 32
<212> TYPE: PRT
<213> ORGANISM: Artificial sequence
<220> FEATURE:
<223> OTHER INFORMATION: Humanized TRU-016

<400> SEQUENCE: 154

Arg Val Thr Met Thr Thr Asp Thr Ser Thr Ser Thr Ala Tyr Met Glu
1 5 10 15

Leu Arg Ser Leu Arg Ser Asp Asp Thr Ala Val Tyr Tyr Cys Ala Arg
20 25 30

<210> SEQ ID NO 155
<211> LENGTH: 32
<212> TYPE: PRT
<213> ORGANISM: Artificial sequence
<220> FEATURE:
<223> OTHER INFORMATION: Humanized TRU-016

<400> SEQUENCE: 155

Arg Val Thr Ile Thr Ala Asp Glu Ser Thr Ser Thr Ala Tyr Met Glu
1 5 10 15

Leu Ser Ser Leu Arg Ser Glu Asp Thr Ala Val Tyr Tyr Cys Ala Arg
20 25 30

<210> SEQ ID NO 156
<211> LENGTH: 32
<212> TYPE: PRT
<213> ORGANISM: Artificial sequence
<220> FEATURE:
<223> OTHER INFORMATION: Humanized TRU-016

<400> SEQUENCE: 156

Arg Val Thr Ile Thr Ala Asp Lys Ser Thr Ser Thr Ala Tyr Met Glu
1 5 10 15

Leu Ser Ser Leu Arg Ser Glu Asp Thr Ala Val Tyr Tyr Cys Ala Arg
20 25 30

<210> SEQ ID NO 157
<211> LENGTH: 32
<212> TYPE: PRT
<213> ORGANISM: Artificial sequence
<220> FEATURE:
<223> OTHER INFORMATION: Humanized TRU-016

<400> SEQUENCE: 157

Arg Val Thr Ile Thr Ala Asp Thr Ser Thr Asp Thr Ala Tyr Met Glu
1 5 10 15

Leu Ser Ser Leu Arg Ser Glu Asp Thr Ala Val Tyr Tyr Cys Ala Thr
20 25 30

<210> SEQ ID NO 158
<211> LENGTH: 32
<212> TYPE: PRT
<213> ORGANISM: Artificial sequence
<220> FEATURE:
<223> OTHER INFORMATION: Humanized TRU-016

<400> SEQUENCE: 158

```
Gln Val Thr Ile Ser Ala Asp Lys Ser Ile Ser Thr Ala Tyr Leu Gln
1               5                   10                  15

Trp Ser Ser Leu Lys Ala Ser Asp Thr Ala Met Tyr Tyr Cys Ala Arg
            20                  25                  30
```

<210> SEQ ID NO 159
<211> LENGTH: 32
<212> TYPE: PRT
<213> ORGANISM: Artificial sequence
<220> FEATURE:
<223> OTHER INFORMATION: Humanized TRU-016

<400> SEQUENCE: 159

```
His Val Thr Ile Ser Ala Asp Lys Ser Ile Ser Thr Ala Tyr Leu Gln
1               5                   10                  15

Trp Ser Ser Leu Lys Ala Ser Asp Thr Ala Met Tyr Tyr Cys Ala Arg
            20                  25                  30
```

<210> SEQ ID NO 160
<211> LENGTH: 32
<212> TYPE: PRT
<213> ORGANISM: Artificial sequence
<220> FEATURE:
<223> OTHER INFORMATION: Humanized TRU-016

<400> SEQUENCE: 160

```
Arg Phe Val Phe Ser Leu Asp Thr Ser Val Ser Thr Ala Tyr Leu Gln
1               5                   10                  15

Ile Ser Ser Leu Lys Ala Glu Asp Thr Ala Val Tyr Tyr Cys Ala Arg
            20                  25                  30
```

<210> SEQ ID NO 161
<211> LENGTH: 11
<212> TYPE: PRT
<213> ORGANISM: Artificial sequence
<220> FEATURE:
<223> OTHER INFORMATION: Humanized TRU-016

<400> SEQUENCE: 161

```
Trp Gly Gln Gly Thr Leu Val Thr Val Ser Ser
1               5                   10
```

<210> SEQ ID NO 162
<211> LENGTH: 11
<212> TYPE: PRT
<213> ORGANISM: Artificial sequence
<220> FEATURE:
<223> OTHER INFORMATION: Humanized TRU-016

<400> SEQUENCE: 162

```
Trp Gly Arg Gly Thr Leu Val Thr Val Ser Ser
1               5                   10
```

<210> SEQ ID NO 163
<211> LENGTH: 11
<212> TYPE: PRT

<213> ORGANISM: Artificial sequence
<220> FEATURE:
<223> OTHER INFORMATION: Humanized TRU-016

<400> SEQUENCE: 163

Trp Gly Gln Gly Thr Met Val Thr Val Ser Ser
1 5 10

<210> SEQ ID NO 164

<400> SEQUENCE: 164

000

<210> SEQ ID NO 165

<400> SEQUENCE: 165

000

<210> SEQ ID NO 166

<400> SEQUENCE: 166

000

<210> SEQ ID NO 167

<400> SEQUENCE: 167

000

<210> SEQ ID NO 168
<211> LENGTH: 11
<212> TYPE: PRT
<213> ORGANISM: Artificial sequence
<220> FEATURE:
<223> OTHER INFORMATION: Humanized TRU-016

<400> SEQUENCE: 168

Trp Gly Gln Gly Thr Thr Val Thr Val Ser Ser
1 5 10

<210> SEQ ID NO 169
<211> LENGTH: 11
<212> TYPE: PRT
<213> ORGANISM: Artificial sequence
<220> FEATURE:
<223> OTHER INFORMATION: Humanized TRU-016

<400> SEQUENCE: 169

Trp Gly Lys Gly Thr Thr Val Thr Val Ser Ser
1 5 10

<210> SEQ ID NO 170
<211> LENGTH: 23
<212> TYPE: PRT
<213> ORGANISM: Artificial sequence
<220> FEATURE:
<223> OTHER INFORMATION: Humanized TRU-016

<400> SEQUENCE: 170

Glu Ile Val Met Thr Gln Ser Pro Ala Thr Leu Ser Val Ser Pro Gly
1 5 10 15

Glu Arg Ala Thr Leu Ser Cys
20

<210> SEQ ID NO 171
<211> LENGTH: 23
<212> TYPE: PRT
<213> ORGANISM: Artificial sequence
<220> FEATURE:
<223> OTHER INFORMATION: Humanized TRU-016

<400> SEQUENCE: 171

```
Glu Ile Val Leu Thr Gln Ser Pro Ala Thr Leu Ser Leu Ser Pro Gly
1               5                   10                  15

Glu Arg Ala Thr Leu Ser Cys
            20
```

<210> SEQ ID NO 172
<211> LENGTH: 23
<212> TYPE: PRT
<213> ORGANISM: Artificial sequence
<220> FEATURE:
<223> OTHER INFORMATION: Humanized TRU-016

<400> SEQUENCE: 172

```
Asp Ile Gln Met Thr Gln Ser Pro Ser Ser Leu Ser Ala Ser Val Gly
1               5                   10                  15

Asp Arg Val Thr Ile Thr Cys
            20
```

<210> SEQ ID NO 173

<400> SEQUENCE: 173

000

<210> SEQ ID NO 174

<400> SEQUENCE: 174

000

<210> SEQ ID NO 175
<211> LENGTH: 23
<212> TYPE: PRT
<213> ORGANISM: Artificial sequence
<220> FEATURE:
<223> OTHER INFORMATION: Humanized TRU-016

<400> SEQUENCE: 175

```
Asn Ile Gln Met Thr Gln Ser Pro Ser Ala Met Ser Ala Ser Val Gly
1               5                   10                  15

Asp Arg Val Thr Ile Thr Cys
            20
```

<210> SEQ ID NO 176

<400> SEQUENCE: 176

000

<210> SEQ ID NO 177
<211> LENGTH: 23
<212> TYPE: PRT
<213> ORGANISM: Artificial sequence
<220> FEATURE:
<223> OTHER INFORMATION: Humanized TRU-016

<400> SEQUENCE: 177

Ala Ile Gln Leu Thr Gln Ser Pro Ser Ser Leu Ser Ala Ser Val Gly
1 5 10 15

Asp Arg Val Thr Ile Thr Cys
20

<210> SEQ ID NO 178
<211> LENGTH: 23
<212> TYPE: PRT
<213> ORGANISM: Artificial sequence
<220> FEATURE:
<223> OTHER INFORMATION: Humanized TRU-016

<400> SEQUENCE: 178

Asp Ile Gln Leu Thr Gln Ser Pro Ser Phe Leu Ser Ala Ser Val Gly
1 5 10 15

Asp Arg Val Thr Ile Thr Cys
20

<210> SEQ ID NO 179
<211> LENGTH: 23
<212> TYPE: PRT
<213> ORGANISM: Artificial sequence
<220> FEATURE:
<223> OTHER INFORMATION: Humanized TRU-016

<400> SEQUENCE: 179

Ala Ile Arg Met Thr Gln Ser Pro Phe Ser Leu Ser Ala Ser Val Gly
1 5 10 15

Asp Arg Val Thr Ile Thr Cys
20

<210> SEQ ID NO 180
<211> LENGTH: 23
<212> TYPE: PRT
<213> ORGANISM: Artificial sequence
<220> FEATURE:
<223> OTHER INFORMATION: Humanized TRU-016

<400> SEQUENCE: 180

Ala Ile Gln Met Thr Gln Ser Pro Ser Ser Leu Ser Ala Ser Val Gly
1 5 10 15

Asp Arg Val Thr Ile Thr Cys
20

<210> SEQ ID NO 181
<211> LENGTH: 23
<212> TYPE: PRT
<213> ORGANISM: Artificial sequence
<220> FEATURE:
<223> OTHER INFORMATION: Humanized TRU-016

<400> SEQUENCE: 181

Asp Ile Gln Met Thr Gln Ser Pro Ser Thr Leu Ser Ala Ser Val Gly
1 5 10 15

Asp Arg Val Thr Ile Thr Cys
20

<210> SEQ ID NO 182
<211> LENGTH: 15
<212> TYPE: PRT
<213> ORGANISM: Artificial sequence
<220> FEATURE:
<223> OTHER INFORMATION: Humanized TRU-016

<400> SEQUENCE: 182

Trp Tyr Gln Gln Lys Pro Gly Gln Ala Pro Arg Leu Leu Ile Tyr
1 5 10 15

<210> SEQ ID NO 183

<400> SEQUENCE: 183

000

<210> SEQ ID NO 184
<211> LENGTH: 15
<212> TYPE: PRT
<213> ORGANISM: Artificial sequence
<220> FEATURE:
<223> OTHER INFORMATION: Humanized TRU-016

<400> SEQUENCE: 184

Trp Tyr Gln Gln Lys Pro Gly Lys Ala Pro Lys Leu Leu Ile Tyr
1 5 10 15

<210> SEQ ID NO 185
<211> LENGTH: 15
<212> TYPE: PRT
<213> ORGANISM: Artificial sequence
<220> FEATURE:
<223> OTHER INFORMATION: Humanized TRU-016

<400> SEQUENCE: 185

Trp Tyr Gln Gln Lys Pro Gly Lys Val Pro Lys Leu Leu Ile Tyr
1 5 10 15

<210> SEQ ID NO 186
<211> LENGTH: 15
<212> TYPE: PRT
<213> ORGANISM: Artificial sequence
<220> FEATURE:
<223> OTHER INFORMATION: Humanized TRU-016

<400> SEQUENCE: 186

Trp Tyr Gln Gln Lys Pro Gly Lys Ala Pro Lys Arg Leu Ile Tyr
1 5 10 15

<210> SEQ ID NO 187
<211> LENGTH: 15
<212> TYPE: PRT
<213> ORGANISM: Artificial sequence
<220> FEATURE:
<223> OTHER INFORMATION: Humanized TRU-016

<400> SEQUENCE: 187

Trp Phe Gln Gln Lys Pro Gly Lys Val Pro Lys His Leu Ile Tyr
1 5 10 15

<210> SEQ ID NO 188
<211> LENGTH: 15
<212> TYPE: PRT
<213> ORGANISM: Artificial sequence
<220> FEATURE:
<223> OTHER INFORMATION: Humanized TRU-016

<400> SEQUENCE: 188

Trp Phe Gln Gln Lys Pro Gly Lys Ala Pro Lys Ser Leu Ile Tyr
1 5 10 15

<210> SEQ ID NO 189

<400> SEQUENCE: 189

000

<210> SEQ ID NO 190

<400> SEQUENCE: 190

000

<210> SEQ ID NO 191
<211> LENGTH: 15
<212> TYPE: PRT
<213> ORGANISM: Artificial sequence
<220> FEATURE:
<223> OTHER INFORMATION: Humanized TRU-016

<400> SEQUENCE: 191

```
Trp Tyr Gln Gln Lys Pro Ala Lys Ala Pro Lys Leu Phe Ile Tyr
1               5                   10                  15
```

<210> SEQ ID NO 192

<400> SEQUENCE: 192

000

<210> SEQ ID NO 193

<400> SEQUENCE: 193

000

<210> SEQ ID NO 194
<211> LENGTH: 32
<212> TYPE: PRT
<213> ORGANISM: Artificial sequence
<220> FEATURE:
<223> OTHER INFORMATION: Humanized TRU-016

<400> SEQUENCE: 194

```
Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30
```

<210> SEQ ID NO 195
<211> LENGTH: 32
<212> TYPE: PRT
<213> ORGANISM: Artificial sequence
<220> FEATURE:
<223> OTHER INFORMATION: Humanized TRU-016

<400> SEQUENCE: 195

```
Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30
```

<210> SEQ ID NO 196
<211> LENGTH: 32
<212> TYPE: PRT
<213> ORGANISM: Artificial sequence
<220> FEATURE:
<223> OTHER INFORMATION: Humanized TRU-016

<400> SEQUENCE: 196

```
Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30


<210> SEQ ID NO 197
<211> LENGTH: 32
<212> TYPE: PRT
<213> ORGANISM: Artificial sequence
<220> FEATURE:
<223> OTHER INFORMATION: Humanized TRU-016

<400> SEQUENCE: 197

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30


<210> SEQ ID NO 198
<211> LENGTH: 32
<212> TYPE: PRT
<213> ORGANISM: Artificial sequence
<220> FEATURE:
<223> OTHER INFORMATION: Humanized TRU-016

<400> SEQUENCE: 198

Gly Val Pro Ser Arg Phe Ser Gly Ser Gly Ser Gly Thr Glu Phe Thr
1               5                   10                  15

Leu Thr Ile Ser Ser Leu Gln Pro Glu Asp Phe Ala Thr Tyr Tyr Cys
            20                  25                  30


<210> SEQ ID NO 199

<400> SEQUENCE: 199

000


<210> SEQ ID NO 200

<400> SEQUENCE: 200

000


<210> SEQ ID NO 201

<400> SEQUENCE: 201

000


<210> SEQ ID NO 202

<400> SEQUENCE: 202

000


<210> SEQ ID NO 203
<211> LENGTH: 32
<212> TYPE: PRT
<213> ORGANISM: Artificial sequence
<220> FEATURE:
<223> OTHER INFORMATION: Humanized TRU-016

<400> SEQUENCE: 203

Gly Val Pro Ser Arg Phe Ser Gly Ser Gly Ser Gly Thr Asp Tyr Thr
1               5                   10                  15
```

```
Leu Thr Ile Ser Ser Leu Gln Pro Glu Asp Phe Ala Thr Tyr Tyr Cys
            20                  25                  30


<210> SEQ ID NO 204

<400> SEQUENCE: 204

000


<210> SEQ ID NO 205
<211> LENGTH: 32
<212> TYPE: PRT
<213> ORGANISM: Artificial sequence
<220> FEATURE:
<223> OTHER INFORMATION: Humanized TRU-016

<400> SEQUENCE: 205

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30


<210> SEQ ID NO 206
<211> LENGTH: 10
<212> TYPE: PRT
<213> ORGANISM: Artificial sequence
<220> FEATURE:
<223> OTHER INFORMATION: Humanized TRU-016

<400> SEQUENCE: 206

Phe Gly Gln Gly Thr Lys Val Glu Ile Lys
1               5                   10


<210> SEQ ID NO 207
<211> LENGTH: 10
<212> TYPE: PRT
<213> ORGANISM: Artificial sequence
<220> FEATURE:
<223> OTHER INFORMATION: Humanized TRU-016

<400> SEQUENCE: 207

Phe Gly Gln Gly Thr Lys Leu Glu Ile Lys
1               5                   10


<210> SEQ ID NO 208
<211> LENGTH: 10
<212> TYPE: PRT
<213> ORGANISM: Artificial sequence
<220> FEATURE:
<223> OTHER INFORMATION: Humanized TRU-016

<400> SEQUENCE: 208

Phe Gly Pro Gly Thr Lys Val Asp Ile Lys
1               5                   10


<210> SEQ ID NO 209
<211> LENGTH: 10
<212> TYPE: PRT
<213> ORGANISM: Artificial sequence
<220> FEATURE:
<223> OTHER INFORMATION: Humanized TRU-016

<400> SEQUENCE: 209

Phe Gly Gly Gly Thr Lys Val Glu Ile Lys
1               5                   10
```

<210> SEQ ID NO 210
<211> LENGTH: 10
<212> TYPE: PRT
<213> ORGANISM: Artificial sequence
<220> FEATURE:
<223> OTHER INFORMATION: Humanized TRU-016

<400> SEQUENCE: 210

Phe Gly Gln Gly Thr Arg Leu Glu Ile Lys
1               5                   10

<210> SEQ ID NO 211

<400> SEQUENCE: 211

000

<210> SEQ ID NO 212

<400> SEQUENCE: 212

000

<210> SEQ ID NO 213
<211> LENGTH: 7
<212> TYPE: PRT
<213> ORGANISM: Artificial sequence
<220> FEATURE:
<223> OTHER INFORMATION: Humanized TRU-016

<400> SEQUENCE: 213

Ser Val Gly Pro Met Asp Val
1               5

<210> SEQ ID NO 214

<400> SEQUENCE: 214

000

<210> SEQ ID NO 215
<211> LENGTH: 7
<212> TYPE: PRT
<213> ORGANISM: Artificial sequence
<220> FEATURE:
<223> OTHER INFORMATION: Humanized TRU-016

<400> SEQUENCE: 215

Ser Val Gly Pro Phe Asp Pro
1               5

<210> SEQ ID NO 216
<211> LENGTH: 7
<212> TYPE: PRT
<213> ORGANISM: Artificial sequence
<220> FEATURE:
<223> OTHER INFORMATION: Humanized TRU-016

<400> SEQUENCE: 216

Ser Val Gly Pro Phe Gln His
1               5

<210> SEQ ID NO 217
<211> LENGTH: 7
<212> TYPE: PRT
<213> ORGANISM: Artificial sequence
<220> FEATURE:

-continued

<223> OTHER INFORMATION: Humanized TRU-016

<400> SEQUENCE: 217

Ser Val Gly Pro Phe Asp Val
1 5

<210> SEQ ID NO 218
<211> LENGTH: 7
<212> TYPE: PRT
<213> ORGANISM: Artificial sequence
<220> FEATURE:
<223> OTHER INFORMATION: Humanized TRU-016

<400> SEQUENCE: 218

Ser Val Gly Pro Phe Asp Ile
1 5

<210> SEQ ID NO 219
<211> LENGTH: 7
<212> TYPE: PRT
<213> ORGANISM: Artificial sequence
<220> FEATURE:
<223> OTHER INFORMATION: Humanized TRU-016

<400> SEQUENCE: 219

Ser Val Gly Pro Phe Asp Leu
1 5

<210> SEQ ID NO 220

<400> SEQUENCE: 220

000

<210> SEQ ID NO 221
<211> LENGTH: 5
<212> TYPE: PRT
<213> ORGANISM: Artificial Sequence
<220> FEATURE:
<223> OTHER INFORMATION: Linker peptide

<400> SEQUENCE: 221

Gly Gly Gly Gly Ser
1 5

<210> SEQ ID NO 222
<211> LENGTH: 10
<212> TYPE: PRT
<213> ORGANISM: Artificial Sequence
<220> FEATURE:
<223> OTHER INFORMATION: Linker peptide

<400> SEQUENCE: 222

Gly Gly Gly Gly Ser Gly Gly Gly Gly Ser
1 5 10

<210> SEQ ID NO 223
<211> LENGTH: 15
<212> TYPE: PRT
<213> ORGANISM: Artificial Sequence
<220> FEATURE:
<223> OTHER INFORMATION: Linker peptide

<400> SEQUENCE: 223

Gly Gly Gly Gly Ser Gly Gly Gly Gly Ser Gly Gly Gly Gly Ser
1 5 10 15

-continued

```
<210> SEQ ID NO 224
<211> LENGTH: 20
<212> TYPE: PRT
<213> ORGANISM: Artificial Sequence
<220> FEATURE:
<223> OTHER INFORMATION: Linker peptide

<400> SEQUENCE: 224

Gly Gly Gly Gly Ser Gly Gly Gly Gly Ser Gly Gly Gly Gly Ser Gly
1               5                   10                  15

Gly Gly Gly Ser
            20


<210> SEQ ID NO 225
<211> LENGTH: 25
<212> TYPE: PRT
<213> ORGANISM: Artificial Sequence
<220> FEATURE:
<223> OTHER INFORMATION: Linker peptide

<400> SEQUENCE: 225

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25


<210> SEQ ID NO 226
<211> LENGTH: 30
<212> TYPE: PRT
<213> ORGANISM: Artificial Sequence
<220> FEATURE:
<223> OTHER INFORMATION: Linker peptide

<400> SEQUENCE: 226

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30
```

B-CELL REDUCTION USING CD37-SPECIFIC AND CD20-SPECIFIC BINDING MOLECULES

The present application is a continuation of U.S. application Ser. No. 11/493,132, filed Jul. 25, 2005, which claims benefit under 35 U.S.C. § 119 of U.S. Patent Application No. 60/702,499, which was filed Jul. 25, 2005, Unites States Patent Application No. 60/798,344, which was filed May 16, 2006, each of which is incorporated herein by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is EMER_012_03US_SubSeqList_ST25.txt. The text file is 228 KB, was created on Apr. 12, 2013, and is being submitted electronically via EFS-Web.

FIELD OF THE INVENTION

The present invention generally provides methods for B-cell reduction in an individual using CD37-specific binding molecules. In particular, the invention provides methods for B-cell reduction using CD37-specific binding molecules alone, or a combination of CD37-specific binding molecules and CD20-specific binding molecules, in some instances a synergistic combination. The invention further provides materials and methods for treatment of diseases involving aberrant B-cell activity.

BACKGROUND OF THE INVENTION

In its usual role, the human immune system protects the body from damage from foreign substances and pathogens. One way in which the immune system protects the body is by production of specialized cells called B lymphocytes or B-cells. B-cells produce antibodies that bind to, and in some cases mediate destruction of, a foreign substance or pathogen.

In some instances though, the human immune system and specifically the B lymphocytes of the human immune system go awry and disease results. There are numerous cancers that involve uncontrolled proliferation of B-cells. There are also numerous autoimmune diseases that involve B-cell production of antibodies that, instead of binding to foreign substances and pathogens, bind to parts of the body. Such antibodies are sometimes called autoantibodies. In addition, there are numerous autoimmune and inflammatory diseases that involve B-cells in their pathology, for example, through inappropriate B-cell antigen presentation to T-cells, or through other pathways involving B-cells. For example, autoimmune-prone mice deficient in B-cells do not develop autoimmune kidney disease, vasculitis or autoantibodies. See Shlomchik et al., *J. Exp. Med.,* 180:1295-306 (1994). Interestingly, these same autoimmune-prone mice which possess B-cells but are deficient in immunoglobulin production, do develop autoimmune diseases when induced experimentally as described by Chan et al., *J. Exp. Med.,* 189: 1639-48 (1999), indicating that B-cells play an integral role in development of autoimmune disease.

B-cells can be identified by molecules on their cell surface. CD20 was the first human B-cell lineage-specific surface molecule identified by a monoclonal antibody. It is a non-glycosylated, hydrophobic 35 kDa B-cell transmembrane phosphoprotein that has both its amino and carboxy ends situated inside the cell. See, Einfeld et al., EMBO J., 7:711-17 (1998). CD20 is expressed by all normal mature B-cells, but is not expressed by precursor B-cells or plasma cells. Natural ligands for CD20 have not been identified, and the function of CD20 in B-cell biology is still incompletely understood.

Another B-cell lineage-specific cell surface molecule is CD37. CD37 is a heavily glycosylated 40-52 kDa protein that belongs to the tetraspanin transmembrane family of cell surface antigens. It traverses the cell membrane four times forming two extracellular loops and exposing its amino and carboxy ends to the cytoplasm. CD37 is highly expressed on normal antibody-producing (slg+)B-cells, but is not expressed on pre-B-cells or plasma cells. The expression of CD37 on resting and activated T cells, monocytes and granulocytes is low and there is no detectable CD37 expression on NK cells, platelets or erythrocytes. See, Belov et al., Cancer Res., 61(11):4483-4489 (2001); Schwartz-Albiez et al., J. Immunol., 140(3): 905-914 (1988); and Link et al., J. Immunol., 137(9): 3013-3018 (1988). Besides normal B-cells, almost all malignancies of B-cell origin are positive for CD37 expression, including CLL, NHL, and hairy cell leukemia [Moore et, al., Journal of Pathology, 152: 13-21 (1987); Merson and Brochier, Immunology Letters, 19: 269-272 (1988); and Faure et al., American Journal of Dermatopathology, 12 (3): 122-133 (1990)]. CD37 participates in regulation of B-cell function, since mice lacking CD37 were found to have low levels of serum IgG1 and to be impaired in their humoral response to viral antigens and model antigens. It appears to act as a nonclassical costimulatory molecule or by directly influencing antigen presentation via complex formation with MHC class II molecules. See Knobeloch et al., Mol. Cell. Biol., 20(15):5363-5369 (2000). CD37 also seems to play a role in TCR signaling. See Van Spriel et al., J. Immunol., 172: 2953-2961 (2004).

Research and drug development has occurred based on the concept that B-cell lineage-specific cell surface molecules such as CD37 or CD20 can themselves be targets for antibodies that would bind to, and mediate destruction of, cancerous and autoimmune disease-causing B-cells that have CD37 or CD20 on their surfaces. Termed "immunotherapy," antibodies made (or based on antibodies made) in a non-human animal that bind to CD37 or CD20 were given to a patient to deplete cancerous or autoimmune disease-causing B-cells.

One antibody to CD37 has been labeled with $^{131}$I and tested in clinical trials for therapy of NHL. See Press et al., J. Clin. Oncol., 7(3): 1027-1038 (1989); Bernstein et al., Cancer Res. (Suppl.), 50: 1017-1021 (1990); Press et al., Front. Radiat. Ther. Oncol., 24: 204-213 (1990); Press et al., Adv. Exp. Med. Biol., 303: 91-96 (1991) and Brown et al., Nucl. Med. Biol., 24: 657-663 (1997). The antibody, MB-1, is a marine IgG1 monoclonal antibody that lacks Fc effector functions such as antibody-dependent cellular cytotoxicity (ADCC) and MB-1 did not inhibit tumor growth in an in vivo xenograft model unless it had been labeled with an isotope (Buchsbaum et al., Cancer Res., 52(83): 6476-6481 (1992). Favorable biodistribution of $^{131}$I-MB-1 was seen in lymphoma patients who had lower tumor burdens (<1 kg) and therapy of these patients resulted in complete tumor remissions lasting from 4 to 11 months (Press et al., 1989 and Bernstein et al. 1990).

In addition, an immunoconjugate composed of the drug adriamycin linked to G28-1, another anti-CD37 antibody, has been evaluated in mice and showed effects through internalization and intracellular release of the drug. See Braslawsky et al., Cancer Immunol. Immunother., 33(6): 367-374 (1991).

Various groups have investigated the use of anti-CD20 antibodies to treat B-cell related diseases. One treatment consists of anti-CD20 antibodies prepared in the form of radionuclides for treating B-cell lymphoma (e.g., $^{131}$I-labeled anti-CD20 antibody), as well as a $^{89}$Sr-labeled form for the palliation of bone pain caused by prostate and breast cancer metastases [Endo, *Gan To Kagaku Ryoho,* 26: 744-748 (1999)].

Another group developed a chimeric monoclonal antibody specific for CD20, consisting of heavy and light chain variable regions of mouse origin fused to human IgG1 heavy chain and human kappa light chain constant regions. The chimeric antibody reportedly retained the ability to bind to CD20 and the ability to mediate ADCC and to fix complement. See, Liu et al., J. Immunol. 139:3521-26 (1987). Yet another chimeric anti-CD20 antibody was made from IDEC hybridoma C2B8 and was named rituximab. The mechanism of anti-tumor activity of rituximab is thought to be a combination of several activities, including ADCC, complement fixation, and triggering of signals that promote apoptosis in malignant B-cells, although the large size of the chimeric antibody prevents optimal diffusion of the molecule into lymphoid tissues that contain malignant B-cells, thereby limiting its anti-tumor activities. ADCC is a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. Complement fixation, or complement-dependent cytotoxicity (CDC) is the ability of a molecule to lyse a target in the presence of complement. The complement activation pathway is initiated by the binding of the first component of the complement system (C1q) to a molecule (e.g. an antibody) complexed with a cognate antigen. The large size of rituximab prevents optimal diffusion of the molecule into lymphoid tissues that contain malignant B-cells, thereby limiting these anti-tumor activities.

Rituximab, typically administered in 4 weekly infusions, is currently used to treat low-grade or follicular B-cell non-Hodgkin's lymphoma [McLaughlin at al., Oncology, 12: 1763-1777 (1998); Leget et al., Curr. Opin, Onco1., 10: 548-551 (1998)] and in relapsed stage III/IV follicular lymphoma [White et al., Pharm. Sci. Technol. Today, 2: 95-101 (1999)]. Other disorders treatable with rituximab include follicular centre cell lymphoma (FCC), mantle cell lymphoma (MCL), diffuse large cell lymphoma (DLCL), and small lymphocytic lymphoma (SLL) [Nguyen et al., Eur J. Haematol., 62:76-82 (1999)]. Rituximab administered in weekly infusions is also used to treat CLL [Lin et al., Sem Oncol., 30:483-92 (2003)].

Anti-CD20 antibodies have also been used to treat patients suffering from autoimmune diseases associated with B-cell production of autoantibodies. For example, rituximab has demonstrated significant clinical benefit in depleting CD20+ B-cells in patients with multiple autoimmune/inflammatory diseases including RA [Edwards, N Engl J. Med., 350:2546-2548 (2004); Cambridge et al., Arthritis Rheum., 48:2146-54 (2003)]. RA patients received continued doses of methotrexate (MTX) and a 4 dose course of rituximab infusion (Edwards, supra). These patients showed improved American College of Rheumatology (ACR) responses compared to control groups.

In a trial for the treatment of systemic lupus erythematosus (SLE) [Leandro et al., Arthritis Rheum., 46:2673-2677 (2002)], patients were administered two infusions of high dose rituximab, and demonstrated B-cell reduction and improved disease state. In a second study of B-cell reduction in SLE [Looney at al., Arthritis Rheum., 50:2580-2589 (2004)], patients were given a single infusion of 100 mg/m2 (low dose), a single infusion of 375 mg/m2 (intermediate dose), or as 4 infusions (1 week apart) of 375 mg/m2 (high dose) rituximab. These patients demonstrated B-cell reduction and improved disease scores, but the treatment did not alter the level of autoantibody. Trials of rituximab have also been carried out in Waldenstrom's macroglobulinemia [Treon at al., Immunother., 24:272-279 (2000)], where patients showed increased hematocrit (HCT) and platelet (PLT) counts after 4 infusions of rituximab.

Recent reports of rituximab treatment in patients suffering from multiple sclerosis, an autoimmune disease affecting the central nervous system, indicate that a course of treatment depletes peripheral B-cells but has little effect on B-cells in cerebrospinal fluid. See Monson et al., Arch. Neural., 62: 258-264 (2005).

Additional publications concerning the use of rituximab include: Stashi et al. "Rituximab chimeric anti-CD20 monoclonal antibody treatment for adults with chronic idiopathic thrombocytopenic purpura" Blood 98:952-957 (2001); Matthews, R. "Medical Heretics" New Scientist (7 Apr. 2001); Leandro at al. "Clinical outcome in 22 patients with rheumatoid arthritis treated with B lymphocyte depletion" Ann Rheum Dis 61:833-888 (2002); Leandro et al. "Lymphocyte depletion in rheumatoid arthritis: early evidence for safety, efficacy and dose response. Arthritis and Rheumatism 44(9): S370 (2001); Leandro et al. "An open study of B lymphocyte depletion in systemic lupus erythematosus", Arthritis Rheum. 46:2673-2677 (2002); Edwards et al., "Sustained improvement in rheumatoid arthritis following a protocol designed to deplete B lymphocytes" Rheumatology 40:205-211 (2001); Edwards et al. "B-lymphocyte depletion therapy in rheumatoid arthritis and other autoimmune disorders" Biochem. Soc. Trans. 30(4):824-828 (2002); Edwards et al. "Efficacy and safety of rituximab, a B-cell targeted chimeric monoclonal antibody: A randomized, placebo controlled trial in patients with rheumatoid arthritis. Arthritis Rheum. 46: S197 (2002); Levine et al., "1 gM antibody-related polyneuropathies: B-cell depletion chemotherapy using rituximab" Neurology 52: 1701-1704 (1999); DeVita et al. "Efficacy of selective B-cell blockade in the treatment of rheumatoid arthritis" Arthritis Rheum 46:2029-2033 (2002); Hidashida et al. "Treatment of DMARD-Refractory rheumatoid arthritis with rituximab." Presented at the Annual Scientific Meeting of the American College of Rheumatology; October 24-29; New Orleans, La. 2002; Tuscano, J. "Successful treatment of Infliximab-refractory rheumatoid arthritis with rituximab" Presented at the Annual Scientific Meeting of the American College of Rheumatology; October 24-29; New Orleans, La. 2002.

Problems associated with rituximab therapy remain. For example, the majority of cancer patients treated with rituximab relapse, generally within about 6-12 months, and fatal infusion reactions within 24 hours of rituximab infusion have been reported. These fatal reactions followed an infusion reaction complex that included hypoxia, pulmonary infiltrates, acute respiratory distress syndrome, myocardial infarction, ventricular fibrillation or cardiogenic shock. Acute renal failure requiring dialysis with instances of fatal outcome has also been reported in the setting of tumor lysis syndrome following treatment with rituximab, as have severe mucocutaneous reactions, some with fatal outcome. Additionally, high doses of rituximab are required for intravenous injection because the molecule is large, approximately 150 kDa, and, as noted above, diffusion into the lymphoid tissues where many tumor cells reside is limited.

Because normal mature B-cells also express CD37 and CD20, normal B-cells are depleted by anti-CD37 (Press et al., 1989) or anti-CD20 antibody therapy [Reff et al., Blood 83:435-445 (1994)]. After treatment is completed, however, normal B-cells can be regenerated from CD37- and CD20-negative B-cell precursors; therefore, patients treated with anti-CD37 or anti-CD20 therapy do not experience significant immunosuppression.

Monoclonal antibody technology and genetic engineering methods have led to development of immunoglobulin molecules for diagnosis and treatment of human diseases. Protein engineering has been applied to improve the affinity of an antibody for its cognate antigen, to diminish problems related to immunogenicity, and to alter an antibody's effector functions. The domain structure of immunoglobulins is amenable to engineering, in that the antigen binding domains and the domains conferring effector functions may be exchanged between immunoglobulin classes and subclasses. Immunoglobulin structure and function are reviewed, for example, in Harlow et al., Eds., Antibodies: A Laboratory Manual, Chapter 14, Cold Spring Harbor Laboratory, Cold Spring Harbor (1988). An extensive introduction as well as detailed information about all aspects of recombinant antibody technology can be found in the textbook "Recombinant Antibodies" (John Wiley & Sons, NY, 1999). A comprehensive collection of detailed antibody engineering lab Protocols can be found in R. Kontermann and S. Dübel (eds.), "The Antibody Engineering Lab Manual" (Springer Verlag, Heidelberg/New York, 2000).

Recently, smaller immunoglobulin molecules have been constructed to overcome problems associated with whole immunoglobulin therapy. Single chain Fv (scFv) comprise an antibody heavy chain variable domain joined via a short linker peptide to an antibody light chain variable domain [Huston et al., *Proc. Natl. Aced. Sci. USA,* 85: 5879-5883 (1988)]. In addition to variable regions, each of the antibody chains has one or more constant regions. Light chains have a single constant region domain. Thus, light chains have one variable region and one constant region. Heavy chains have several constant region domains. The heavy chains in IgG, IgA, and IgD antibodies have three constant region domains, which are designated CH1, CH2, and CH3, and the heavy chains in IgM and IgE antibodies have four constant region domains, CH1, CH2, CH3 and CH4. Thus, heavy chains have one variable region and three or four constant regions.

The heavy chains of immunoglobulins can also be divided into three functional regions: the Fd region (a fragment comprising V.sub.H and CH1, i.e., the two N-terminal domains of the heavy chain), the hinge region, and the Fc region (the "fragment crystallizable" region, derived from constant regions and formed after pepsin digestion). The Fd region in combination with the light chain forms an Fab (the "fragment antigen-binding"). Because an antigen will react stereochemically with the antigen-binding region at the amino terminus of each Fab the IgG molecule is divalent, i.e., it can bind to two antigen molecules. The Fc contains the domains that interact with immunoglobulin receptors on cells and with the initial elements of the complement cascade. Thus, the Fc fragment is generally considered responsible for the effector functions of an immunoglobulin, such as complement fixation and binding to Fc receptors.

Because of the small size of scFv molecules, they exhibit very rapid clearance from plasma and tissues and more effective penetration into tissues than whole immunoglobulin. An anti-tumor scFv showed more rapid tumor penetration and more even distribution through the tumor mass than the corresponding chimeric antibody [Yokota et al., *Cancer Res.,* 52, 3402-3408 (1992)]. Fusion of an scFv to another molecule, such as a toxin, takes advantage of the specific antigen-binding activity and the small size of an scFv to deliver the toxin to a target tissue. [Chaudary et al., *Nature,* 339:394 (1989); Batra et al., *Mol. Cell. Biol.,* 11:2200 (1991)].

Despite the advantages of scFv molecules, several drawbacks to their use exist. While rapid clearance of scFv may reduce toxic effects in normal cells, such rapid clearance may prevent delivery of a minimum effective dose to the target tissue. Manufacturing adequate amounts of scFv for administration to patients has been challenging due to difficulties in expression and isolation of scFv that adversely affect the yield. During expression, scFv molecules lack stability and often aggregate due to pairing of variable regions from different molecules. Furthermore, production levels of scFv molecules in mammalian expression systems are low, limiting the potential for efficient manufacturing of scFv molecules for therapy [Davis et al, *J Biol. Chem.,* 265:10410-10418 (1990); Traunecker et al., *EMBO J,* 10: 3655-3659 (1991). Strategies for improving production have been explored, including addition of glycosylation sites to the variable regions [Jost, C. R. U.S. Pat. No. 5,888,773, Jost et al, *J. Biol. Chem.,* 69: 26267-26273 (1994)].

Another disadvantage to using scFv for therapy is the lack of effector function. An scFv without the cytolytic functions, ADCC and complement dependent-cytotoxicity (CDC), associated with the constant region of an immunoglobulin may be ineffective for treating disease. Even though development of scFv technology began over 12 years ago, currently no scFv products are approved for therapy.

Alternatively, it has been proposed that fusion of an scFv to another molecule, such as a toxin, could take advantage of the specific antigen-binding activity and the small size of an scFv to deliver the toxin to a target tissue. Chaudary et al., *Nature* 339:394 (1989); Batra et al., *Mol. Cell. Biol.* 11:2200 (1991). Conjugation or fusion of toxins to scFvs has thus been offered as an alternative strategy to provide potent, antigen-specific molecules, but dosing with such conjugates or chimeras can be limited by excessive and/or non-specific toxicity due to the toxin moiety of such preparations. Toxic effects may include supraphysiological elevation of liver enzymes and vascular leak syndrome, and other undesired effects. In addition, immunotoxins are themselves highly immunogenic upon administration to a host, and host antibodies generated against the immunotoxin limit potential usefulness for repeated therapeutic treatments of an individual.

Other engineered fusion proteins, termed small, modular immunopharmaceutical (SMIP™) products, are described in co-owned US Patent Publications 2003/133939., 2003/0118592, and 2005/0136049, and co-owned International Patent Publications WO02/056910, WO2005/037989., and WO2005/017148, which are all incorporated by reference herein. SMIP products are novel binding domain-immunoglobulin fusion proteins that feature a binding domain for a cognate structure such as an antigen, a counterreceptor or the like; an IgG1, IGA or IgE hinge region polypeptide or a mutant IgG1 hinge region polypeptide having either zero, one or two cysteine residues; and immunoglobulin CH2 and CH3 domains. SMIP products are capable of ADCC and/or CDC.

Although there has been extensive research carried out on antibody-based therapies, there remains a need in the art for improved methods to treat diseases associated with aberrant B-cell activity. The methods of the present invention described and claimed herein provide such improved methods as well as other advantages.

SUMMARY OF THE INVENTION

The present invention provides methods for reducing B-cells using CD37-specific binding molecules. In some methods of the invention, use of combinations of CD37-specific binding molecules (one or more CD37-specific binding molecules) and CD20-specific binding molecules (one or more CD20-specific binding molecules) results in increased B-cell reduction. In some of these methods, the combinations are synergistic. In a related aspect, the invention provides a method of treating an individual having, or suspected of having, a disease associated with aberrant B-cell activity.

The present invention also provides humanized CD37-specific binding molecules (e.g., humanized TRU-016 constructs) and methods for reducing B-cells using these molecules. In some embodiments of the methods of the invention, uses of combinations of humanized TRU-016 constructs with one or more CD20-specific binding molecules is contemplated. In another aspect, the invention provides methods of treating individuals having, or suspected of having, a disease associated with aberrant B-cell activity. Related aspects of the invention are drawn to methods of preventing any such disease and methods of ameliorating a symptom associated with such a disease comprising administering a dose of a humanized CD37-specific binding molecule effective to treat or prevent such disease, or to ameliorate a symptom of such disease.

"Aberrant B-cell activity" refers to B-cell activity that deviates from the normal, proper, or expected course. For example, aberrant. B-cell activity may include inappropriate proliferation of cells whose DNA or other cellular components have become damaged or defective. Aberrant B-cell activity may include cell proliferation whose characteristics are associated with a disease caused by, mediated by, or resulting in inappropriately high levels of cell division, inappropriately low levels of apoptosis, or both. Such diseases may be characterized, for example, by single or multiple local abnormal proliferations of cells, groups of cells or tissue(s), whether cancerous or non-cancerous, benign or malignant. Aberrant B-cell activity may also include aberrant antibody production, such as production of autoantibodies, or overproduction of antibodies typically desirable when produced at normal levels. It is contemplated that aberrant B-cell activity may occur in certain subpopulations of B-cells and not in other subpopulations. Aberrant B-cell activity may also include inappropriate stimulation of T-cells, such as by inappropriate B-cell antigen presentation to T-cells or by other pathways involving B-cells.

"Treatment" or "treating" refers to either a therapeutic treatment or prophylactic/preventative treatment. A therapeutic treatment may improve at least one symptom of disease in an individual receiving treatment or may delay worsening of a progressive disease in an individual, or prevent onset of additional associated diseases.

A "therapeutically effective dose" or "effective dose" of a CD20-specific binding molecule refers to that amount of the compound sufficient to result in amelioration of one or more symptoms of the disease being treated. When applied to an individual active ingredient, administered alone, a therapeutically effective dose refers to that ingredient alone. When applied to a combination, a therapeutically effective dose refers to combined amounts of the active ingredients that result in the therapeutic effect, whether administered serially or simultaneously. The invention specifically contemplates that one or more specific binding molecules may be administered according to methods of the invention, each in an effective dose.

"An individual having, or suspected of having, a disease associated with aberrant B-cell activity" is an individual in whom a disease or a symptom of a disorder may be caused by aberrant B-cell activity, may be exacerbated by aberrant B-cell activity, or may be relieved by regulation of B-cell activity. Examples of such diseases are a B-cell cancer (for example, B-cell lymphoma, a B-cell leukemia or a B-cell myeloma), a disease characterized by autoantibody production or a disease characterized by inappropriate T-cell stimulation caused by inappropriate B-cell antigen presentation to T-cells or caused by other pathways involving B-cells.

In one exemplary aspect, an individual treated by methods of the invention demonstrates a response to treatment that is better than, or improved relative to, the response to treatment with rituximab. A response which is improved over treatment with rituximab refers to a clinical response wherein treatment by a method of the invention results in a clinical response in a patient that is better than a clinical response in a patient receiving rituximab therapy, such as rituximab. An improved response is assessed by comparison of clinical criteria well-known in the art and described herein. Exemplary criteria include, but are not limited to, duration of B cell depletion, reduction in B cell numbers overall, reduction in B cell numbers in a biological sample, reduction in tumor size, reduction in the number of tumors, existing and/or appearing after treatment, and improved overall response as assessed by patients themselves and physicians, e.g., using an International Prognostic Index. The improvement may be in one or more than one of the clinical criteria. An improved response with the method of the invention may be due to an inadequate response to previous or current treatment with rituximab, for example, because of toxicity and/or inadequate efficacy of the rituximab treatment.

B-cell cancers include B-cell lymphomas [such as various forms of Hodgkin's disease, non-Hodgkins lymphoma (NHL) or central nervous system lymphomas], leukemias [such as acute lymphoblastic leukemia (ALL), chronic lymphocytic leukemia (CLL), Hairy cell leukemia and chronic myoblastic leukemia] and myelomas (such as multiple myeloma). Additional B cell cancers include small lymphocytic lymphoma, B-cell prolymphocytic leukemia, lymphoplasmacytic lymphoma, splenic marginal zone lymphoma, plasma cell myeloma, solitary plasmacytoma of bone, extraosseous plasmacytoma, extra-nodal marginal zone B-cell lymphoma of mucosa-associated (MALT) lymphoid tissue, nodal marginal zone B-cell lymphoma, follicular lymphoma, mantle cell lymphoma, diffuse large B-cell lymphoma, mediastinal (thymic) large B-cell lymphoma, intravascular large B-cell lymphoma, primary effusion lymphoma, Burkitt lymphoma/leukemia, B-cell proliferations of uncertain malignant potential, lymphomatoid granulomatosis, and post-transplant lymphoproliferative disorder.

Disorders characterized by autoantibody production are often considered autoimmune diseases. Autoimmune diseases include, but are not limited to: arthritis, rheumatoid arthritis, juvenile rheumatoid arthritis, osteoarthritis, polychondritis, psoriatic arthritis, psoriasis, dermatitis, polymyositis/dermatomyositis, inclusion body myositis, inflammatory myositis, toxic epidermal necrolysis, systemic scleroderma and sclerosis, CREST syndrome, responses associated with inflammatory bowel disease, Crohn's disease, ulcerative colitis, respiratory distress syndrome, adult respiratory distress syndrome (ARDS), meningitis, encephalitis, uveitis, colitis, glomerulonephritis, allergic conditions, eczema, asthma, conditions involving infiltration of T cells and chronic inflammatory responses, atherosclerosis, autoimmune myocarditis, leukocyte adhesion deficiency, systemic lupus erythematosus (SLE), subacute cutaneous lupus erythematosus, discoid lupus, lupus myelitis, lupus cerebritis, juvenile onset diabetes, multiple sclerosis, allergic encephalomyelitis, neuromyelitis optica, rheumatic fever, Sydenham's chorea, immune responses associated with acute and delayed hypersensitivity mediated by cytokines and T-lymphocytes, tuberculosis, sarcoidosis, granulomatosis including Wegener's granulomatosis and Churg-Strauss disease, agranulocytosis, vasculitis (including hypersensitivity vasculitis/angiitis, ANCA and rheumatoid vasculitis), aplastic anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopertia, leukopenia, diseases involving leukocyte diapedesis, central nervous system (CNS) inflammatory disorders, multiple organ injury syndrome, myasthenia gravis, antigen-antibody complex mediated diseases, anti-glomerular basement membrane disease, anti-phospholipid antibody syndrome, allergic neuritis, Behcet disease, Castleman's syndrome, Goodpasture's syndrome, Lambert-Eaton Myasthenic Syndrome, Reynaud's syndrome, Sjorgen's syndrome, Stevens-Johnson syndrome, solid organ transplant rejection, graft versus host disease (GVHD), pemphigoid bullous, pemphigus, autoimmune polyendocrinopathies, seronegative spondyloarthropathies, Reiter's disease, stiff-man syndrome, giant cell arteritis, immune complex nephritis, IgA nephropathy, IgM polyneuropathies or IgM mediated neuropathy, idiopathic thrombocytopenic purpura (ITP), thrombotic thrombocytopenic purpura (TTP), Henoch-Schonlein purpura, autoimmune thrombocytopenia, autoimmune disease of the testis and ovary including autoimmune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes also referred to as insulin-dependent diabetes mellitus (IDDM) and Sheehan's syndrome; autoimmune hepatitis, lymphoid interstitial pneumonitis (HIV), bronchiolitis obliterans (non-transplant) vs NSIP, Guillain-Barre' Syndrome, large vessel vasculitis (including polymyalgia rheumatica and giant cell (Takayasu's) arteritis), medium vessel vasculitis (including Kawasaki's disease and polyarteritis nodosa), polyarteritis nodosa (PAN) ankylosing spondylitis, Berger's disease (IgA nephropathy), rapidly progressive glomerulonephritis, primary biliary cirrhosis, Celiac sprue (gluten enteropathy), cryoglobulinemia, cryoglobulinemia associated with hepatitis, amyotrophic lateral sclerosis (ALS), coronary artery disease, familial Mediterranean fever, microscopic polyangiitis, Cogan's syndrome, Whiskott-Aldrich syndrome and thromboangiitis obliterans.

Rheumatoid arthritis (RA) is a chronic disease characterized by inflammation of the joints, leading to swelling, pain, and loss of function. Patients having RA for an extended period usually exhibit progressive joint destruction, deformity, disability and even premature death.

Crohn's disease and a related disease, ulcerative colitis, are the two main disease categories that belong to a group of illnesses called inflammatory bowel disease (IBD). Crohn's disease is a chronic disorder that causes inflammation of the digestive or gastrointestinal (GI) tract. Although it can involve any area of the GI tract from the mouth to the anus, it most commonly affects the small intestine and/or colon. In ulcerative colitis, the GI involvement is limited to the colon.

Crohn's disease may be characterized by antibodies against neutrophil antigens, i.e., the "perinuclear anti-neutrophil antibody" (pANCA), and Saccharomyces cervisiae, i.e. the "anti-Saccharomyces cervisiae antibody" (ASCA). Many patients with ulcerative colitis have the pANCA antibody in their blood, but not the ASCA antibody, while many Crohn's patients exhibit ASCA antibodies, and not pANCA antibodies. One method of evaluating Crohn's disease is using the Crohn's disease Activity Index (CDAI), based on 18 predictor variables scores collected by physicians. CDAI values of 150 and below are associated with quiescent disease; values above that indicate active disease, and values above 450 are seen with extremely severe disease [Best et al., "Development of a Crohn's disease activity index." Gastroenterology 70:439-444 (1976)]. However, since the original study, some researchers use a 'subjective value' of 200 to 250 as an healthy score.

Systemic Lupus Erythematosus (SLE) is an autoimmune disease caused by recurrent injuries to blood vessels in multiple organs, including the kidney, skin, and joints. In patients with SLE, a faulty interaction between T cells and B-cells results in the production of autoantibodies that attack the cell nucleus. There is general agreement that autoantibodies are responsible for SLE, so new therapies that deplete the B-cell lineage, allowing the immune system to reset as new B-cells are generated from precursors, would offer hope for long lasting benefit in SLE patients.

Multiple sclerosis (MS) is also an autoimmune disease. It is characterized by inflammation of the central nervous system and destruction of myelin, which insulates nerve cell fibers in the brain, spinal cord, and body. Although the cause of MS is unknown, it is widely believed that autoimmune T cells are primary contributors to the pathogenesis of the disease. However, high levels of antibodies are present in the cerebral spinal fluid of patients with MS, and some theories predict that the B-cell response leading to antibody production is important for mediating the disease.

Autoimmune thyroid disease results from the production of autoantibodies that either stimulate the thyroid to cause hyperthyroidism (Graves' disease) or destroy the thyroid to cause hypothyroidism (Hashimoto's thyroiditis). Stimulation of the thyroid is caused by autoantibodies that bind and activate the thyroid stimulating hormone (TSH) receptor. Destruction of the thyroid is caused by autoantibodies that react with other thyroid antigens.

Sjogren's syndrome is an autoimmune disease characterized by destruction of the body's moisture-producing glands.

Immune thrombocytopenic purpura (ITP) is caused by autoantibodies that bind to blood platelets and cause their destruction.

Myasthenia Gravis (MG) is a chronic autoimmune neuromuscular disorder characterized by autoantibodies that bind to acetylcholine receptors expressed at neuromuscular junctions leading to weakness of the voluntary muscle groups.

Psoriasis, is characterized by autoimmune inflammation in the skin and also associated with arthritis in 30% of cases, scleroderma, inflammatory bowel disease, including Crohn's disease and ulcerative colitis, Also contemplated is the treatment of idiopathic inflammatory myopathy (IIM), including dermatomyositis (DM) and polymyositis (PM). Inflammatory myopathies have been categorized using a number of classification schemes. Miller's classification schema (Miller, *Rheum Dis Din North Am.* 20:811-826, 1994) identifies 2 idiopathic inflammatory myopathies (IIM), polymyositis (PM) and dermatomyositis (DM).

Polymyositis and dermatomyositis are chronic, debilitating inflammatory diseases that involve muscle and, in the case of DM, skin. These disorders are rare, with a reported annual incidence of approximately 5 to 10 cases per million adults and 0.6 to 3.2 cases per million children per year in the United States (Targoff, *Curr Probl Dermatol.* 1991, 3:131-180). Idiopathic inflammatory myopathy is associated with significant morbidity and mortality, with up to half of affected adults noted to have suffered significant impairment (Gottdiener et al., *Am J. Cardiol.* 1978, 41:1141-49). Miller (*Rheum Dis Clin North Am.* 1994, 20:811-826 and *Arthritis and Allied Conditions*, Ch. 75, Eds. Koopman and Moreland, Lippincott Williams and Wilkins, 2005) sets out five groups of criteria used to diagnose IIM, i.e., Idiopathic Inflammatory Myopathy Criteria (IIMC) assessment, including muscle weakness, muscle biopsy evidence of degeneration, elevation of serum levels of muscle-associated enzymes, electromagnetic triad of myopathy, evidence of rashes in dermatomyositis, and also includes evidence of autoantibodies as a secondary criteria.

IIM associated factors, including muscle-associated enzymes and autoantibodies include, but are not limited to, creatine kinase (CK), lactate dehydrogenase, aldolase, C-reactive protein, aspartate aminotransferase (AST), alanine aminotransferase (ALT), and antinuclear autoantibody (ANA), myositis-specific antibodies (MSA), and antibody to extractable nuclear antigens.

A "binding molecule" according to the invention can be, for example, a protein (a "protein" may be polypeptide or peptide), nucleic acid, carbohydrate, lipid, or small molecule compound that binds to a target. A type of proteinaceous binding molecule contemplated by the invention is an antibody or an antibody fragment that retains binding activity. A binding molecule may be modified according to methods standard in the art to improve its binding affinity, diminish its immunogenicity, alter its effector functions and/or improve its availability in the body of an individual. Such modifications may include, for example, amino acid sequence modifications or expression as a fusion protein. Such fusion proteins are also binding molecules according to the invention. An exemplary binding molecule of the invention is a small modular immunopharmaceutical (SMIP™).

A binding molecule that is "specific" for a target binds to that target with a greater affinity than any other target. For example, a CD37-specific binding molecule binds to CD37 with a greater affinity than to any other target and a CD20-specific binding molecule binds to CD20 with a greater affinity than to any other target. Binding molecules of the invention may have affinities for their targets of a Ka of greater than or equal to about $10^4$ $M^{-1}$, preferably of greater than or equal to about $10^5$ $M^{-1}$, more preferably of greater than or equal to about $10^6$ $M^{-1}$ and still more preferably of greater than or equal to about $10^7$ $M^{-1}$. Affinities of even greater than about $10^7$ $M^{-1}$ are still more preferred, such as affinities equal to or greater than about $10^7$ $M^{-1}$, about $10^8$ $M^{-1}$, and about $10^9$ $M^{-1}$, and about $10^{10}$ $M^{-1}$. Affinities of binding molecules according to the present invention can be readily determined using conventional techniques, for example those described by Scatchard et al., Ann. N.Y. Acad. Sci. 51:660 (1949).

Certain CD37-specific binding molecules contemplated by the invention have affinities for CD37 of about 0.5 to about 10 nM. Certain CD20-specific binding molecules contemplated by the invention have affinities for CD20 of about 1 to about 30 nM.

Another characteristic of certain CD37-binding molecules and CD20-binding molecules contemplated by the invention is they exhibit a half life in circulation of about 7 to about 30 days.

CD37-specific antibodies that characterized the CD37 antigen in the Thrid HLDA Workshop were HD28, G28-1, HH1, BI14, WR17 and F93G6. See, Ling and MacLennan, pp. 302-335 in Leucocyte Typing III. White Cell Differentiation Antigens, Oxford University Press (1987). Other CD37-specific antibodies that have been described include RFB-7, Y29/55, MB-1, M-B371, M-B372 and IPO-24. See, Moldenhaurer, J. Biol., Regul. Homeost. Agents, 14: 281-283 (2000) which states that all these antibodies recognize only one CD37 epitope. Schwartz-Albiez et al., 14: 905-914 (1988) indicates that the epitope is situated in the carbohydrate moiety of CD37. Another CD37-specific antibody is S-B3 (Biosys).

Patents and patent publications describing CD20 antibodies include U.S. Pat. Nos. 5,776,456, 5,736,137, 6,399,061, and 5,843,439, as well as US patent application Nos. US 2002/0197255A1 and US 2003/0021781A1 (Anderson et al.); U.S. Pat. No. 6,455,043B1 and WO00/09160 (Grillo-Lopez, A.); WO00/27428 (Grillo-Lopez and White); WO00/27433 (Grillo-Lopez and Leonard); WO00/44788 (Braslawsky et al.); WO01/10462 (Rastetter, W.); WO01/10461 (Rastetter and White); WO01/10460 (White and Grillo-Lopez); US appln No. US2002/0006404 and WO02/04021 (Hanna and Hariharan); US appln No. US2002/0012665 A1 and WO01/74388 (Hanna, N.); US appln No. US2002/0009444A1, and WO01/80884 (Grillo-Lopez, A.); WO01/97858 (White, C.); US appln No. US2002/0128488A1 and WO02/34790 (Reff, M.);WO02/060955 (Braslawsky et al.);WO02/096948 (Braslawsky et al.); WO02/079255 (Reff and Davies); U.S. Pat. No. 6,171,58681, and WO98/56418 (Lam et al.); WO98/58964 (Raju, S.); WO99/22764 (Raju, S.);WO99/51642, U.S. Pat. Nos. 6,194,551B1, 6,242,195B1, 6,528,624B1 and 6,538,124 (Idusogie et al.); WO00/42072 (Presta, L.); WO00/67796 (Curd et al.); WO01/03734 (Grillo-Lopez et al.); US appln No. US 2002/0004587A1 and WO01/77342 (Miller and Presta); US appln No. US2002/0197256 (Grewal, I.); U.S. Pat. Nos. 6,090,365B1, 6,287,537B1, 6,015,542, 5,843,398, and 5,595,721, (Kaminski et al.); U.S. Pat. Nos. 5,500,362, 5,677,180, 5,721,108, and 6,120,767 (Robinson et al.); U.S. Pat. No. 6,410,391B1 (Raubitschek et al.); U.S. Pat. No. 6,224,866B1 and WO00/20864 (Barbera-Guillem, E.); WO01/13945 (Barbera-Guillem, E.); WO00/67795 (Goldenberg); WO00/74718 (Goldenberg and Hansen); WO00/76542 (Golay et al.); WO01/72333 (Wolin and Rosenblatt); U.S. Pat. No. 6,368,596B1 (Ghetie et al.); US Appin No. US2002/0041847A1, (Goldenberg, D.); US Appln no. US2003/0026801A1 (Weiner and Hartmann); WO02/102312 (Engleman, E.), each of which is expressly incorporated herein by reference. See, also, U.S. Pat. No. 5,849,898 and EP appln No. 330,191 (Seed et al.); U.S. Pat. No. 4,861,579 and EP332,865A2 (Meyer and Weiss); and WO95/03770 (Bhat et al.).

Rituximab has been approved for human clinical use as Rituxan®. Rituxan® is considered to be a CD20-specific binding molecule of the invention.

Small, modular immunopharmaceuticals (SMIPs) are considered to be one type of binding molecules of the invention. Methods for making SMIPs have been described previously in co-owned U.S. application Ser. No. 10/627,556 and US Patent Publ. 20030133939, 20030118592, and 20050136049, which are incorporated herein by reference in their entirety. SMIPs are novel binding domain-immunoglobulin fusion proteins that generally feature a binding domain for a cognate structure such as an antigen, a counterreceptor or the like, an IgG1, IGA or IgE hinge region polypeptide or a mutant IgG1 hinge region polypeptide having either zero, one or two cysteine residues, and immunoglobulin CH2 and CH3 domains. In one embodiment, the binding domain molecule has one or two cysteine (Cys) residues in the hinge region. In a related embodiment, when the binding domain molecule comprises two Cys residues, the first Cys, which is involved in binding between the heavy chain and light chain, is not deleted or substituted with an amino acid.

The binding domain of molecules useful in methods of the invention are contemplated as having one or more binding regions, such as variable light chain and variable heavy chain binding regions derived from one or more immunoglobulin superfamily members, such as an immunoglobulin. These regions, moreover, are typically separated by linker peptides, which may be any linker peptide known in the art to be compatible with domain or region joinder in a binding molecule. Exemplary linkers are linkers based on the $Gly_4Ser$ linker motif, such as $(Gly_4Ser)_n$, where n=1-5. The molecules for use in the methods of the invention also contain sufficient amino acid sequence derived from a constant region of an immunoglobulin to provide an effector function, preferably ADCC and/or CDC. Thus, the molecules will have a sequence derived from a CH2 domain of an immunoglobulin or CH2 and CH3 domains derived from one or more immunoglobulins. SMIPs are capable of ADCC and/or CDC but are compromised in their ability to form disulfide-linked multimers.

The invention includes humanized CD37-specific SMIP polypeptides that exhibit at least 80 percent identity to the polypeptide set forth in SEQ ID NO: 2, wherein the humanized CD37-specific SMIP polypeptide binds CD37. In one aspect, the humanized CD37-specific SMIP polypeptides comprise any amino acid sequence selected from the group consisting of SEQ ID NOS: 6, 8, 10, 12, 14, 16, 18, 20, 22, 24, 26, 28, 30, 32, 34, 36, 38, 40, 42, 44, 46, 48, 50, 52, 54, 56, 58, 60, 80, 82, 84, 86, and 88. In another aspect, the humanized CD37-specific SMIP polypeptides comprise at least one amino acid modification in a complementarity-determining region (CDR) selected from the group consisting of: light chain CDR1, heavy chain CDR1, light chain CDR2, heavy chain CDR2, light chain CDR3, and heavy chain CDR3.

In one embodiment, the invention includes a humanized CD37-specific SMIP polypeptide, wherein CDR1 of the light chain comprises the amino acid sequence of SEQ ID NO: 61 (RASENVYSYLA). The invention also includes a humanized CD37-specific SMIP polypeptide, wherein CDR1 of the light chain comprises the amino acid sequence of SEQ ID NO: 62 (RTSENVYSYLA). The invention further includes a humanized CD37-specific SMIP polypeptide, wherein CDR1 of the heavy chain comprises the amino acid sequence of SEQ ID NO: 63 (GYMNM).

In another embodiment, the invention includes a humanized CD37-specific SMIP polypeptide, wherein CDR2 of the light chain comprises the amino acid sequence of SEQ ID NO: 64 (FAKTLAE). The invention also includes a humanized CD37-specific SMIP polypeptide, wherein CDR2 of the heavy chain comprises the amino acid sequence of SEQ ID NO: 65 (N 1DPYYGGTTTYNRKFKG).

In a further embodiment, the invention includes a humanized CD37-specific SMIP polypeptide, wherein CDR3 of the light chain comprises the amino acid sequence of SEQ ID NO: 66 (QHHSDNPWT). The invention further includes a humanized CD37-specific SMIP polypeptide, wherein CDR3 of the heavy chain comprises the amino acid sequence of SEQ ID NO: 67 (SVGPFDY). The invention further includes a humanized CD37-specific SMIP polypeptide, wherein CDR3 of the heavy chain comprises the amino acid sequence of SEQ ID NO: 68 (SVGPFDS). The invention also includes a humanized CD37-specific SMIP polypeptide, wherein CDR3 of the heavy chain comprises the amino acid sequence of SEQ ID NO: 69 (SVGPMDY).

In another aspect, the invention includes a humanized CD37-specific SMIP polypeptide comprising at least one, at least two, or at least three sequence(s) of the light chain CDR amino acid sequences selected from the group consisting of SEQ ID NOS: 61, 62, 64, and 66. In yet another embodiment, the invention includes a humanized CD37-specific SMIP polypeptide comprising a light chain CDR1 amino acid sequence of SEQ ID NOS: 61 or 62, or a variant thereof in which one or two amino acids of SEQ ID NOS: 61 or 62 has been changed; a light chain CDR2 amino acid sequence of SEQ ID NO: 64, or a variant thereof in which one or two amino acids of SEQ ID NO: 64 has been changed; and a light chain CDR3 amino acid sequence of SEQ ID NO: 66, or a variant thereof in which one or two amino acids of SEQ ID NO: 66 has been changed.

In still another aspect, the invention includes a humanized CD37-specific SMIP polypeptide comprising at least one, at least two, or at least three of the heavy chain CDR amino acid sequences selected from the group consisting of SEQ ID NOS: 63, 65, and 67-69. In a further embodiment, the invention includes a humanized CD37-specific SMIP polypeptide comprising a heavy chain CDR1 amino acid sequence of SEQ ID NO: 63, or a variant thereof in which one or two amino acids of SEQ ID NO: 63 has been changed; a heavy chain CDR2 amino acid sequence of SEQ ID NO: 65, or a variant thereof in which one or two amino acids of SEQ ID NO: 65 has been changed; and a heavy chain CDR3 amino acid sequence selected from the group consisting of SEQ ID NOS: 67-69, or a variant thereof in which one or two amino acids of any one of SEQ ID NOS: 67-69 has been changed.

The invention also includes humanized CD37-specific SMIP polypeptides comprising at least one amino acid modification in a framework region (FR) selected from the group consisting of: light chain FR1, heavy chain FR1, light chain FR2, heavy chain FR2, light chain FR3, heavy chain FR3, light chain FR4, and heavy chain FR4. In one embodiment, the invention includes a humanized CD37-specific SMIP polypeptide, wherein the first framework region (FR1) of the light chain comprises the amino acid sequence of SEQ ID NO: 70 (EIVLTQSPATLSLSPGERATLSC). In another embodiment, the invention includes a humanized CD37-specific SMIP polypeptide, wherein FR1 of the heavy chain comprises the amino acid sequence of SEQ ID NO: 71 (EVQLVQSGAEVKKPGESLKISCKGSGYSFT). In still another embodiment, the invention includes a humanized CD37-specific SMIP polypeptide, wherein FR2 of the light chain comprises the amino acid sequence of SEQ ID NO: 72 (WYQQKPGQAPRLLIY). In a further embodiment, the invention includes a humanized CD37-specific SMIP polypeptide, wherein FR2 of the heavy chain comprises the amino acid sequence of SEQ ID NO: 73 (WVRQMPGKGLEWMG). In yet another embodiment, the invention includes a humanized CD37-specific SMIP polypeptide, wherein FR3 of the light chain comprises the amino acid sequence of SEQ ID NO: 74 (GIPARFSGSGSGTDFTLTISSLEPEDFAVYYC). In yet another embodiment, the invention includes a humanized CD37-specific SMIP polypeptide, wherein FR3 of the heavy chain comprises the amino acid sequence of SEQ ID NO: 75 (QVTISADKSISTAYLQWSSLKASDTAMYYCAR). In yet another embodiment, the invention includes a humanized CD37-specific SMIP polypeptide, wherein FR4 of the light chain comprises the amino acid sequence of SEQ ID NO: 76 (FGQGTKVEIK). In yet another embodiment, the invention includes a humanized CD37-specific SMIP polypeptide, wherein FR4 of the heavy chain comprises the amino acid sequence of SEQ ID NO: 77 (WGQGTLVTVSS). In yet another embodiment, the invention includes a humanized CD37-specific SMIP polypeptide, wherein FR4 of the heavy chain comprises the amino acid sequence of SEQ ID NO: 78 (WGRGTLVTVSS).

The invention further includes humanized CD37-specific SMIP polypeptides comprising at least one, at least two, or at least three sequence(s) of the light chain FR amino acid sequences selected from the group consisting of SEQ ID NOS: 70, 72, 74, and 76. In one embodiment, the invention includes a humanized CD37-specific SMIP polypeptide comprising a light chain FR1 amino acid sequence of SEQ ID NO: 70, or a variant thereof in which one or two amino acids of SEQ ID NO: 70 has been changed; a light chain FR2 amino acid sequence of SEQ ID NO: 72, or a variant thereof in which one or two amino acids of SEQ ID NO: 72 has been changed; a light chain FR3 amino acid sequence of SEQ ID NO: 74, or a variant thereof in which one or two amino acids of SEQ ID NO: 74 has been changed; and a light chain FR4 amino acid sequence of SEQ ID NO: 76, or a variant thereof in which one or two amino acids of SEQ ID NO: 76 has been changed.

In addition, the invention includes humanized CD37-specific SMIP polypeptides comprising at least one, at least two, or at least three sequence(s) of the heavy chain FR amino acid sequences selected from the group consisting of SEQ ID NOS: 71, 73, 75, 77, and 78. In one embodiment, the invention includes a humanized CD37-specific SMIP polypeptide comprising a heavy chain FR1 amino acid sequence of SEQ ID NO: 71, or a variant thereof in which one or two amino acids of SEQ ID NO: 71 has been changed; a heavy chain FR2 amino acid sequence of SEQ ID NO: 73, or a variant thereof in which one or two amino acids of SEQ ID ND: 73 has been changed; a heavy chain FR3 amino acid sequence of SEQ ID ND: 75, or a variant thereof in which one or two amino acids of SEQ ID NO: 75 has been changed; and a heavy chain FR4 amino acid sequence of SEQ ID NOS: 77 or 78, or a variant thereof in which one or two amino acids of SEQ ID NOS: 77 or 78 has been changed.

The invention also includes an isolated nucleic acid molecule comprising a nucleotide sequence encoding a humanized CD37-specific SMIP polypeptide that exhibits at least 80 percent identity to the polypeptide set forth in SEQ ID NO: 2, wherein the humanized CD37-specific SMIP polypeptide binds CD37. Such an isolated nucleic acid molecule may comprise a nucleotide sequence selected from the group consisting of: SEQ ID NOS: 5, 7, 9, 11, 13, 15, 17, 19, 21, 23, 25, 27, 29, 31, 33, 35, 37, 39, 41, 43, 45, 47, 49, 51, 53, 55, 57, 59, 79, 81, 83, 85, and 87. In one embodiment, the invention includes vectors that comprise these nucleic acid molecules and host cells that comprise the vectors.

The invention also includes processes of producing the polypeptides described herein, comprising culturing the host cells under suitable conditions to express the polypeptides, and optionally isolating the polypeptides from the culture.

In yet another aspect, the invention includes compositions comprising the humanized CD37-specific SMIP polypeptides of the invention and a pharmaceutically acceptable carrier.

The invention further includes using the CD37-specific SMIP or CD37-specific binding molecules described herein in any of the methods of the invention. Such methods include the use of any of the CD37-specific SMIP or CD37-specific binding molecule comprising an amino acid sequence selected from the group consisting of SEQ ID NOS: 6, 8, 10, 12, 14, 16, 18, 20, 22, 24, 26, 28, 30, 32, 34, 36, 38, 40, 42, 44, 46, 48, 50, 52, 54, 56, 58, 60, 80, 82, 84, 86, and 88:

In yet another aspect, the invention includes kits for reducing B-cells comprising the compositions of the invention; and protocols for using the kits to reduce B cells. Such kits may further comprise one or more CD20-specific binding molecule(s). The invention contemplates that such a CD20-specific binding molecule is TRU-015.

The invention also includes humanized CD37-specific SMIP polypeptides comprising a CDRI, a CDR2, and a CDR3, that exhibits at least 80 percent identity to the polypeptide set forth in SEQ ID NO: 2. Such CD37-specific SMIP polypeptides may further comprise a human framework domain separating each of CDR1, CDR2, and CDR3.

In another aspect, the invention includes a humanized CD37-specific SMIP polypeptide that exhibits at least 80 percent identity to the polypeptide set forth in SEQ ID NO: 2, wherein the humanized CD37-specific SMIP polypeptide binds CD37 and comprises a hinge region polypeptide comprising an amino acid sequence selected from the group consisting of SEQ ID NOS: 90, 92, 94, 96, 98, 100, 102, 104, 106, 108 110, 112, 114, 115, 116, 118, 120, 122, 124, 126 and 127.

The invention also contemplates a humanized CD37-specific SMIP polypeptide that exhibits at least 80 percent identity to the polypeptide set forth in SEQ ID NO: 2, wherein the humanized CD37-specific SMIP polypeptide binds CD37 and comprises a linker comprising $(Gly_4Ser)_n$, wherein n is 1, 2, 3, 4, 5, or 6.

In still a further aspect, the invention includes a humanized CD37-specific SMIP polypeptide, wherein CDR1 of the light chain comprises the amino acid sequence selected from the group consisting of SEQ ID NOS: 128 (RTSQNVYSYLA), 129 (RTSESVYSYLA), 130 (RASQSVYSYLA), 131 (RASQSVYSYLA) and 132 (RASQSVSYYLA). In another embodiment, the invention includes a humanized CD37-specific SMIP polypeptide, wherein CDR1 of the heavy chain comprises the amino acid sequence selected from the group consisting of SEQ ID NOS: 133 (SYMNM) and 134 (SYWIG). In a further embodiment, the invention includes a humanized CD37-specific SMIP polypeptide, wherein CDR2 of the light chain comprises the amino acid sequence selected from the group consisting of SEQ ID NOS: 135 (AASSLQS), 136 (GASTRAT) and 137 (DASNRAT). In still another embodiment, the invention includes a humanized CD37-specific SMIP polypeptide, wherein CDR2 of the heavy chain comprises the amino acid sequence selected from the group consisting of SEQ ID NOS: 138 (IIYPGDSDTRYSPSFQG) and 139 (RIDPSDSYTNYSPSFQG).

The invention also includes a humanized CD37-specific SNP polypeptide, wherein CDR3 of the light chain comprises the amino acid sequence of SEQ ID NO: 220 (QHHSDNPWT). In another embodiment, the invention includes a humanized CD37-specific SMIP polypeptide, wherein CDR3 of the heavy chain comprises the amino acid sequence selected from the group consisting of SEQ ID NOS: 211 (SVGPMDY), 212 (SVGPFDY), 213 (SVGPMDV), 214 (SVGPFDS), 215 (SVGPFDP), 216 (SVGPFQH), 217 (SVGPFDV), 218 (SVGPFD1) and 219 (SVGPFDL).

In still a further aspect, the invention includes CD37-specific SMIP polypeptides with alternative framework regions. in one aspect, the invention includes a humanized CD37-specific SMIP polypeptide, wherein FR1 of the light chain comprises the amino acid sequence selected from the group consisting of SEQ ID NOS: 170-181. In another aspect, the invention includes a humanized CD37-specific SMIP polypeptide, wherein FR1 of the heavy chain comprises the amino acid sequence selected from the group consisting of SEQ ID NOS: 140-146. In a still further aspect, the invention includes a humanized CD37-specific SMIP polypeptide, wherein FR2 of the light chain comprises the amino acid sequence selected from the group consisting of SEQ ID NOS: 182-193. In yet another aspect, the invention includes a humanized CD37-specific SMIP polypeptide, wherein FR2 of the heavy chain comprises the amino acid sequence selected from the group consisting of SEQ ID NOS: 147-153. In an additional aspect, the invention includes a humanized CD37-specific SMIP polypeptide, wherein FR3 of the light chain comprises the amino acid sequence selected from the group consisting of SEQ ID NOS: 194-205. In yet another aspect, the invention includes a humanized CD37-specific SMIP polypeptide, wherein FR3 of the heavy chain comprises the amino acid sequence selected from the group consisting of SEQ ID NOS: 154-160. In a further aspect, the invention includes a humanized CD37-specific SMIP polypeptide, wherein FR4 of the light chain comprises the amino acid sequence selected from the group consisting of SEQ ID NOS: 206-210. In yet another aspect, the invention includes a humanized CD37-specific SMIP polypeptide, wherein FR4 of the heavy chain comprises the amino acid sequence selected from the group consisting of SEQ ID NOS: 161-169.

Exemplary CD37-specific SMIPs useful in the invention include, but are not limited to: G28-1 scFv (SSS-S)H WCH2 WCH3, consists of a G28-1 single chain Fv in which all three cysteine residues in the connection or hinge regions are mutated to serine residues, and wild type CH2 and CH3 domains; G28-1 scFv IgAH WCH2 WCH3, comprising an IgA hinge and WT IgG1 domains; 028-1 scFv VHL11S (SSS-S)H WCH2 CH3 in which all three cysteine residues in the connection or hinge regions are mutated to serine residues and the leucine at position 11 of the heavy chain variable region is substituted with a serine; G28-1 scFv VH L11S(CSS-S)H WCH2 CH3, in which cysteine residues were substituted at the second and third positions with serine; G28-1 scFv VHL11S(CSC-S)H WCH2 CH3, in which cysteine residues were substituted at the second position with serine; G28-1 scFv VH11S(SSC-P)H WCH2 WCH3 (referred to as TRU-016 herein), in which the first and second cysteine residues in the connection or hinge regions are mutated to serine residues and the leucine at position 11 of the heavy chain variable region is substituted with a serine; G28-1 scFv VH11S(SCS-S)H WCH2 WCH3, in which the first and third cysteine residues in the hinge regions are mutated to serine residues; 028-1 scFv VHL11S (CCS-P)H WCH2 WCH3, in which the third cysteine residue in the hinge region is substituted with a serine; G28-1scFv VHL11S(SCC-P)H WCH2 WCH3, in which the first cysteine is substituted with a serine; 028-1 scFv VH L11S mIgE CH2 CH3 CH4, comprising mouse IgE CH 2-4 regions in which the leucine at position 11 of the heavy chain variable region is substituted with a serine; G28-1 scFv VH LI 1S mIgA WIgACH2 T4-CH3, comprising a mouse IgA hinge with a wild type IgA CH2 and a truncated IgA CH3 domain lacking the 4 carboxy amino acids GTCY; G28-1 scFv VHL11S hIgE CH2 CH3 CH4, comprising IgE CH regions in which the leucine at position 11 of the heavy chain variable region is substituted with a serine; and G28-1 scFv VHL11S hIgAH WIgACH2 TCH3, comprising an IgA hinge, a wild type IgA CH2 and a truncated IgA CH2 and a truncated IgA CH3 domain lacking the 4 carboxy amino acids GTCY.

Exemplary CD20-specific SMIPs useful in the invention include SMIPs derived from the anti-CD20 monoclonal antibody 2H7 described in US Patent Publ. 2003133939. and 20030118592. The SMIPs include 2H7scFv-Ig or a derivative thereof. Derivatives includes CytoxB-MHWTG1C, which has a human IgG1 Fc domain and a mutant IgG1 hinge domain; CytoxB-MHMG1C, which comprises a mutated Fc domain; MG1H/MG1C, which comprises an Fc receptor with a mutated leucine residue 234; CytoxB-IgAHWTHG1C, comprising a portion of the human IgA hinge fused to wild-type human Fc domain; 2H7 scFv-llama IgG1, comprising the llama IgG1 hinge and CH2CH3 regions, 2H7 scFv-llama IgG2, comprising the llama IgG2 hinge and CH2CH3 regions; 2H7 scFv-llama IgG3, comprising the llama IgG3 hinge and CH2CH3 regions.

2H7 scFv MTH(SSS) WTCH2CH3, in which all three cysteine residues in the connection or hinge regions are mutated to serine residues, and wild type CH2 and CH3 domains; 2H7 scFv MTH(SSC), in which the first two cysteine residues were substituted with serine residues; 2H7 scFv MTH(SCS), in which the first and third cysteines were substituted with serine residues; 2H7 scFv MTH(CSS) WTCH2CH3, in which cysteine residues were substituted at the second and third positions with serine; 2H7 scFv VH11SER IgG MTH(SSS) WTCH2CH3, in which the leucine at position 11 in the heavy chain variable region is substituted with serine; 2H7 scFv IgA hinge-IgG1 CH2-CH3, comprising an IgA hinge region and WT IgG1 domains; 2H7 scFv IgA hinge-CH2-CH3, comprising IgA hinge, CH2-3 regions; 2H7 IgAWH IgACH2-T4-CH3, comprising an IgA hinge, a wild type IgA CH2 and a truncated IgA CH3 domain lacking the 4 carboxy amino acids GTCY.

Derivatives with mutations in the IgG CH3 region include 2H7 scFv MTH WTCH2 MTCH3 Y405, in which phenylalanine residue at position 405 (numbering according to Kabat et al. supra) was substituted with tyrosine; 2H7 scFv MTH WTCH2 MTCH3 A405, in which phenylalanine position at 405 was substituted with an alanine; scFv MTH WTCH2 MTCH3 A407, in which tyrosine residue at position 407 was substituted with an alanine; scFv MTH WTCH2 MTCH3 Y405A407, comprising the two mutations; and scFv MTH WTCH2 MTCH3 A405A407 comprising two mutations.

2H7 scFv MTH(CCS) WTCH2CH3 is a construct with the third cysteine residue in the IgG1 hinge region substituted with a serine residue. The 2H7 scFv IgG MTH (555)

MTCH2WTCH3 SMIP comprises mutant hinge (MT (55S)) and a mutant CH2 domain in which the proline at residue 238 (according to Ward et al.) was substituted with a serine.

2H7scFv-Ig derivatives also include 2H7 scFv mutants with point mutations in the variable heavy chain region. The following constructs all comprise mutations in which the leucine at position 11 in the heavy chain variable region is substituted with serine: 2H7 scFv VH11SER IgG MTH (SSS-S) WTCH2CH3, 2H7scFv VHL11S(CSS-S)H WCH2 WCH3, comprising a mutated hinge region as set out above; 2H7scFv VHL115 (CSC-5) H WCH2 WCH3 comprising a mutated hinge region as set out above; 2H7 scFv VHL115 IgAH IgACH2 T4-CH3, comprises the IgA hinge, WT IgA CH2 and truncated IgA CH3; 2H7 scFv VHL11S IgECH2 CH3 CH4, comprising the IgE CH 2-4 regions; 2H7 VHL115 scFv (SSS-S) 1gECH3CH4, comprising a mutated hinge region and IgE CH3 and CH4 regions; 2H7 scFv VH L11S mlgE CH2 CH3 CH4, comprises mouse IgE regions; 2H7 scFv VH L11S mIgAH WIGACH2 T4-CH3 comprises the mutations described above and a mouse IgA constant region consisting of a wild type CH2 region and a mutated CH3 region; 2H7 scFv VH L115 (55S-5) H K3225 CH2 WCH3 comprises a mutation in the human IgG1 CH2 region at residue 322, where lysine was changed to serine; 2H7 scFv VH L11S(CSS-S)H K3225 CH2 WCH3 comprises a mutated hinge region as described above, and a mutated CH2 region as previously described; 2H7 scFv VH L11S (SSS-S)H P331S CH2 WCH3, comprises a mutated hinge region as described above, and a mutated CH2 region in which praline at residue 331 was changed to a serine; 2H7 scFv VH L11S(CSS-S)H P331S CH2 WCH3 comprises a mutated hinge region and a praline to serine mutation at residue 331 in the CH2 region; 2H7 scFv VH L11S(SSS-S)H T256N CH2 WCH3, comprises a mutated hinge region and a threonine to asparagine mutation at residue 256 in the CH2 region; 2H7 scFv VH L11S(SSS-S)H RTPE/QNAK (255-258) CH2 WCH3, comprises a mutated hinge region and a series of mutations in which residues 255-258 have been mutated from arginine, threonine, praline, glutamic acid to glutamine, asparagines, alanine and lysine, respectively; 2H7 scFv VH L11S(SSS-S)H K290Q CH2 WCH3, comprises a mutated hinge regions and a lysine to glutamine change at position 290; 2H7 scFv VH L11S(SSS-S)H A339P CH2 WCH3, comprises a mutated hinge region and an alanine to praline change at position 339; SMIP 2H7 scFv (SSS-S)H P238SCH2 WCH3, comprises a mutated hinge region and an proline to serine change at position 238 in CH2, which is the same as 2H7 scFv IgG MTH(SSS) MTCH2WTCH3. 2H7 scFv IgAH IGAHCH2 TI8CH3 comprises a wild type IgA hinge and CH2 region and a CH3 region with an 18 amino acid truncation at the carboxy end.

A binding molecule of the invention may comprise a native or engineered extracellular domain from another protein which improves the binding molecule activity. In one embodiment, the extracellular domain is selected from the group consisting of CD154 and CTLA4.

A "synergistic combination" of CD37-specific binding molecules and CD20-specific binding molecules is a combination that has an effect that is greater than the sum of the effects of the binding molecules when administered alone.

In one aspect of the invention, the binding molecules are administered in one or more pharmaceutical compositions. To administer the binding molecules to human or test animals, it is preferable to formulate the binding molecules in a composition comprising one or more pharmaceutically acceptable carriers. The phrase "pharmaceutically or pharmacologically acceptable" refer to molecular entities and compositions that do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like.

In addition, compounds may form solvates with water or common organic solvents. Such solvates are contemplated as well.

The binding molecule compositions may be administered orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramusclar, intramammary, intraperitoneal, intrathecal, retrobulbar, intrapulmonary injection and or surgical implantation at a particular site is contemplated as well. Generally, compositions are essentially free of pyrogens, as well as other impurities that could be harmful to the recipient. Injection, especially intravenous, is preferred.

Pharmaceutical compositions of the present invention containing binding molecules used in a method of the invention may contain pharmaceutically acceptable carriers or additives depending on the route of administration. Examples of such carriers or additives include water, a pharmaceutical acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, glycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof, as appropriate, depending on the dosage form of the present invention.

Formulation of the pharmaceutical composition will vary according to the route of administration selected (e.g., solution, emulsion). An appropriate composition comprising the antibody to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers.

A variety of aqueous carriers, e.g., water, buffered water, 0.4% saline, 0.3% glycine, or aqueous suspensions may contain the active compound in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate.

The binding molecule compositions can be lyophilized for storage and reconstituted in a suitable carrier prior to use. This technique has been shown to be effective with conventional immunoglobulins. Any suitable lyophilization and reconstitution techniques can be employed. It will be appreciated by those skilled in the art that lyophilization and reconstitution can lead to varying degrees of antibody activity loss and that use levels may have to be adjusted to compensate.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above.

The concentration of binding molecule in these formulations can vary widely, for example from less than about 0.5%, usually at or at least about 1% to as much as 15 or 20% by weight and will be selected primarily based on fluid volumes, viscosities, etc., in accordance with the particular mode of administration selected. Thus, a typical pharmaceutical composition for parenteral injection could be made up to contain 1 mL sterile buffered water, and 50 mg of antibody. A typical composition for intravenous infusion could be made up to contain 250 mL of sterile Ringer's solution, and 150 mg of antibody. Actual methods for preparing parenterally administrable compositions will be known or apparent to those skilled in the art and are described in more detail in, for example, Remington's Pharmaceutical Science, 15th ed., Mack Publishing Company, Easton, Pa. (1980). An effective dosage of antibody is within the range of 0.01 mg to 1000 mg per kg of body weight per administration.

The pharmaceutical compositions may be in the form of a sterile injectable aqueous, oleaginous suspension, dispersions or sterile powders for the extemporaneous preparation of sterile injectable solutions or dispersions. The suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane dial. The carrier can be a solvent or dispersion medium containing, for example, water, ethanol, polyol (for example, glycerol, propylene glycol, and liquid polyethylene glycol, and the like), suitable mixtures thereof, vegetable oils, Ringer's solution and isotonic sodium chloride solution, In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

In all cases the form must be sterile and must be fluid to the extent that easy syringability exists. The proper fluidity can be maintained, for example, by the use of a coating, such as lecithin, by the maintenance of the required particle size in the case of dispersion and by the use of surfactants. It must be stable under the conditions of manufacture and storage and must be preserved against the contaminating action of microorganisms, such as bacteria and fungi. The prevention of the action of microorganisms can be brought about by various antibacterial an antifungal agents, for example, parabens, chlorobutanol, phenol, sorbic acid, thimerosal, and the like. In many cases, it will be desirable to include isotonic agents, for example, sugars or sodium chloride. Prolonged absorption of the injectable compositions can be brought about by the use in the compositions of agents delaying absorption, for example, aluminum monostearate and gelatin.

Compositions useful for administration may be formulated with uptake or absorption enhancers to increase their efficacy. Such enhancers include for example, salicylate, glycocholateilinoleate, glycholate, aprotinin, bacitracin, SDS, caprate and the like. See, e.g., Fix (*J. Pharm. Sci.,* 85:1282-1285, 1996) and Oliyai and Stella (*Ann. Rev. Pharmacol. Toxicol.,* 32:521-544, 1993).

In addition, the properties of hydrophilicity and hydrophobicity of the compositions contemplated for use in the invention are well balanced, thereby enhancing their utility for both in vitro and especially in vivo uses, while other compositions lacking such balance are of substantially less utility. Specifically, compositions contemplated for use in the invention have an appropriate degree of solubility in aqueous media which permits absorption and bioavailability in the body, while also having a degree of solubility in lipids which permits the compounds to traverse the cell membrane to a putative site of action. Thus, antibody compositions contemplated are maximally effective when they can be delivered to the site of target antigen activity.

In one aspect, methods of the invention include a step of administration of a binding molecule composition.

Methods of the invention are performed using any medically-accepted means for introducing a therapeutic directly or indirectly into a mammalian individual, including but not limited to injections, oral ingestion, intranasal, topical, transdermal, parenteral, inhalation spray, vaginal, or rectal administration. The term parenteral as used herein includes subcutaneous, intravenous, intramuscular, and intracisternal injections, as well as catheter or infusion techniques. Administration by, intradermal, intramammary, intraperitoneal, intrathecal, retrobulbar, intrapulmonary injection and or surgical implantation at a particular site is contemplated as well.

In one embodiment, administration is performed at the site of a cancer or affected tissue needing treatment by direct injection into the site or via a sustained delivery or sustained release mechanism, which can deliver the formulation internally. For example, biodegradable microspheres or capsules or other biodegradable polymer configurations capable of sustained delivery of a composition (e.g., a soluble polypeptide, antibody, or small molecule) can be included in the formulations of the invention implanted near the cancer.

Therapeutic compositions may also be delivered to the patient at multiple sites. The multiple administrations may be rendered simultaneously or may be administered over a period of time. In certain cases it is beneficial to provide a continuous flow of the therapeutic composition. Additional therapy may be administered on a period basis, for example, hourly, daily, weekly or monthly.

Binding molecule compositions of the invention may comprise one, or may comprise more than one, binding molecules. Also contemplated by the present invention is the administration of binding molecule compositions in conjunction with a second agent, Second agents contemplated by the invention are listed in paragraphs below.

A second agent may be a B-cell-associated molecule. Other B-cell-associated molecules contemplated by the invention include binding molecules which bind to B-cell surface molecules that are not CD37 or CD20. B-cell-associated molecules, include but are not limited to, CD19 (B-lymphocyte antigen CD19, also referred to as B-lymphocyte surface antigen B4, or Leu-12), CD21, CD22 (B-cell receptor CD22, also referred to as Leu-14, B-lymphocyte cell adhesion molecule, or BL-CAM), CD23, CD40 (B-cell surface antigen CD40, also referred to as Tumor Necrosis Factor receptor superfamily member 5, CD40L receptor, or Bp50), CD80 (T lymphocyte activation antigen CD80, also referred to as Activation 37-1 antigen, B7, B7-1, or BB1), CD86 (T lymphocyte activation antigen CD86, also referred to as Activation B7-2 antigen, B70, FUN-1, or BU63), CD137 (also referred to as Tumor Necrosis Factor receptor superfamily member 9), CD152 (also referred to as cytotoxic T-lymphocyte protein 4 or CTLA-4), L6 (Tumor-associated antigen L6, also referred to as Transmembrane 4 superfamily member 1, Membrane component surface marker 1, or M3S1), CD30 (lymphocyte activation antigen CD30, also referred to as Tumor Necrosis Factor receptor superfamily member 8, CD30L receptor, or Ki-1), CD50 (also referred to as Intercellular adhesion molecule-3 (ICAM3), or ICAM-R), CD54 (also referred to as Intercellular adhesion molecule-1 (ICAMI), or Major group rhinovirus receptor), 37-H1 (ligand for an immunoinhibitory receptor expressed by activated T cells, B-cells, and myeloid cells, also referred to as PD-L1; see Dong, et al., "B7-H1, a third member of the B7 family, co-stimulates T-cell proliferation and interleukin-10 secretion," *Nat. Med.,* 5:1365-1369 (1999), CD134 (also referred to as Tumor Necrosis Factor receptor superfamily member 4, OX40, OX4OL receptor, ACT35 antigen, or TAX-transcriptionally activated glycoprotein 1 receptor), 41 BB (4-1 BB ligand receptor, T-cell antigen 4-1 BB, or T-cell antigen ILA), CD153 (also referred to as Tumor Necrosis Factor ligand superfamily member 8, CD30 ligand, or CD3O-L), CD154 (also referred to as Tumor Necrosis Factor ligand superfamily member 5, TNF-related activation protein, TRAP, or T cell antigen Gp39) and Toll receptors. The above list of construct targets and/or target antigens is exemplary only and is not exhaustive.

Cytokines and growth factors are second agents contemplated by the invention and include, without limitation, one or more of TNF, 1L-1, IL-2, IL-3, 1L-4, 1L-5, IL-6, IL-7, IL-8, IL-9, IL-10, IL-11, 1L-12, IL-13, IL-14, 1L-15, IL-16, 1L-17,1L-18, IFN, G-CSF, Meg-CSF, GM-CSF, thrombopoietin, stem cell factor, and erythropoietin. Pharmaceutical compositions in accordance with the invention may also include other known angiopoietins, for example Ang-1, Ang-2, Ang-4, Ang-Y, and/or the human angiopoietin-like polypeptide, and/or vascular endothelial growth factor (VEGF). Growth factors for use in pharmaceutical compositions of the invention include angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor a, cytokine-induced neutrophil chemotactic factor 1, cytokine-induced neutrophil chemotactic factor 2α, cytokine-induced neutrophil chemotactic factor 2β, β endothelial cell growth factor, endothelin 1, epidermal growth factor, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor acidic, fibroblast growth factor basic, glial cell line-derived neutrophic factor receptor α1, glial cell line-derived neutrophic factor receptor α2, growth related protein, growth related protein a, growth-related protein β, growth related protein γ, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor a, nerve growth factor, nerve growth factor receptor, neurotrophin-3, neurotrophin-4, placenta growth factor, placenta growth factor 2, platelet derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor a, platelet derived growth factor receptor β, pre-B cell growth stimulating factor, stem cell factor, stem cell factor receptor, transforming growth factor a, transforming growth factor β, transforming growth factor β1, transforming growth factor β1.2, transforming growth factor β2, transforming growth factor β3, transforming growth factor β5, latent transforming growth factor β1, transforming growth factor β binding protein I, transforming growth factor β binding protein II, transforming growth factor β binding protein III, tumor necrosis factor receptor type I, tumor necrosis factor receptor type 11, urokinase-type plasminogen activator receptor, vascular endothelial growth factor, and chimeric proteins and biologically or immunologically active fragments thereof.

Examples of chemotherapeutic agents contemplated as second agents include, but are not limited to, alkylating agents, such as nitrogen mustards (e.g., mechlorethamine, cyclophosphamide, ifosfamide, melphalan, and chlorambucil); nitrosoureas (e.g., carmustine (BCNU), lomustine (CCNU), and semustine (methyl-CCNU)); ethyleneimines and methyl-melamines (e.g., triethylenemelamine (TEM), triethylene thiophosphoramide (thiotepa), and hexamethylmelamine (HMM, altretamine)); alkyl sulfonates (e.g., buslfan); and triazines (e.g., dacabazine (DTIC)); antimetabolites, such as folic acid analogs (e.g., methotrexate, trimetrexate, and pemetrexed (multi-targeted antifolate)); pyrimidine analogs (such as 5-fluorouracil (5-FU), fluorodeoxyuridine, gemcitabine, cytosine arabinoside (AraC, cytarabine), 5-azacylidine, and 2,2'-difluorodeoxycytidine); and purine analogs (e.g., 6-mercaptopurine, 6-thioguanine, azathioprine, 2'-deoxycoformycin (pentostatin), erythrohydroxynonyiadenine (EHNA), fludarabine phosphate, 2-chlorodeoxyadenosine (cladribine, 2-CdA)); Type 1 topoisomerase inhibitors such as camptothecin (CPT), topotecan, and irinotecan; natural products, such as epipodophylotoxins (e.g., etoposide and teniposide); and vinca alkaloids (e.g., vinblastine, vincristine, and vinorelbine); anti-tumor antibiotics such as actinomycin D, doxorubicin, and bieomycin; radiosensitizers such as 5-bromodeozyuridine, 5-iododeoxyuridine, and bromodeoxycytidine; platinum coordination complexes such as cisplatin, carboplatin, and oxaliplatin; substituted ureas, such as hydroxyurea; and methylhydrazine derivatives such as N-methylhydrazine (MIH) and procarbazine.

Non-limiting examples of chemotherapeutic agents, radiotherapeutic agents and other active and ancillary agents are also shown in Table 1.

TABLE 1

| |
|---|
| Alkylating agents |
| Nitrogen mustards |
| Mechlorethamine |
| Cyclophosphamide |
| ifosfamide |
| melphalan |
| chlorambucil |
| Nitrosoureas |
| carmustine (BCNU) |
| lomustine (CCNU) |
| semustine (methyl-CCNU) |
| Ethylenemine/Methyl-melamine |
| thriethylenemelamine (TEM) |
| triethylene thiophosphoramide (thiotepa) |
| hexamethylmelamine (HMM, altretamine) |
| Alkyl sulfonates |
| busulfan |
| Triazines |
| dacarbazine (DTIC) |
| Antimetabolites |
| Folic Acid analogs |
| methotrexate |
| Trimetrexate |
| Pemetrexed (Multi-targeted antifolate) |
| Pyrimidine analogs |
| 5-fluorouracil |
| fluorodeoxyuridine |
| gemcitabine |
| cytosine arabinoside (AraC, cytarabine) |
| 5-azacytidine |
| 2,2'-difluorodeoxy-cytidine |
| Purine analogs |
| 6-mercaptopurine |
| 6-thioguanine |
| azathioprine |
| 2'-deoxycoformycin (pentostatin) |
| erythrohydroxynonyl-adenine (EHNA) |
| fludarabine phosphate |
| 2-chlorodeoxyadenosine (cladribine, 2-CdA) |
| Type I Topoisomerase Inhibitors |
| camptothecin |
| topotecan |
| irinotecan |
| Biological response modifiers |
| G-CSF |
| GM-CSF |
| Differentiation Agents |
| retinoic acid derivatives |
| Hormones and antagonists |
| Adrenocorticosteroids/antagonists |
| prednisone and equivalents |
| dexamethasone |
| ainoglutethimide |
| Progestins |
| hydroxyprogesterone caproate |
| medroxyprogesterone acetate |
| megestrol acetate |
| Estrogens |
| diethylstilbestrol |
| ethynyl estradiol/equivalents |

TABLE 1-continued

| |
|---|
| Antiestrogen |
| tamoxifen |
| Androgens |
| testosterone propionate |
| fluoxymesterone/equivalents |
| Antiandrogens |
| flutamide |
| gonadotropin-releasing |
| hormone analogs |
| Leuprolide |
| Nonsteroidal antiandrooens |
| flutamide |
| Natural products |
| Antimitotic drugs |
| Taxanes |
| paclitaxel |
| Vinca alkaloids |
| vinblastine (VLB) |
| vincristine |
| vinorelbine |
| Taxotere ® (docetaxel) |
| estramustine |
| estramustine phosphate |
| Epipodophylotoxins |
| etoposide |
| teniposide |
| Antibiotics |
| actimomycin D |
| daunomycin (rubido-mycin) |
| doxorubicin (adria-mycin) |
| mitoxantroneidarubicin |
| bleomycin |
| splicamycin (mithramycin) |
| mitomycinC |
| dactinomycin |
| aphidicolin |
| Enzymes |
| L-asparaginase |
| L-arginase |
| Radiosensitizers |
| metronidazole |
| misonidazole |
| desmethylmisonidazole |
| pimonidazole |
| etanidazole |
| nimorazole |
| RSU 1069 |
| EO9 |
| RB 6145 |
| SR4233 |
| nicotinamide |
| 5-bromodeozyuridine |
| 5-iododeoxyuridine |
| bromodeoxycytidine |
| Miscellaneous agents |
| Platinium coordination complexes |
| cisplatin |
| Carboplatin |
| oxaliplatin |
| Anthracenedione |
| mitoxantrone |
| Substituted urea |
| hydroxyurea |
| Methylhydrazine derivatives |
| N-methylhydrazine (MIH) |
| procarbazine |

TABLE 1-continued

| |
|---|
| Adrenocortical suppressant |
| mitotane (o,p'-DDD) |
| ainoglutethimide |
| Cytokines |
| interferon (a, β, γ) |
| interleukin-2 |
| Photosensitizers |
| hematoporphyrin derivatives |
| Photofrin ® |
| benzoporphyrin derivatives |
| Npe6 |
| tin etioporphyrin (SnET2) |
| pheoboride-a |
| bacteriochlorophyll-a |
| naphthalocyanines |
| phthalocyanines |
| zinc phthalocyanines |
| Radiation |
| X-ray |
| ultraviolet light |
| gamma radiation |
| visible light |
| infrared radiation |
| microwave radiation |

Second agents glucocorticoids, the invention for treatment of autoimmune diseases are referred to as immunosuppressive agents, which act to suppress or mask the immune system of the individual being treated. Immunosuppressive agents include, for example, non-steroidal anti-inflammatory drugs (NSAIDs), analgesics, glucocorticoids, disease-modifying antirheumatic drugs (DMARDs) for the treatment of arthritis, or biologic response modifiers. Compositions in the DMARD description are also useful in the treatment of many other autoimmune diseases aside from RA.

Exemplary NSAIDs are chosen from the group consisting of ibuprofen, naproxen, naproxen sodium, Cox-2 inhibitors such as VIOXX® (rofecoxib) and CELEBREX® (celecoxib), and sialylates. Exemplary analgesics are chosen from the group consisting of acetaminophen, oxycodone, tramadol and proporxyphene hydrochloride. Exemplary glucocorticoids are chosen from the group consisting of cortisone, dexamethasone, hydrocortisone, methylprednisolone, prednisolone, or prednisone. Exemplary biological response modifiers include, but are not limited to, molecules directed against cell surface markers (e.g., CD4, CD5, etc.), cytokine inhibitors, such as the TNF antagonists (e.g. etanercept (ENBREL®), adalimumab (HUMIRA®) and infliximab (REMICADE®)), chemokine inhibitors and adhesion molecule inhibitors. The biological response modifiers include monoclonal antibodies as well as recombinant forms of molecules. Exemplary DMARDs include, but are not limited to, azathioprine, cyclophosphamide, cyclosporine, methotrexate, penicillamine, leflunomide, sulfasalazine, hydroxychloroquine, Gold [oral (auranofin) and intramuscular] and minocycline.

It is contemplated the binding molecule composition and the second agent may be given simultaneously in the same formulation. Alternatively, the agents are administered in a separate formulation but concurrently, with concurrently referring to agents given within 30 minutes of each other.

In another aspect, the second agent is administered prior to administration of the binding molecule composition. Prior administration refers to administration of the second agent within the range of one week prior to treatment with the antibody, up to 30 minutes before administration of the antibody. It is further contemplated that the second agent is administered subsequent to administration of the binding molecule composition. Subsequent administration is meant to describe administration from 30 minutes after antibody treatment up to one week after antibody administration.

It is further contemplated that when the binding molecule is administered in combination with a second agent, wherein the second agent is a cytokine or growth factor, or a chemotherapeutic agent, the administration may also include use of a radiotherapeutic agent or radiation therapy. The radiation therapy administered in combination with an antibody composition is administered as determined by the treating physician, and at doses typically given to patients being treated for cancer.

The amounts of binding molecule in a given dose will vary according to the size of the individual to whom the therapy is being administered as well as the characteristics of the disorder being treated. In exemplary treatments, it may be necessary to administer about 1 mg/day, about 5 mg/day, about 10 mg/day, about 20 mg/day, about 50 mg/day, about 75 mg/day, about 100 mg/day, about 150 mg/day, about 200 mg/day, about 250 mg/day, about 500 mg/day or about 1000 mg/day. The doses may also be administered based on weight of the patient, at a dose of about 0.01 to about 50 mg/kg. In a related embodiment, the binding molecule may be administered in a dose range of about 0.015 to about 30 mg/kg. In an additional embodiment, the binding molecule is administered in a dose of about 0.015, about 0.05, about 0.15, about 0.5, about 1.5, about 5, about 15 or about 30 mg/kg.

These compositions may be administered in a single dose or in multiple doses. Standard dose-response studies, first in animal models and then in clinical testing, reveal optimal dosages for particular disease states and patient populations.

The administration of the binding molecule composition decreases the B-cell population by at least 20% after a single dose of treatment. In one embodiment, the B-cell population is decreased by at least about 20, about 30, about 40, about 50, about 60, about 70, about 80, about 90 or about 100%. B-cell reduction is defined as a decrease in absolute B-cell count below the lower limit of the normal range. B-cell recovery is defined as a return of absolute B-cell count to either of the following: 70% of subject's baseline value or normal range.

The administration of CD20-specific binding molecules also results in enhanced apoptosis in particular B-cell subsets. Apoptosis refers to the induction of programmed cell death of a cell, manifested and assessed by DNA fragmentation, cell shrinkage, cell fragmentation, formation of membrane vesicles, or alteration of membrane lipid composition as assessed by annexin V staining.

Further, the administration of binding molecule compositions of the invention results in desired clinical effects in the disease or disorder being treated. For example, in patients affected by rheumatoid arthritis, in one aspect the administration improves the patient's condition by a clinically significant amount [e.g., achieves the American College of Rheumatology Preliminary Detection of Improvement (ACR20)], and/or an improvement of 20% in tender and swollen joint and 20% improvement in 3/5 remaining ACR measures (Felson et al., *Arthritis Rheum.* 1995, 38:727-35). Biological measures for improvement in an RA patient after administration of CD37-specific and CD20-specific binding molecules include measurement of changes in cytokine levels, measured via protein or RNA levels. Cytokines of interest include, but are not limited to, TNF-α, IL-1, interferons, Blys, and APRIL. Cytokine changes may be due to reduced B cell numbers or decreased activated T cells. In RA patients, markers relevant to bone turnover (bone resorption or erosion) are measured before and after administration of CD20-specific binding molecules. Relevant markers include, but are not limited to, alkaline phosphatase, osteocalcin, collagen breakdown fragments, hydroxyproline, tartrate-resistant acid phosphatase, and RANK ligand (RANKL). Other readouts relevant to the improvement of RA include measurement of C reactive protein (CRP) levels, erythrocyte sedimentation rate (ESR), rheumatoid factor, CCP (cyclic citrullinated peptide) antibodies and assessment of systemic B cell levels and lymphocyte count via flow cytometry. Specific factors can also be measured from the synovium of RA patients, including assessment of B cell levels in synovium from synovium biopsy, levels of RANKL and other bone factors and cytokines set out above.

In a related aspect, the effects of combination administration on other diseases is measured according to standards known in the art. For example, it is contemplated that Crohn's disease patients treated according to the invention achieve an improvement in Crohn's Disease Activity Index (CDAI) in the range of about 50 to about 70 units, wherein remission is at 150 units (Simonis et al, *Scand. J. Gastroent.* 1998, 33:283-8). A score of 150 or 200 is considered normal, while a score of 450 is considered a severe disease score. It is further desired that administration of the CD37-specific and CD20-specific binding molecules results in a reduction in perinuclear anti-neutrophil antibody (pANCA) and anti-Saccharomyces cervisiae antibody (ASCA) in individuals affected by inflammatory bowel disease.

It is further contemplated that adult and juvenile myositis patients treated according to the invention achieve an improvement in core set of evaluations, such as 3 out of 6 of the core set measured improved by approximately 20%, with not more than 2 of the core measurements worse by approximately 25% (see Rider et al., *Arthritis Rheum.* 2004, 50:2281-90).

It is further contemplated that SLE patients treated according to the invention achieve an improvement in Systemic Lupus Activity Measure (SLAM) or SLE Disease Activity Index (SLEDAI) score of at least 1 point (Gladman et al, *J Rheumatol* 1994, 21:1468-71) (Tan et al., Arthritis Rheum. 1982, 25:1271-7). A SLAM score of >5, or SLEDAI score >2 is considered clinically active disease. A response to treatment may be defined as improvement or stabilization over the in 2 disease activity measures (the SLE Disease Activity Index [SLEDAI] and the Systemic Lupus Activity Measure) and 2 quality of life measures (patient's global assessment and the Krupp Fatigue Severity Scale) (Petri et al., *Arthritis Rheum.* 2004, 50:2858-68.) It is further contemplated that administration of the binding molecule to SLE patients results in a reduction in anti-double-stranded DNA antibodies. Alternatively, improvement may be gauged using the British Isles Lupus Assessment Group Criteria (BILAG).

It is further contemplated that multiple sclerosis patients treated according to the invention achieve an improvement in clinical score on the Kurtzke Expanded Disability status scale (EDSS) (Kurtzke, F., *Neurology* 1983, 33:1444-52) of at least 0.5, or a delay in worsening of clinical disease of at least 1.0 on the Kurtzke scale (Rudick et al., *Neurology* 1997, 49:358-63).

It is further contemplated that patients suffering from IIM receiving CD37-specific and CD20-specific binding molecules achieve a reduction in at least one of five criteria set out in the Idiopathic Inflammatory Myopathy Criteria (MC) assessment (Miller, F., supra). It is further contemplated that administration to IIM patients results in a reduction in IIM associated factors selected from the group consisting of creatine kinase (CK), lactate dehydrogenase, aldolase, C-reactive protein, aspartate aminotransferase (AST), alanine aminotransferase (ALT), and antinuclear autoantibody (ANA), myositis-specific antibodies (MSA), and antibody to extractable nuclear antigens. Alternatively, patients meet 3 out of 6 of the criteria set out in Rider et al., Arthritis Rheum., 50(7):2281-2290 (2004), with worsening in no more than 2 criteria.

In some embodiments, patients suffering from a B cell cancer receive treatment according to the invention and demonstrate an overall beneficial response to the treatment, based on clinical criteria well-known and commonly used in the art, and as described below, such as a decrease in tumor size, decrease in tumor number and/or an improvement in disease symptoms.

Exemplary clinical criteria are provided by the U.S. National Cancer Institute (NCI), which has divided some of the classes of cancers into the clinical categories of "indolent" and "aggressive" lymphomas. Indolent lymphomas include follicular cell lymphomas, separated into cytology "grades," diffuse small lymphocytic lymphoma/chronic lymphocytic leukemia (CLL), lymphoplasmacytoid/Waldenstrom's Macroglobulinemia, Marginal zone lymphoma and Hairy cell leukemia. Aggressive lymphomas include diffuse mixed and large cell lymphoma, Burkitt's lymphoma/diffuse small non-cleaved cell lymphoma, Lymphoblastic lymphoma, Mantle cell lymphoma and AIDS-related lymphoma. In some cases, the International Prognostic Index (IPI) is used in cases of aggressive and follicular lymphoma. Factors to consider in the IPI include Age (<60 years of age versus >60 years of age), serum lactate dehydrogenase (levels normal versus elevated), performance status (0 or 1 versus 2-4) (see definition below), disease stage (I or II versus III or IV), and extranodal site involvement (0 or 1 versus 2-4). Patients with 2 or more risk factors have less than a 50% chance of relapse-free and overall survival at 5 years.

Performance status in the aggressive 1P1 is defined as follows:

Grade Description: 0 Fully active, able to carry on all pre-disease performance without restriction; 1 Restricted in physically strenuous activity but ambulatory and able to carry out work of a light or sedentary nature, e.g., light house work, office work; 2 Ambulatory and capable of all selfcare but unable to carry out any work activities, up to and about more than 50% of waking hours; 3 Capable of only limited selfcare, confined to bed or chair more than 50% of waking hours; 4 Completely disabled, unable to carry on any selfcare, totally confined to bed or chair; and, 5 Dead. (See., The International Non-Hodgkin's Lymphoma Prognostic Factors Project. A predictive model for aggressive non-Hodgkin's lymphoma. N Engl J. Med. 329:987-94, 1993)

Typically, the grade of lymphoma is clinically assessed using the criterion that low-grade lymphoma usually presents as a nodal disease and is often indolent or slow-growing. Intermediate- and high-grade disease usually presents as a much more aggressive disease with large extranodal bulky tumors.

The Ann Arbor classification system is also used to measure progression of tumors, especially non-Hodgkins lymphomas. In this system, stages I, II, III, and IV of adult NHL can be classified into A and B categories depending on whether the patient has well-defined generalized symptoms (B) or not (A). The B designation is given to patients with the following symptoms: unexplained loss of more than 10% body weight in the 6 months prior to diagnosis, unexplained fever with temperatures above 38° C. and drenching night sweats. Definitions of the stages are as follows: Stage I-involvement of a single lymph node region or localized involvement of a single extralymphatic organ or site. Stage II-involvement of two or more lymph node regions on the same side of the diaphragm or localized involvement of a single associated extralymphatic organ or site and its regional lymph nodes with or without other lymph node regions on the same side of the diaphragm. Stage III-involvement of lymph node regions on both sides of the diaphragm, possibly accompanying localized involvement of an extralymphatic organ or site, involvement of the spleen, or both. Stage IV-disseminated (multifocal) involvement of one or more extralymphatic sites with or without associated lymph node involvement or isolated extralymphatic organ involvement with distant (non-regional) nodal involvement. For further details, see The International Non-Hodgkin's Lymphoma Prognostic Factors Project: A predictive model for aggressive non-Hodgkin's lymphoma, New England J. Med. (1993) 329:987-994.

In one aspect, a therapeutic effect of the methods according to the invention is determined by the level of response, for example a partial response is defined as tumor reduction to less than one-half of its original size. A complete response is defined as total elimination of disease confirmed by clinical or radiological evaluation. In one embodiment, the individual receiving treatment according to the invention demonstrates at least a partial response to treatment.

According to the Cheson criteria for assessing NHL developed in collaboration with the National Cancer Institute (Cheson et al., *J Clin Oncol.* 1999, 17:1244; Grillo-Lopez et al., *Ann Oncol.* 2000, 11:399-408), a complete response is obtained when there is a complete disappearance of all detectable clinical and radiographic evidence of disease and disease-related symptoms, all lymph nodes have returned to normal size, the spleen has regressed in size, and the bone marrow is cleared of lymphoma.

An unconfirmed complete response is obtained when a patient shows complete disappearance of the disease and the spleen regresses in size, but lymph nodes have regressed by more than 75% and the bone marrow is indeterminate. An unconfirmed complete response meets and exceeds the criteria for partial response. An overall response is defined as a reduction of at least 50 percent in overall tumor burden.

Similar criteria have been developed for various other forms of cancers or hyperproliferative diseases and are readily available to a person of skill in the art. See, e.g., Cheson et al., *Clin Adv Hematol Oncol.* 2006, 4:4-5, which describes criteria for assessing CLL; Cheson et al., *J Clin Oncol.* 2003, 21:4642-9, which describes criteria for AML; Cheson et al., *Blood* 2000, 96:3671-4, which describes criteria for myelodysplastic syndromes.

In another aspect, a therapeutic response in patients having a B cell cancer is manifest as a slowing of disease progression compared to patients not receiving therapy. Measurement of slowed disease progression or any of the above factors may be carried out using techniques well-known in the art, including bone scan, CT scan, gallium scan, lymphangiogram, MRI, PET scans, ultrasound, and the like.

It will also be apparent that dosing may be modified if traditional therapeutics are administered in combination with therapeutics of the invention.

As an additional aspect, the invention includes kits which comprise one or more compounds or compositions useful in the methods of the invention packaged in a manner which facilitates their use to practice methods of the invention. In a simplest embodiment, such a kit includes a compound or composition described herein as useful for practice of a method of the invention packaged in a container such as a sealed bottle or vessel, with a label affixed to the container or included in the package that describes use of the compound or composition to practice the method of the invention. Preferably, the compound or composition is packaged in a unit dosage form. The kit may further include a device suitable for administering the composition according to a preferred route of administration or for practicing a screening assay. The kit may include a label that describes use of the binding molecule composition(s) in a method of the invention.

The present invention also comprises articles of manufacture. Such articles comprise CD37-specific binding molecules or CD37-specific and CD20-specific binding molecules, optionally together with a pharmaceutical carrier or diluent, and at least one label describing a method of use of the binding molecules according to the invention. Such articles of manufacture may also optionally comprise at least one second agent for administration in connection with the binding molecules.

The present invention also calls for use of a composition comprising a CD37-specific binding molecule or CD37-specific and CD20-specific binding molecules in the manufacture of a medicament for the treatment or prophylaxis of a disease involving aberrant B-cell activity.

BRIEF DESCRIPTION OF THE DRAWING

FIG. 10 shows the effect of TRU-016 on RITUXAN (rituximab) in a CDC assay.

FIGS. 20A and 20B show the percent CD19 positive (FIG. 20A) or CD40 positive (FIG. 20B) cells following a 48 or 72 hour incubation with TRU016 or rituximab. FIG. 20C shows the percent reduction from the original number of lymphocytes expressing the indicated CD antigen (i.e. CD19, CD40 or CD3 positive) after incubation of PBMCs with TRU-016 (at 1 μg/ml) for 24 and 72 hours.

FIG. 30A shows the consensus amino acid sequence of humanized TRU-016 construct no. 019001 (SEQ ID NO: 6) and TRU-016 (SEQ ID NO: 2) with Kabat numbering;

FIG. 30B shows amino acid sequence alignments of three humanized TRU-16 constructs (019001, 019008, and 109009).

FIG. 31 shows the DNA and amino acid sequence alignments of three humanized constructs of TRU-016 (019001, 019041, and 019044).

FIG. 32A-32D shows the FASTA formatted sequence alignments of the same three humanized constructs of TRU-016 (019001, 019041, and 019044).

EXAMPLES

Additional aspects and details of the invention will be apparent from the following examples, which are intended to be illustrative rather than limiting. Example 1 describes the production of a CD37-specific binding molecule; Example 2 demonstrates that TRU-016 and various CD37-specific antibodies recognize the same or overlapping epitopes; Example 3 shows that TRU-016 is deficient in binding C1q and activating the classical complement activation pathway; Example 4 demonstrates activity and binding of TRU-016 muitimers; Example 5 describes the production of a CD20-specific binding molecule; Example 6 shows that combinations of TRU-016 with TRU-015 or RITUXAN (rituximab) synergistically increase apoptosis in B cells; Example 7 shows that combinations of TRU-016 with CD20-specific antibodies or SMIPs synergistically increase CDC; Example 8 demonstrates that TRU-016 augments the ADCC and the CDC activity of CD20-specific antibodies and SMIPS; Example 9 demonstrates that TRU-016 induces apoptosis in B cells; Example 10 shows that combinations of a CD37-specific SMIP with a CD20-specific antibody synergistically reduce tumor volume in a murine tumor xenograft model; Example 11 shows that a CD37-specific SMIP alone also reduces tumor volume in a murine tumor xenograft model; Example 12 demonstrates that TRU-016 does not affect the CDC activity of other B cell surface receptors; Example 13 demonstrates that TRU-016 does not augment the CDC activity of various targeted receptors, including MHCII, CD19, CD80/86, and CD40; Example 14 provides additional data showing that TRU-016 increases survival in vivo in mice with tumors; Example 15 demonstrates that TRU-016 potentiates fludarabine-induced cell death in CLL cells in vitro; Example 16 shows that TRU-016 induces direct cytotoxicity in RITUXAN (rituximab) resistant cells; Example 17 shows that TRU-016 induces tyrosine phosphorylation in CD19+ primary CLL B cells; and Example 18 provides humanized TRU-016 molecules.

Example 1

Production of a CD37-Specific Binding Molecule

CD37-specific SMIPs are described in commonly owned U.S. Pat. No. 7,829,084 and U.S. Patent Application Publication No. 2003/133939, U.S. Pat. Nos 7,754,208 and 7,829, 084. An exemplary SMIP, TRU-016, is produced as described below.

TRU-016 [G28-1 scFv VH11S(SSC—P)H WCH2 WCH3] is a recombinant single chain protein that binds to the CD37 antigen. The binding domain was based on the G28-1 antibody sequence previously disclosed in the patent publications listed in the preceding paragraph, which disclosure is incorporated herein by reference. The binding domain is connected to the effector domain, the CH2 and CH3 domains of human IgG1, through a modified hinge region. TRU-016 exists as a dimer in solution and the dimer has a theoretical molecular weight of approximately 106,000 daltons.

Figure 1A:
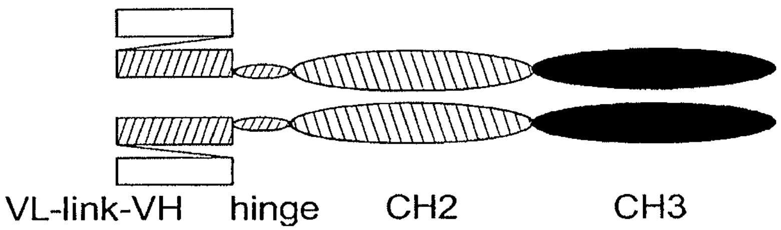
FIG. 1A diagrams the structure of the TRU-016 molecule.

Total RNA from the G28-1 hybridoma was isolated using Trizol RNA (Gibco) reagent according to the manufacturer's instructions. cDNA was prepared using 51 μg RNA, random primers and Superscript II Reverse Transcriptase (GIBCO BRL). The variable domains were cloned using pools of degenerate primers for the different murine VK or VH gene families. The variable domains from the G28-1 hybridoma were cloned into PCR 2.1 TOPO cloning vectors (Invitrogen) and DNA from transformants with correct size inserts was sequenced. Heavy and light chain variable regions from correct clones were then used as templates for sewing PCR amplification of a G28-1 scFv joined together in the VL-VH orientation with a 15 as (gly4ser)3 linker. The anti-CD37 scFv was attached to a modified human IgG1 hinge, CH2, and CH3 domains (see FIG. 1A). In order to ensure adequate expression by mammalian cells, modifications of the variable regions were selected that allowed significant increases in expression by mammalian cells. Specifically, a leucine was changed to a serine at position 11 of the scFV. The predicted mature peptide is 473 amino acids long.

The polynucleotide sequence encoding TRU-016 and the amino acid sequence of TRU-016 are respectively set out in SEQ ID NOs: 1 and 2.

TRU-016 was produced by recombinant DNA technology in a Chinese hamster ovary (CHO) mammalian cell expression system. Transfected CHO cells that produce the SMIP were cultured in a bioreactor using proprietary media.

TRU-016 SMIPs were purified from CHO culture supernatants by Protein A affinity chromatography. Using dPBS, a 50 mL rProtein A FF sepharose column (GE Healthcare rProtein A Sepharose FF, Catalog #17-0974-04) was equilibrated at 5.0 mls/min (150 cm/hr) for 1.5 column volumes (CV). The culture supernatant was loaded to the rProtein A Sepharose FF column at a flow rate of 1.7mls/min using the AKTA Explorer 100 Air (GE healthcare AKTA Explorer 100 Air, Catalog #18-1403-00), capturing the recombinant. TRU-016. The column was washed with dPBS for 5 Column Volumes (CV), then 1.0 M NaCl, 20 mM Sodium Phosphate, pH 6.0, and then with 25 mM NaCl, 25 mM NaOAc, pH 5.0. These washing steps removed nonspecifically bound CHO host cell proteins from the rProtein A column that contribute to product precipitation after elution.

The recombinant TRU-016 was eluted from the column with 100 mM Glycine, pH 3.5. 10 mL fractions of the eluted product were recovered and the eluted product was then brought to pH 5.0 with 20% of the eluted volume of 0.5 M 2-(N-Morpholino)ethanesulfonic acid (MES) pH6.0. This eluted product was prepared for GPC purification by concentration of the sample to approximately 25 mg/mL TRU-016 and then filter sterilized in preparation for GPC purification.

Purified protein was then subjected to GPC size exclusion chromatography (SEC) to achieve further purification of the TRU-016 (dimer) molecule from higher molecular weight aggregates. Using dPBS, an XK 50/100 column (GE healthcare XK 50/100 empty chromatography column, Catalog #18-8753-01) containing 1 L of Superdex 200 FF sepharose was equilibrated at 12.6 mls/min (38 cm/hr) for 1.5 column volumes (CV). A maximum volume of 54 mls (3% CV) of sample was applied to the column. The column continued to run at 12.6 ml/min and the eluted protein was fractionated in 40 mL fractions. Each fraction was analyzed for product quality using an analytic HPLC, and the eluted fractions were pooled for >95% POI (non-aggregated) TRU-016. This resultant pool was filter sterilized at 0.22 μm. The material was then concentrated and formulated with 20 mM sodium phosphate and 240 mM sucrose, with a resulting pH of 6.0. The composition is filtered before filling into glass vials at a concentration of 10 mg/mL. Each glass vial contains 5 mL of TRU-016 (50 mg/vial).

Figure 1B:
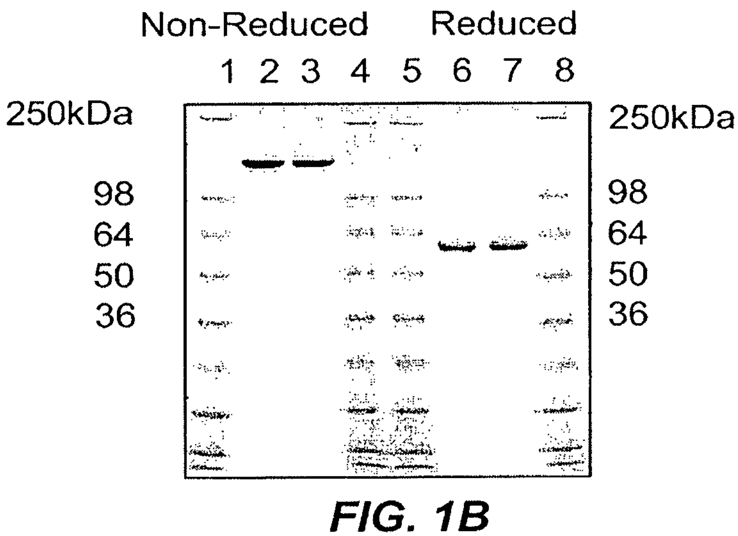
FIG. 1B shows the results of SDS-PAGE analysis, demonstrating that the expressed protein migrates at a Mr of approximately 110 kDa under nonreducing conditions, and approximately 52 kDa when subjected to reducing conditions.

TRU-016 protein was also subject to SDS-PAGE analysis on 4-20% Novex Tris-glycine gels (Invitrogen, San Diego, Calif.). Samples were loaded using Novex Tris-glycine SOS sample buffer (2×) under reducing (addition of 1/10 volume NuPAGE sample reducing agent) or non-reducing conditions after heating at 95° C. for 3 minutes, followed by electrophoresis at 150V for 90 minutes. Electrophoresis was performed using 1×Novex Tris-Glycine SDS Running Buffer (Invitrogen). Gels were stained after electrophoresis in Coomassie SOS PAGE R-250 stain for 30 minutes with agitation, and destained for at least one hour. The predicted molecular weight of the mature peptide is 51.5 kDa. Under reducing conditions, fusion protein migrates at the expected molecular weight. Under non-reducing conditions, the molecule migrates at approximately 150 kDa (FIG. 1B).

Experiments were also performed to determine that the binding specificity of the parent antibody to the CD37 cell surface receptor is preserved in TRU-016. Human PBMCs were isolated over LSM density gradients and incubated with unconjugated TRU-016 and PE-conjugated anti-human CD19. Cells were washed and incubated with 1:100 FITC GAH IgG (Fc specific) for 45 minutes on ice. Cells were washed and analyzed by two-color flow cytometry on a FACsCalibur instrument using Cell Quest software. Cells were gated for B lymphocytes or non-B lymphocytes by CD19 staining.

Figure 1C:
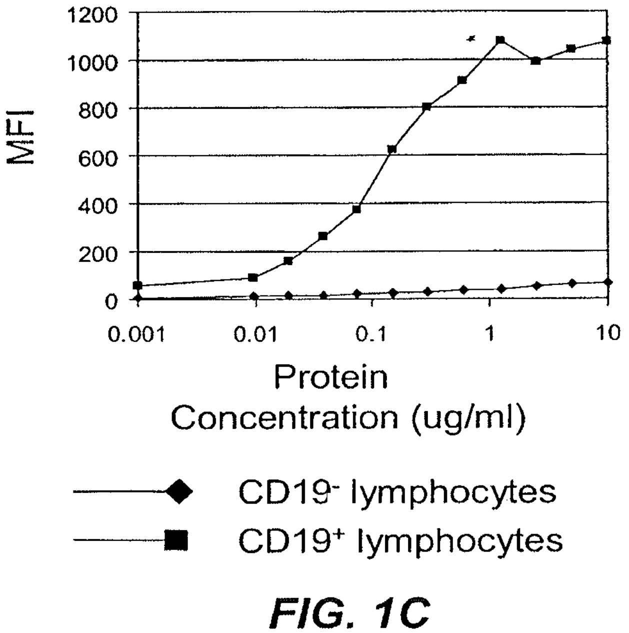

With increasing concentrations of TRU-016, the FITC signal on the B lymphocyte (CD19 positive gate) increased rapidly from 0.01-1.0 μg/ml, until it reached saturation at approximately 1 μg/mL or a mean fluorescence intensity (MFI) of 1000. In contrast, the staining of the non-B lymphocyte population is detectable, but very low, and increases slowly with increasing concentration of scFvlg. Thus, the staining pattern of the G28-1 murine monoclonal antibody is preserved with TRU-016 (FIG. 1C).

The CD37-binding molecules according to the invention describe structures (binding domains derived from antibodies, hinge variants, CH2CH3 regions being the same or different, and various isotypes).

Example 2

TRU-016 and Various CD37-Specific Antibodies Bind the Same or Overlapping Epitopes on CD37

Experiments were performed to identify the CD37 epitope bound by TRU-016 and other previously described CD37-specific antibodies.

Unconjugated MB371 (#555457) and FITC-conjugated MB371 (#555456) were obtained from BD Pharmingen (San Jose, Calif.), FITC-conjugated BL14 (#0457) from Immunotech/Beckman Coulter (Fullerton, Calif.), FITC-conjugated NMN46 (#RDI-CBL 136FT) and unconjugated NMN46 (#RDI-CBL 136) from RD1 (Flanders, N.J.), FITC-conjugated IP024 (#186-040) and unconjugated IPO-24 (#186-020) from Ancell Corporation (Bayport, Minn.), F1TC-conjugated HH1 (#3081) and unconjugated HH1 (#3080) from DiaTec.Com (Oslo, Norway) and FITC-conjugated WR17 (YSRTMCA483F) and unconjugated WR17 (YSRTMCA483S) from Accurate Chemical & Scientific (Westbury, N.Y.). TRU-016 protein was produced as described in Example 1.

TRU-016 was conjugated to FITC at Trubion using a Molecular Probes Fluororeporter FITC Labeling Kit (F6434) according to manufacturer's instructions as follows: TRU-016 protein peak of interest (POI) at 13.5 mg/mL was adjusted to 5 mg/mL with PBS. 1 mg (200 ul) was added to kit tubes with a stirbar, and 1M $NaHCO3$ (adjusted to pH 8.5 with 6N NaOH), was added to a final concentration of 0.1M. 50 ul DMSO was added to 370 ug of FITC and was added to the tubes at molar ratios of 15, 20, 30 and 40 FITC: protein using the following formula to determine the ul of FITC to add: [ul of FITC solution to add=5 mg/mL protein×0.2 mL×389×100×desired molar ratio/Molecular weight of TRU-016 (110,000)].

Reactions were shielded from light and stirred continuously for 75 minutes at room temperature. Reactions were added to spin columns prepared as described in the kit and spun at 1100 g for 5 minutes to buffer exchange into PBS with azide and remove unconjugated FITC. The OD at 280 nM and 494 nM was determined with 2 ul drops on the Nanodrop; the extinction coefficient for TRU-016 was experimentally determined for this instrument by reading dilutions of the starting unconjugated SMIP, the concentration of each of the conjugates was 4.25 mg/ml and the following FITC:protein rations were determined: 2.7 FITC/TRU-016 at a ratio of 15; 3.7 FITC/TRU-016 at a ratio of 20; 4.4 FITC/TRU-016 at a ratio of 30; and 5.1 FITC/TRU-016 at a ratio of 40.

BSA was added to 3 mg/mL to help stabilize the protein. Binding of each fraction was assessed at dilutions ranging from 100-24,300× on Ramos and 3200-25,600 on human PBMC. All bound, but the MR30 ratio was chosen for further use since it gave a high MR that was well maintained over the titration range used, indicating that binding avidity was least affected in this reaction.

Figures 2A, 2B, 2C, 2D, 2E:
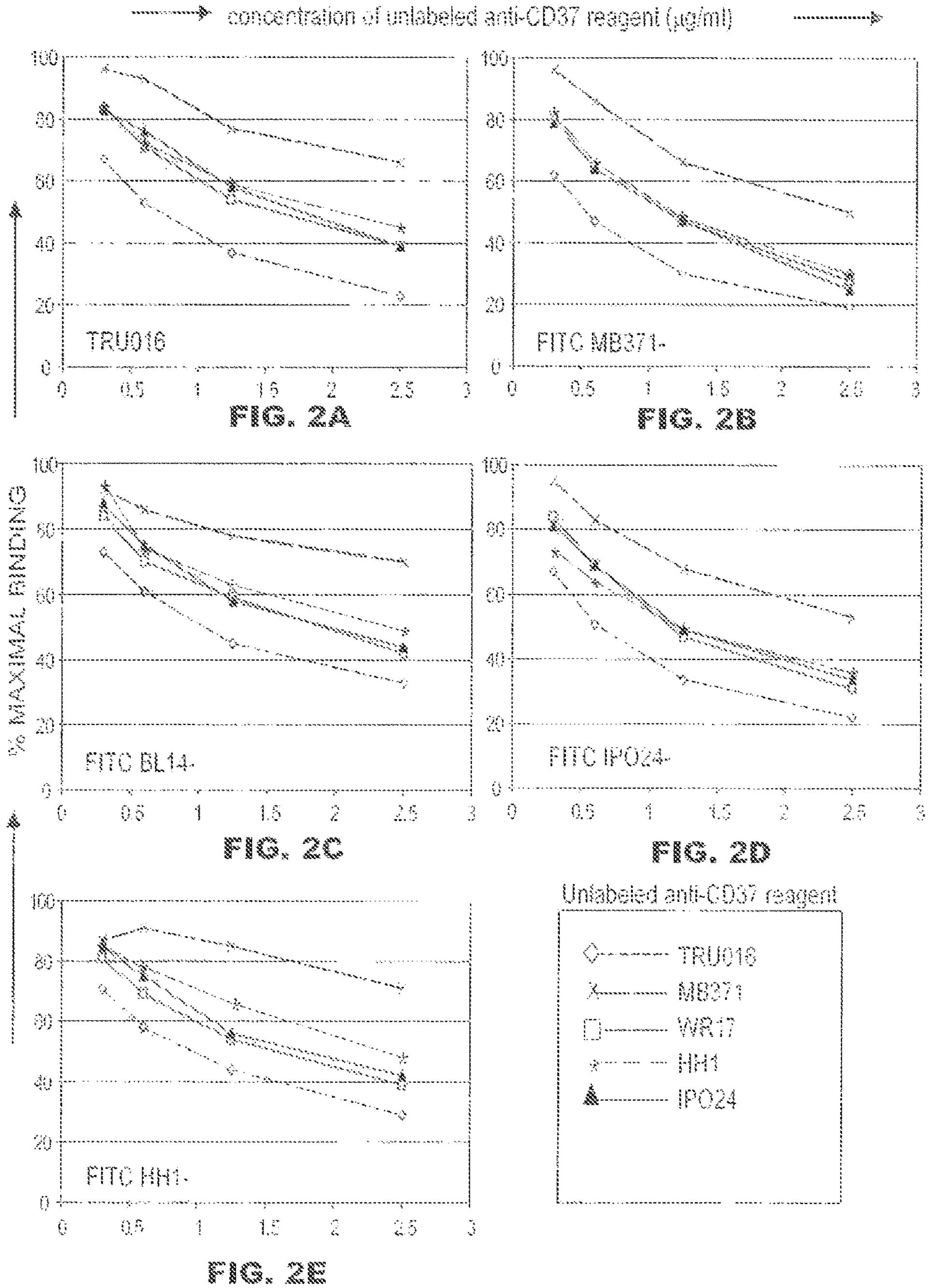
FIG. 2A-E shows binding inhibition by different CD37 targeted reagents.

FITC labeled antibody conjugates were titrated from 10 μg/mL to 10 pg/mL in an initial binding study to determine the optimal amounts to use in the blocking studies. The level chosen was just below saturating amounts, and was kept constant in the subsequent assays, while levels of blocking antibody were increased over a 10-fold range. Data were plotted as percent of maximal binding versus concentration of blocking antibody, so that higher levels indicate less efficient blocking, while lower levels indicate more efficient blocking activity. All of the antibodies tested showed blocking activity of the maximal binding observed without unlabeled reagents (FIG. 2).

BJAB-cells, a B lymphoblastoid B-cell line, (courtesy of Ed Clark, University of Washington) were then stained with a panel of various clones of anti-CD37 MAbs, including MB371, BL14, NMN46, IPO24, HH1, WR17, and the TRU-016 SMIP.

For competitive binding assays, $2.5\times10^5$ BJAB cells were incubated in 96-well V-bottom plates in staining media (PBS with 2% mouse sera) with the FITC-conjugated anti-CD37 MAbs at 1.25 μg/mL in the presence of unconjugated anti-CD37 MAb at the indicated concentrations (2.5, 1.25, 0.6, or 0.3 μg/ml) or staining media for 45 minutes on ice in the dark. Blocking antibodies and FITC labeled antibody conjugates were added to reactions prior to addition of cells. The cells were then washed 2½ times with PBS and fixed with 1% paraformaldehyde (#19943, USB, Cleveland, Ohio). The cells were analyzed by flow cytometry using a FACsCalibur instrument and CellQuest software (BD Biosciences, San Jose, Calif.).

For FACs cross blocking assays, $2.5\times10^5$ BJAB cells were incubated in 96-well V-bottom plates in staining media (PBS with 2% mouse sera) in the presence of unconjugated anti-CD37 MAb at 5 μg/mL staining media for 45 minutes at room temperature in the dark. F1TC-conjugated anti-CD37 MAbs were then added to a final concentration of 2 μg/ml, resulting in a dilution of the unlabelled reagents to 3.3 μg/ml. The reactions were then further incubated for 45 minutes at room temperature in the dark. Reactions were washed 2.5 times with PBS and fixed in 1% paraformaldehyde in PBS (#19943, USB, Cleveland, Ohio). Cells were analyzed by flow cytometry on a FACsCalibur instrument using Cell Quest software (BD Biosciences, San Jose, Calif.).

For cell binding assays, cells were suspended in PBS (#14040-133, Gibco/Invitrogen, Grand Island N.Y.) containing 2% FBS (#16140-071, Gibco/Invitrogen, Grand Island, N.Y.), (staining media) at a concentration of approximately $4\times10^6$ cells/mL. Cells were then plated and test samples, diluted in staining media, were then added 1:1 to the final designated concentrations. Reactions were incubated for 45 minutes on ice. Samples were centrifuged and washed 2 times with PBS. FITC goat anti-human IgG (#H10501, CalTag, Burlingame Calif.) was added at a final dilution of 1:50, and incubated 45 minutes on ice. Samples were centrifuged, washed in PBS, then fixed in 200 μl 1% paraformaldehyde in PBS (#19943, USB, Cleveland, Ohio). Cells were analyzed by flow cytometry on a FACs Calibur instrument using Cell Quest software (BD Biosciences, San Jose, Calif.).

Each antibody showed dose dependent inhibition of binding, indicating that all the molecules tested bind to an identical or closely related epitope. A different potency for inhibition of binding was observed for each antibody. TRU-016 SMIP had the highest level of blocking activity of all molecules tested, while HH1 gave an intermediate level of blocking activity, and WR17, IPO24 blocked better than MB371; but showed less effective blocking than the other two unlabeled molecules (FIG. 2).

In addition to analysis of blocking activity, a similar series of experiments was performed in which various CD37 targeted antibodies were tested for their ability to compete with one another for binding to the CD37 receptor. The results from these experiments, like results obtained in the blocking studies for all the molecules tested, indicated that the various CD37 targeted antibodies and TRU-016 have the same or closely overlapping epitopes.

Example 3

TRU-016 is Deficient in Binding C1q and Activating the Classical Complement Activation Pathway Experiments were performed to explore why the TRU-016 dimer peak fails to mediate significant levels of complement dependent killing of B cell targets. One possibility was that TRU-016 dimer shows reduced binding to components of the complement cascade relative to normal human IgG1 antibody. Thus, experiments were performed to determine if TRU-016 activates the classical complement activation pathway by looking for TRU-016 binding to C1q. C1q, is a subunit of the C1 enzyme complex that activates the serum complement system, and is the recognition component of the classical complement activation pathway.

C1q binding studies were performed as previously described (Cragg et al., Blood 2004, 103:2738-2743). Briefly, Ramos B-cells in Iscoves media (#12440-053, Gibco/Invitrogen, Grand island, NY) with no serum were plated in 96-well V bottom plates at $5\times10^5$/well in 100 μl. Cells were incubated with reagents for 15 minutes at 37° C., and normal human serum (NHS, #A113, Quidel Corp., San Diego, Calif.) diluted in Iscoves was then added at a volume of 50 μl to each well for a final concentration of 10, 5, 2.5, or 1.25% human serum. Fifty μl of media was added to the control well. For cobra venom factor (CVF) experiments, CVF was added to human serum complement samples at 20 Units CVF/mL of serum for 90 minutes at 37° C. prior to addition of serum to complement assays, and the dilution of serum by CVF accounted for when making sample dilutions.

The cells plus complement source were incubated for an additional 5 minutes at 37° C., and washed 2 times with cold PBS (#14040-133, Gibco/Invitrogen, Grand Island, N.Y.) via centrifugation and resuspended in 100 μl of PBS. Fifty μl from each well was transferred to a second plate for second step control staining. Both plates were stained for 15 minutes in the dark on ice with either FITC sheep anti-HU C1q (#C7850-06A, US Biological, Swampscott, Mass.) or RTC Sheep IgG (#11904-56P, US Biological, Swampscott, Mass.). Samples were washed, resuspended in cold PBS, and read immediately on a FACsCalibur flow cytometer and analyzed with Cell Quest software (Becton Dickinson, San Jose, Calif.).

Figure 3A:
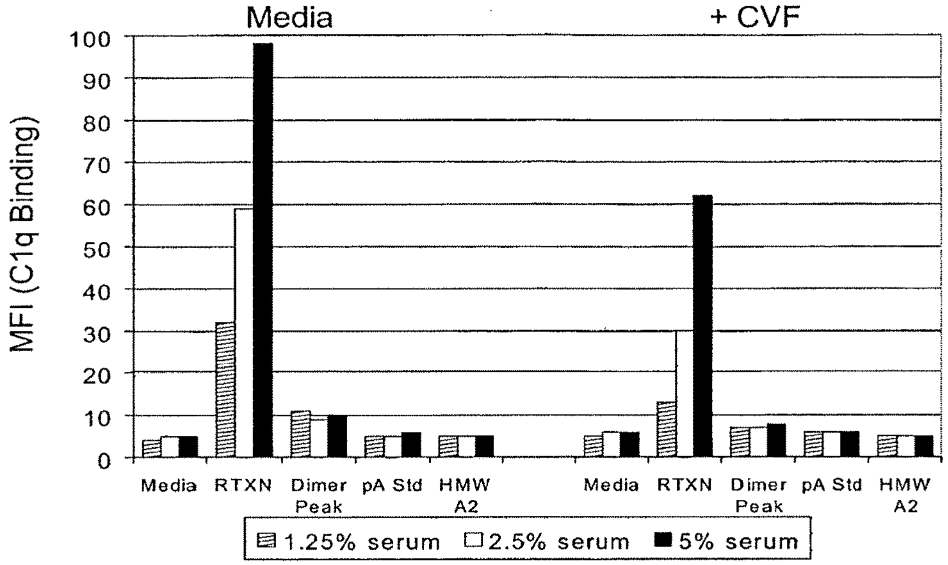
FIG. 3A demonstrates FITC C1q binding to TRU-016 molecular forms incubated with Ramos B Cells in normal human serum with and without cobra venom factor (CVF)

FITC C1q does not bind well to any subfractions of SEC purified TRU-016, although the higher molecular weight (HMW) or A2 aggregate fraction does show more binding than the other forms (FIG. 3A). In contrast, RITUXAN (rituximab) showed a significant level of C1q binding, particularly at lower levels of NHS. The presence of CVF failed to completely block this binding, although the MFI levels are reduced significantly compared to media alone.

Figure 3B:
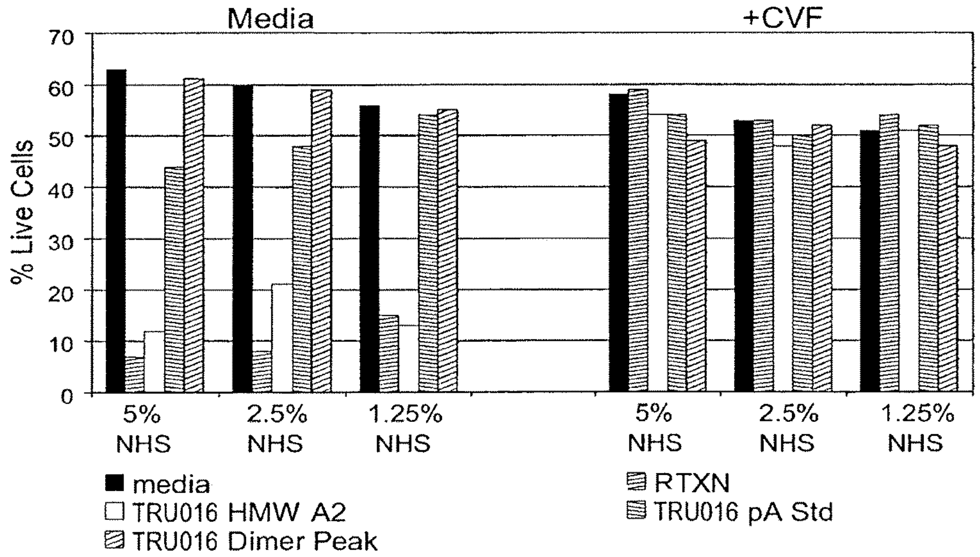
FIG. 3B shows CDC activity of TRU-016 molecular forms incubated with Ramos B Cells in normal human serum with and without CVF.

CDC assays were then performed to compare the ability of the different subfractions of the TRU-016 purified forms and RITUXAN (rituximab) to mediate cell killing in the presence or absence of CVF and human serum complement (FIG. 3B). CDC assays were performed using propidium iodide staining to discriminate between live and dead cells after incubations of target cells with antibody, fusion proteins, ascites fluid, TRU-016 molecular forms, or media, and a source of complement such as human serum. Briefly, $3\times10^5$ Ramos B-cells were pre-incubated with test reagents for 30-45 minutes at 37° C. prior to addition of complement. The prebound samples were centrifuged, washed, and resuspended in Iscoves with human serum (#A113, Quidel, San Diego, Calif.) at the indicated concentrations, then incubated for 90 minutes at 37° C. Samples were washed and propidium iodide (#P-16063,Molecular Probes, Eugene, Oreg.) was added to a final concentration of 0.5 μg/ml in PBS. The cells were incubated with the propidium iodide for 15 minutes at room temperature in the dark and then analyzed by flow cytometry on a FACsCalibur instrument with CellQuest software (Becton Dickinson).

Cell killing mediated by both the A2 fraction of TRU-016 and RITUXAN (rituximab) was significantly reduced in the presence of CVF despite its failure to completely block C1q binding (FIG. 3B).

Figure 3C:
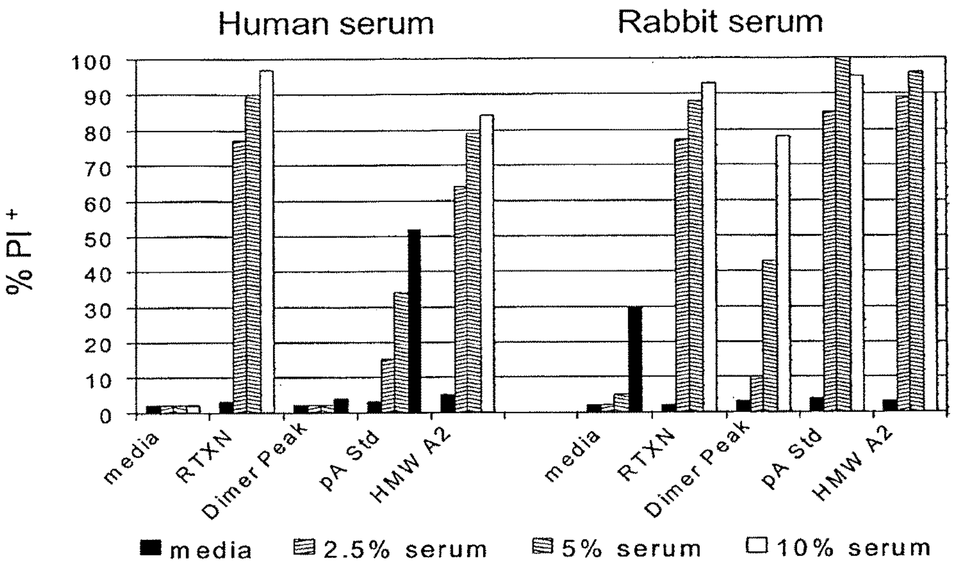
FIG. 3C shows CDC activity of TRU-016 molecular forms incubated with Ramos B cells and human or rabbit complement.

Human and rabbit complement were then compared for their CDC activity in the presence of the TRU-016. The CDC activity of TRU-016 molecular forms incubated with Ramos B cells and human or rabbit complement was measured (FIG. 3C). Ramos B cells were added to wells in serum free media. RITUXAN (rituximab) or the dimer, HMW A2, or pA fractions of TRU-016 were added to cells to give a final concentration of 10 μg/ml, and incubated for 15 minutes at 37° C., prior to washing 1.5× in serum free media and addition of normal human serum (NHS) or rabbit complement (Pelfreez) at 10, 5, or 2.5%. Cells plus complement source were incubated 90 minutes at 37° C. Cells were washed once with cold PBS and propidium iodide (Molecular Probes #P3566) added to a final concentration of 0.5 μg/mL in cold PBS. Cells with PI were incubated in the dark at RT for 15 minutes and analyzed by flow cytometry.

The origin of the complement fraction affects the CDC results obtained (FIG. 3C). Rabbit complement mediated higher levels of CDC than human complement in the presence of TRU-016 molecular forms. Interestingly, the dimer form of the TRU-016 mediated good CDC using rabbit complement, but very low CDC activity in the presence of human complement.

Example 4

Activity and Binding of TRU-016 Multimers

Experiments were performed to examine the biological activity of multimeric forms of TRU-016 (TRU-016 multimers) in solution. First, to determine the size of TRU-016 fusion protein in solution, protein A purified material was analyzed by SEC HPLC and revealed that TRU-016 exists in multiple forms in solution (FIG. 4).

Figure 4A:
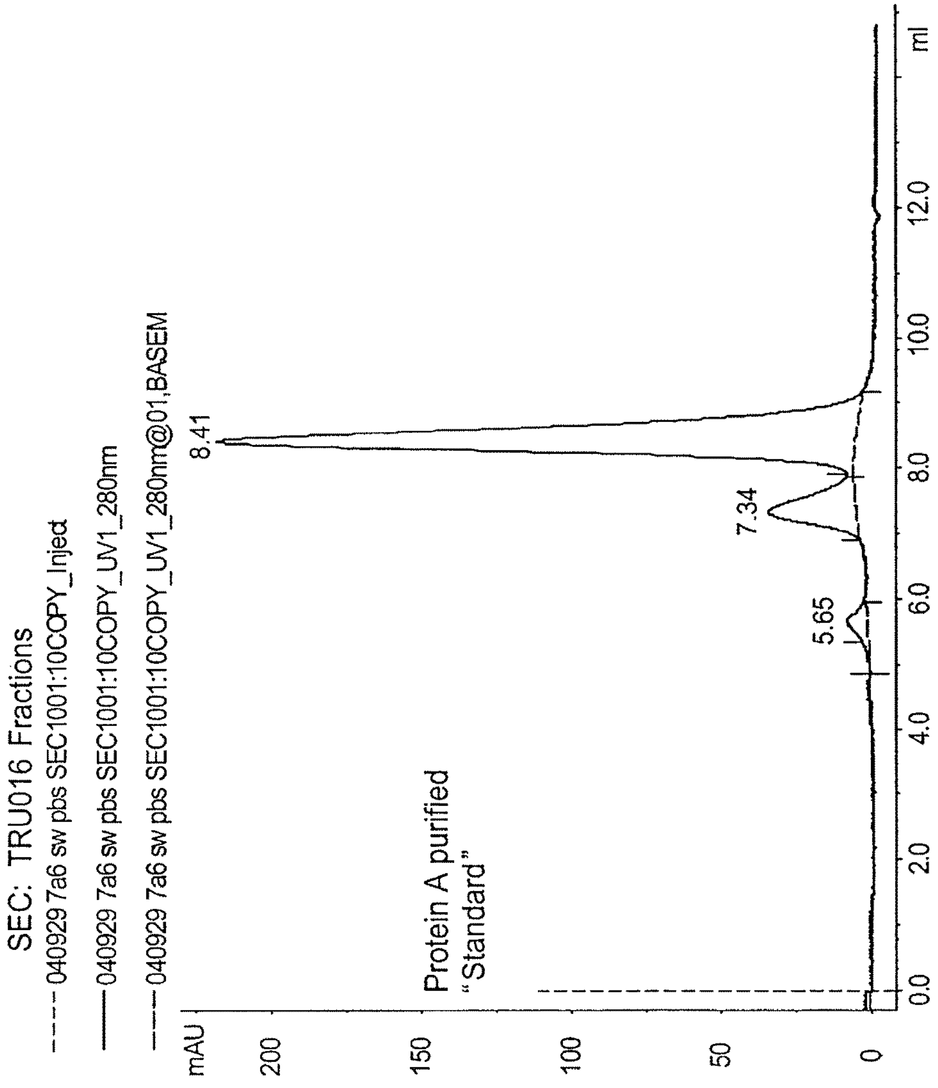
FIGS. 4A and 4B shows the protein A purified material analyzed by SEC HPLC (FIG. 4A) and HPLC size exclusion chromatography (SEC) traces obtained from GPC purification of the TRU-016 (FIG. 4B), plotting absorbance versus retention time for the different fractions collected.
Figure 4B:
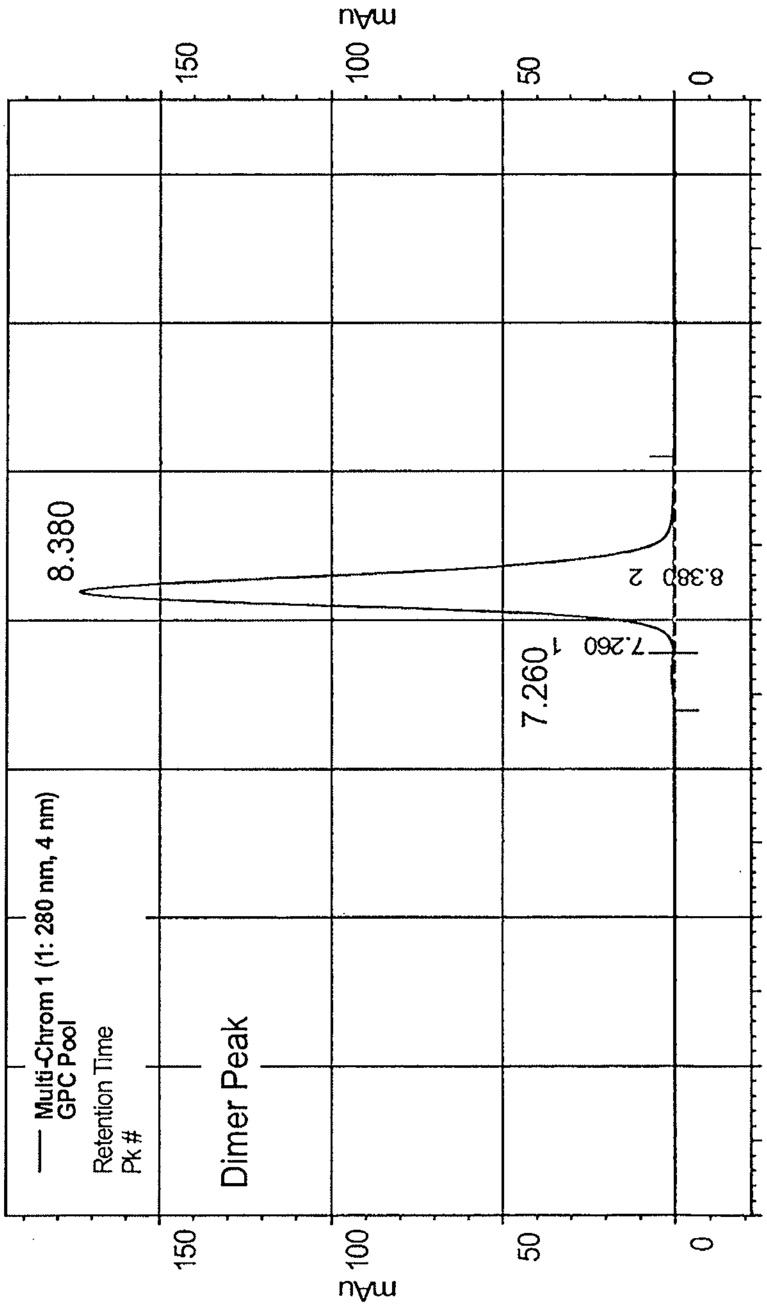
Figure 4C:
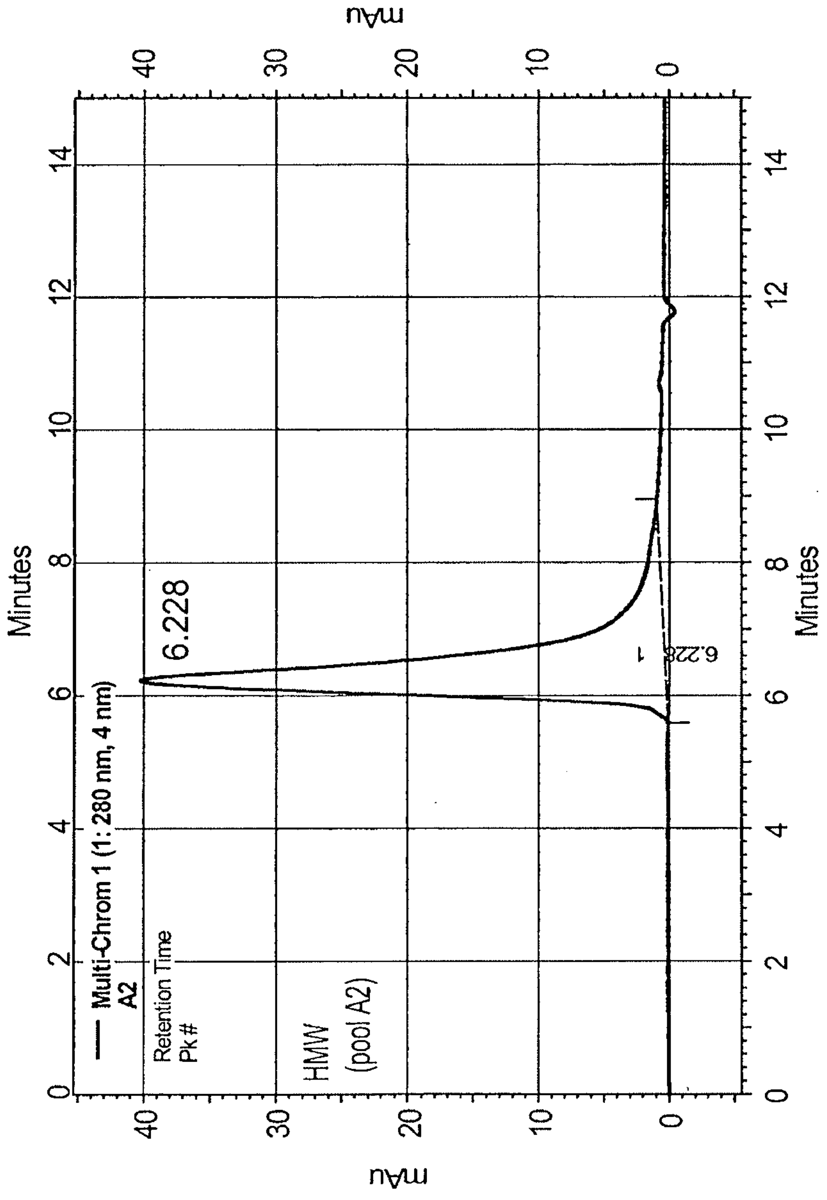
FIG. 4C shows the HPLC SEC traces obtained from HMW or A2 pools

HPLC size exclusion chromatography (SEC) traces were obtained from GPC purification of TRU-016, plotting absorbance versus retention time for the different fractions collected (FIG. 4). TRU-016 was purified from cell culture supernatants initially by affinity chromatography using Protein A Sepharose. The recombinant molecule was eluted from the column with 100 mM glycine, pH 3.5. 10 mL fractions of the eluted product were recovered and the eluted product was then brought to pH 5.0 with 20% of the eluted volume of 0.5 M 2-(N-Morpholino)ethanesulfonic acid (MES) pH6.0. The eluate was prepared for GPC purification by concentration of the sample to approximately 25 mg/mL TRU-016 and then filter sterilized in preparation for GPC purification. Size exclusion chromatography was performed on a GE Healthcare AKTA Explorer 100 Air apparatus, using a GE healthcare XK column and Superdex 200 preparative grade (GE Healthcare).

The HMW or A2 pools exhibited a retention time of approximately 6.23 minutes, while the most prominent form showed a retention time of 8.38 minutes. The reference standard used here (pA standard or std) is protein A purified material containing both dimers and HMW mulitimer forms, as shown in the first panel of FIG. 4. The most prominent form, migrating at a retention time of 8.38 minutes, most likely corresponds to the dimer molecule seen on non-reduced SDS-PAGE, and several minor forms most likely correspond to multimers that associate through non-covalent interactions as they are not evident on nonreducing SDS-PAGE. To separate these different forms of TRU-016, material obtained from protein A sepharose affinity chromatography of culture supernatants was further purified by GPC and HPLC fractionation to isolate the dimer form (identified as "dimers" or "dimer peak") from higher molecular weight multimers (identified as HMW or A2 agg fraction). Each of these three subfractions was then analyzed separately for functional activity in vitro using binding, ADCC, and CDC assays.

To explore whether the fractions isolated from SEC showed different binding properties, each fraction of TRU 016 SEC was tested for binding to Ramos cells. To determine the binding properties of SEC fractions, cells were suspended in staining media at a concentration of approximately $4\times10^6$ cells/mL and then plated at 50 μl/well ($2\times10^5$ cells/well) in staining media. Serial dilutions of SEC fractions were then added to sequential wells, incubated for 45 minutes, washed, and binding activity was detected using FITC goat anti-human IgG. Samples were fixed in 200 μl 1% paraformaldehyde in PBS. Cells were analyzed by flow cytometry on a FACsCalibur instrument using Cell Quest software (BD Biosciences, San Jose, Calif.) (FIG. 5A).

To determine the CDC activity of SEC fractions, cells were suspended at $5\times10^5$ cells/well in 75 μl IMDM. TRU 016 SEC fractions (75 μl) were added to the cells at twice the concentrations indicated. Binding reactions were allowed to proceed for 45 minutes prior to centrifugation and washing in serum free Iscoves. Cells were resuspended in Iscoves with human serum (#A113, Quidel, San Diego, Calif.) at the indicated concentrations. The cells were incubated 60 minutes at 37° C., washed, and resuspended in staining media with 0.5 μg/mL propidium iodide (PI, #P-16063, Molecular Probes, Eugene Oreg.). Samples were incubated 15 minutes at room temperature in the dark prior to analysis by flow cytometry using a FACsCalibur and CellQuest software (Becton Dickinson) (FIG. 5B).

To determine the ADCC activity of SEC fractions, BJAB, Ramos, and Daudi lymphoblastoid B cells ($10^7$) cells were labeled with 500 μCi/mL $^{51}$Cr sodium chromate for 2 hours at 37° C. in IMDM/10% FBS. PBMCs were isolated from heparinized, human whole blood by fractionation over Lymphocyte Separation Media (LSM, ICN Biomedical) gradients. Reagent samples were added to RPMI media with 10% FBS and five serial dilutions for each reagent were prepared. For combinations, the reagents were premixed and diluted prior to addition to the wells. The $^{51}$Cr labeled BJAB were added at ($2\times10^4$ cells/well). The PBMCs were then added at ($5\times10^5$ cells/well) for a final ratio of 25:1 effectors (PBMC): targets (BJAB). Reactions were set up in quadruplicate wells of a 96 well plate. TRU-016 SEC fractions were added to wells at a final concentration ranging from 10 ng/mL to 20 μg/mL as indicated on the graphs. Each data series plots a different SEC fraction at the titration ranges described. Reactions were allowed to proceed for 6 hours at 37° C. in 5% $CO_2$ prior to harvesting and counting. CPM released was measured on a Packard TopCounNXT from 50 μl dried culture supernatant. Percent specific killing was calculated by subtracting (cpm [mean of quadruplicate samples] of sample—cpm spontaneous release)/(cpm maximal release-cpm spontaneous release)x100 (FIG. 5C).

Figure 5A:
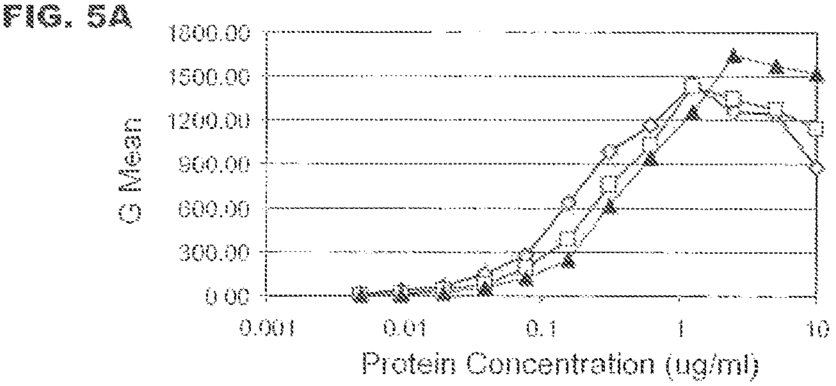
FIG. 5A shows the binding properties of SEC fractions.
Figure 5B:
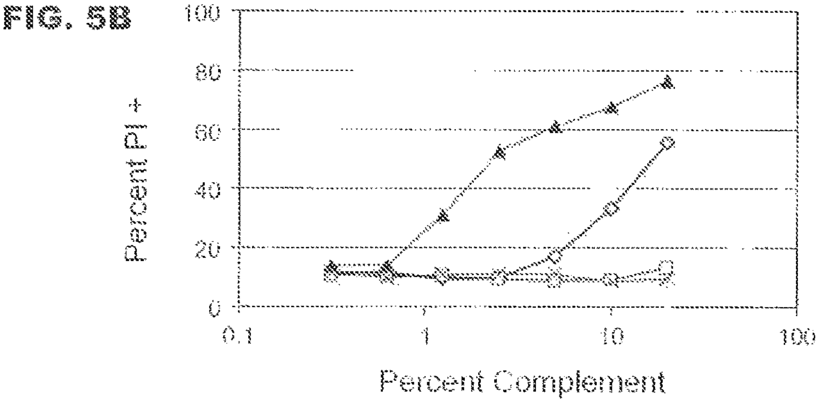
FIG. 5B shows the CDC activity of SEC fractions.
Figure 5C:
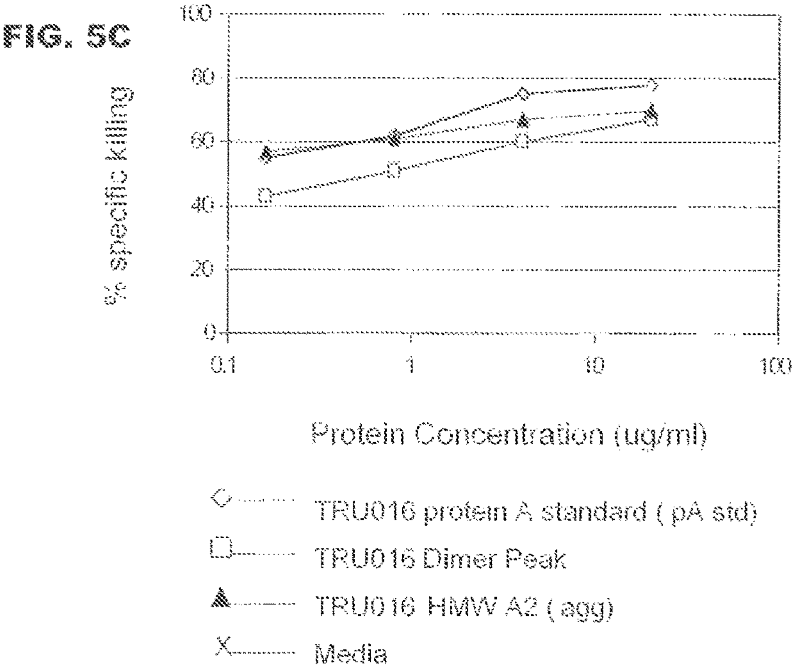
FIG. 5C shows the ADCC activity of SEC fractions.

FIG. 5A shows the titration curves of the different SEC fractions binding to Ramos cells. All of the fractionated molecules bound to CD37 with similar binding curves except at the highest concentrations tested, where the HMW material exhibited better binding (higher fluorescence intensity) than the pA standard and the dimer peak forms.

Experiments were also performed to determine if the TRU 016 SEC fractions exhibited different levels of functional activity such as CDC and ADCC mediated target cell killing. The graph shown in FIG. 5B indicates that only the purified HMW multimer fraction mediated significant levels of CDC activity against Ramos B cells using human complement. The pA standard exhibited some CDC activity at higher concentrations, while the dimer peak form showed very little or no CDC activity at all concentrations tested.

ADCC assays were performed on serial dilutions of various TRU-016 size fractions using labeled BJAB B cells as targets and human PBMC as effector cells. TRU 016 SEC fractions were present in wells at a final concentration ranging from 10 ng/mL to 20 μg/mL as indicated in the graph shown in FIG. 5C. Each data series plotted a different SEC fraction at the titration ranges described. Data were plotted as % specific killing versus protein concentration. All of the SEC subfractions, including the pA standard, HMW or A2 fraction, and dimer peak, mediated potent, dose-dependent ADCC against BJAB target cells. Similar results were also obtained using Ramos cells as labeled targets (data not shown).

Example 5

Production of a CD20-specific Binding Molecule

CD20-specific SMIPs are described in co-owned US Patent Publications 2003/133939, 2003/0118592 and 2005/0136049. Production of an exemplary CD20-specific SMIP, TRU-015, is described below.

TRU-015 is a recombinant (murine/human) single chain protein that binds to the CD20 antigen. The binding domain was based on a publicly available human CD20 antibody sequence. The binding domain is connected to the effector domain, the CH2 and CH3 domains of human IgG1, through a modified CSS hinge region. TRU-015 exists as a dimer in solution and the dimer has a theoretical molecular weight of approximately 106,000 daltons. The nucleotide sequence encoding TRU-015 and the amino acid sequence of TRU-015 are respectively set out in SEQ ID NOs: 3 and 4.

Referring to the amino acid sequence set out in SEQ ID NO: 4, TRU-015 comprises the 2e12 leader peptide cloning sequence from amino acids 1-23; the 2H7 murine anti-human CD20 light chain variable region with a lysine to serine (VHL11S) amino acid substitution at residue 11 in the variable region, which is reflected at position 34; an asp-gly3-ser-(gly4ser)2 linker beginning at residue 129, with the linker having an additional serine at the end to incorporate the SacI restriction site for cassette shuffling; the 2H7 murine anti-human CD20 heavy chain variable region, which lacks a serine residue at the end of the heavy chain region, i.e., changed from VTVSS to VTVS; a human IgG1 Fc domain, including a modified hinge region comprising a (CSS) sequence, and wild type CH2 and CH3 domains.

The CHO cells that produce TRU-015 were cultured in a bioreactor using proprietary media. TRU-015 was purified using a series of chromatography and filtration steps including a virus reduction filter. The material was then concentrated and formulated with 20 mM sodium phosphate and 240 mM sucrose, with a resulting pH of 6.0. The composition is filtered before filling into glass vials at a concentration of 10 mg/mL. Each glass vial contained 5 mL of TRU-015 (50 mg/vial).

Example 6

Combinations of TRU-016 with TRU-015 or RITUXAN (rituximab) Synergistically Increase Apoptosis in B Cells Experiments examining the effect of B cell targeted SMIPS on B cell line apoptosis were performed. Each SMIP was tested individually and then in combination. Samples were analyzed at both 24 and 48 hours after initiation of incubation reactions. Annexin/PI Analysis was performed as follows: BJAB (courtesy of Ed Clark, University of Washington), Ramos (ATCC#CRL-1596), and Daudi cells were incubated 24 or 48 hours at 37° C. in 5% $CO_2$ in Iscoves (Gibco) complete media with 10% FBS at $3\times10^5$ cells/mL and 20 μg/mL SMIP protein. In addition, 20 μg/mL goat anti-human IgG was added to reactions in order to cross link reagents on the cell surface. Cells were then stained with Annexin V-FITC and propidium iodide using the BD Pharmigen Apoptosis Detection Kit I (#556547), and processed according to kit instructions. Briefly, cells were washed twice with cold PBS and resuspended in "binding buffer" at $1\times10^6$ cells/mL. One hundred microliters of the cells in binding buffer were then stained with 5 μl of Annexin V-FITC and 5 μl of propidium iodide. The cells were gently vortexed and incubated in the dark at room temperature for 15 minutes. Four hundred microliters of binding buffer was then added to each sample. They were then read and analyzed on a FACsCalibur (Becton Dickinson) instrument using Cell Quest software (Becton Dickinson).

Table 2 below shows that in the presence of crosslinking, treatment with TRU-016 had a more significant effect on apoptosis of cell lines than TRU-015 alone, although both molecules when used alone do induce some apoptosis. The increase varies depending on the cell line.

TABLE 2

| Bjab | Annexin V Positive |
|---|---|
| No SMIP | 17.5 |
| CD20 SMIP | 27 |
| CD37 SMIP | 30.6 |
| CD19 SMIP | 29.1 |
| CD20 + CD37 SMIP | 41 |
| CD20 + CD19 SMIP | 37.1 |
| CD37 + CD19 SMIP | 35.3 |

| Ramos | AnnexinV Positive | Plus GAM AnnexinV positive |
|---|---|---|
| cells alone | 3 | 3.3 |
| CD20 MAb | 1.4 | 3.1 |
| CD37 Mab | 18.3 | 8.7 |
| CD19 MAb | 3.7 | 3.1 |
| CD40 MAb | 3.9 | 8.3 |
| CD20 + CD37 | 32.3 | 35.7 |
| CD20 + CD19 | 5 | 10.5 |
| CD20 + CD40 | 5.7 | 19.4 |
| CD19 + CD37 | 26.9 | 50 |
| CD19 + CD40 | 8.2 | 18.4 |

Example 7

Combinations of TRU-016 with CD20-specific Antibodies or SMIPs Synergistically Increase CDC Experiments were performed to determine the CDC activity of combinations of TRU-016 with CD20-specific antibodies or SMIPS against B cells. The amount of reagents chosen for combination experiments was 0.5 μg/mL TRU-016 while that of TRU-015 was also 0.5 μg/ml. The concentration of RITUXAN (rituximab) was usually 0.04-0.06 μg/mL because of its higher activity in single reagent CDC experiments. In some experiments, the concentration of CD20 reagent was held constant at a suboptimal concentration, while the concentration of TRU-016 was varied to explore the minimal levels of CD37 directed reagent required to observe augmentation effects on CDC.

Cells were suspended in Iscoves (#12440-053, Gibco/Invitrogen, Granland, N.Y.) at $5\times10E^5$ cells/well in 75 μl. TRU-016 (75 μl), TRU-015, RITUXAN (rituximab), or combinations of these reagents were added to the cells at twice the concentrations indicated. Binding reactions were allowed to proceed for 45 minutes prior to centrifugation and washing in serum free Iscoves. Cells were resuspended in Iscoves with human serum (#A113, Quidel, San Diego, Calif.) at the indicated concentrations. The cells were incubated 60 minutes at 37° C. Cells were washed by centrifugation and resuspended in 125 μl PBS with 2% FBS (#16140-071, Gibco, Invitrogen, Grand Island, N.Y.), staining media. The cells were transferred to FACS cluster tubes (#4410, CoStar, Corning, N.Y.) and 125 μl staining media with 5 μl propidium iodide (PI, #P-16063, Molecular Probes, Eugene Oreg.) was added. Samples were incubated 15 minutes at room temperature in the dark prior to analysis by flow cytometry using a FACsCalibur and CellQuest software (Becton Dickinson).

Figure 6:
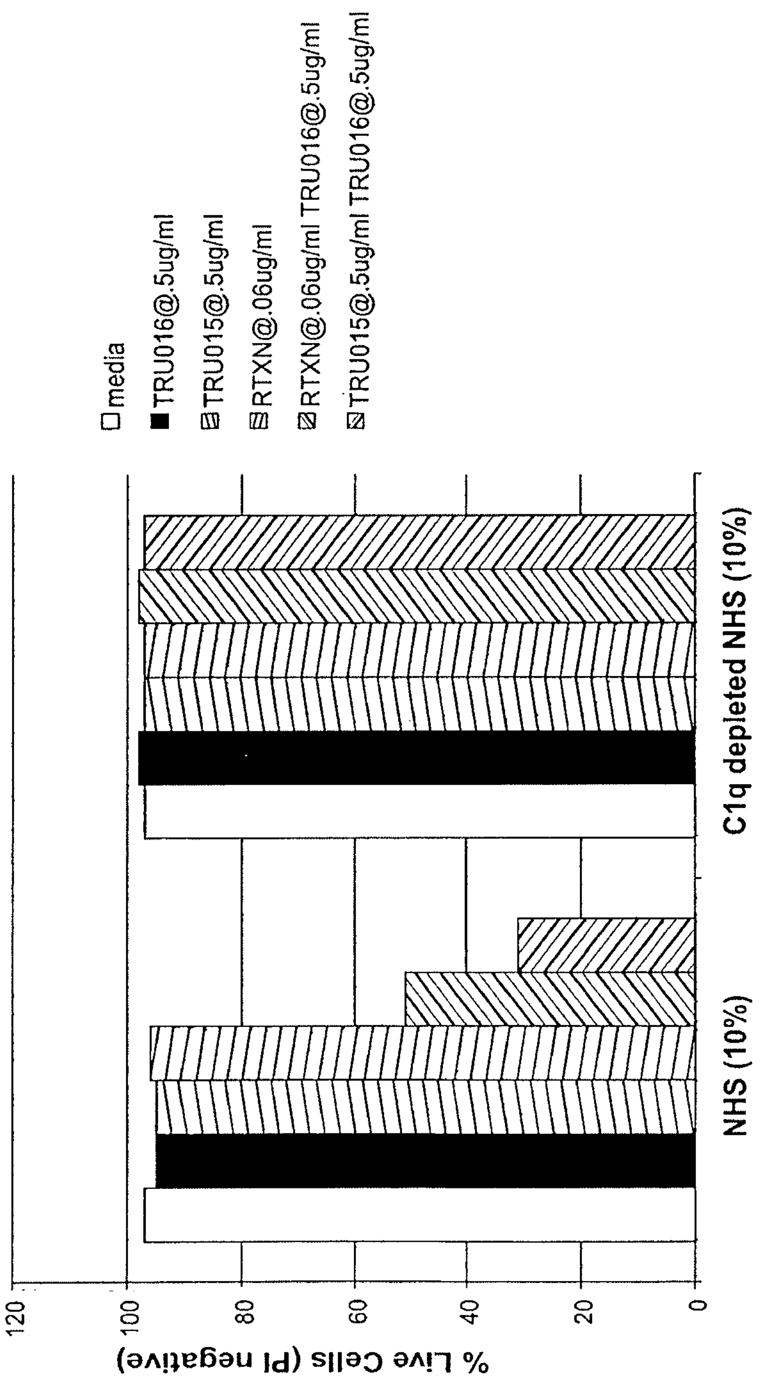
FIG. 6 shows the CDC activity ofTRU-015, RITUXAN (rituximab), TRU-016, or a combination thereof on Ramos B cells.

FIG. 6 shows that at suboptimal concentrations for killing as a single agent, TRU-015 and RITUXAN (rituximab) exhibit high levels of CDC activity when combined with TRU-016. TRU-016 alone fails to mediate CDC unless aggregates are present. Depletion of C1q from the reactions results in the elimination of all CDC activity observed.

Figure 7:
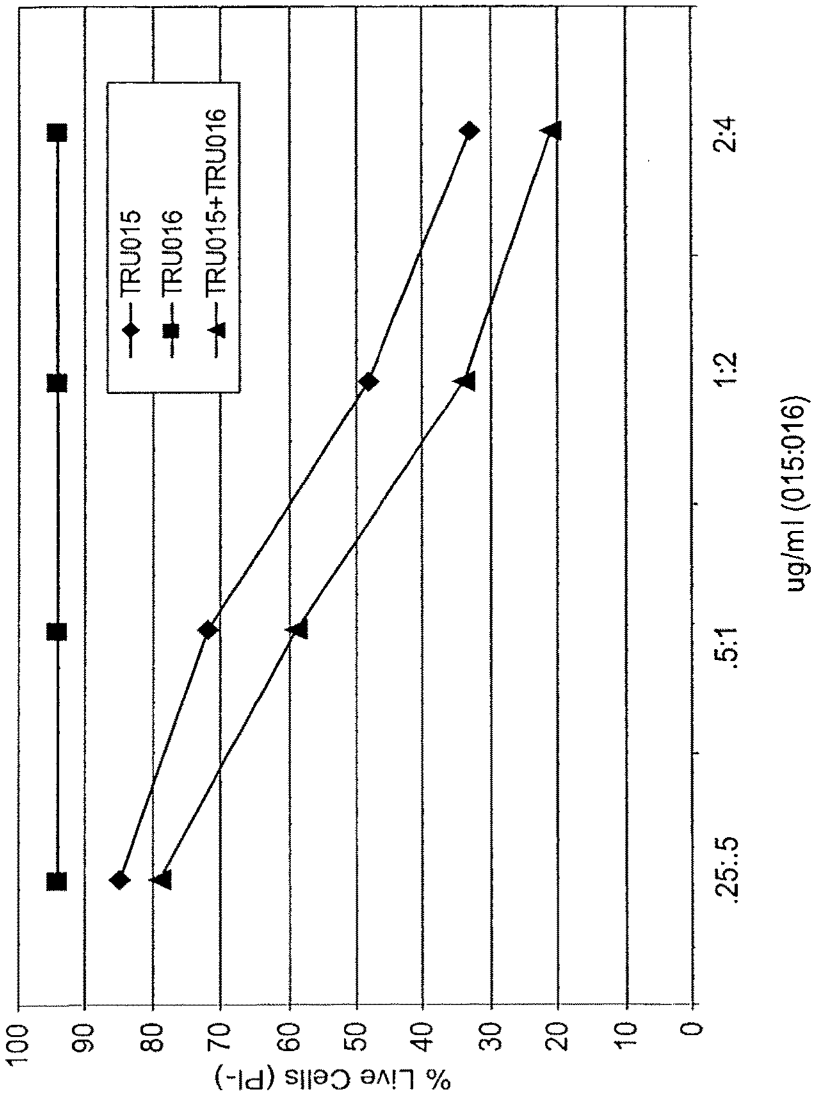
FIG. 7 shows that the effect of TRU-016 on CDC activity of TRU-015 on DHL-4 B cells.

FIG. 7 shows a combination experiment performed on DHL-4 B cells. Addition of TRU-016 to the CDC reactions results in a downward shift to the TRU-015 killing curve, demonstrating more effective killing at each concentration tested even though TRU-016 exhibits little or no activity alone.

Figure 8:
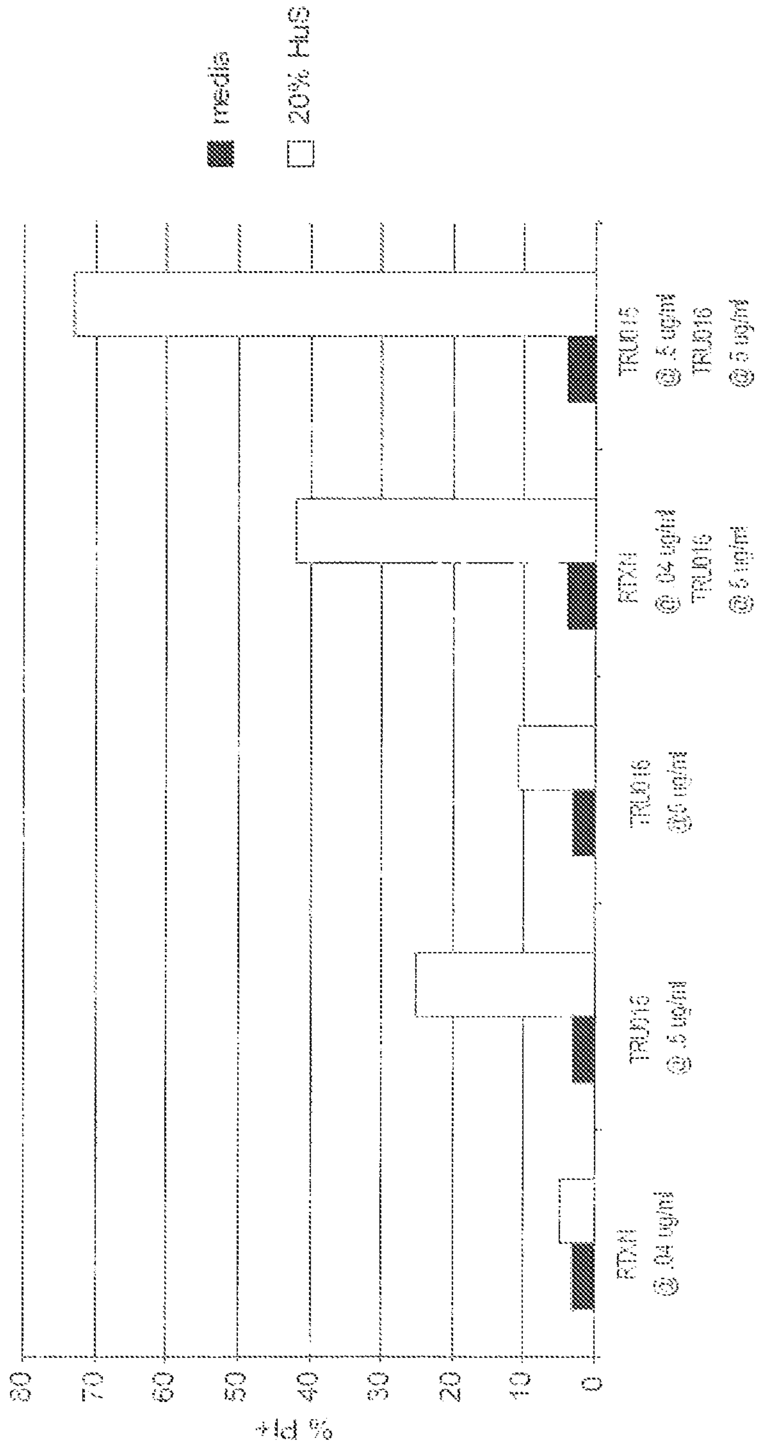
FIG. 8 shows the effect of TRU-016 on the CDC activity of TRU-015 and RITUXAN (rituximab).

FIG. 8 shows another CDC experiment where the sample reagents were mixed at the following ratios: 0.5 μ/mL TRU-015, 0.5 μg/mL TRU-016, and 0.06 μg/mL RITUXAN (rituximab). Again, the single agents are used at suboptimal concentrations in order to see augmentation effects in the presence of TRU-016. For both TRU-015 and RITUXAN (rituximab), TRU-016 enhances the level of CDC killing when added to the assays.

Figure 9:
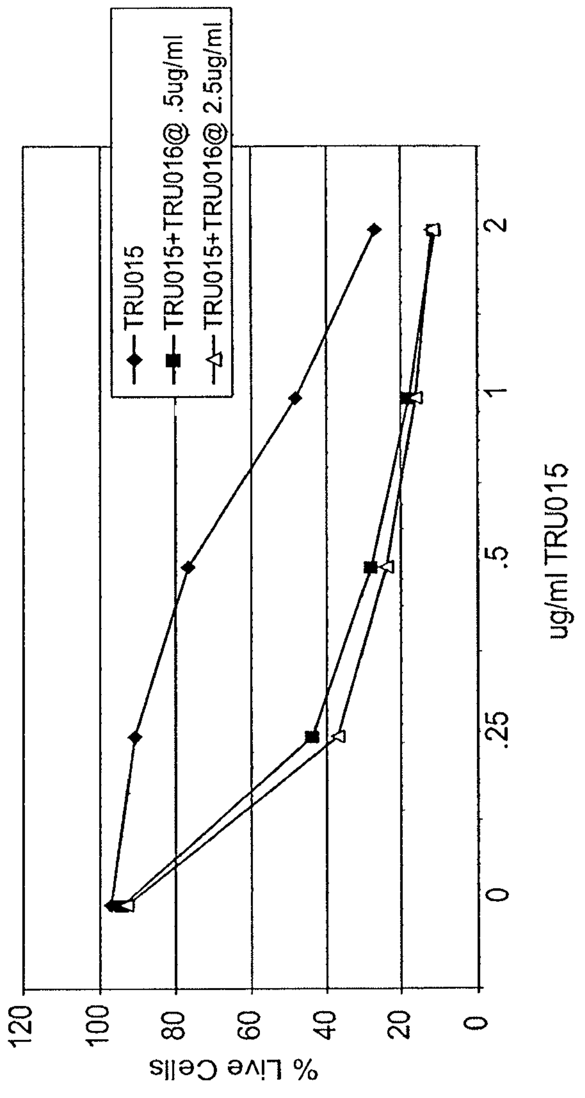
FIG. 9 shows the effect of TRU-016 on TRU-015 in a CDC assay.
Figure 10:
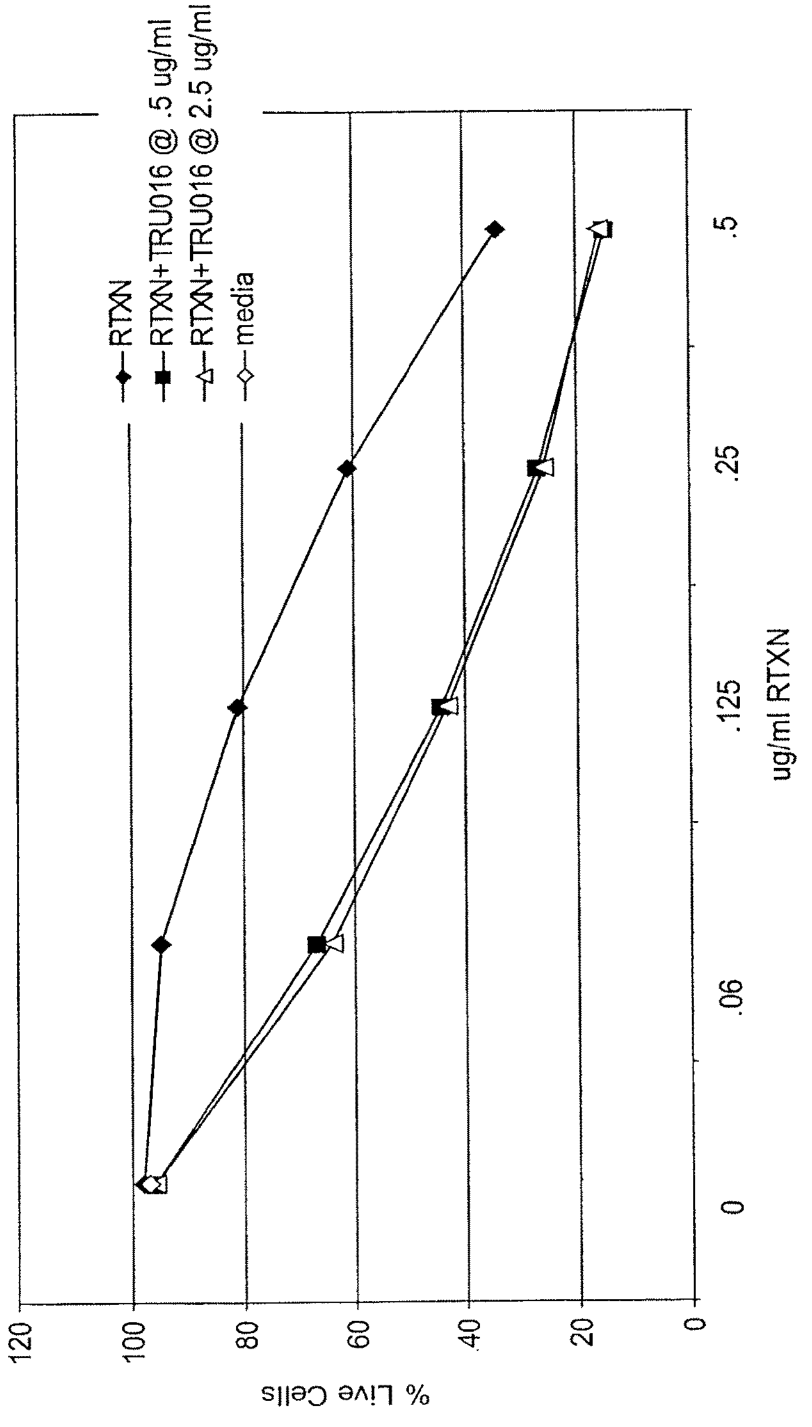
FIG. 10 shows that the TRU-016 molecule demonstrates high level, specific binding to human peripheral blood B lymphocytes, and a much lower level of binding to other subpopulations of cells in the non-B cell lymphocyte gate (CD19 negative population) when analyzed by flow cytometry.

FIGS. 9 and 10 show graphical representations of the data for CDC assays where the concentration of TRU-015 or RITUXAN (rituximab) was kept constant and TRU-016 concentration was increased. Again, CDC activity was greater when TRU-016 was added to the reactions, but increasing the concentration of TRU-016 to 2.5 μg/mL from 0.5 μg/mL did not significantly increase the CDC-mediated killing in these experiments.

Example 8

TRU-016 Augments the ADCC and the CDC Activity of CD20-Specific Antibodies and SMIPs Experiments were performed to determine if combinations of TRU-016 SMIP with CD20-specific antibodies or SMIPs could augment ADCC and CDC activity against B cell targets.

BJAB, Ramos, and Daudi lymphoblastoid B cells (10E7) cells were labeled with 500 μCi/mL $^{51}Cr$ sodium chromate for 2 hours at 37° C. in IMDM/10% FBS. The labeled BJAB cells were washed three times in RPMI/10% FBS and resuspended at 4×10E5 cells/mL in RPMI. Heparinized, human whole blood was obtained from anonymous, in-house donors and PBMC isolated by fractionation over Lymphocyte Separation Media (LSM, ICN Biomedical) gradients. Buffy coats were harvested and washed twice in RPMI/10% FBS prior to resuspension in RPMI/10% FBS at a final concentration of 3×10E6 cells/ml. Cells were counted by trypan blue exclusion using a hemacytometer prior to use in subsequent assays. Reagent samples were added to RPMI media with 10% FBS at 4 times the final concentration and five serial dilutions for each reagent were prepared. For combinations, the reagents were premixed and diluted prior to addition to the wells. These reagents were then added to 96 well U bottom plates at 50 μl/well for the indicated final concentrations. The $^{51}Cr$ labeled BJAB were added to the plates at 50 μl/well (2×10E4 cells/well). The PBMCs were then, added to the plates at 100 μl/well (3×10E5 cells/well) for a final ratio of 15:1 effectors (PBMC):target (BJAB).

Effectors and targets were added to media alone to measure background killing. The $^{51}Cr$ labeled BJAB were added to media alone to measure spontaneous release of $^{51}Cr$ and to media with 5% NP40 (#28324, Pierce, Rockford, Ill.) to measure maximal release of $^{51}Cr$. Reactions were set up in quadruplicate wells of a 96-well plate. SMIPs were added to wells at a final concentration ranging from 12 ng/mL to 101 μg/mL as indicated on the graphs. For SMIP combinations, the reagents were mixed prior to addition to the wells. Each data series plots a different single SMIP or combination at the titration ranges described. Reactions were allowed to proceed for 6 hours at 37° C. in 5% $CO_2$ prior to harvesting and counting. Fifty μl of the supernatant from each well was then transferred to a Luma Plate 96 (#6006633, Perkin Elmer, Boston, Mass.) and dried overnight at room temperature. CPM released was measured on a Packard TopCounNXT. Percent specific killing was calculated by subtracting (cpm {mean of quadruplicate samples} of sample—cpm spontaneous release)/(cpm maximal release-cpm spontaneous release)×100.

Figure 11:
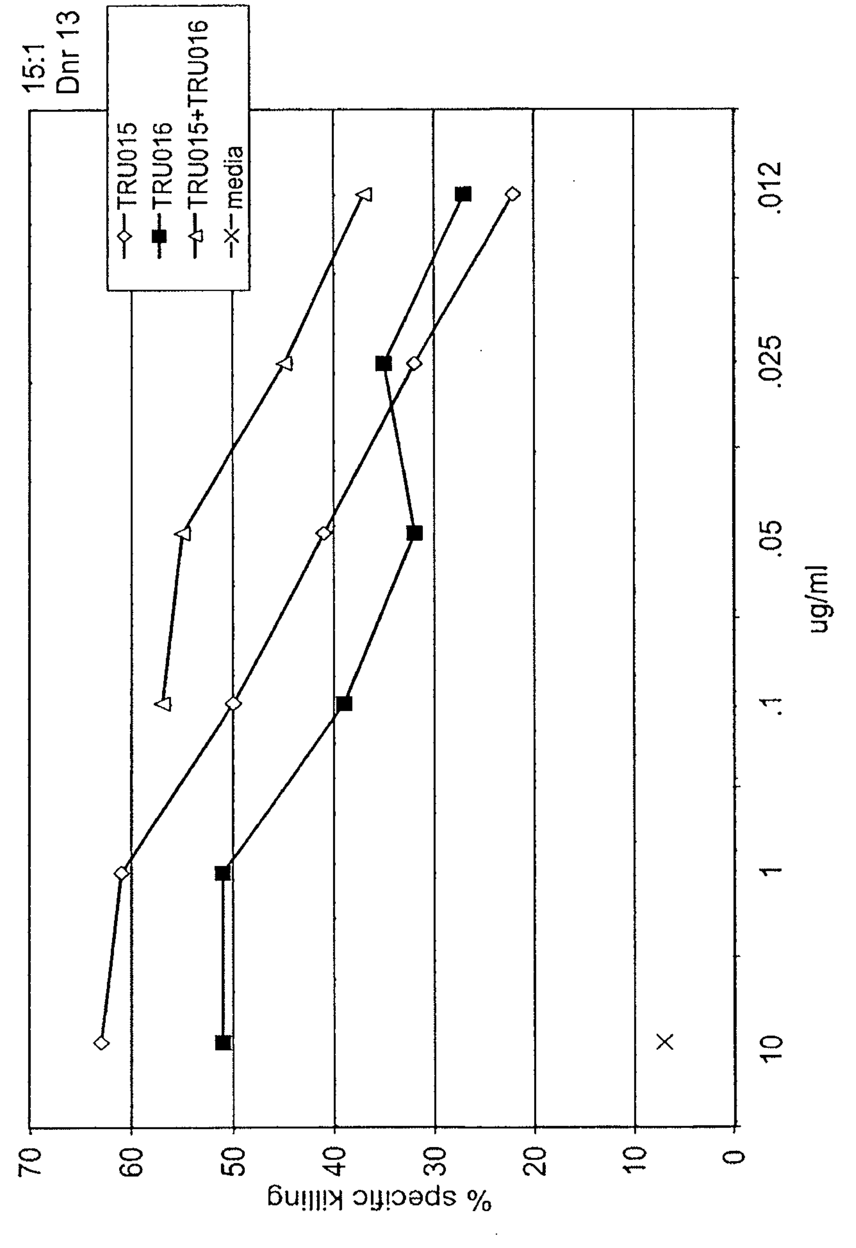
FIG. 11 shows the interaction of TRU-015 and TRU-016 in an ADCC assay using BJAB cells.
Figure 12:
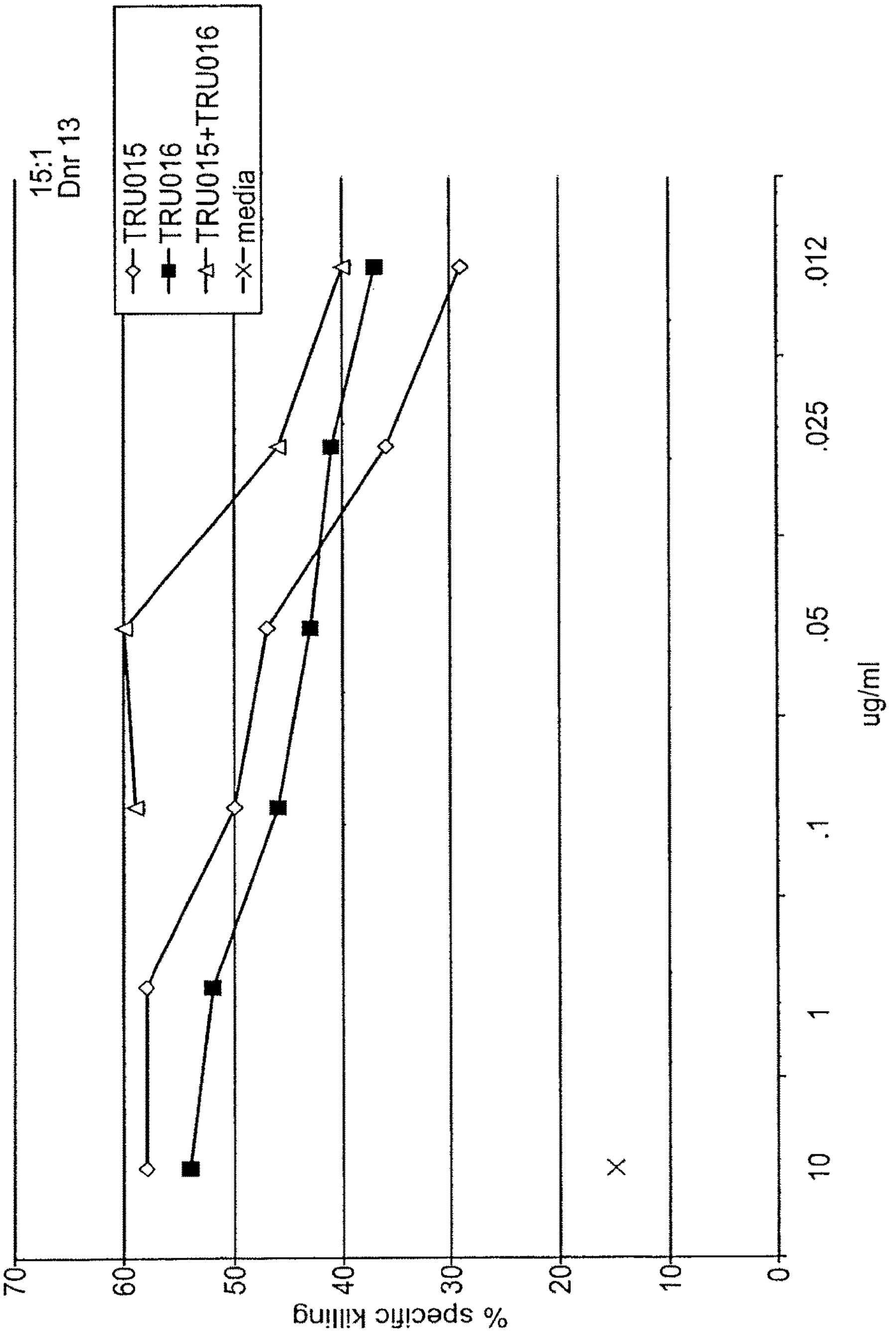
FIG. 12 shows the interaction of TRU-015 and TRU-016 in an ADCC assay using Daudi cells.
Figure 13:
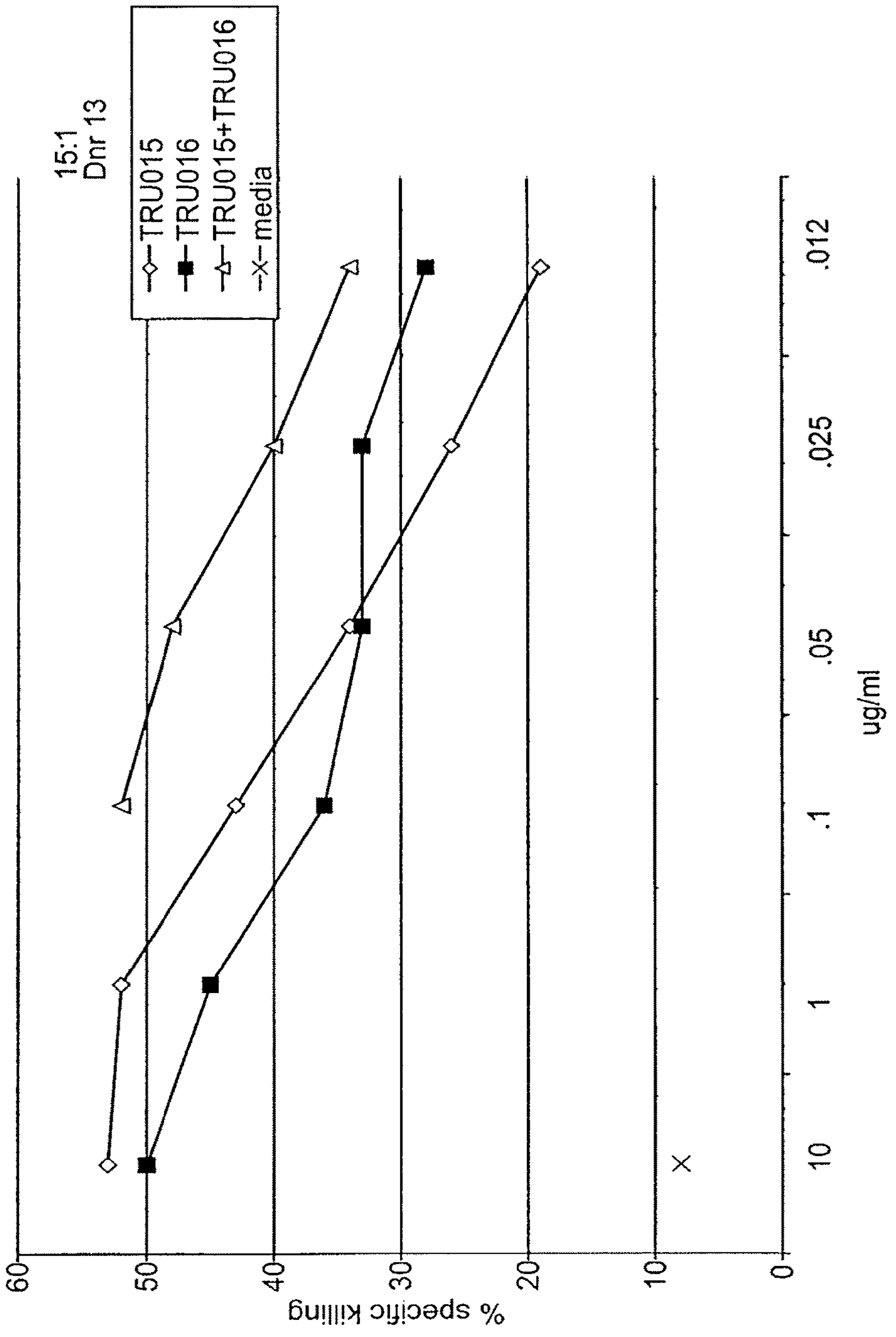
FIG. 13 shows the interaction of TRU-015 and TRU-016 in an ADCC assay using Ramos cells.

Data were plotted as % specific killing versus SMIP concentration. The effector to target ratio is indicated on each figure, and the target cell line was also indicated. FIGS. 11, 12, and 13 show data for experiments on different cell lines (BJAB, Daudi, and Ramos) where the same donor was used.

Figure 14:
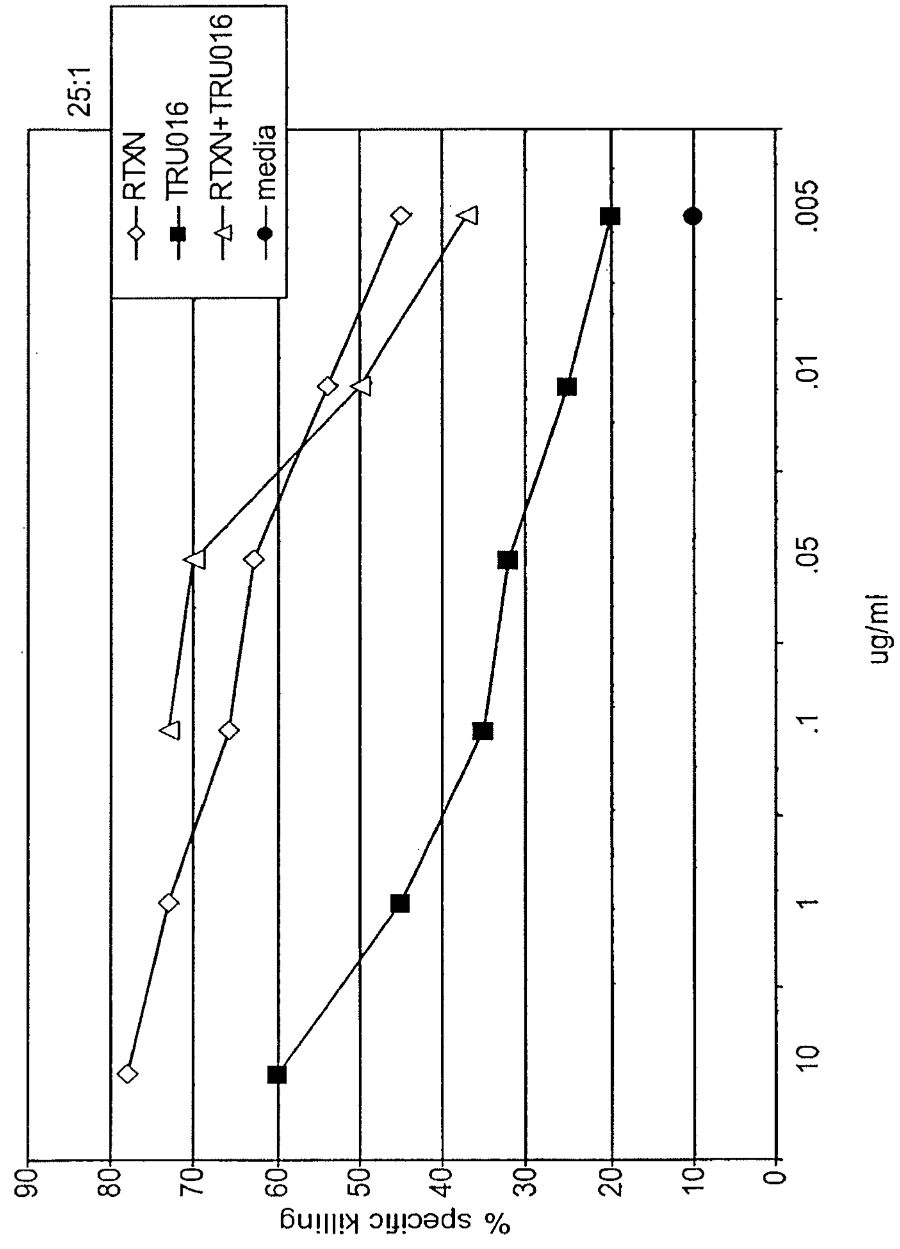
FIG. 14 shows the effect of RITUXAN (rituximab), TRU-016, and a combination thereof on the specific killing of BJAB cells.
Figure 15:
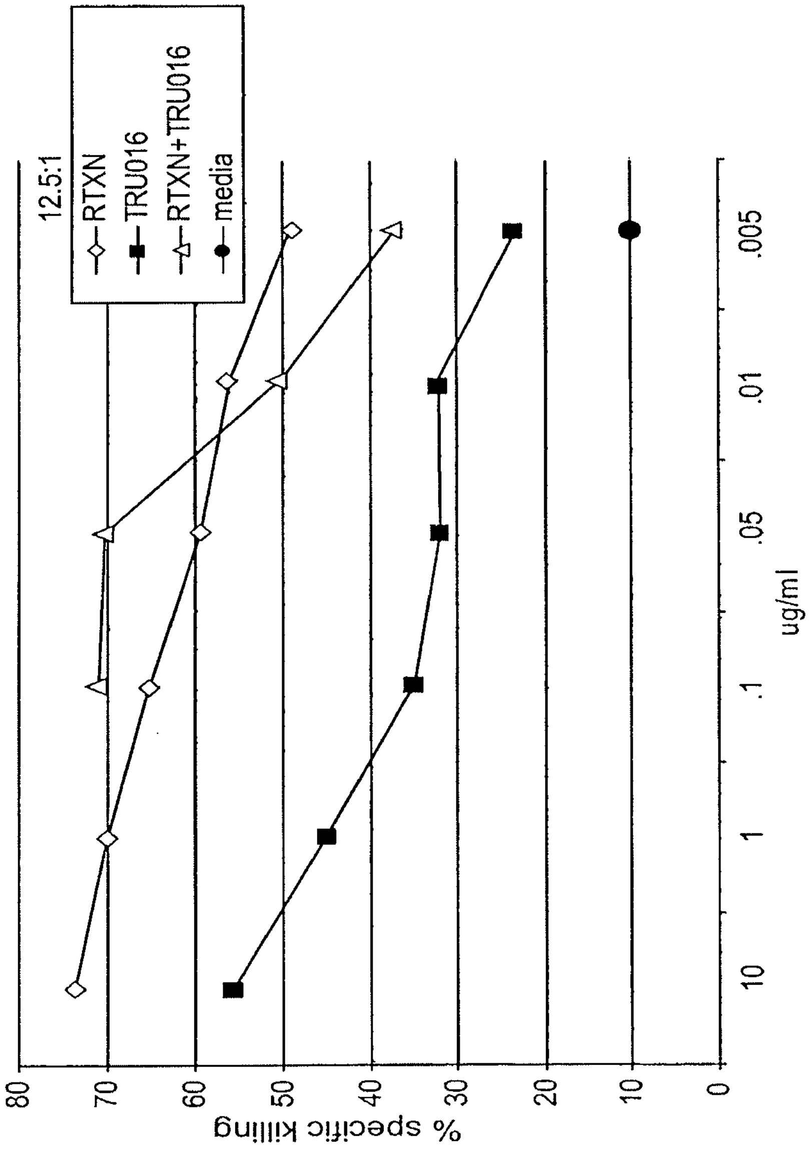
FIG. 15 shows the effect of RITUXAN (rituximab), TRU-016, and a combination thereof on the specific killing of BJAB cells.
Figure 16:
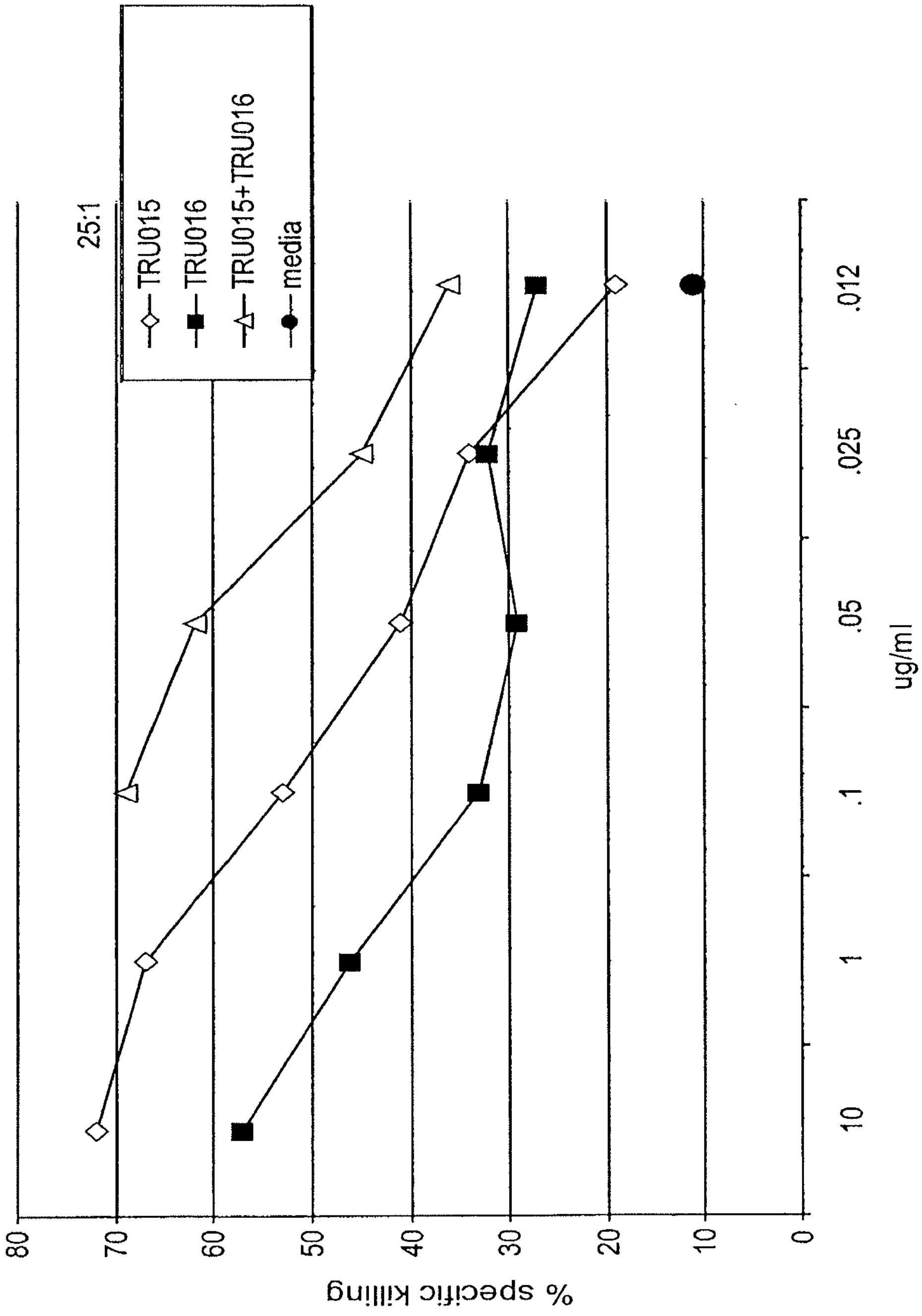
FIG. 16 shows the effect of TRU-015, TRU-016, and a combination thereof on the specific killing of BJAB cells.
Figure 17:
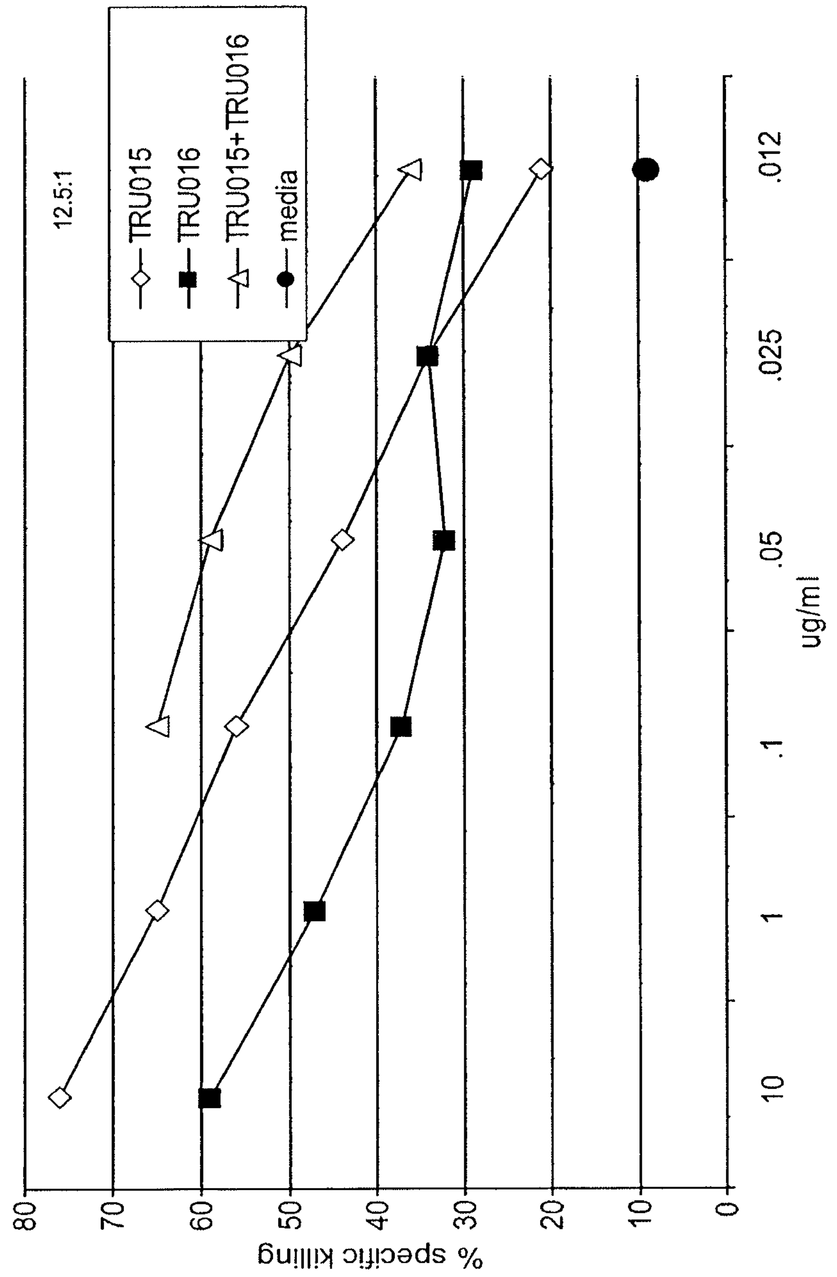
FIG. 17 shows the effect of TRU-015, TRU-016, and a combination thereof on the specific killing of BJAB cells.

In FIGS. 14 and 15 (RITUXAN (rituximab)+TRU-016) and FIGS. 16 and 17 (TRU-015+TRU-016) data is presented for experiments in which the target cell line used was BJAB. The specific killing observed for each combination was greater than either single reagent alone at the same concentration, indicating that the CD20 and CD37 targeted SMIPs augment the killing mediated by the other, although the augmentation effect is not completely additive.

Thus, TRU-016 can enhance CD20-specific SMIP or CD20-specific antibody ADCC mediated killing of B cells.

Initial experiments to explore the effects of combinations of TRU-016 with CD20-directed antibodies were designed to determine the relative amounts of each reagent to use so that CDC synergy could be detectable. Ramos cells were suspended in IMDM, and TRU-016, RITUXAN (rituximab), or combinations of these reagents were added to the cells to the final concentrations indicated in FIG. 18. Binding reactions were allowed to proceed for 45 minutes prior to centrifugation and washing in serum free Iscoves. Cells were resuspended in Iscoves with 10% NHS. The cells were incubated 60 minutes at 37° C. In experiments shown in FIG. 18A-C, cells were washed by centrifugation and resuspended in staining media containing 0.5 μg/mL propidium iodide (PI, #P-16063, Molecular Probes, Eugene Oreg.). Samples were incubated 15 minutes at room temperature in the dark prior to analysis by flow cytometry using a FACsCalibur and CellQuest software (Becton Dickinson).

Figure 18A:
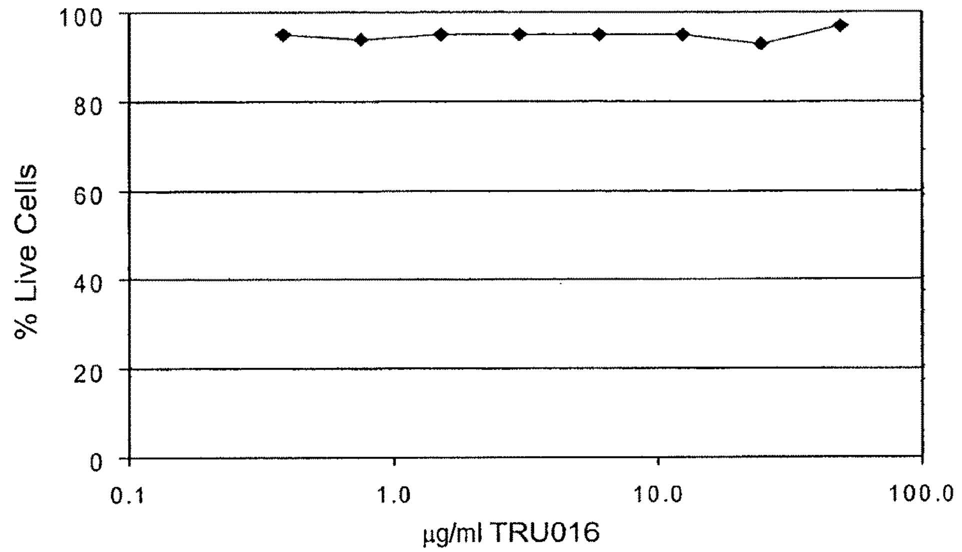
FIG. 18A-D shows that TRU-016 dimer forms do not mediate CDC alone, but potentiate the CDC activity of Rituximab in vitro.

The more highly purified TRU-016 dimer peak is a poor mediator of CDC when used alone, as shown in FIG. 18A by the flat dose-response curve even at high concentrations. Because CD20 directed reagents were efficient inducers of CDC activity, non saturating amounts of the CD20 directed reagents were desirable in combination experiments, so that synergy between the reagents could be detected. From these initial studies, the usual amount of reagent chosen for combination experiments was 0.5 μg/mL or 2 μg/mL TRU-016. The concentration of RITUXAN(rituximab) was usually 0.04-0.06 μg/mL because of its higher activity in single reagent CDC experiments. In some experiments, the concentration of CD20 reagent was held constant at a suboptimal concentration, while the concentration of TRU 016 was varied to explore the minimal levels of CD37 directed reagent required to observe augmentation effects on CDC. Thus, TRU-016 alone fails to mediate CDC unless aggregates are present.

Figure 18B:
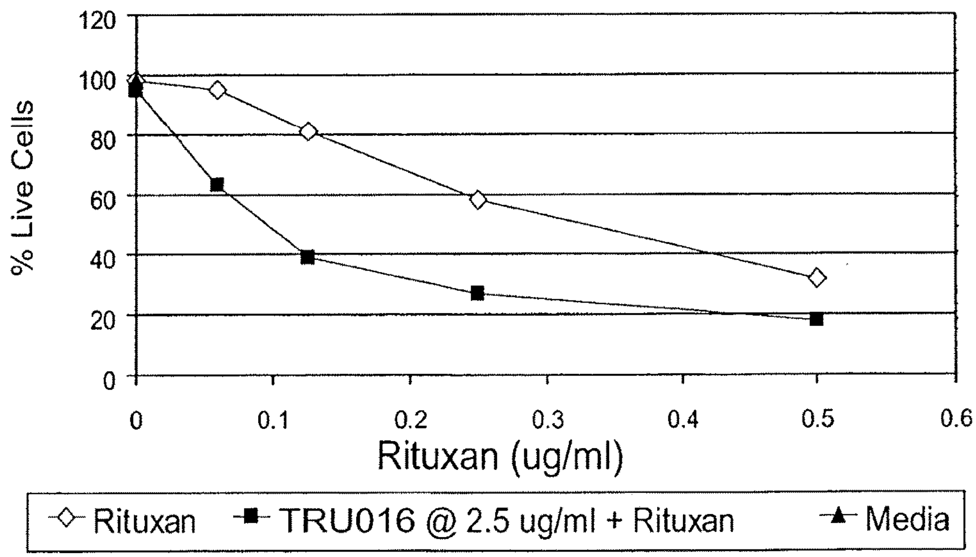

FIG. 18B shows a graph of the percentage of live cells (PI negative) observed over the titration range indicated (0.06-0.5 μg/ml) when RITUXAN(rituximab) is used alone or in combination with TRU-016 at 2.51 μg/ml. RITUXAN (rituximab), when used at a range of suboptimal doses for killing as a single agent, exhibits higher levels of CDC activity at each concentration when combined with TRU-016 (FIG. 18B). Depletion of C1q from the reactions results in the elimination of all CDC activity observed (FIG. 3B).

Figure 18C:
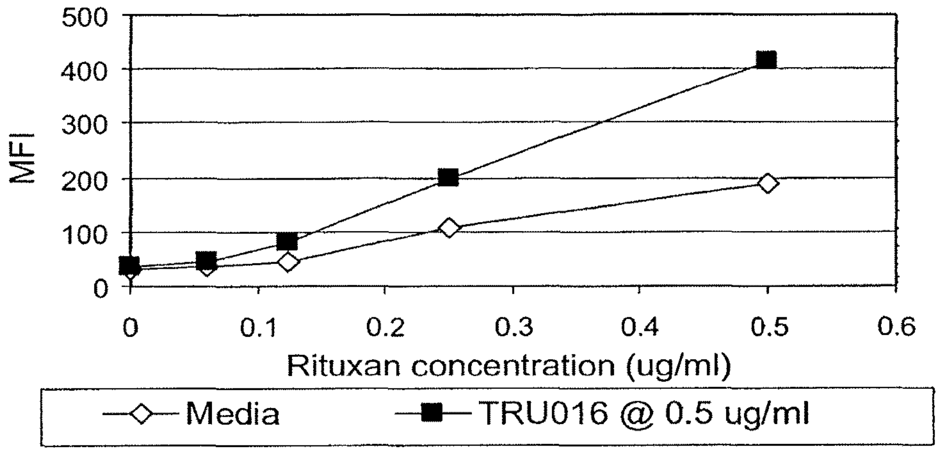

In FIG. 18C, samples were also incubated with FITC anti-C1q for 45 minutes on ice prior to analysis by flow cytometry. Lymphocyte gating was on compromised cells. The percentage of cells in this gate increased with increasing RITUXAN (rituximab) concentration, and the relative MFI for this population of cells was graphed. FIG. 18C shows the results of a CDC experiment where the sample reagents were mixed at the following ratios: 0.5 μg/mL for TRU-016, and RITUXAN (rituximab) concentrations ranging from 0.06 μg/mL to 0.5 μg/mL, and cells stained with PI prior to flow cytometry. The results show a dose dependent increase in MFI with increasing doses of RITUXAN (rituximab). The addition of TRU-016 dimer forms resulted in an additional increase in the MFI at each concentration of RITUXAN (rituximab). A similar series of CDC assays were performed, keeping the concentration of RITUXAN (rituximab) constant and increasing the TRU-016 concentration. Again, CDC activity was greater when TRU-016 was added to the RITUXAN (rituximab) reactions, but increasing the concentration of TRU-016 to 2.5 μg/mL from 0.5 μg/mL did not significantly increase the CDC mediated killing in these experiments (data not shown).

Figure 18D:
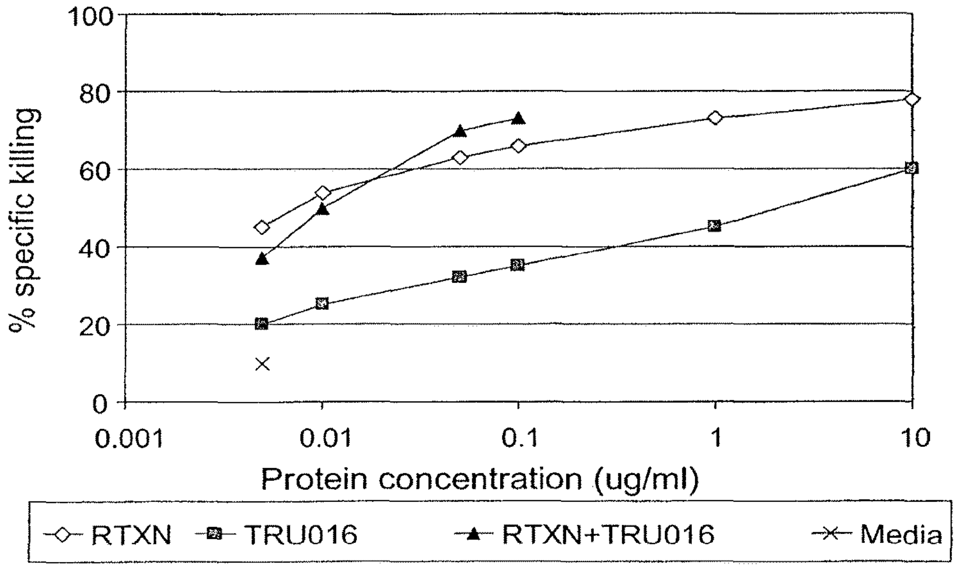

RITUXAN (rituximab) and TRU-016 proteins used alone and in combination with one another were compared for their ADCC activity in vitro using a similar concentration range as that used for the CDC assays. FIG. 18D shows the results of an ADCC assay with labeled Ramos cell targets and human PBMC effector cells at an effector to target ratio of 25:1, using TRU-016 or RITUXAN (rituximab), alone and in combination with one another over the concentration ranges indicated. Similar data were obtained at an effector: target ratio of 12.5:1. Both the TRU-016 dimer form and RITUXAN (rituximab) mediate significant levels of ADCC against Ramos cells expressing the CD20 and CD37 target antigens; however, the combination of the two reagents does not result in significant augmentation in the level of killing.

Example 9

TRU-016 Induces Apoptosis in B Cells

Experiments examining the effect of TRU-016 on B cell line apoptosis were performed. Initial assays of the effects on apoptosis of TRU-016 molecules targeted to different B cell receptors were performed using protein A purified material that still contained higher order aggregates. After 24 hour treatment with CD37 antibodies or engineered TRU-016 molecules, similar patterns of increased apoptosis were observed in multiple experiments using annexin V positive cell percentages as a measure of apoptotic activity and both Ramos and BJAB cells as binding targets (data not shown).

Figure 19A:
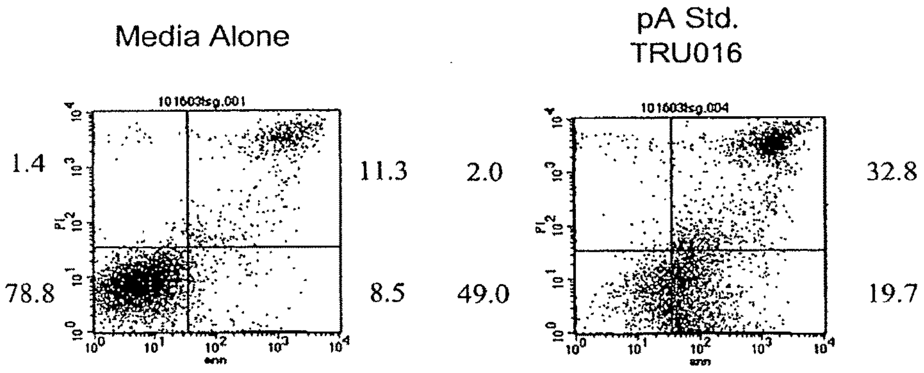
FIG. 19A-B demonstrates that protein A purified TRU-016 induces apoptosis of Ramos and Daudi cells, while dimer forms require crosslinking.

FIG. 19A demonstrate that apoptosis is significantly increased after incubation of B cell lines with unfractionated TRU-016. FIG. 19A shows a dot plot of Annexin V-PI staining of Ramos cells after incubation for 24 hours with the TRU-016 (10 μg/mL). The % of annexin V-PI double positive cells increased from 11.3% of the total population to 32.8%, and the % of annexin V positive-PI negative cells increased from 8.5% to 19.7%, indicating that apoptosis is induced after exposure to TRU-016. Similar data were obtained whether Ramos or BJAB cells were used as the binding targets in these assays.

Figure 19B:
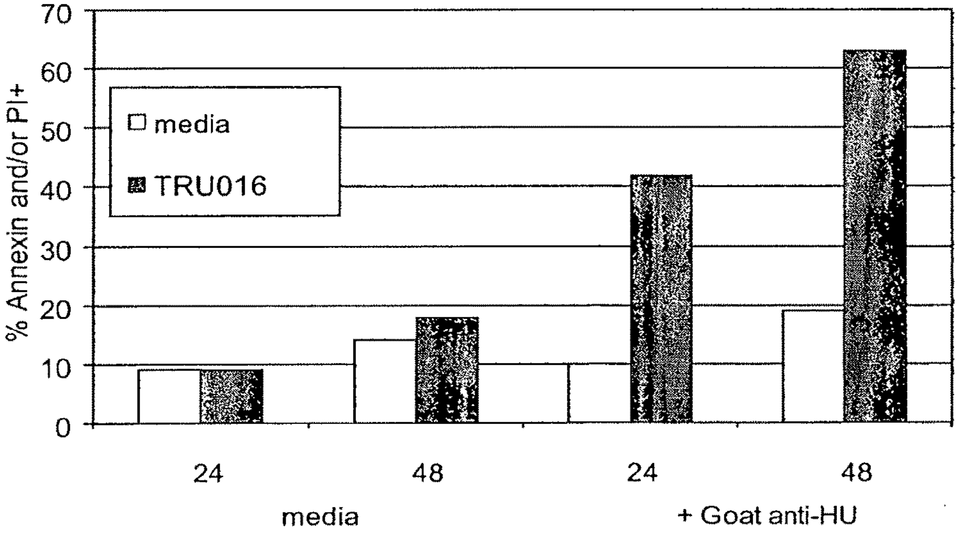

Further experiments examining the effect of TRU-016 on B cell line apoptosis were performed using the more highly purified dimer form of TRU-016 (FIG. 19B). Samples were analyzed at both 24 and 48 hours after initiation of incubation reactions. Annexin/PI analysis was performed on several cell types using 20 μg/mL TRU-016 protein. Because apoptosis was reduced using the dimer form of TRU-016, 20 μg/mL goat anti-human IgG was added to reactions in order to cross link reagents on the cell surface. Cells were then stained with Annexin V-FITC and propidium iodide. The data shown in FIG. 19B demonstrates that the TRU-016 dimer peak induces apoptosis of Daudi cells after 24-48 hours, but that the presence of a crosslinking agent such as anti-human IgG results in a significant increase in the level of CD37 targeted apoptosis.

Figure 20A:
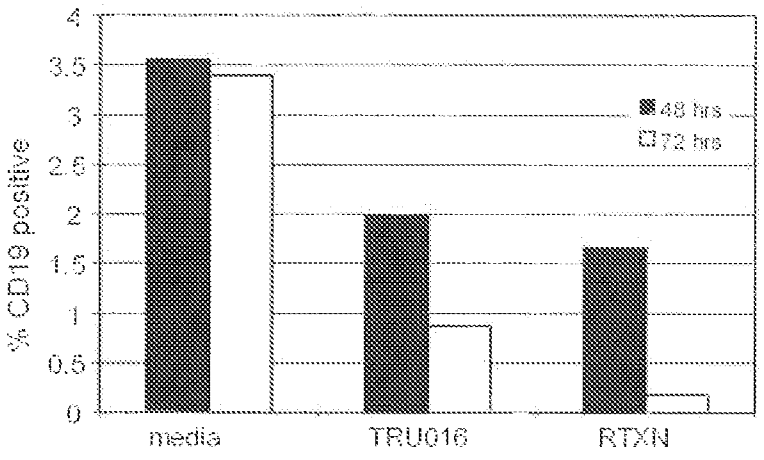
FIGS. 20A, 20B, and 20C shows that TRU-016 preferentially depletes normal B cells from PBMC cultures.
Figure 20B:
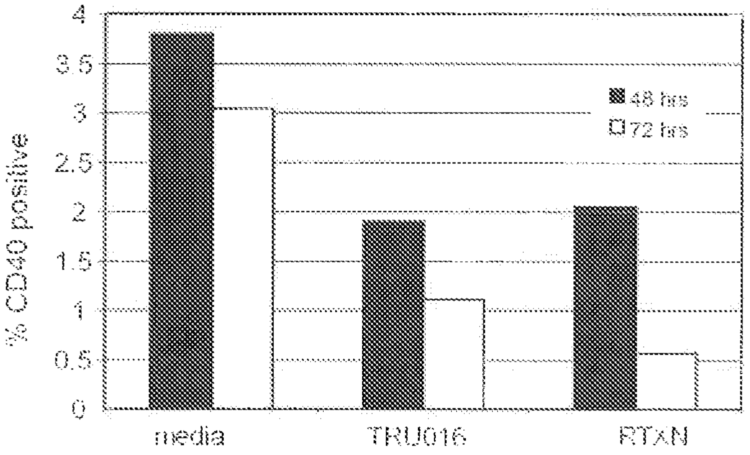

Experiments were also performed to determine the effect of TRU-016 on normal human B cells in culture using human PBMCs. FIGS. 20A and 20B shows results from one such experiment, with columnar graphs of the percentage of CD19 or CD40 positive lymphocytes (B cells) present in PBMC cultures treated for 48-72 hours with media alone, TRU-016, or RITUXAN (rituximab).

Figure 20C:
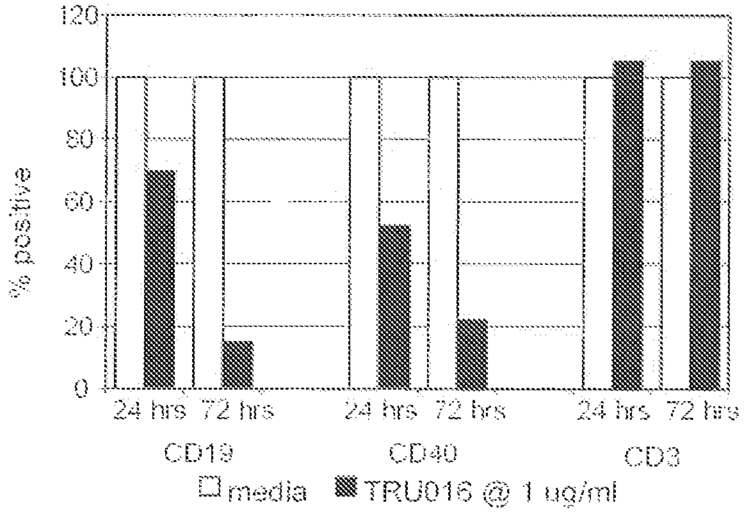

Human PBMCs were isolated from whole blood by LSM density centrifugation. Cells were incubated for 48 or 72 hours with 1 μg/mL of RITUXAN (rituximab) or TRU-016. A portion of the incubation reaction was harvested at 48 hours and again at 72 hours after initiation of the experiment. PBMCs were washed and incubated with FITC anti-CD19, FITC anti-CD40, or FITC anti-CD3 for 45 minutes on ice. The percentage of total lymphocytes staining with these reagents was then tabulated and compared to PBMC samples incubated under similar conditions but without test reagents, and stained as for the treated samples. FIGS. 20A and B show columnar graphs of the fraction of the total lymphocyte population (%) which give a positive FACs signal after 48 and 72 hours with the indicated reagents. FIG. 20C shows a composite graph from a similar experiment, showing the percent reduction from the original number of lymphocytes expressing the indicated CD antigen (i.e. CD19, CD40 or CD3 positive) after incubation of PBMCs with TRU-016 (at 1 μg/ml) for 24 and 72 hours.

In the presence of crosslinking, treatment with the TRU-016 dimer form or RITUXAN (rituximab) resulted in a reduction in the percentage of B lymphocytes in PBMC cultures as measured by positive staining for CD19 and CD40. Although the percentage of B lymphocytes in culture was low at the outset of the experiment, coculture with RITUXAN (rituximab) or TRU-016 decreased the number of CD19 and CD40 positive lymphocytes in the PBMC culture by approximately 1.5-2 fold after 48 hours, and by more than 3 fold after 72 hours. This general pattern of B cell depletion after 48-72 hours was reproducible in all normal PBMC cultures tested, regardless of the initial starting percentage of B lymphocytes in these cultures, which ranged from approximately 3% to as much as 7% of the total lymphocytes, depending on the sample.

FIG. 20C shows a columnar graph of the percentage depletion of B lymphocytes compared to T lymphocytes in short term PBMC cultures incubated with TRU-016 for 24 to 72 hours. These data indicate that the TRU-016 is capable of specific depletion of CD37 positive B lymphocytes from normal peripheral blood cultures, and that the low level of binding by TRU-016 to non-B lymphocytes (FIG. 1C) is insufficient to mediate significant depletion of these lymphocytes from the cell population.

Example 10

Combinations of TRU-016 and Rituximab Synergistically Reduce Tumor Volume in a Murine Tumor Xenograft Model Mouse tumor xenograft studies exploring combination therapies were performed using nude mice (Harlan) and Ramos or Daudi human tumor lines. Ramos or Daudi tumor cells were grown in T150 flasks in IMDM/10% FBS until they reached 80% confluency. Five million ($5\times10^6$) cells were used as a tumor inoculum per mouse. Cells were injected subcutaneously in the right flank using PBS in a total volume of 0.1 ml or $5.0\times1\ 0^7$/ml. Nude mice were allowed to develop tumors and sorted into groups based on tumor size/volume. For each treatment group, 12 mice with a mean tumor volume of approximately 222 $mm^3$ (range =152-296$mm^3$) were used. Some mean tumor volumes ranging from 237-251 $mm^3$ were also used. Animals were injected intravenously (IV) at days 0, 2, 4, 6, and 8 with one of the following reagents: TRU-016 GPC POI (peak of interest), 200 μg/mouse; RITUXAN (rituximab), 200μg/mouse, or human IgG (control) at 200 or 400 μg/mouse as single reagents, or as the following combinations of reagents: RITUXAN (rituximab)+TRU-016 at 100 μg each per mouse; or RITUXAN (rituximab)+TRU-016 at 200 μg each per mouse. Tumor volume was measured daily with calipers until completion of the experiment (sacrifice or regression). Tumor volume as a function of treatment time was plotted for each animal and results were also averaged within each group.

Similar studies were also performed using smaller tumors, with mice sorted into groups with smaller mean tumor volume ranging between 153-158 $mm^3$, and with larger tumors but using Daudi cells rather than Ramos cells. These studies were performed in an AAALAC accredited animal facility and animal use program in accordance with guidelines from an Institutional Animal Care and Use Committee (IACUC).

Figure 21:
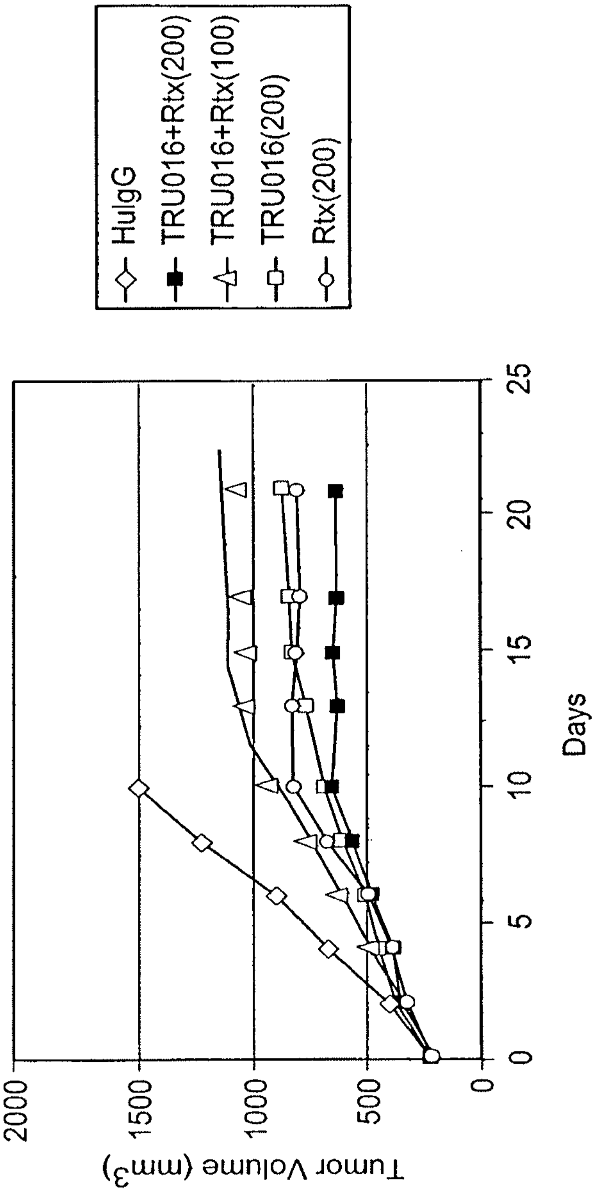
FIG. 21 demonstrates the efficacy of TRU-016 compared to hulgG, RITUXAN (rituximab), and the combination treatment of TRU-016 and RITUXAN (rituximab) on tumor volume in animals.

FIG. 21 graphs the efficacy of TRU-016 compared to huIgG, RITUXAN (rituximab), and the combinations at 100 μg and 200μg each averaged over each group of 12 animals. Tumor volume was plotted as a function of time after treatment with the IV injection(s). The average tumor volume after treatment with TRU-016 was smaller than that observed using the negative control (huIgG). When % survival or % tumor free animals were graphed, the higher dose combination therapy exhibited higher anti-tumor activity in this in vivo tumor model. However, at the lower dose (100μg each), the combination therapy was not as effective as each single reagent at a higher dose.

These data indicate that TRU-016 therapy, when used in combination with RITUXAN (rituximab) at the appropriate doses, will have greater efficacy in treating patient tumors than RITUXAN (rituximab) therapy alone.

Example 11

TRU-016 Reduces Tumor Volume and Increases Survival in a Murine Tumor Xenograft Model Mouse tumor xenograft studies were performed using nude mice (Harlan) and Ramos or Daudi human tumor lines. Three different studies were performed based on tumor type and tumor size at the time of treatment with the TRU-016 or other test reagent. Ramos or Daudi tumor cells were grown and ($5\times10^6$) cells were injected subcutaneously in the right flank to inoculate each treated mouse with the tumor. Nude mice were allowed to develop tumors and sorted into groups based on tumor size/volume. In the first study, for each treatment group, 12 mice with a mean tumor volume of 155-237 $mm^3$ were used. Animals were injected intravenously (IV) at days 0, 2, 4, 6, and 8 with one of the following reagents: Rituximab, 200 μg/mouse; TRU-016 GPC dimer peak, 200 μg/mouse; or human IgG (control), 400 μg/mouse. Tumor volume was measured daily with calipers until completion of the experiment (sacrifice or regression). Tumor volume as a function of treatment time was plotted for each animal and results were also averaged within each group. Group averages were shown in FIG. 22A, while FIG. 22B shows a comparison of the percent survival data for each group of mice as a function of time.

Figure 22A:
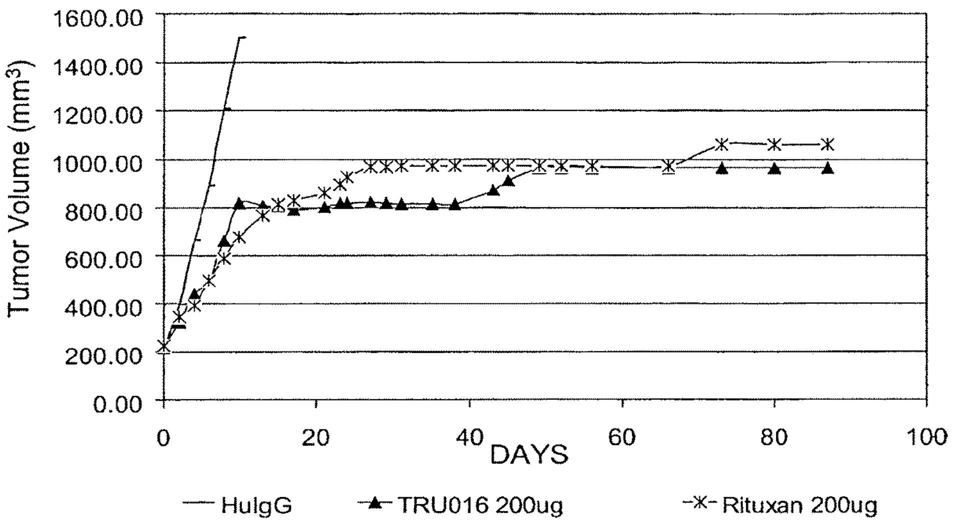
FIGS. 22A and B shows that TRU-016 dimer forms exhibit significant anti-tumor activity, as measured by effect on tumor volume and percent survival in a mouse xenograft tumor model.
Figure 22B:
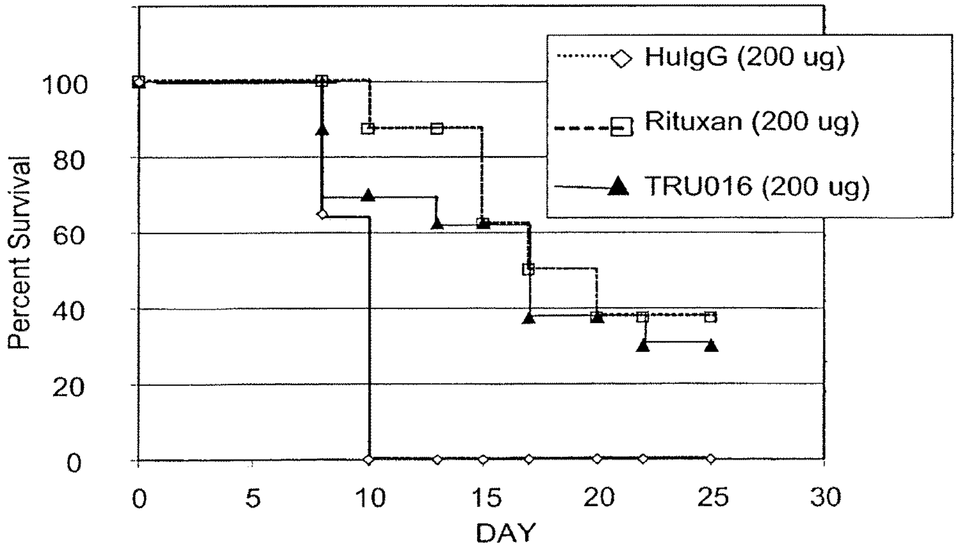

FIG. 22A shows the efficacy ofTRU-016 compared to huIgG and RITUXAN (rituximab) in the Ramos tumor model, averaged over each group of 12 animals. Tumor volume was plotted as a function of time after treatment with the IV injection(s). The average tumor volume after treatment with the TRU-016 was smaller than that observed using the negative control (huIgG). FIG. 22A graphs the survival curves for the different treatment groups, comparing huIgG, RITUXAN (rituximab), and TRU-016. Administration of TRU-016, utilizing the more demanding Ramos tumor model with increased baseline tumor volume, resulted in an inhibition of tumor growth rate relative to human IgG (data not shown). Administration of TRU-016 to mice with the smaller Ramos tumors resulted in both an inhibition of tumor growth and increased median survival times.

Example 12

TRU-016 does not Affect the CDC Activity of Other B Cell Surface Receptors

To determine whether the TRU-016 molecule augments the level of CDC activity resulting from treatment with antibodies to other B cell surface receptors, in addition to CD20, such as MHCII, CD19, CD80/86, and CD40, a panel of experiments was performed similar to those just described for CD20-CD37 directed combinations.

Ramos cells were added to wells in Iscoves complete media with 10% FBS. The MAbs (reagent B: HD37-anti CD19, reagent C, 9.4-anti-CD45), fusion protein (reagent D: CTLA-4 mulg-IgG2a, Ancell #501-820), and ascites fluid (reagent A: HB10a-anti-MHC11), were added at the indicated dilutions (see FIG. 23) and duplicate reactions were set up with and without Rituximab (at 0.05 μg/ml) or TRU-016 (at 2 μg/ml) added. Reactions were incubated for 30 minutes at 37° C. The cells were washed and NHS was added to a final concentration of 10% in serum free media. Cells were incubated for 90 minutes at 37° C. with the complement source. The cells were washed; propidium iodide was added to a final concentration of 0.5 μg/mL in PBS; the cells were incubated in the dark at room temperature for 15 minutes; and then cells were assayed by flow cytometry. Each graph in panels A-D of FIG. 23 plots the % PI positive cells over the titration ranges indicated.

Figure 23A:
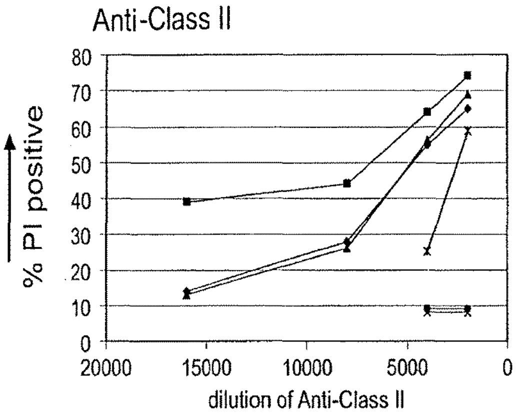
FIGS. 23A, 23B, 23C and 23D demonstrates that TRU-016 dimers do not augment CDC activity resulting from treatment with MHCII (FIG. 23A), CD19 (FIG. 23B), CD45 (FIG. 23C), or CD80/86 (FIG. 23D; treatment with the CD80/86 specific reagent CTLA4Ig is shown) specific reagents.
Figure 23B:
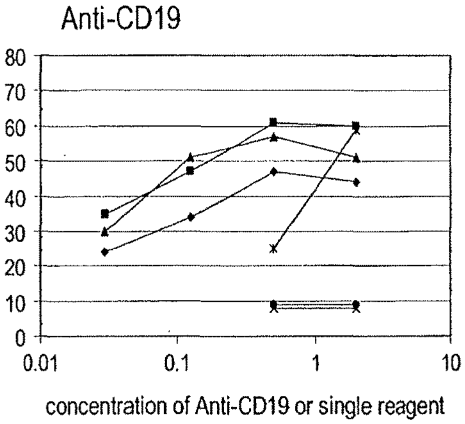
Figure 23B:
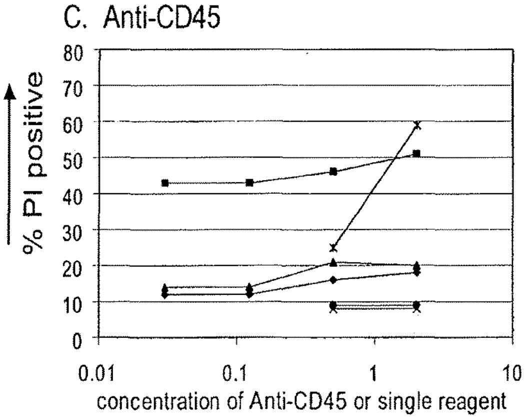
Figure 23C:
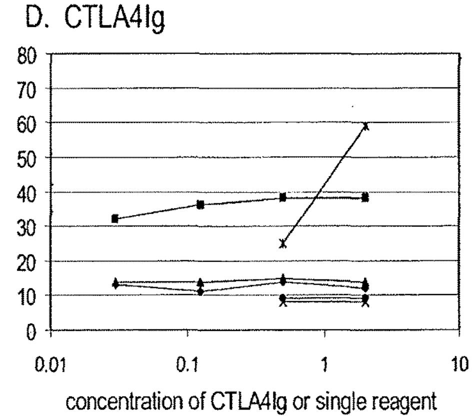
Figure 23D:
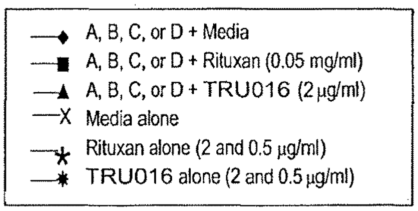

In general, the data indicate that there was not a significant difference in the level of CDC activity when antibodies directed to these receptors were used alone or in combination with the TRU-016 (FIG. 23AD). There may be a slight increase in CDC levels for the CD19 and CD45directed reagents when used with TRU-016 at suboptimal concentrations. However, the differences in CDC levels are not nearly as significant as those observed for the CD20-CD37combination. In addition to the augmentation of CDC when CD20 and CD37 directed reagents are used in combination, there appears to be augmentation in the level of killing observed using combinations of anti-classll (HB 10a), anti-CD19, anti-CD45 (9.4) or CTLA4Ig with RITUXAN (rituximab) at the suboptimal dose.

Example 13

TRU-016 Does Not Augment the CDC Activity of Other Targeted Receptors, Including MHCII, CD19, CD80186, and CD40

To determine whether the TRU-016 molecule augments the level of CDC activity resulting from treatment with antibodies to other B cell surface receptors, in addition to CD20, a panel of experiments was performed similar to those described for CD20-CD37 directed combinations (see Example 8). The results of these experiments are shown in FIG. 23. In general, there was not a significant difference in the level of CDC activity when antibodies directed to these receptors were used alone or in combination with the TRU-016. CDC levels slightly increased in response to CD19 and CD45 directed reagents when used with TRU-016 at suboptimal concentrations. However, the differences in CDC levels were not nearly as significant as those observed for the CD20-CD37 combination (see Example 8). In addition to the augmentation of CDC when CD20 and CD37 directed reagents are used in combination, there appeared to be augmentation in the level of killing observed. using combinations of anti-MHCII (HB10a), antiCD19, anti-CD45 (9.4) or CTLA4Ig with RITUXAN (rituximab) at the suboptimal dose.

Example 14

TRU-016 Increases Survival in a Murine Tumor Xenograft Model

Mouse tumor xenograft studies beyond those described in Example 11 were performed to examine the efficacy of TRU-016 in increasing long-term survival using nude mice (Harlan) and either Ramos or Daudi human tumor cell lines.

Figure 24:
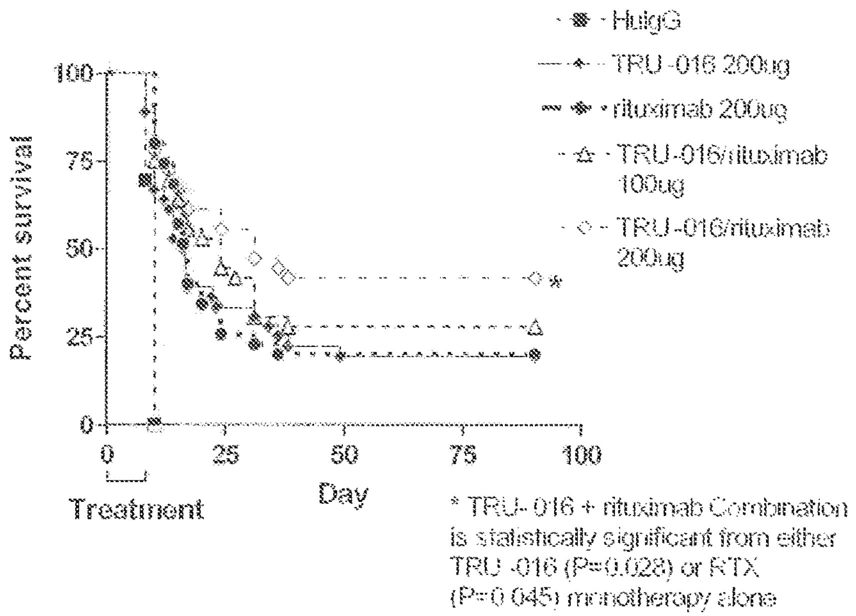
FIG. 24 shows the percent survival of mice with Ramos tumors (up to 90 days) after treatment with TRU-016, rituximab, or a combination thereof.
Figure 25:
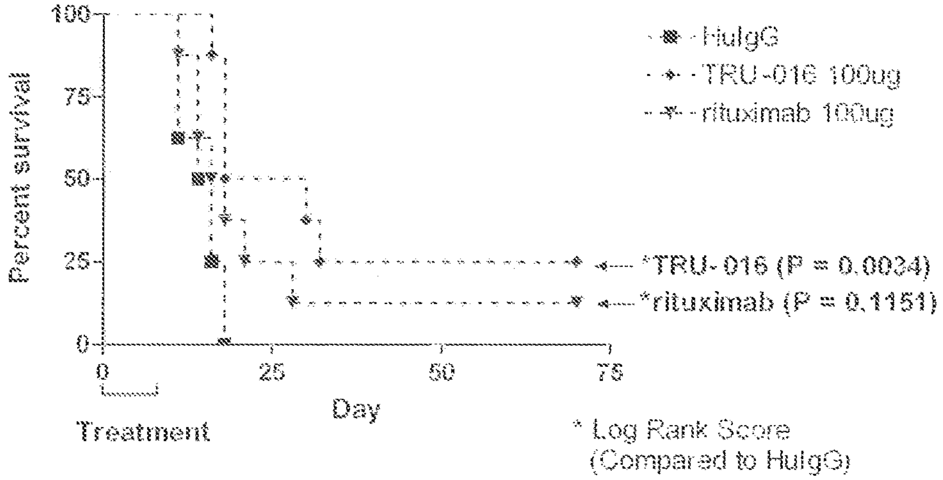
FIGS. 25 and 26 show the percent survival of mice with Daudi tumors (up to 90 days) after treatment with TRU-016 or rituximab.
Figure 26:
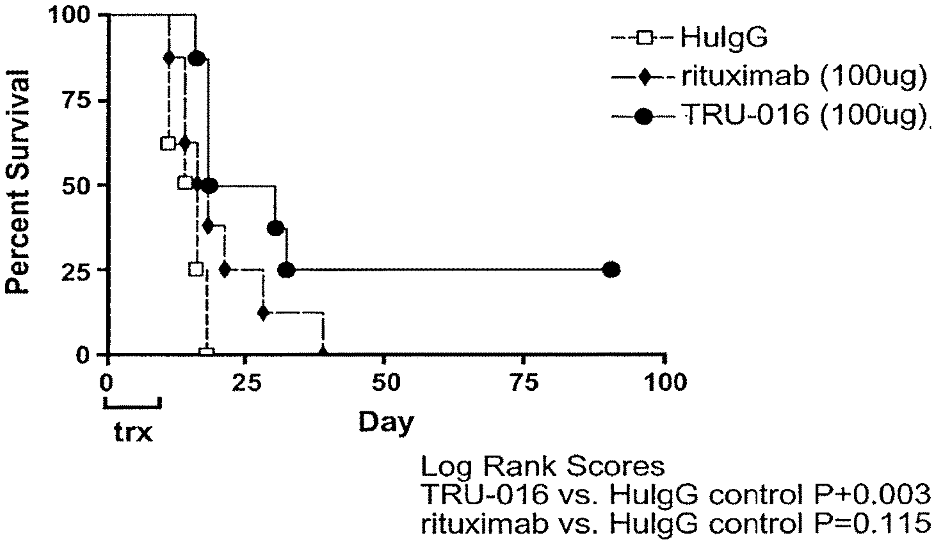

Ramos and Daudi tumor cells were separately grown and ($5\times10^6$) cells were injected subcutaneously in the right flank of mice to initiate the formation of mouse tumor xenografts. After tumor development, mice were sorted into groups based on tumor size/volume (day 0). Animals were injected intravenously (IV) at days 0, 2, 4, 6, and 8 with one of the following reagents: rituximab, 200 μg/mouse; TRU-016, 200 μg/mouse; rituximab+TRU-016 at 100 or 200 μg/mouse; or human IgG (control), 400 μg/mouse. Tumor volume was blindly measured three times weekly with calipers until completion of the experiment (sacrifice or regression). Tumor volume as a function of treatment time was plotted for each animal and results were averaged within each group. FIG. 24 shows the percent survival of mice with Ramos tumors (up to 90 days) after treatment with TRU-016, rituximab, or a combination thereof. The combination treatment with TRU-016+rituximab significantly increased median survival time versus treatment with single agent therapy alone. FIGS. 25 and 26 show the percent survival of mice with Daudi tumors (up to 90 days) after treatment with TRU-016 or rituximab. Treatment with TRU-016 increased median survival time in established Daudi tumors (FIG. 25). TRU-016 was more effective than rituximab in maintaining survival in mice with Daudi tumors (FIG. 26).

Administration of TRU-016 as a single agent in mice with established Ramos tumors demonstrated an inhibition of tumor growth and improved survival times equivalent to rituximab administered as a single agent, and was superior to HuIgG control-treated mice. Pooled data from 3 experiments demonstrated that TRU-016 and rituximab combination therapy resulted in a statistically significantly improvement in survival time compared to TRU-016 ($p=0.028$) or rituximab ($p=0.045$) monotherapies. Complete tumor regressions were also enhanced for the TRU-016 and rituximab combination groups. Forty-two percent of the TRU-016+rituximab 200 μg combination group were able to achieve long-term complete regression of their tumors compared to a 20% tumor regression rate in mice treated with either TRU-016 or rituximab alone (see Table 3 and FIG. 24).

TABLE 3

Survival after Treatment in Established Ramos Tumors

| | Percentage of Tumor- Free Mice at Day 90 | Median Survival Time (Days) |
|---|---|---|
| TRU-016 + rituximab (200 μg) | 42 | 31 |
| TRU-016 + rituximab (100 μg) | 25 | 24 |
| TRU-016 (200 μg) | 20 | 16 |
| Rituximab (200 μg) | 20 | 17 |
| HuIgG | 0 | 10 |

Reduction in tumor growth and improved survival time were found after TRU-016 treatment in the Daudi tumor xenograft model (see Table 4 and FIGS. 25 and 26). TRU-016 administration significantly enhanced survival time compared to the control group. An increase in percentage of tumor-free mice was also observed with SMIP-016 treatment in this model compared to both control and rituximab groups.

TABLE 4

Survival, after Treatment in Established Daudi Tumors

| | Percentage of Tumor Free Mice at Day 90 | Median Survival Time (Days) |
|---|---|---|
| TRU-016 (100 μg) | 25 | 24 |
| Rituximab (100 μg) | 0 | 17 |
| HuIgG | 0 | 15 |

Treatment with a CD37-directed SMIP (TRU-016) is as effective as rituximab monotherapy in reducing tumor volume and increasing survival time in the Ramos tumor xenograft model. TRU-016+rituximab combination therapy demonstrated enhanced benefit in reducing tumor volume and significantly improving survival time compared to either rituximab or TRU-016 monotherapy in the Ramos tumor xenograft model. In the Daudi xenograft model, TRU-016-treated mice demonstrated a statistically significant increase in median survival time compared to HulgG controls. Treatment with rituximab did not extend survival times compared to control mice. These data highlight the efficacy of a CD37-directed therapy in these NHL xenograft models.

Example 15

TRU-016 Potentiates Fludarabine-Induced Cell Death in CLL Cells In Vitro

Fludarabine is a chemotherapy drug used in the treatment of hematological malignancies. Fludarabine is a purine analog that inhibits DNA synthesis by interfering with ribonucleotide reductase and DNA polymerase. Fludarabine is active against both dividing and resting cells. Fludarabine is highly effective in the treatment of chronic lymphocytic leukemia (CLL), producing higher response rates than alkylating agents such as chlorambucil alone (Rai et al., N. Engl. J. Med. 343:1750-1757, 2000). Fludarabine is used in various combinations with cyclophosphamide, mitoxantrone, dexamethasone and rituximab in the treatment of indolent lymphoma and non-Hodgkins lymphoma. However, resistance to fludarabine has also been observed in treatment. Fludarabine induces caspase-dependent apoptosis in CLL cells, and apoptosis mediated by TRU-016 appears to be independent of caspase activation. The present study examined the effect of TRU-016 with fludarabine on CLL cells.

Figure 27:
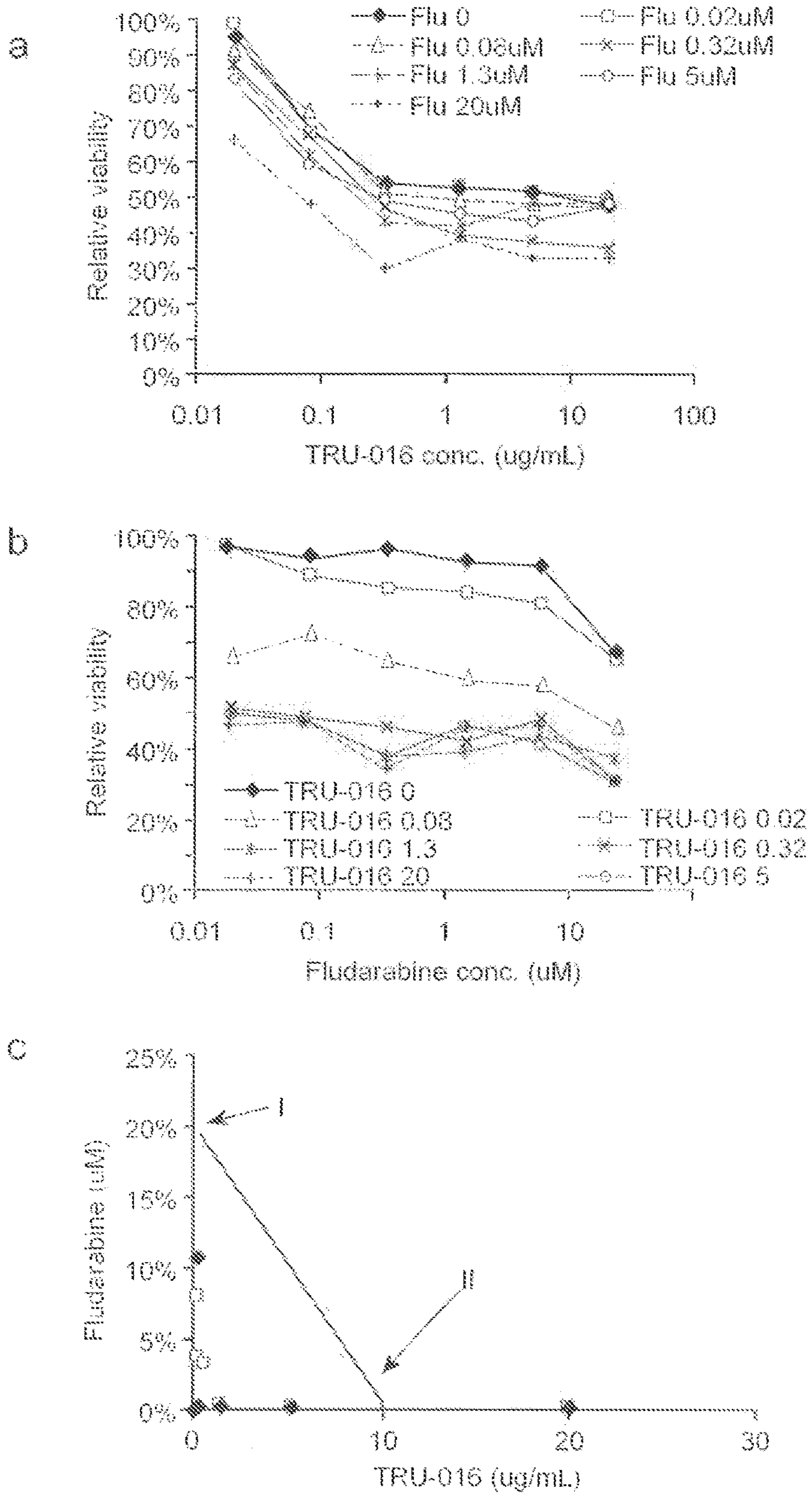
FIG. 27 shows that TRU-016 effectively reduced relative cell viability in cells treated with fludarabine, thereby potentiating the cytotoxic effect of fludarabine

Cells were treated with TRU-016 at dosages ranging from 0.1-100 μg/mL and with fludarabine at dosages ranging from 0-20 μM (see FIG. 27). TRU-016 was provided by Trubion Pharmaceuticals (Seattle, Wash.). Fludarabine (F-araA) was purchased from SIGMA (St. Louis, Mo.). RPMI 1640 media was purchased from Invitrogen (Carlsbad, Calif.). Fluorescein isothiocyanate (FITC)-labeled annexin V, and propidium iodide (P1) were purchased from BD Pharmingen, San Diego, Calif. 13-(4,5-dimethylthiazol-2-yl)-2,5-diphenyltetrazolium bromide (MTT) was purchased from Sigma (St. Louis, Mo.). B-CLL cells were isolated immediately following donation using ficoll density gradient centrifugation (Ficoll-Paque Plus, Amersham Biosciences, Piscataway, N.J.). Isolated mononuclear cells were incubated in RPM' 1640 media supplemented with 10% heat-inactivated fetal bovine serum (FBS, Hyclone Laboratories, Logan, Utah), 2 mM L-glutamine (Invitrogen, Carlsbad, Calif.), and penicillin (100 U/mL)/streptomycin (100 μg/ml; Sigma-Aldrich, St. Louis) at 37° C. in an atmosphere of 5% CO2. Freshly isolated B-CLL cells were used for all the experiments described herein except for the surface staining. For those samples with less than 90% B cells, negative selection was applied to deplete non-B cells using B cell Isolation Kit 11 (Miltenyi Biotec, Auburn, Calif.) or by "Rosette-Sep" kit from Stem Cell Technologies (Vancouver, British Columbia, Canada) according to the manufacture suggested protocol. Raji (Human Burkitt's lymphoma cell line) cell line was purchased from ATCC and maintained in RPM' 1640 media containing 10% FBS, supplemented with penicillin, streptomycin and glutamine. Cells were split 1:3 when the cell density reached 1×106/mL. Media was changed the night before each study to assure fresh cells being used.

Cells were treated in vitro as described herein. 1:4 serial dilution of fludarabine (44, 11, 2.8, 0.7, 0.17 and 0.04 μM) was prepared in a 6-well plate by transferring 2 mL of drug-containing media to the next well containing 6 mL blank media. In a separate 6-well plate, 1:4 serial dilution of TRU-016 (44, 11, 2.8, 0.7, 0.17, and 0.04 μg/ml) in media was prepared using the same dilution method. From each of the plates, 0.45 mL media was transferred to a designed well in a 48-well plate to make a mixed drug solution in media (0.9 mL total in each well). Suspended CLL cells in media at a density of 1×107 cells/mL (0.1 mL) were then added to the 0.9 mL media in each well to make a final density of 1×106 cells/mL. For Raji cells, the final cell density was 5×104 cells/mL. Thus, the cell suspension used was 5×105 cells/mL. For the MTT assays, drug serial dilutions were prepared in 96-well plates, and transferred to other 96-well plates for incubation with cells. The total volume for incubation is 200 μL (90 pL of fludarabine solution, 90 pL of TRU-016 solution, and 20 μL cell suspension). Cell viability was assessed using MTT assays at 48 hr, and apoptosis was measured using Annexin V/PI at 24 hr.

MTT assays were performed to measure cell viability as described herein. Briefly, 106 CLL cells were seeded to 96-well plates. Cells were incubated for 48 hours. 50 μl of MTT working solution (2 mg/ml, prepared from 5 mg/mL MTT reagent mixed with RPMI 1640 2:3 v/v) was added to each well, and the cells were incubated for 8 hours. Plates were centrifuged and supernatant was removed and dissolved in 100 pl lysis solution. Samples were measured with a plate reader at 0.D.540. Cell viability was expressed as the percentage of viability compared with media control.

The apoptosis of CLL cells after incubation with antibodies was measured using annexin V-FITC/propidium iodide (P1) staining with FACS analysis. 5×105 cells in 200pl 1× binding buffer (BD Pharmingen) were stained with 5pL annexin V (BD Pharmingen) and 5pL P1 (BD Pharmingen), and kept in the dark at room temperature for 15 minutes before suspension with 300pl 1× buffer and analyzed by flow cytometry. Cells without staining, cells stained only with Annexin V, and cells stained only with PI were prepared. For all flow cytometry experiments, FACS analysis was performed using a Beckman-Coulter EPICS XL cytometer (Beckman-Coulter, Miami, Fla.). Fluorophores were excited at 488 nm. FITC-fluorescence was measured with FL1, while PI and PE fluorescence was measured with FL3. System II software package (Beckman-Coulter) was applied to analyze the data. The counted cell number was set at 10,000 for each sample.

A synergistic effect was determined by use of the isobologram method. To identify synergy, the effect of a drug combination was compared to the effect of each drug alone. This is based on the equation: Ca/Ca,b+Cb/Cb,a=CI, where Ca and Cb are the concentration of drug A and drug B alone, respectively, to produce a desired effect (e.g. 50% cell death). Ca,b and Cb,a are the concentrations of drug A and drug B in a combination, respectively, to produce the same effect. CI is the combination index. The concentrations of fludarabine and TRU-016, which elicit 50% death (1050) were determined and are shown in FIG. 27C [1050 of Fludarabine (I) and IC50 of TRU-016 (11)1 The straight line between these two points on the axes is the line of additive effect. Subsequently, different combinations of fludarabine and TRU-016 that achieve 50% cell death were also determined from the viability study and plotted to the same graph. When points fall below the additivity line, synergy is indicated. When points rise above the line, antagonism is indicated. When points are on the line, additivity is indicated.

FIG. 27 shows that TRU-016 effectively reduced relative cell viability in cells treated with fludarabine, thereby potentiating the cytotoxic effect of fludarabine alone. Thus, this study provides evidence that TRU-016 can be co-administered with fludarabine, resulting in increased effectiveness (i.e., synergistic reduction of CLL cells) in the treatment of hematological malignancies.

Example 16

TRU-016 Induces Direct Cytotoxicity in Rituximab-Resistant Cells

As disclosed herein, rituximab is a monoclonal antibody used in the treatment of NHL, FCC, MCL, DLCL, SLL, and CLL. The present study was undertaken to determine the efficacy of TRU-016 in inducing direct cytotoxicty in cells resistant to rituximab.

Rituximab-resistant cells (1×106 cells) (Raji 4RH and RL 4RH, supplied by Dr. Myron S. Czuczman, Roswell Park Cancer Institute, Buffalo, N.Y.) were treated with herceptin (10 μg/mL), rituximab (10 μg/mL), or TRU-016 (5 μg/mL) in the presence of a five-fold excess of goat anti-human IgG for 24 hours. Direct cytoxicity was measured by annexin/PI staining and cell viability (percent) was calculated relative to control cells (cells treated with herceptin).

Figure 28:
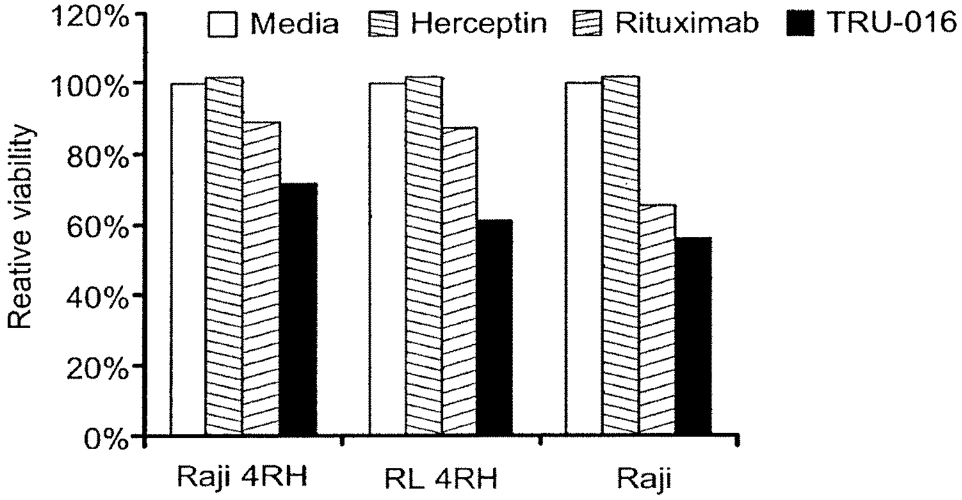
FIG. 28 shows that TRU-016 induced greater cell toxicity than herceptin or rituximab in rituximab-resistant cell lines.

TRU-016 induced greater cell toxicity than rituximab in rituximab-resistant cell lines (see FIG. 28). Thus, TRU-016 is an effective agent for inducing cytoxicity in rituximab-resistant cells, making it useful as a therapeutic in diseases characterized by or involving rituximab-resistant cells, such as some B cells.

Example 17

TRU-016 Induces Tyrosine Phosphorylation in CD19+ Primary CLL B Cells

To determine how TRU-016 induces signal transduction in B cells, experiments were performed to examine the effect of TRU-016 on tyrosine phosphorylation.

Freshly isolated CD19+ cells (−50−100×106) from CLL patients were suspended at a concentration of 5×106/ml PBS. Cells were then incubated for 10 minutes at 37° C., 5% CO2, with control, trastuzumab (herceptin), or TRU-016 at a final concentration of 5 ug/ml. Cells were spun down, supernatant was removed, and cells were resuspended in fresh PBS of initial volume. Goat anti-human Fc fragment specific crosslinker (25 ug/ml) was added and cells were incubated for an additional 5 minutes. Cells were again spun down, supernatant was removed, and cells were lysed in 1 ml of RIPA lysis buffer with protease and phosphatase inhibitors (10 mM Tris, ph7.4, 150 mM NaCl,1% Triton X-100, 1% deoxycholic acid, 0.1% SDS and 5 mM EDTA all final concentrations. Sigma protease inhibitor cocktail cat#P-8340; Sigma phosphatase inhibitor cocktail: serine/threonine phosphatase inhibitor cocktail pat#P-2850; and tyrosine phosphatase inhibitor cat#P-5726;PMSF (100 mM) were all used. The inhibitors were added to the lysis buffer immediately prior to use at a 1:100 dilution. Protein concentration in the lysates was quantified by the bicin choninic acid (BCA) method (Pierce, Rockford, Ill.). The control arid treated protein samples (SOug total protein) were separated by two-dimensional gel electrophoresis (pH Range 3-10)

(1st Dimension) and 10% SDS-PAGE (2nd Dimension). The protein was transferred to 0.2 Nm nitrocellulose membranes (Schleicher & Schuell, Keene, N.H.) and subjected to immunoblot analysis using anti-phosphotyrosine antibody clone 4G10 (Upstate Biotechnology), using standard protocol. Horseradish peroxidase (HRP)-conjugated goat anti-rabbit IgG was used as a secondary antibody. Detection of the phosphoprotein was made with chemiluminescent substrate (SuperSignal, Pierce Inc. Rockford, Ill.).

Figure 29:
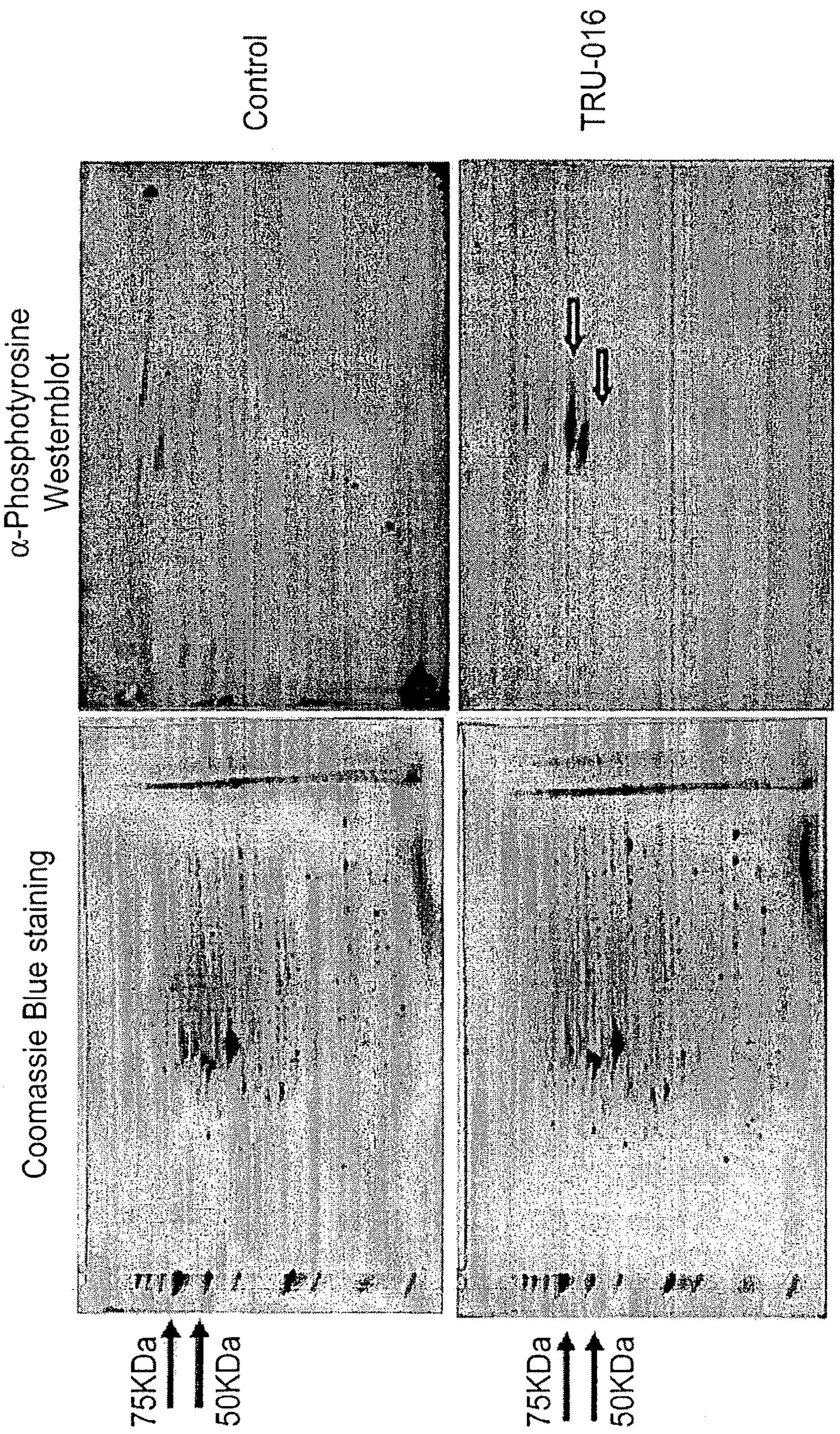
FIG. 29 shows that TRU-016 induced tyrosine phosphorylation in CD19+ primary CLL B cells.

TRU-016 induced tyrosine phosphorylation in CD19+ primary CLL B cells, as shown by two-dimensional gel analysis (see FIG. 29). Thus, these experiments show that one way that TRU-016 acts is via a tyrosine phosphorylation pathway.

Example 18

Humanized TRU-016 Molecules

As set out in Example 1, CD37-specific SMIPs (such as TRU-016) are described in co-owned U.S. application Ser. No. 10/627,556 and U.S. Patent Application Publication Nos. 2003/133939, 2003/0118592 and 2005/0136049. Those descriptions are incorporated by reference herein. An exemplary CD37-specific SMIP, TRU-016 polypeptide (SEQ ID NO: 2), was produced and described therein. The present example provides humanized TRU-016 SMIPs.

Humanized antibodies are known in the art and are discussed in United States Patent Application Publication No. 2006/0153837. The present application uses the techniques involved in antibody humanization (discussed below) to humanize SMIPs, and particularly to humanize TRU-016.

"Humanization" is expected to result in an antibody that is less immunogenic, with complete retention of the antigen-binding properties of the original molecule. In order to retain all of the antigen-binding properties of the original antibody, the structure of its antigen binding site should be reproduced in the "humanized" version. This can be achieved by grafting only the nonhuman CDRs onto human variable framework domains and constant regions, with or without retention of critical framework residues (Jones et al, Nature 321:522 (1986); Verhoeyen et al, Science 239:1539 (1988)) or by recombining the entire nonhuman variable domains (to preserve ligand-binding properties), but "cloaking" them with a human-like surface through judicious replacement of exposed residues (to reduce antigenicity) (Padlan, Molec. Immunol. 28:489 (1991)).

Essentially, humanization by CDR grafting involves recombining only the CDRs of a non-human antibody onto a human variable region framework and a human constant region. Theoretically, this should substantially reduce or eliminate immunogenicity (except if allotypic or idiotypic differences exist). However, it has been reported that some framework residues of the original antibody also may need to be preserved (Reichmann et al, Nature, 332:323 (1988); Queen et al, Proc. Natl. Acad. Sci. USA, 86:10,029 (1989)).

The framework residues that need to be preserved are amenable to identification through computer modeling. Alternatively, critical framework residues may potentially be identified by comparing known antigen-binding site structures (Padlan, Malec. Immun., 31(3):169-217 (1994)), incorporated herein by reference.

The residues that potentially affect antigen binding fall into several groups. The first group comprises residues that are contiguous with the antigen site surface, which could therefore make direct contact with antigens. These residues include the amino-terminal residues and those adjacent to the CDRs. The second group includes residues that could alter the structure or relative alignment of the CDRs, either by contacting the CDRs or another peptide chain in the antibody. The third group comprises amino acids with buried side chains that could influence the structural integrity of the variable domains. The residues in these groups are usually found in the same positions (Padlan, 1994, supra) although their positions as identified may differ depending on the numbering system (see Kabat et al, "Sequences of proteins of immunological interest, 5th ed., Pub. No. 91-3242, U.S. Dept. Health & Human Services, NIH, Bethesda, Md., 1991).

Although the present invention is directed to the humanization of SMIPs and not antibodies, knowledge about humanized antibodies in the art is applicable to the SMIPs according to the invention. Some examples of humanized TRU-016 molecules are set out in Table 5 below.

To make humanized TRU-016 constructs of the invention, the mouse framework regions of TRU-016 were aligned to human VH1 and VH5 framework residues for the heavy chain and VK1 and VK3 for the light chain. Best matches were analyzed for framework compatibility with the CDRs of the mouse variable regions. Although there were several equally compatible combinations to chose from, we had previous success using the VK3 (C01668), VH5-51 (Z12373) combination, so the humanized anti-CD37 SMIPs were designed using these human frameworks joined by a 15aa Gly4Ser ((g4s)3) scFv linker. The VK3 construct was constructed with JK1 as a preferred FR4 match and the VH5 was constructed with JH2 coding for FR4, as with previously-described constructs. SMIPs were constructed de novo using overlapping oligonucleotide PCR. Full-length products were cloned into the SMIP expression vector in frame with the human IgG1 hinge, CH2, and CH3. These clones were sequence verified, transfected into COS-7 cells and 3-day conditioned media tested for binding to the 8-cell lymphoma line, Ramos. In order to increase humanization, changes were incorporated into CDR1 of the light chain at positions L25, L27 and L28 and were well tolerated, showing equal binding activity with the original humanized molecule 019001. Further DNA constructs were made in a similar fashion to alter the CDR3 of the VH region by incorporating germline amino acids, H100-H102, encoded by various human JH regions. Constructs were examined for expression level and degree of binding to CD37 on Ramos cells.

TABLE 5

Humanized TRU-016 Constructs

| Construct No. | Description | Linker | Hinge | DMA SEQ ID NO: | AA SEQ ID NO: |
|---|---|---|---|---|---|
| 019001 | Vk3: VH5-51 | 15aa gly4ser | SSC-P | 5 | 6 |
| 019002 | Vk3: VH5-51 Linker (TG-SS) | 15aa gly4ser | SSC-P | 7 | 8 |
| 019003 | Vk3: VH5-51 VH V11S | 15aa gly4ser | SSC-P | 9 | 10 |
| 019004 | Vk3: VH5-51 VK3, cdr1 (E →Q) | 15aa gly4ser | SSC-P | 11 | 12 |
| 019005 | Vk3: VH5-51 VK3, cdr1 (N →S) | 15aa gly4ser | SSC-P | 13 | 14 |
| 019006 | Vk3: VH5-51 VK3, cdr1 (T → A) | 15aa gly4ser | SSC-P | 15 | 16 |
| 019010 | mVk: VH5-5a | 15aa gly4ser | SSC-P | 17 | 18 |

TABLE 5-continued

Humanized TRU-016 Constructs

| Construct No. | Description | Linker | Hinge | DMA SEQ ID NO: | AA SEQ ID NO: |
|---|---|---|---|---|---|
| 019011 | Vk3: mVH (linker G-S mutation) | 15aa gly4ser | SSC-P | 19 | 20 |
| 019017 | Vk3: VH5 VH3 FW1 | 15aa gly4ser | SSC-P | 21 | 22 |
| 019018 | mVH: Vk3 | 15aa gly4ser | SSC-P | 23 | 24 |
| 019019 | Vk3: mVH (019011 with 2H7 Leader) | 15aa gly4ser | SSC-P | 25 | 26 |
| 019021 | mVH: Vk3 | 15aa gly4ser | SSC-P | 27 | 28 |
| 019023 | Vk3: mVH (fixed 019011 GS4 mutation) | 15aa gly4ser | SSC-P | 29 | 30 |
| 019024 | Vk3: mVH (fixed 019011 GS4 mutation) | 15aa gly4ser | SSC-P | 31 | 32 |
| 019025 | Vk3: VH5 VH3 FW1 | 15aa gly4ser | SSC-P | 33 | 34 |
| 019026 | Vk3: VH5 VH3 FW1 | 15aa gly4ser | SSC-P | 35 | 36 |
| 019032 | Vk3: VH5 VH3-13 FW1 | 15aa gly4ser | SSC-P | 37 | 38 |
| 019033 | Vk3: VH5 VH3-13 FW1 | 15aa gly4ser | SSC-P | 39 | 40 |
| 019034 | Vk3: VH5 VH3-13 L11S FW1 | 15aa gly4ser | SSC-P | 41 | 42 |
| 019035 | Vk3: VH5 VH3-13 L11S FW1 | 15aa gly4ser | SSC-P | 43 | 44 |
| 019037 | Vk3(CDR-L1 changes): VH5 | 15aa gly4ser | SSC-P | 45 | 46 |
| 019041 | 019006 - CDR-H3 JH4 | 15aa gly4ser | SSC-P | 47 | 48 |
| 019043 | 019006 - CDR-H3 JH6 | 15aa gly4ser | SSC-P | 49 | 50 |
| 019044 | 019006 - CDR-H3 JH5a | 15aa gly4ser | SSC-P | 51 | 52 |
| 019045 | 019006 - CDR-H3 JH5b | 15aa gly4ser | SSC-P | 53 | 54 |
| 019046 | 019006 - CDR-H3 JH1 | 15aa gly4ser | SSC-P | 55 | 56 |
| 019047 | 019006 - CDR-H3 JH3a | 15aa gly4ser | SSC-P | 57 | 58 |
| 019048 | 019006 - CDR-H3 JH3b | 15aa gly4ser | SSC-P | 59 | 60 |
| 019049 | 019006 - CDR-H3 JH2 | 15aa gly4ser | SSC-P | 79 | 80 |
| 019050 | 019006 - CDR-H2 changes | 15aa gly4ser | SSC-P | 81 | 82 |
| 019051 | 019044 | 20aa gly4ser | CPPCP | 83 | 84 |
| 019008 | | | | 85 | 86 |
| 019009 | | | | 87 | 88 |

The amino acid consensus sequence of humanized TRU-016 construct no. 019001 (SEQ ID NO: 6; H016-019001) and non-humanized TRU-016 (SEQ ID NO: 2; 016-G28-1) is shown with Kabat numbering in FIG. 30A. FIG. 30 B shows the amino acid sequence alignments of humanized TRU-016 construct nos. 019001 (SEQ ID NO: 6), 019008 (SEQ ID NO: 86), and 019009 (SEQ ID NO: 88).

DNA and amino acid sequence alignments of three humanized constructs of TRU 016 (019001, 019041, and 019044), demonstrating high CD37-specific binding to Ramos B cells are shown in FIG. 31.

FASTA formatted DNA and amino acid sequence alignments of the same three humanized constructs of TRU-016 (019001, 019041, and 019044) are shown in FIG. 32.

Additional hinge regions (Table 6) and framework regions (Table 7) that may be used in the humanized TRU-016 molecules of the invention are provided below.

TABLE 6

Hinge Regions for Humanized TRU-016 SMIPs

| Hinge description | DNA or Amino Acid Sequence | SEQ ID NO: |
|---|---|---|
| ccc(p)-hlgG1 (DNA) | gagcccaaatcttgtgacaaaactcacacatgtccaccgtgccca | 89 |
| ccc(p)-hlgG1 (AA | EPKSCDKTHTCPPCP | 90 |
| scc(p)-hlgG1 (DNA) | gagcccaaatcttctgacaaaactcacacatgtccaccgtgccca | 91 |
| scc(p)-hlgG1 (AA) | EPKSSDKTHTCPPCP | 92 |
| scc(s)-hlgG1 (DNA) | gagcccaaatcttctgacaaaactcacacatgtccaccgtgctca | 93 |
| scc(s)-hlgG1 (AA) | EPKSSDKTHTCPPCS | 94 |
| scs(s)-hlgG1 (DNA) | gagcccaaatcttgtgacaaaactcacacatgtccaccgagctca | 95 |

TABLE 6-continued

| Hinge Regions for Humanized TRU-016 SMIPs | | |
|---|---|---|
| Hinge description | DNA or Amino Acid Sequence | SEQ ID NO: |
| scs(s)-hlgG1 (AA) | EPKSSDKTHTCPPSS | 96 |
| sss(p)-hlgG1 (DNA) | gagcccaaatcttctgacaaaactcacacatctccaccgagccca | 97 |
| sss(p)-hlgG1 (AA) | EPKSSDKTHTSPPSP | 98 |
| sss(s)-hlgG1 (DNA) | gagcccaaatcttctgacaaaactcacacatctccaccgagctca | 99 |
| sss(s)-hlgG1 (AA) | EPKSSDKTHTSPPSS | 100 |
| csc(p)-hlgG1 (DNA) | gagcccaaatcttgtgacaaaactcacacatctccaccgtgccca | 101 |
| csc(p)-hlgG1 (AA) | EPKSCDKTHTSPPCP | 102 |
| csc(s)-hlgG1 (DNA) | gagcccaaatcttgtgacaaaactcacacatctccaccgtgctca | 103 |
| csc(s)-hlgG1 (AA) | EPKSCDKTHTSPPCS | 104 |
| ssc(p)-hlgG1 (DNA) | gagcccaaatcttctgacaaaactcacacatctccaccgtgccca | 105 |
| ssc(p)-hlgG1 (AA) | EPKSSDKTHTSPPCP | 106 |
| scs(s)-hlgG1 (DNA) | gagcccaaatcttctgacaaaactcacacatctccaccgtgctca | 107 |
| scs(s)-hlgG1 (AA) | EPKSSDKTHTSPPCS | 108 |
| css(p)-hlgG1 (DNA) | gagcccaaatcttgtgacaaaactcacacatctccaccgagccca | 109 |
| css(p)-hlgG1 (AA) | EPKSCDKTHTSPPSP | 110 |
| css(s)-hlgG1 (DNA) | gagcccaaatcttgtgacaaaactcacacatctccaccgagctca | 111 |
| css(s)-hlgG1 (AA) | EPKSCDKTHTSPPSS | 112 |
| scs(s)-hlgG1 (DNA) | gagcccaaatcttgtgacaaaactcacacatgtccaccgagctca | 113 |
| scs(s)-hlgG1 (AA) | EPKSSDKTHTCPPSS | 114 |
| hlgA1 | VPSTPPTPSPSTPPTPSPS | 115 |
| hlgA2 | VPPPPP | 116 |
| hlgG3 (DNA) | gagctcaaaactcctctcggggatacgacccatacgtgtccccgc tgtcctgaaccgaagtcctgcgatacgcctccgccatgtccacggt gcccagagcccaaatcatgcgatacgcccccaccgtgtccccgc tgtcctgaaccaaagtcatgcgataccccaccaccatgtccaagatgccca | 117 |

TABLE 6-continued

Hinge Regions for Humanized TRU-016 SMIPs

| Hinge description | DNA or Amino Acid Sequence | SEQ ID NO: |
|---|---|---|
| hlgG3 (AA) | ELKTPLGDTTHTCPRCPEPKSCDTPPPCPRCP EPKSCDTPPPCPRCPEPKSCDTPPPCPRCP | 118 |
| lgG315hscc (DNA) | gagcccaaatcttctgacacacctcccccatgcccacggtgcccc | 119 |
| lgG315hscc (AA) | EPKSSDTPPPCPRCP | 120 |
| lgG315hcss (DNA) | gagcccaaatcttgtgacacacctcccccatccccacggtcccca | 121 |
| fgG315hcss (AA) | EPKSCDTPPPSPRSP | 122 |
| lgG315hsss (DNA) | gagcccaaatcttctgacacacctcccccatccccacggtcccca | 123 |
| lgG315hsss (AA) | EPKSSDTPPPSPRSP | 124 |
| lgG3hl5csc (DNA) | gagcccaaatcttgtgacacacctcccccatccccacggtgccca | 125 |
| lgG3hl5csc (AA) | EPKSCDTPPPSPRCP | 126 |
| hlgD | ESPKAQASSVPTAQPQAEGSLAKATTAPATTR NTGRGGEEKKKEKEKEEQEERETKTP | 127 |

TABLE 7

Framework Regions for Humanized TRU-016 SMIPs

| V-region | Human VH Framework Regions for anti-CD37 Humanization | SEQ ID NO: |
|---|---|---|
| | FR1 | |
| VH1 | QVQLVQSGAEVKKPGASVKVSCKASGYTFT | 140 |
| VH1 | QVQLVQSGAEVKKPGSSVKVSCKASGGTFS | 141 |
| VH1 | QVQLVQSGAEVKKPGSSVKVSCKASGGIFS | 142 |
| VH1 | EVQLVQSGAEVKKPGATVKISCKVSGYTFT | 143 |
| VH5 | EVQLVQSGAEVKKPGESLKISCKGSGYSFT | 144 |
| VH5 | EVQLVQSGAFVKKPGESLRISCKGSGYSFT | 145 |
| VH7 | QVQLVQSGSELKKPGASVKVSCKASGYTFT | 146 |
| | FR2 | |
| VH1 | WVRQAPGQGLEWMG | 147 |
| VH1 | WVRQAPGQGLEWMG | 148 |
| VH1 | WVRQAPGQGLEWMG | 149 |
| VH1 | WVQQAPGKGLEWMG | 150 |
| VH5 | WVRQMPGKGLEWMG | 151 |
| VH5 | WVRQMPGKGLEWMG | 152 |
| VH7 | WVRQAPGQGLEWMG | 153 |
| | FR3 | |
| VH1 | RVTMTTDTSTSTAYMELRSLRSDDTAVYYCAR | 154 |
| VH1 | RVTITADESTSTAYMELSSLRSEDTAVYYCAR | 155 |
| VH1 | RVTITADKSTSTAYMELSSLRSEDTAVYYCAR | 156 |
| VH1 | RVTITADTSTDTAYMELSSLRSEDTAVYYCAT | 157 |
| VH5 | QVTISADKSISTAYLQWSSLKASDTAMYYCAR | 158 |
| VH5 | HVTISADKSISTAYLQWSSLKASDTAMYYCAR | 159 |
| VH7 | RFVFSLDTSVSTAYLQISSLKAEDTAVYYCAR | 160 |
| | FR4 | |
| | WGQGTLVTVSS | 161 |
| | WGRGTLVTVSS | 162 |
| | WGQGTMVTVSS | 163 |

TABLE 7-continued

Framework Regions for Humanized TRU-016 SMIPs

| | | |
|---|---|---|
| | WGQGTMVTVSS | 164 |
| | WGQGTLVTVSS | 165 |
| | WGQGTLVTVSS | 166 |
| | WGQGTLVTVSS | 167 |
| | WGQGTTVTVSS | 168 |
| | WGKGTTVTVSS | 169 |
| | Human VK Framework Regions for anti-CD37 Humanization | |
| | FR1 | |
| VK3 | EIVMTQSPATLSVSPGERATLSC | 170 |
| VK3 | EIVLTQSPATLSLSPGERATLSC | 171 |
| VK1 | DIQMTQSPSSLSASVGDRVTITC | 172 |
| VK1 | DIQMTQSPSSLSASVGDRVTITC | 173 |
| VK1 | DIQMTQSPSSLSASVGDRVTITC | 174 |
| VK1 | NIQMTQSPSAMSASVGDRVTITC | 175 |
| VK1 | DIQMTQSPSSLSASVGDRVTITC | 176 |
| VK1 | AIQLTQSPSSLSASVGDRVTITC | 177 |
| VK1 | DIQLTQSPSFLSASVGDRVTITC | 178 |
| VK1 | AIRMTQSPFSLSASVGDRVTITC | 179 |
| VK1 | AIQMTQSPSSLSASVGDRVTITC | 180 |
| VK1 | DIQMTQSPSTLSASVGDRVTITC | 181 |
| | FR2 | |
| VK3 | WYQQKPGQAPRLLIY | 182 |
| VK3 | WYQQKPGQAPRLLIY | 183 |
| VK1 | WYQQKPGKAPKLLIY | 184 |
| VK1 | WYQQKPGKAPKLLIY | 185 |
| VK1 | WYQQKPGKAPKRLIY | 186 |
| VK1 | WFQQKPGKVPKHLIY | 187 |
| VK1 | WFQQKPGKAPKSLIY | 188 |
| VK1 | WYQQKPGKAPKLLIY | 189 |
| VK1 | WYQQKPGKAPKLLIY | 190 |

TABLE 7-continued

| Framework Regions for Humanized TRU-016 SMIPs | | |
|---|---|---|
| VK1 | WYQQKPAKAPKLFIY | 191 |
| VK1 | WYQQKPGKAPKLLIY | 192 |
| VK1 | WYQQKPGKAPKLLIY | 193 |
| | FR3 | |
| VK3 | GIPARFSGSGSGTEFTLTISSLQSEDFAVYYC | 194 |
| VK3 | GIPARFSGSGSGTDFTLTISSLEPEDFAVYYC | 195 |
| VK1 | GVPSRFSGSGSGTDFTLTISSLQPEDFATYYC | 196 |
| VK1 | GVPSRFSGSGSGTDFTLTISSLQPEDVATYYC | 197 |
| VK1 | GVPSRFSGSGSGTEFTLTISSLQPEDFATYYC | 198 |
| VK1 | GVPSRFSGSGSGTEFTLTISSLQPEDFATYYC | 199 |
| VK1 | GVPSRFSGSGSGTDFTLTISSLQPEDFATYYC | 200 |
| VK1 | GVPSRFSGSGSGTDFTLTISSLQPEDFATYYC | 201 |
| VK1 | GVPSRFSGSGSGTEFTLTISSLQPEDFATYYC | 202 |
| VK1 | GVPSRFSGSGSGTDYTLTISSLQPEDFATYYC | 203 |
| VK1 | GVPSRFSGSGSGTDFTLTISSLQPEDFATYYC | 204 |
| VK1 | GVPSRFSGSGSGTEFTLTISSLQPDDFATYYC | 205 |
| | FR4 | |
| | FGQGTKVEIK | 206 |
| | FGQGTKLEIK | 207 |
| | FGPGTKVDIK | 208 |
| | FGGGTKVEIK | 209 |
| | FGQGTRLEIK | 210 |

Numerous modifications and variations in the invention as set forth in the above illustrative examples are expected to occur to those skilled in the art. Consequently only such limitations as appear in the appended claims should be placed on the invention.

DNA and Amino Acid Sequences for SEQ ID NOS: 79-88

| Construct # | SEQ ID NO: | DNA or Amino Acid Sequence |
|---|---|---|
| 019049 | 79 | aagcttgccgccatggaagccccagcgcagcttctcttcctcctgctactctgg<br>ctcccagataccaccggagaaattgtgttgacacagtctccagccaccctgtct<br>ttgtctccaggcgaaagagccaccctctcctgccgagcaagtgaaaatgttta<br>cagctacttagcctggtaccaacagaaacctggccaggctcctaggctcctca<br>tctattttgcaaaaaccttagcagaaggaattccagccaggttcagtggcagtg<br>gatccgggacagacttcactctcaccatcagcagcctagagcctgaagatttt<br>gcagtttattactgtcaacatcattccgataatccgtggacattcggccaaggga<br>ccaaggtggaaatcaaaggtggcggtggctcgggcggtggtggat<br>ctggaggaggtgggaccggtgaggtgcagctggtgcagtctggagcagagg<br>tgaaaaagcccggagagtctctgaagatttcctgtaagggatccggttactcat<br>tcactggctacaatatgaactgggtgcgccagatgcccgggaaaggcctcga<br>gtggatgggcaatattgatccttattatggtggtactacctacaaccggaagttc<br>aagggccaggtcactatctccgccgacaagtccatcagcaccgcctacctgc<br>aatggagcagcctgaaggcctcggacaccgccatgtattactgtgcacgctc<br>agtcggccctttcgacctctggggcagaggcaccctggtcactgtctcctctgat<br>caggagcccaaatcttctgacaaaactcacacatctccaccgtgcccagcac<br>ctgaactcctgggtggaccgtcagtcttcctcttccccccaaaacccaaggac<br>accctcatgatctcccggacccctgaggtcacatgcgtggtggtggacgtgag<br>ccacgaagaccctgaggtcaagttcaactggtacgtggacggcgtggaggt<br>gcataatgccaagacaaagccgcgggaggagcagtacaacagcacgtac<br>cgtgtggtcagcgtcctcaccgtcctgcaccaggactggctgaatggcaagg<br>agtacaagtgcaaggtctccaacaaagccctcccagcccccatcgagaaaa<br>ccatctccaaagccaaagggcagccccgagaaccacaggtgtacaccctg<br>cccccatcccgggatgagctgaccaagaaccaggtcagcctgacctgcctg<br>gtcaaaggcttctatccaagcgacatcgccgtggagtgggagagcaatggg<br>cagccggagaacaactacaagaccacgcctcccgtgctggactccgacgg<br>ctccttcttcctctacagcaagctcaccgtggacaagagcaggtggcagcag<br>gggaacgtcttctcatgctccgtgatgcatgaggctctgcacaaccactacac<br>gcagaagagcctctc cctgtctccgggtaaatgatctaga |
| 019049 | 80 | MEAPAQLLFLLLLWLPDTTGEIVLTQSPATLSLSPGERA<br>TLSCRASENVYSYLAWYQQKPGQAPRLLIYFAKTLAEGI<br>PARFSGSGSGTDFTLTISSLEPEDFAVYYCQHHSDNPW<br>TFGQGTKVEIKGGGGSGGGGSGGGGTGEVQLVQSGA<br>EVKKPGESLKISCKGSGYSFTGYNMNWVRQMPGKGLE<br>WMGNIDPYYGGTTYNRKFKGQVTISADKSISTAYLQWS<br>SLKASDTAMYYCARSVGPFDLWGRGTLVTVSSDQEPK<br>SSDKTHTSPPCPAPELLGGPSVFLFPPKPKDTLMISRTP<br>EVTCVVVDVSHEDPEVKFNWYVDGVEVHNAKTKPREE<br>QYNSTYRVVSVLTVLHQDWLNGKEYKCKVSNKALPAPI<br>EKTISKAKGQPREPQVYTLPPSRDELTKNQVSLTCLVK<br>GFYPSDIAVEWESNGQPENNYKTTPPVLDSDGSFFLYS<br>KLTVDKSRWQQGNVFSCSVMHEALHNHYTQKSLSLSP<br>GK |
| 019050 | 81 | aagcttgccgccatggaagccccagctcagcttctcttcctcctgctactctggc<br>tcccagataccaccggagaaattgtgttgacacagtctccagccaccctgtcttt<br>gtctccaggcgaaagagccaccctctcctgccgagcaagtgaaaatgtttac<br>agctacttagcctggtaccaacagaaacctggccaggctcctaggctcctcat<br>ctattttgcaaaaaccttagcagaaggaattccagccaggttcagtggcagtg<br>gatccgggacagacttcactctcaccatcagcagcctagagcctgaagatttt |

-continued

DNA and Amino Acid Sequences for SEQ ID NOS: 79-88

| Construct # | SEQ ID NO: | DNA or Amino Acid Sequence |
|---|---|---|
| | | gcagtttattactgtcaacatcattccgataatccgtggacattcggccaaggga<br>ccaaggtggaaatcaaaggtggcggtggctcgggcggtggtggatctggag<br>gaggtggggctagcgaggtgcagctggtgcagtctggagcagaggtgaaa<br>aagcccggagagtctctgaagatttcctgtaagggatccggttactcattcacta<br>gctacaatatgaactgggtgcgccagatgcccgggaaaggcctggagtgga<br>tgggcaatattgatccttattatggtggtactaactacgcccagaagttccaggg<br>ccaggtcactatctccgccgacaagtccatcagcaccgcctacctgcaatgg<br>agcagcctgaaggcctcggacaccgccatgtattactgtgcacgctcagtcg<br>gccctatggactactggggccgcggcaccctggtcactgtctcctctgatcagg<br>agcccaaatcttctgacaaaactcacacatctccaccgtgcccagcacctga<br>actcctgggtggaccgtcagtcttcctcttccccccaaaacccaaggacaccct<br>catgatctcccggacccctgaggtcacatgcgtggtggtggacgtgagccac<br>gaagaccctgaggtcaagttcaactggtacgtggacggcgtggaggtgcata<br>atgccaagacaaagccgcgggaggagcagtacaacagcacgtaccgtgtg<br>gtcagcgtcctcaccgtcctgcaccaggactggctgaatggcaaggagtaca<br>agtgcaaggtctccaacaaagccctcccagcccccatcgagaaaaccatct<br>ccaaagccaaagggcagccccgagaaccacaggtgtacaccctgcccccc<br>atcccgggatgagctgaccaagaaccaggtcagcctgacctgcctggtcaa<br>aggcttctatccaagcgacatcgccgtggagtgggagagcaatgggcagcc<br>ggagaacaactacaagaccacgcctcccgtgctggactccgacggctccttc<br>ttcctctacagcaagctcaccgtggacaagagcaggtggcagcaggggaac<br>gtcttctcatgctccgtgatgcatgaggctctgcacaaccactacacgcagaa<br>gagc ctctccctgtctccgggtaaaatga |
| 019050 | 82 | MEAPAQLLFLLLLWLPDTTGEIVLTQSPATLSLSPGERA<br>TLSCRASENVYSYLAWYQQKPGQAPRLLIYFAKTLAEGI<br>PARFSGSGSGTDFTLTISSLEPEDFAVYYCQHHSDNPW<br>TFGQGTKVEIKGGGGSGGGGSGGGGTGEVQLVQSGA<br>EVKKPGESLKISCKGSGYSFTGYNMNWVRQMPGKGLE<br>WMGNIDPYYGGTTYNRKFKGQVTISADKSISTAYLQWS<br>SLKASDTAMYYCARSVGPFDLWGRGTLVTVSSDQEPK<br>SSDKTHTSPPCPAPELLGGPSVFLFPPKPKDTLMISRTP<br>EVTCVVVDVSHEDPEVKFNWYVDGVEVHNAKTKPREE<br>QYNSTYRVVSVLTVLHQDWLNGKEYKCKVSNKALPAPI<br>EKTISKAKGQPREPQVYTLPPSRDELTKNQVSLTCLVK<br>GFYPSDIAVEWESNGQPENNYKTTPPVLDSDGSFFLYS<br>KLTVDKSRWQQGNVFSCSVMHEALHNHYTQKSLSLSP<br>GK |
| 019051 | 83 | aagcttgccgccatggaagccccagcgcagcttctcttcctcctgctactctgg<br>ctcccagataccaccggagaaattgtgttgacacagtctccagccaccctgtct<br>ttgtctccaggcgaaagagccaccctctcctgccgagcaagtgagaatgttta<br>cagctacttagcctggtaccaacagaaacctggccaggctcctaggctcctca<br>tctattttgcaaaaaccttagcagaagggattccagccagattcagtggcagtg<br>gttccgggacagacttcactctcaccatcagcagcctagagcctgaagattttg<br>cagtttattactgtcaacatcattccgataatccgtggacattcggccaagggac<br>caaggtggaaatcaaaggtggcggtggctcgggcggtggtggatctggagg<br>aggtgggagcggaggaggagctagcgaggtgcagctggtgcagtctgga<br>gcagaggtgaaaaagcccggagagtctctgaagatttcctgtaagggatccg<br>gttactcattcactggctacaatatgaactgggtgcgccagatgcccgggaaa<br>ggcctcgaatggatgggcaatattgatccttattatggtggtactacctacaacc<br>ggaagttcaagggccaggtcactatctccgccgacaagtccatcagcaccgc<br>ctacctgcaaggagcagcctgaaggcctcggacaccgccatgtattactgtg<br>cacgctcagtcggccctttcgactcctggggccagggcaccctggtcactgtct<br>cgagttgtccaccgtgcccagcacctgaactcctgggtggaccgtcagtcttcc<br>tcttccccccaaaacccaaggacaccctcatgatctcccggacccctgaggtc<br>acatgcgtggtggtggacgtgagccacgaagaccctgaggtcaagttcaact<br>ggtacgtggacggcgtggaggtgcataatgccaagacaaagccgcgggag<br>gagcagtacaacagcacgtaccgtgtggtcagcgtcctcaccgtcctgcacc<br>aggactggctgaatggcaaggagtacaagtgcaaggtctccaacaaagcc<br>ctcccagcccccatcgagaaaaccatctccaaagccaaagggcagccccg<br>agaaccacaggtgtacaccctgcccccatcccgggatgagctgaccaagaa<br>ccaggtcagcctgacctgcctggtcaaaggcttctatccaagcgacatcgccg<br>tggagtgggagagcaatgggcagccggagaacaactacaagaccacgcc<br>tcccgtgctggactccgacggctccttcttcctctacagcaagctcaccgtgga<br>caagagcaggtggcagcaggggaacgtcttctcatgctccgtgatgcatgag<br>gctctgcacaaccactacacgcagaagagcctctccctgtctccgggtaaatg<br>actc taga |
| 019051 | 84 | MEAPAQLLFLLLLWLPDTTGEIVLTQSPATLSLSPGERA<br>TLSCRASENVYSYLAWYQQKPGQAPRLLIYFAKTLAEGI<br>PARFSGSGSGTDFTLTISSLEPEDFAVYYCQHHSDNPW<br>TFGQGTKVEIKGGGGSGGGGSGGGGSGGGASEVQLV |

-continued

DNA and Amino Acid Sequences for SEQ ID NOS: 79-88

| Construct # | SEQ ID NO: | DNA or Amino Acid Sequence |
|---|---|---|
| | | QSGAEVKKPGESLKISCKGSGYSFTGYNMNWVRQMP<br>GKGLEWMGNIDPYYGGTTYNRKFKGQVTISADKSISTA<br>YLQWSSLKASDTAMYYCARSVGPFDSWGQGTLVTVSS<br>CPPCPAPELLGGPSVFLFPPKPKDTLMISRTPE<br>VTCVVVDVSHEDPEVKFNWYVDGVEVHNAKTKPREEQ<br>YNSTYRVVSVLTVLHQDWLNGKEYKCKVSNKALPAPIE<br>KTISKAKGQPREPQVYTLPPSRDELTKNQVSLTCLVKG<br>FYPSDIAVEWESNGQPENNYKTTPPVLDSDGSFFLYSK<br>LTVDKSRWQQGNVFSCSVMHEALHNHYTQKSLSLSPG<br>K |
| 019008 | 85 | aagcttgccgccatggaagccccagctcagcttctcttcctcctgctactctggc<br>tcccagataccaccggagaaattgtgttgacacagtctccagccaccctgtcttt<br>gtctccaggcgaaagagccaccctctcctgccgaacaagtgaaaatgtttac<br>agctacttagcctggtaccaacagaaacctggccaggctcctaggctcctcat<br>ctattttgcaaaaaccttagcagaaggaattccagccaggttcagtggcagtg<br>gatccgggacagacttcactctcaccatcagcagcctagagcctgaagatttt<br>gcagtttattactgtcaacatcattccgataatccgtggacattcggccaaggga<br>ccaaggtggaaatcaaaggtggcggtggctcgggcggtggtggatctggag<br>gaggtgggaccggtgaggtgcagctggtgcagtctggagcagaggtgaaa<br>aagcccggagagtctctgaagatttcctgtaagggatccggttactcattcactg<br>gctacaatatgaactgggtgcgccagatgcccgggaaaggcctggagtgga<br>tgggcaatattgatccttattatggtggtactacctacaaccggaagttcaaggg<br>ccaggtcactatctccgccgacaagtccatcagcaccgcctacctgcaatgg<br>agcagcctgaaggcctcggacaccgccatgtattactgtgcacgctcagtcg<br>gccctatggactactggggccgcggcaccctggtcactgtctcctctgatcagg<br>agcccaaatcttctgacaaaactcacacatctccaccgtgcccagcacctga<br>actcctgggtggaccgtcagtcttcctcttccccccaaaacccaaggacaccct<br>catgatctcccggacccctgaggtcacatgcgtggtggtggacgtgagccac<br>gaagaccctgaggtcaagttcaactggtacgtggacggcgtggaggtgcata<br>atgccaagacaaagccgcgggaggagcagtacaacagcacgtaccgtgtg<br>gtcagcgtcctcaccgtcctgcaccaggactggctgaatggcaaggagtaca<br>agtgcaaggtctccaacaaagccctcccagcccccatcgagaaaaccatct<br>ccaaagccaaagggcagccccgagaaccacaggtgtacacctgcccccat<br>cccgggatgagctgaccaagaaccaggtcagcctgacctgcctggtcaaag<br>gcttctatccaagcgacatcgccgtggagtgggaga<br>gcaatgggcagccggagaacaactacaagaccacgcctcccgtgctggac<br>tccgacggctccttcttcctctacagcaagctcaccgtggacaagagcaggtg<br>gcagcaggggaacgtcttctcatgctccgtgatgcatgaggctctgcacaacc<br>actacacgcagaagagc ctctccctgtctccgggtaaatga |
| 019008 | 86 | MEAPAQLLFLLLLWLPDTTGEIVLTQSPATLSLSPGERA<br>TLSCRTSENVYSYLAWYQQKPGQAPRLLIYFAKTLAEGI<br>PARFSGSGSGTDFTLTISSLEPEDFAVYYCQHHSDNPW<br>TFGQGTKVEIKGGGGSGGGGSGGGGASEVQLVQSGA<br>EVKKPGESLKISCKGSGYSFTGYNMNWVRQMPGKGLE<br>WMGNIDPYYGGTTYNRKFKGQVTISADKSISTAYLQWS<br>SLKASDTAMYYCARSVGPMDYWGRGTLVTVSSDQEPK<br>SSDKTHTSPPCPAPELLGGPSVFLFPPKPKDTLMISRTP<br>EVTCVVVDVSHEDPEVKFNWYVDGVEVHNAKTKPREE<br>QYNSTYRVVSVLTVLHQDWLNGKEYKCKVSNKALPAPI<br>EKTISKAKGQPREPQVYTLPPSRDELTKNQVSLTCLVK<br>GFYPSDIAVEWESNGQPENNYKTTPPVLDSDGSFFLYS<br>KLTVDKSRWQQGNVFSCSVMHEALHNHYTQKSLSLSP<br>GK |
| 019009 | 87 | aagcttgccgccatggaagccccagctcagcttctcttcctcctgctactctggc<br>tcccagataccaccggtgaaattgtgttgacacagtctccagccaccctgtcttt<br>gtctccaggcgaaagagccaccctctcctgccgaacaagtgaaaatgtttac<br>agctacttagcctggtaccaacagaaacctggccaggctcctaggctcctcat<br>ctattttgcaaaaacettagcagaaggaattccagccaggttcagtggcagtg<br>gatccgggacagacttcactctcaccatcagcagcctagagcctgaagatttt<br>gcagtttattactgtcaacatcattccgataatccgtggacattcggccaaggga<br>ccaaggtggaaatcaaaggtggcggtggctcgggcggtggtggatctggag<br>gaggtggggctagcgaggtgcagctggtgcagtctggagcagaggtgaaa<br>aagcccggagagtctctgaggatttcctgtaagggatccggttactcatteact<br>ggctacaatatgaactgggtgcgccagatgcccgggaaaggcctggagtgg<br>atgggcaatattgatccttattatggtggtactacctacaaccggaagttcaagg<br>gccaggtcactatctccgccg<br>acaagtccatcagcaccgcctacctgcaatggagcagcctgaaggcctcgg<br>acaccgccatgtattactgtgcacgctcagtcggccctatggactactggggcc<br>gcggcaccctggtcactgtctcctctgatcaggagcccaaatcttctgacaaaa<br>ctcacacatctccaccgtgcccagcacctgaactcctgggtggaccgtcagtc |

-continued

DNA and Amino Acid Sequences for SEQ ID NOS: 79-88

| Construct # | SEQ ID NO: | DNA or Amino Acid Sequence |
|---|---|---|
| | | ttcctcttcccccaaaacccaaggacaccctcatgatctcccggacccctga ggtcacatgcgtggtggtggacgtgagccacgaagaccctgaggtcaagttc aactggtacgtggacggcgtggaggtgcataatgccaagacaaagccgcg ggaggagcagtacaacagcacgtaccgtgtggtcagcgtcctcaccgtcctg caccaggactggctgaatggcaaggagtacaagtgcaaggtctccaacaa agccctcccagcccccatcgagaaaaccatctccaaagccaaagggcagc cccgagaaccacaggtgtacaccctgcccccatcccgggatgagctgacca agaaccaggtcagcctgacctgcctggtcaaaggcttctatccaagcgacat cgccgtggagtgggagagcaatgggcagccggagaacaactacaagacc acgcctcccgtgctggactccgacggctccttcttcctctacagcaagctcacc gtggacaagagcaggtggcagcaggggaacgtcttctcatgctccgtgatgc atgaggctctgcacaaccactacacgcagaagagcctctccctgtctccgggt aaatga |
| 019009 | 88 | MEAPAQLLFLLLLWLPDTTGEIVLTQSPATLSLSPGERA TLSCRTSENVYSYLAWYQQKPGQAPRLLIYFAKTLAEGI PARFSGSGSGTDFTLTISSLEPEDFAVYYCQHHSDNPW TFGQGTKVEIKGGGGSGGGGSGGGGASEVQLVQSGA EVKKPGESLRISCKGSGYSFTGYNMNWVRQMPGKGLE WMGNIDPYYGGTTYNRKFKGQVTISADKSISTAYLQWS SLKASDTAMYYCARSVGPMDYWGRGTLVTVSSDQEPK SSDKTHTSPPCPAPELLGGPSVFLFPPKPKDTLMISRTP EVTCVVVDVSHEDPEVKFNWYVDGVEVHNAKTKPREE QYNSTYRVVSVLTVLHQDWLNGKEYKCKVSNKALPAPI EKTISKAKGQPREPQVYTLPPSRDELTKNQVSLTCLVK GFYPSDIAVEWESNGQPENNYKTTPPVLDSDGSFFLYS KLTVDKSRWQQGNVFSCSVMHEALHNHYTQKSLSLSP GK |

The invention claimed is:

1. A method for treating a disease or disorder associated with aberrant B-cell activity, the method comprising administering to a subject in need thereof an effective amount of a humanized or chimeric CD37-specific binding molecule derived from G28-1 and comprising a binding domain and immunoglobulin CH2 and CH3 domains, wherein the binding domain comprises a light chain CDR1 comprising the amino acid sequence of SEQ ID NO: 61; a light chain CDR2 comprising the amino acid sequence of SEQ ID NO: 64; a light chain CDR3 comprising the amino acid sequence of SEQ ID NO: 66; a heavy chain CDR1 comprising the amino acid sequence of SEQ ID NO: 63; a heavy chain CDR2 comprising the amino acid sequence of SEQ ID NO: 65; and a heavy chain CDR3 comprising the amino acid sequence of SEQ ID NO: 67 or 68;

wherein said CD37-specific binding molecule specifically binds human CD37 on the surface of a B-cell in the subject.

2. The method of claim 1, wherein the disease or disorder is a B cell cancer or an autoimmune disease.

3. The method of claim 2, wherein the B cell cancer is selected from the group consisting of Hodgkin's disease, non-Hodgkins lymphoma (NHL), central nervous system lymphomas, leukemias, myelomas, small lymphocytic lymphoma, B-cell 'prolymphocytic leukemia, lymphoplasmacytic lymphoma, splenic marginal zone lymphoma, plasma cell myeloma, solitary plasmacytoma of bone, extraosseous plasmacytoma, extranodal marginal zone B-cell lymphoma of mucosa-associated (MALT) lymphoid tissue, nodal marginal zone B-cell lymphoma, follicular lymphoma, mantle cell lymphoma, diffuse large B-cell lymphoma, mediastinal (thymic) large B-cell lymphoma, intravascular large B-cell lymphoma, primary effusion lymphoma, Burkitt lymphoma/leukemia, B-cell proliferations of uncertain malignant potential, lymphomatoid granulomatosis, and post-transplant lymphoproliferative disorder.

4. The method of claim 2, wherein the autoimmune disease is selected from the group consisting of rheumatoid arthritis, multiple sclerosis, systemic lupus erythematosus, Crohn's disease, Sjogren's syndrome, Grave's disease, type I diabetes mellitus, psoriasis, immune thrombocytopenic purpura, pemphigus, idiopathic inflammatory myopathy, myasthenis gravis, and Waldenstorm's macroglobinemia.

5. A method of reducing B cell tumor volume in a subject in need thereof, the method comprising administering an effective amount of a humanized or chimeric CD37-specific binding molecule derived from G28-1 and comprising a binding domain and immunoglobulin CH2 and CH3 domains, wherein the binding domain comprises a light chain CDR1 comprising the amino acid sequence of SEQ ID NO: 61; a light chain CDR2 comprising the amino acid sequence of SEQ ID NO: 64; a light chain CDR3 comprising the amino acid sequence of SEQ ID NO: 66; a heavy chain CDR1 comprising the amino acid sequence of SEQ ID NO: 63; a heavy chain CDR2 comprising the amino acid sequence of SEQ ID NO: 65; and a heavy chain CDR3 comprising the amino acid sequence of SEQ ID NO: 67 or 68;

wherein said human or chimeric CD37-specific binding molecule specifically binds human CD37 on the surface of a B-cell tumor cell in the subject.

6. A method of inhibiting B cell tumor growth in a subject in need thereof, the method comprising administering an effective amount of a humanized or chimeric CD37-specific binding molecule derived from G28-1 and comprising a binding domain and immunoglobulin CH2 and CH3 domains, wherein the binding domain comprises a light chain CDR1 comprising the amino acid sequence of SEQ ID NO: 61; a light chain CDR2 comprising the amino acid sequence of SEQ ID NO: 64; a light chain CDR3 comprising the amino acid sequence of SEQ ID NO: 66; a heavy chain CDR1 comprising the amino acid sequence of SEQ ID NO: 63; a heavy chain CDR2 comprising the amino acid sequence of SEQ ID NO: 65; and a heavy chain CDR3 comprising the amino acid sequence of SEQ ID NO: 67 or 68;

wherein said humanized or chimeric CD37-specific binding molecule specifically binds human CD37 on the surface of a B-cell tumor cell in the subject.

7. A method of inducing tyrosine phosporylation in B cell cancer cells, the method comprising contacting the B cell cancer cells with a humanized or chimeric CD37-specific binding molecule derived from G28-1 and comprising a binding domain and immunoglobulin CH2 and CH3 domains, wherein the binding domain comprises a light chain CDR1 comprising the amino acid sequence of SEQ ID NO: 61; a light chain CDR2 comprising the amino acid sequence of SEQ ID NO: 64; a light chain CDR3 comprising the amino acid sequence of SEQ ID NO: 66; a heavy chain CDR1 comprising the amino acid sequence of SEQ ID NO: 63; a heavy chain CDR2 comprising the amino acid sequence of SEQ ID NO: 65; and a heavy chain CDR3 comprising the amino acid sequence of SEQ ID NO: 67 or 68;

wherein said humanized or chimeric CD37-specific binding molecule specifically binds human CD37 on the surface of a B-cell cancer cell.

8. The method of claim 3, wherein the leukemia is acute lymphoblastic leukemia (ALL), chronic lymphocytic leukemia (CLL), Hairy cell leukemia or chronic myoblastic leukemia.

* * * * *

UNITED STATES PATENT AND TRADEMARK OFFICE
CERTIFICATE OF CORRECTION

PATENT NO. : 10,143,748 B2
APPLICATION NO. : 13/836103
DATED : December 4, 2018
INVENTOR(S) : Laura Sue Grosmaire et al.

It is certified that error appears in the above-identified patent and that said Letters Patent is hereby corrected as shown below:

On the Title Page

Please delete the following: "(71) Applicant: Emergent Product Development Seattle, LLC, Seattle, WA (US)" and replace with: --(71) Applicant: Aptevo Research and Development LLC, Seattle, WA (US)--

Signed and Sealed this
Fifteenth Day of October, 2019

Andrei Iancu
*Director of the United States Patent and Trademark Office*